US012600997B2

(12) United States Patent
Jennewein et al.

(10) Patent No.: US 12,600,997 B2
(45) Date of Patent: Apr. 14, 2026

(54) FERMENTATIVE PRODUCTION OF SIALYLATED SACCHARIDES

(71) Applicant: Chr. Hansen A/S, Hoersholm (DK)

(72) Inventors: Stefan Jennewein, Bad Honnef (DE); Dirk Wartenberg, Gau-Algesheim (DE)

(73) Assignee: Chr. Hansen A/S, Hoersholm (DK)

( * ) Notice: Subject to any disclaimer, the term of this patent is extended or adjusted under 35 U.S.C. 154(b) by 1323 days.

(21) Appl. No.: 17/058,689

(22) PCT Filed: May 27, 2019

(86) PCT No.: PCT/EP2019/063669
§ 371 (c)(1),
(2) Date: Nov. 25, 2020

(87) PCT Pub. No.: WO2019/228993
PCT Pub. Date: Dec. 5, 2019

(65) Prior Publication Data
US 2021/0198709 A1 Jul. 1, 2021

(30) Foreign Application Priority Data
May 28, 2018 (EP) ..................................... 18174643

(51) Int. Cl.
*C12P 19/28* (2006.01)
*A23L 33/00* (2016.01)

(52) U.S. Cl.
CPC .............. *C12P 19/28* (2013.01); *A23L 33/40* (2016.08)

(58) Field of Classification Search
CPC ......... C12P 19/28; A23L 33/40; C12Y 204/99
See application file for complete search history.

(56) References Cited

U.S. PATENT DOCUMENTS

| | | | | |
|---|---|---|---|---|
| 2003/0157659 A1* | 8/2003 | Koizumi | .................. | C12N 9/90 435/85 |
| 2007/0020736 A1* | 1/2007 | Samain | .................... | C12P 19/04 435/85 |
| 2016/0024543 A1* | 1/2016 | Merighi | .................. | C12N 15/52 435/252.8 |

FOREIGN PATENT DOCUMENTS

| | | |
|---|---|---|
| CN | 1920048 A | 2/2007 |
| CN | 103602627 A | 2/2016 |
| EP | 1541693 A1 | 6/2005 |
| IN | 201917029091 | 7/2018 |
| IN | 202017006703 | 1/2019 |
| IN | 202017010852 | 3/2019 |
| WO | 2007101862 A1 | 9/2007 |
| WO | 2014153253 A1 | 9/2014 |
| WO | 2018122225 A1 | 7/2018 |
| WO | 2019020707 A1 | 1/2019 |
| WO | 2019043029 A1 | 3/2019 |

OTHER PUBLICATIONS

SEQ ID No. 91 search. Pending Patents AA Main search. Performed Jun. 14, 2024. (Year: 2024).*
SEQ ID No. 84 search. Published Applications AA Main search. Performed Apr. 4, 2025. (Year: 2025).*
PCT International Search Report for PCT/EP2019/063669, mailed Jul. 5, 2019.
Nicolas Fierfort and Eric Samain, "Genetic engineering of *Escherichia coli* for the economical production of sialylated oligosaccharides," Journal of Biotechnology, (2008), vol. 134, No. 3-4: 261-265.
Georg A. Sprenger, et al., "Production of human milk oligosaccharides by enzymatic and whole-cell microbial biotransformations," Journal of Biotechnology, (2017), vol. 258: 79-91.
Barbara Petschacher, et al., "Biotechnological production of fucosylated human milk oligosaccharides: Prokaryotic fucosyltransferases and their use in biocatalytic cascades or whole cell conversion systems," Journal of Biotechnology, (2016), vol. 235: 61-83.
Fierfort, et al., "Genetic engineering of *Escherichia coli* for the economical production of sialylated oligosaccharides," Journal of Biotechnology, Apr. 30, 2008, 134(3-4): 261-265, Elsevier, Amsterdam, Netherlands.
International Search Report issued in connection with PCT Application No. PCT/EP2019/063669 dated Jun. 17, 2019.
Petschacher, Barbara et al., "Biotechnological production of fucosylated human milk oligosaccharides: Prokaryotic fucosyltransferases and their use in biocatalytic cascades or whole cell conversion systems," Jounral of Biotechnology, Apr. 1, 2016, 235:61-83, Elsevier, Amsterdam, Netherlands.

(Continued)

*Primary Examiner* — David W Berke-Schlessel
*Assistant Examiner* — Susan E. Fernandez
(74) *Attorney, Agent, or Firm* — Kelly K. Reynolds

(57) ABSTRACT

Disclosed are methods for the fermentative production of a sialylated saccharide and genetically engineered microbial cells for use in said method, wherein the genetically engineered microbial cells comprise (i) a sialic acid biosynthesis pathway comprising a glucosamine-6-phosphate N-acetyltransferase, (ii) a cytidine 5'-monophospho-(CMP)-N-acetylneuraminic acid synthetase; and (iii) a sialyitransferase, for producing sialylated saccharides, as well as the use of said sialylated oligosaccharides for providing nutritional compositions.

17 Claims, 3 Drawing Sheets

Specification includes a Sequence Listing.

(56)                    References Cited

OTHER PUBLICATIONS

Sprenger, Georg et al., "Production of human milk oligosaccharides
by enzymatic and whole-cell microbial biotransformations", Journal
of Biotechnology, 258: 79-91, Jul. 29, 2017, Elsevier, Amsterdam,
Netherlands.
Opposition to Grant in Indian Patent Application No. 202017051809,
dated Aug. 3, 2023 (224 pages).
Kang J et al., 2012, Metabolic Engineering 14, 623-629.

* cited by examiner

FERMENTATIVE PRODUCTION OF SIALYLATED SACCHARIDES

CROSS-REFERENCE TO RELATED APPLICATIONS

This application is the National Stage entry of International Application No. PCT/EP2019/063669, filed 27 May 2019, which claims priority to European Patent Application No. 18174643.9, filed 28 May 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "3000045-024000_Sequence_Listing_ST25.txt" created on 20 Nov. 2020, and 291,602 bytes in size) is submitted concurrently with the instant application, and the entire contents of the Sequence Listing are incorporated herein by reference.

BACKGROUND

Field

The present invention relates to a method for the fermentative production of sialylated saccharides, as well as to recombinant or genetically engineered microbial cells employed therein.

Description of Related Art

More than 150 structurally distinct human milk oligosaccharides (HMOs) have been identified to date. Although HMOs represent only a minor amount of total human milk nutrients, their beneficial effects on the development of breast fed infants became evident over the past decades.

Among the HMOs, sialylated HMOs (SHMOs) were observed to support the resistance to enteropathogenic bacteria and viruses. Interestingly, recent studies further demonstrated a protective effect of long-chained SHMOs against necrotizing enterocolitis, which is one of the most common and lethal diseases in preterm infants. In addition, SHMOs are believed to support an infant's brain development and its cognitive capabilities. Also, sialylated oligosaccharides have been shown to neutralize enterotoxins of various pathogenic microbes including *Escherichia coli, Vibrio cholerae* and *Salmonella*. Further, it was found that sialylated oligosaccharides interfere with the colonization of the gut by *Helicobacter pylori* and thereby prevent or inhibit gastric and duodenal ulcers.

Among the sialylated oligosaccharides, 3'-sialyllactose, 6'-sialyllactose, sialyllacto-N-tetraose a, sialyllacto-N-tetraose b, sialyllacto-N-tetraose c and disialyllacto-N-tetraose are the most prevalent members in human milk.

Since sialylated oligosaccharides have a complex structure, their chemical or (chemo-) enzymatic syntheses are challenging and associated with extensive difficulties, e.g. control of stereochemistry, formation of specific linkages, availability of feedstocks, etc. As a consequence, commercially available sialylated oligosaccharides have been very expensive due to their low quantity in natural sources.

Thus, efforts in metabolic engineering of microorganisms to produce sialylated oligosaccharides have been made, since this approach is the most promising way for producing HMOs in an industrial scale. For the production of SHMOs by microbial fermentation, the microorganism is typically cultivated in the presence of exogenous sialic acid.

International Publication WO 2007/101862 A1 discloses a method for the large scale in vivo synthesis of sialylated oligosaccharides relying on the intracellular UDP-GlcNAc pool by culturing a microorganism in a culture medium, wherein said microorganism comprises heterologous genes encoding CMP-Neu5Ac synthetase, a sialic acid synthase, a GlcNAc-6-phosphate 2 epimerase and a sialyltransferase. In addition, the endogenous genes coding for sialic acid aldolase (NanA) and for ManNac kinase (NanK) were deleted.

International Publication WO 2014/153253 A1 discloses methods and compositions for engineering bacteria to produce sialylated oligosaccharides as well as a method for producing a sialylated oligosaccharide in a bacterium, said bacterium comprises an exogenous sialyltransferase, a deficient sialic acid catabolic pathway, a sialic acid synthetic capability, and a functional lactose permease gene, wherein said bacterium is cultured in the presence of lactose. The sialic acid synthetic capability comprises expressing an exogenous CMP-Neu5Ac synthetase, an exogenous sialic acid synthase, and an exogenous UDP-GlcNAc-2-epimerase.

However, it is desirable to produce sialylated oligosaccharides by microbial fermentation which does not require the presence and/or addition of exogenous sialic acid during fermentation. Also, it is desirable to produce sialylated oligosaccharides by microorganisms which does not require accessing the intracellular pool of UDP-N-acetylglucosamine (UDP-GlcNAc) as this is believed to be energetically beneficial for the cell.

SUMMARY

The object is solved, inter alia, by providing a method for the whole cell fermentative production of sialylated saccharides, which method does not require addition of exogenous sialic acid, and by a genetically engineered microbial cell which can synthesized sialylated saccharides in the absence of exogenous sialic acid.

According to one aspect, a method for the production of a sialylated saccharide is provided which method comprises the steps of a) providing at least one genetically engineered microbial cell which comprises (i) a sialic acid biosynthesis pathway for the intracellular biosynthesis of N-acetylneuraminic acid (Neu5Ac, NeuNAc), wherein said sialic acid biosynthesis pathway comprises a glucosamine-6-phosphate N-acetyltransferase (ii) a cytidine 5'-monophospho-(CMP)-sialic acid synthetase, and (iii) a heterologous sialyltransferase; b) cultivating the at least one genetically engineered microbial cell in a fermentation broth and under conditions permissive for the production of said sialylated saccharide; and optionally c) recovering said sialylated saccharide.

According to another aspect, a genetically engineered microbial cell for producing a sialylated saccharide is provided, wherein the microbial cell comprises (i) a sialic acid biosynthesis pathway for the intracellular biosynthesis of N-acetylneuraminic acid, wherein said sialic acid biosynthesis pathway comprises a glucosamine-6-phosphate N-acetyltransferase; (ii) a cytidine 5'-monophospho-(CMP)-N-acetylneuraminic acid synthetase for transferring the N-acetylneuraminic acid onto cytidine 5'-monophosphate to generate a CMP-activated N-acetylneuraminic acid; and (iii) a heterologous sialyltransferase.

According to another aspect, a sialylated saccharide is provided which is producible by a method or a genetically engineered microbial cell according to the invention.

According to another aspect, a use of a sialylated saccharide which is produced by a method or a genetically engineered microbial cell according to the invention for manufacturing a nutritional composition, preferably an infant composition, is provided.

According to yet another aspect, a nutritional composition containing at least one sialylated saccharide produced by the method or the genetically engineered microbial cell according to the invention is provided.

DETAILED DESCRIPTION

According to a first aspect, a method for the fermentative production of a sialylated saccharide is provided. The method comprises the steps of a) providing at least one genetically engineered microbial cell that is able to synthesize the sialylated saccharide, said at least one genetically engineered microbial cell comprises (i) a sialic acid biosynthesis pathway comprising a glucosamine-6-phosphate N-acetyltransferase; (ii) a cytidine 5'-monophopho-(CMP)-N-acetylneuraminic acid synthetase; and (iii) a heterologous sialyltransferase; b) cultivating the at least one genetically engineered microbial cell in a fermentation broth and under conditions that are permissive for the production of said sialylated saccharide, and optionally c) recovering said sialylated saccharide.

Accordingly, in a second aspect, the invention also concerns a genetically engineered microbial cell for the fermentative production of the sialylated saccharide, wherein the microbial cell comprises (i) a sialic acid biosynthesis pathway for the intracellular biosynthesis of N-acetylneuraminic acid, wherein said sialic acid biosynthesis pathway comprises a glucosamine-6-phosphate N-acetyltransferase; (ii) a cytidine 5'-monophospho-(CMP)-sialic acid synthetase for transferring the N-acetylneuraminic acid onto cytidine 5'-monophosphate to generate a CMP-activated sialic acid; and (iii) a sialyltransferase for transferring the N-acetylneuraminic acid moiety from the CMP-activated sialic acid as donor substrate to an acceptor molecule, which acceptor molecule is a saccharide molecule, resulting in the intracellular biosynthesis of the sialylated saccharide.

Figure 2:
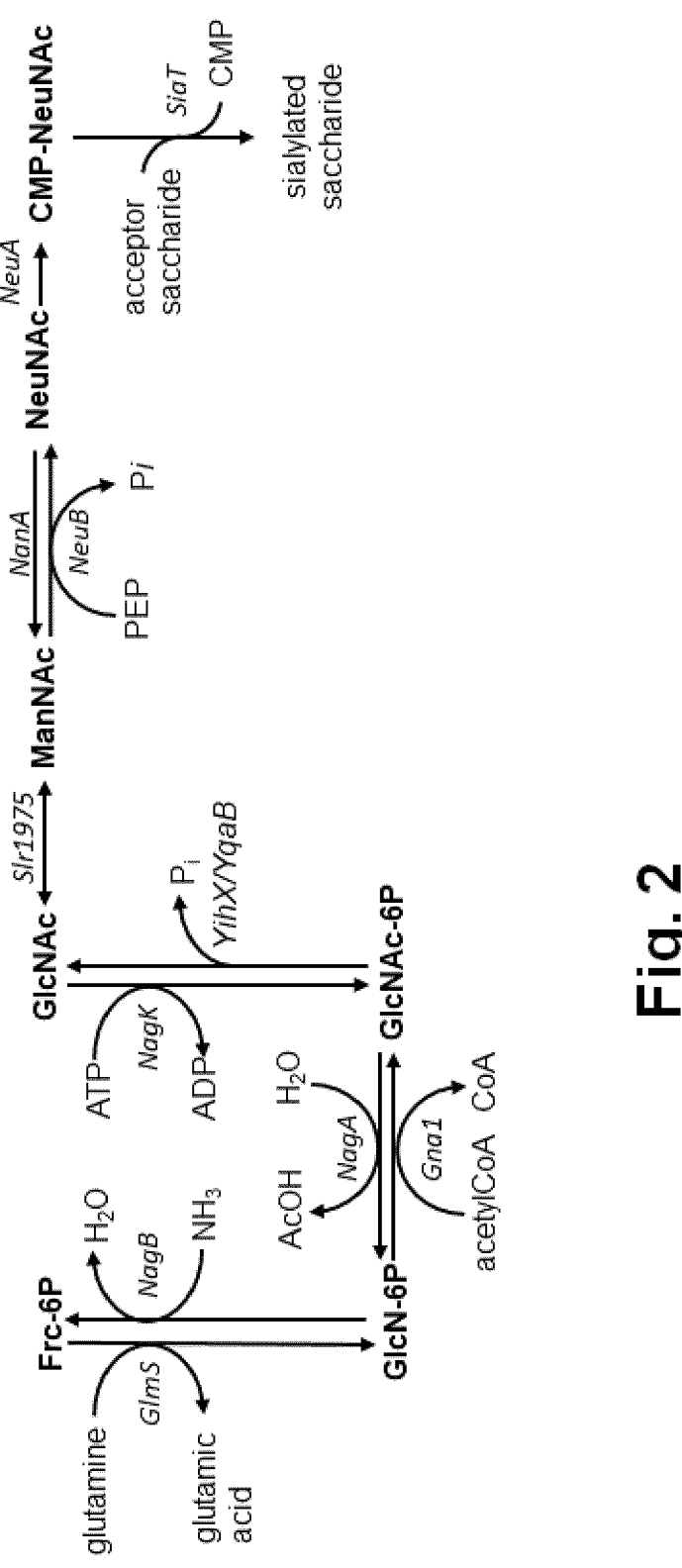
FIG. 2 is a schematic representation of a sialic acid biosynthesis pathway that may be employed by a genetically engineered microbial cell of the invention for the fermentative production of sialylated saccharides.
Figure 3:
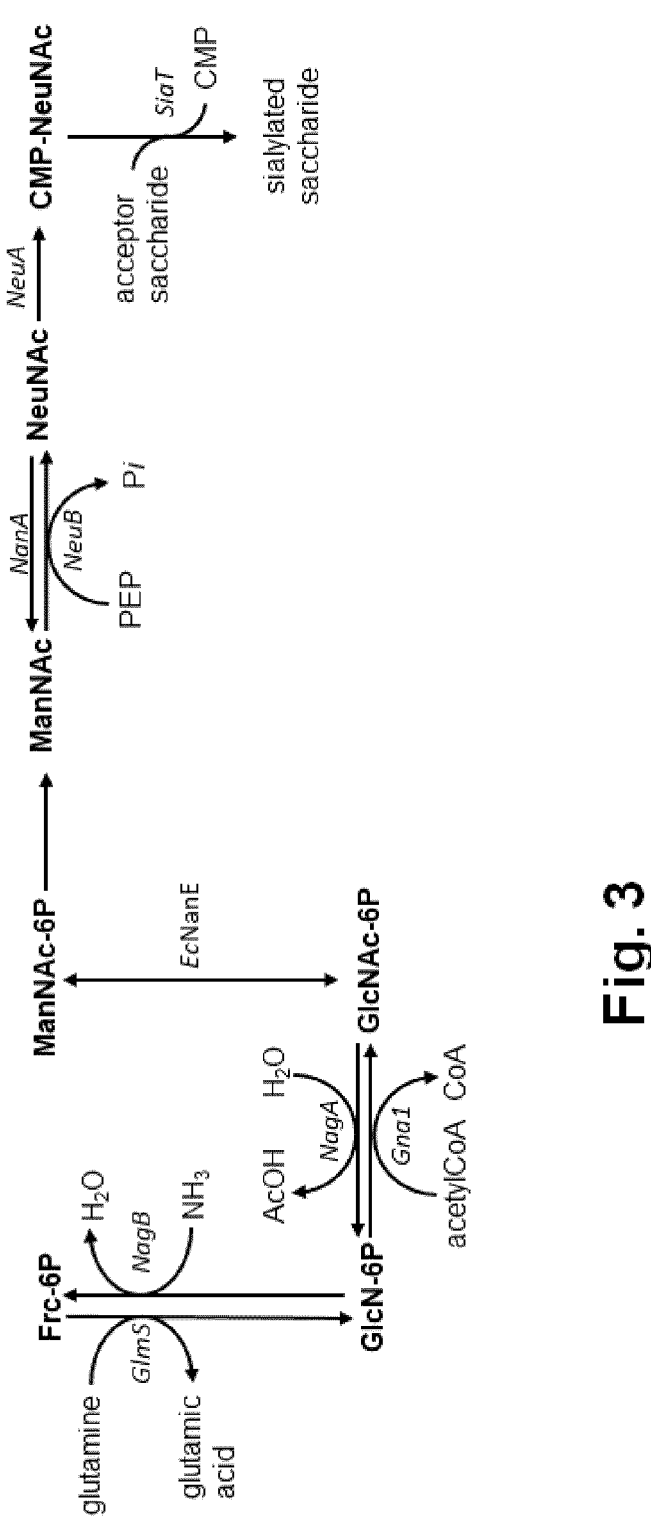
FIG. 3 is a schematic representation of another sialic acid biosynthesis pathway that may be employed by a genetically engineered microbial cell of the invention for the fermentative production of sialylated saccharides.

The genetically engineered microbial cell comprises a sialic acid biosynthesis pathway for the intracellular biosynthesis of N-acetylneuraminic acid which does not utilize UDP-GlcNAc. The genetically engineered microbial cell comprises a sialic acid biosynthesis pathway for the intracellular biosynthesis of N-acetylneuraminic acid which a glucosamine-6-phosphate N-acetyltransferase. A sialic acid biosynthesis pathway using a glucosamine-6-phosphate N-acetyltransferase for the intracellular biosynthesis of N-acetylneuraminic acid does not utilize UDP-GlcNAc for the biosynthesis of sialic acid (FIG. 2 and FIG. 3).

The sialic acid biosynthesis pathway comprises the enzymatic activities of a glutamine:fructose-6-phosphate aminotransferase and an N-acetylneuraminic acid synthase. The sialic acid biosynthesis pathway further comprises a) the enzymatic activities of a glucosamine-6-phosphate N-acetyltransferase, an N-acetylglucosamine-6-phosphate phosphatase and an N-acetylglucosamine 2-epimerase (FIG. 2); and/or b) the enzymatic activities of a glucosamine-6-phosphate N-acetyltransferase, an N-acetylglucosamine-6-phosphate epimerase and an N-acetylmannosamine-6-phosphate phosphatase (FIG. 3). Therefore, it is not necessary that the genetically engineered microbial cell comprises the enzymatic activities of a phosphoglucosamine mutase, an N-acetylglucosamine-1-phosphate uridyltransferase and an UDP N-acetylglucosamine 2-epimerase with concomitant release of UDP (FIG. 1) for intracellular sialic acid biosynthesis. Thus, in an additional and/or alternative embodiment, the genetically engineered microbial cell being capable of synthesizing sialic acid does not comprise one or more enzymatic activities selected from the group consisting of the enzymatic activities of a phosphoglucosamine mutase, an N-acetylglucosamine-1-phosphate uridyltransferase and an UDP N-acetylglucosamine 2-epimerase with concomitant release of UDP.

The enzyme glutamine:fructose-6-phosphate aminotransferase (EC 2.6.1.16) catalyzes the conversion of fructose-6-phosphate (Frc-6P) to glucosamine-6-phosphate (GlcN-6P) using glutamine. This enzymatic reaction is typically considered to be the first step in the hexosamine biosynthesis pathway. Alternative names of the glutamine:fructose-6-phosphate aminotransferase are D-fructose-6-phosphate aminotransferase, GFAT, glucosamine-6-phosphate synthase, hexosephosphate aminotransferase, and L-glutamine-D-fructose-6-phosphate aminotransferase.

In an additional and/or alternative embodiment, the genetically engineered microbial cell possesses a glutamine:fructose-6-phosphate aminotransferase, preferably a heterologous a glutamine:fructose-6-phosphate aminotransferase, more preferably a glutamine:fructose-6-phosphate aminotransferase which is derived from E. coli (E. coli GlmS (UniProtKB—P17169; SEQ ID NO. 67), or a functional variant of the E. coli GlmS. Most preferably, the functional variant is a version of the E. coli GlmS which shows significantly reduced sensitivity to glucosamine-6-phosphate inhibition as the wild-type enzyme does. An example of a functional variant of the E. coli GlmS which shows significantly reduced sensitivity to glucosamine-6-phosphate inhibition is represented by SEQ ID NO. 68).

In an additional and/or alternative embodiment, the genetically engineered microbial cell contains a nucleic acid molecule comprising a nucleotide sequence which encodes a glutamine:fructose-6-phosphate aminotransferase, preferably the E. coli glutamine:fructose-6-phosphate aminotransferase GlmS (SEQ ID NO. 69), or a nucleotide sequence encoding a functional variant is a version of the E. coli GlmS which shows significantly reduced sensitivity to glucosamine-6-phosphate inhibition as compared to the wild-type enzyme (glmS*54 or glmS* (as represented by SEQ ID NO. 70)).

Thus, in an additional and/or alternative embodiment, the genetically engineered microbial cell contains a nucleic acid molecule comprising and expressing a nucleotide sequence selected from the group consisting of i) nucleotide sequences encoding a polypeptide as represented by any one of SEQ ID No. 67 and SEQ ID NO. 68;

ii) nucleotide sequences as represented by any one of SEQ ID NO. 69 and SEQ ID NO. 70;

iii) nucleotide sequences having at least 80%, 90%, 95%, 96%, 97%, 98%, 99% or more than 99% sequence identity to one of the nucleotide sequences encoding a polypeptide as represented by any one of SEQ ID NO. 67 and SEQ ID NO. 68;

iv) nucleotide sequences having at least 80%, 90%, 95%, 96%, 97%, 98%, 99% or more than 99% sequence identity to one of the nucleotide sequences as represented by any one of SEQ ID NO. 69 and SEQ ID NO. 70;

v) nucleotide sequences which are complementary to any one of the nucleotide sequences of i, ii, iii, and iv; and vi) fragments of any one of the nucleotide sequences of i., ii., iii., iv and v.;

wherein said nucleotide sequence is operably linked to at least one nucleic acid expression control sequence effecting transcription and/or translation of said nucleotide sequence in the genetically engineered microbial cell to provide intracellular glutamine:fructose-6-phosphate aminotransferase activity.

In an additional and/or alternative embodiment, the genetically engineered microbial cell possesses glucosamine-6-phosphate N-acetyltransferase activity. Said glucosamine-6-phosphate N-acetyltransferase activity converts GlcN-6P to N-acetylglucosamine-6-phosphate (GlcNAc-6P). An example of a glucosamine-6-phosphate N-acetyltransferase is the *Saccharomyces cerevisiae* Gna1 (UniProtKB-P43577; SEQ ID NO. 77).

In an additional and/or alternative embodiment, the genetically engineered microbial cell contains a glucosamine-6-phosphate N-acetyltransferase, preferably a heterologous glucosamine-6-phosphate N-acetyltransferase, more preferably *S. cerevisiae* Gna1 (encoded by a nucleotide sequence as represented by SEQ ID NO. 78) or a functional variant thereof.

Thus, in an additional and/or alternative embodiment, the genetically engineered microbial cell contains a nucleic acid molecule comprising and expressing a nucleotide sequence selected from the group consisting of i) nucleotide sequences encoding a polypeptide as represented by SEQ ID NO. 77;

ii) a nucleotide sequences as represented by SEQ ID NO. 78;

iii) nucleotide sequences having at least 80%, 90%, 95%, 96%, 97%, 98%, 99% or more than 99% sequence identity to the nucleotide sequences encoding a polypeptide as represented by SEQ ID NO. 77;

iv) nucleotide sequences having at least 80%, 90%, 95%, 96%, 97%, 98%, 99% or more than 99% sequence identity to one of the nucleotide sequences as represented by SEQ ID NO. 78;

v) nucleotide sequences which are complementary to any one of the nucleotide sequences of i., ii., iii, and iv.; and vi) fragments of any one of the nucleotide sequences of i., ii., iii., iv and v.;

wherein said nucleotide sequence is operably linked to at least one nucleic acid expression control sequence effecting transcription and/or translation of said nucleotide sequence in the genetically engineered microbial cell to provide intracellular glucosamine-6-phosphate N-acetyltransferase activity.

In an additional and/or alternative embodiment, the genetically engineered microbial cell possesses a N-acetyl-glucosamine-6-phosphate phosphatase activity. Said N-acetylglucosamine-6-phosphate phosphatase activity converts GlcNAc6P to N-acetylglucosamine (GlcNAc). Examples of an N-acetylglucosamine-6-phosphate phosphatase are sugar phosphatases of the HAD-like superfamily which catalyze the conversion of GlcNAc6P to GlcNAc. The HAD-like superfamily of enzymes is named after the bacterial enzyme halo acid dehydrogenase and includes phosphatases. A suitable phosphatase of the HAD-like superfamily catalyzing the conversion of GlcNAc6P to GlcNAc may be selected from the group consisting of fructose-1-phosphate phosphatase (YqaB, UniProtKB-P77475; SEQ ID NO. 79) and alpha-D-glucose 1-phosphate phosphatase (YihX, UniProtKB—P0A8Y3; SEQ ID No. 80). The *E. coli* YqaB and *E. coli* YihX enzymes are considered to also act on GlcNAc6P (Lee, S. W. and Oh, M. K. (2015) Metabolic Engineering 28:143-150).

In an additional and/or alternative embodiment, the sugar phosphatase of the HAD-like superfamily catalyzing the conversion of GlcNAc-6P to GlcNAc is a heterologous enzyme in the genetically engineered microbial cell. In an additional and/or alternative embodiment, the sugar phosphatase of the HAD-like superfamily catalyzing the conversion of GlcNAc6P to GlcNAc is selected from the group consisting of *E. coli* YqaB, *E. coli* YihX, and functional variants thereof.

In an additional and/or alternative embodiment, the genetically engineered microbial cell contains a nucleic acid molecule which comprises and expresses a nucleotide sequence encoding a sugar phosphatase of the HAD-like superfamily catalyzing the conversion of GlcNAc6P to GlcNAc. In an additional and/or alternative embodiment, the nucleotide sequence encoding the sugar phosphatase of the HAD-like superfamily catalyzing the conversion of GlcNAc6P to GlcNAc is a heterologous nucleotide sequence. In an additional and/or alternative embodiment, the nucleotide sequence encoding the sugar phosphatase of the HAD-like superfamily catalyzing the conversion of GlcNAc6P to GlcNAc encodes the *E. coli* fructose-1-phosphate phosphatase or the *E. coli* alpha-D-glucose 1-phosphate phosphatase or a functional fragment of one of these two enzymes.

The *E. coli* YqaB is encoded by a nucleotide sequence as represented by SEQ ID NO. 81, whereas the *E. coli* YihX is encoded by a nucleotide sequences as represented by SEQ ID NO. 82. Thus, in an additional and/or alternative embodiment, the genetically engineered microbial cell contains a nucleic acid molecule comprising and expressing a nucleotide sequence selected from the group consisting of i) nucleotide sequences encoding a polypeptide as represented by any one of SEQ ID NO. 79 and SEQ ID NO. 80;

ii) nucleotide sequences as represented by any one of SEQ ID NO. 81 and SEQ ID NO. 82;

iii) nucleotide sequences having at least 80%, 90%, 95%, 96%, 97%, 98%, 99% or more than 99% sequence identity to one of the nucleotide sequences encoding a polypeptide as represented by any one of SEQ ID NO. 79 and SEQ ID NO. 80;

iv) nucleotide sequences having at least 80%, 90%, 95%, 96%, 97%, 98%, 99% or more than 99% sequence identity to one of the nucleotide sequences as represented by any one of SEQ ID NO. 81 and SEQ ID NO. 82;

v) nucleotide sequences which are complementary to any one of the nucleotide sequences of i, ii, iii, and iv; and vi) fragments of any one of the nucleotide sequences of i, ii, iii., iv and v.;

wherein said nucleotide sequence is operably linked to at least one nucleic acid expression control sequence effecting transcription and/or translation of said nucleotide sequence in the genetically engineered microbial cell to provide intracellular sugar phosphatase activity which catalyze the conversion of GlcNAc6P to GlcNAc.

In an additional and/or alternative embodiment, the non-naturally-occurring microorganism has been genetically engineered to contain a nucleic acid molecule comprising and expressing a nucleotide sequence encoding a sugar phosphatase of the HAD-like superfamily catalyzing the conversion of GlcNAc6P to GlcNAc or a functional fragment of said HAD phosphatase and/or to comprise a sugar phosphatase of the HAD-like In an additional and/or alternative embodiment, the genetically engineered microbial cell possesses N-acetylglucosamine 2-epimerase activity. N-acetylglucosamine 2-epimerase (EC 5.1.3.8) is an enzyme that catalyzes the conversion of N-acetylglucosamine (GlcNAc) to N-acetylmannosamine (ManNAc). The enzyme is a racemase acting on carbohydrates and their derivatives. The systematic name of this enzyme class is N-acyl-D-glucosamine 2-epimerase. This enzyme participates in amino-sugar metabolism and nucleotide-sugar metabolism, preferably a heterologous N-acetylglucosamine 2-epimerase.

In an additional and/or alternative embodiment, the genetically engineered microbial cell comprises an N-acetylglucosamine 2-epimerase, preferably a heterologous N-acetylglucosamine 2-epimerase. Examples of N-acetylglucosamine 2-epimerases were described from *Anabaena variabilis*, Acaryochloris sp., *Nostoc* sp., *Nostoc punctiforme*, *Bacteroides ovatus* or *Synechocystis* sp. An example of a suitable N-acetylglucosamine 2-epimerase is the N-acetylglucosamine 2-epimerase of *B. ovatus* ATCC 8483 (UniProtKB—A7LVG6, SEQ ID NO. 83) as encoded by gene BACOVA_01816 (SEQ ID NO. 85). Another example is the N-acetylglucosamine 2-epimerase of *Synechocystis* sp. (strain PCC 6803) (UniProtKB-P74124; SEQ ID NO: 84) which is also known as renin-binding protein and is encoded by the sir1975 gene (SEQ ID NO. 86).

In an additional and/or alternative embodiment, the genetically engineered microbial cell contains a nucleic acid molecule comprising a nucleotide sequence which encodes an N-acetylglucosamine 2-epimerase, preferably the N-acetylglucosamine 2-epimerase of *B. ovatus* ATCC 8483 or *Synechocystis* sp. (strain PCC 6803) or a functional variant thereof.

Thus, in an additional and/or alternative embodiment, the genetically engineered microbial cell contains a nucleic acid molecule comprising and expressing a nucleotide sequence selected from the group consisting of i) nucleotide sequences encoding a polypeptide as represented by any one of SEQ ID NO. 83 and SEQ ID NO. 84;

ii) nucleotide sequences as represented by any one of SEQ ID NO. 85 and SEQ ID NO. 86;

iii) nucleotide sequences having at least 80%, 90%, 95%, 96%, 97%, 98%, 99% or more than 99% sequence identity to one of the nucleotide sequences encoding a polypeptide as represented by any one of SEQ ID NO. 83 and SEQ ID NO. 84;

iv) nucleotide sequences having at least 80%, 90%, 95%, 96%, 97%, 98%, 99% or more than 99% sequence identity to one of the nucleotide sequences as represented by any one of SEQ ID NO. 85 and SEQ ID NO. 86;

v) nucleotide sequences which are complementary to any one of the nucleotide sequences of i, ii, iii, and iv; and vi) fragments of any one of the nucleotide sequences of i, ii, iii., iv and v.;

wherein said nucleotide sequence is operably linked to at least one nucleic acid expression control sequence effecting transcription and/or translation of said nucleotide sequence in the genetically engineered microbial cell to provide intracellular N-acetylglucosamine 2-epimerase activity.

In an additional and/or alternative embodiment, the genetically engineered microbial cell possesses N-acetylglucosamine-6-phosphate epimerase activity and N-acetylmannosamine-6-phosphate phosphatase activity. N-acetylglucosamine-6-phosphatase epimerase converts N-acetylglucosamine-6-phosphate (GlcNAc-6P) to N-acetylmannosamine-6-phosphate (ManNAc-6P), whereas N-acetylmannosamine-6-phosphate phosphatase dephosphorylates ManNAc-6P to give N-acetylmannosamine (ManNAc). Possessing N-acetylglucosamine-6-phosphate epimerase activity and N-acetylmannosamine-6-phosphate phosphatase activity provides an additional or alternative way for providing ManNAc for Neu5Ac production.

In an additional and/or alternative embodiment, the genetically engineered microbial cell contains an N-acetyl-glucosamine-6-phosphate epimerase. An example of a suitable N-acetylglucosamine-6-phosphate epimerase is *E. coli* NanE (UniprotKB POA761, SEQ ID NO. 87) as encoded by the *E. coli* nanE gene (SEQ ID NO. 88).

Thus, in an additional and/or alternative embodiment, the genetically engineered microbial cell contains a nucleic acid molecule comprising and expressing a nucleotide sequence encoding an N-acetylglucosamine-6-phosphate epimerase, preferably a nucleotide sequence encoding *E. coli* NanE.

Thus, in an additional and/or alternative embodiment, the genetically engineered microbial cell contains a nucleic acid molecule comprising and expressing a nucleotide sequence selected from the group consisting of i) nucleotide sequences encoding a polypeptide as represented by SEQ ID NO. 87;

ii) a nucleotide sequences as represented by SEQ ID NO. 88;

iii) nucleotide sequences having at least 80%, 90%, 95%, 96%, 97%, 98%, 99% or more than 99% sequence identity to the nucleotide sequences encoding a polypeptide as represented by SEQ ID NO. 87;

iv) nucleotide sequences having at least 80%, 90%, 95%, 96%, 97%, 98%, 99% or more than 99% sequence identity to one of the nucleotide sequences as represented by SEQ ID NO. 88;

v) nucleotide sequences which are complementary to any one of the nucleotide sequences of i, ii, iii, and iv; and vi) fragments of any one of the nucleotide sequences of i, ii, iii, iv and v;

wherein said nucleotide sequence is operably linked to at least one nucleic acid expression control sequence effecting transcription and/or translation of said nucleotide sequence in the genetically engineered microbial cell to provide intracellular N-acetylglucosamine-6-phosphate epimerase activity.

In an additional and/or alternative embodiment, the genetically engineered microbial cell contains an N-acetylmannosamine-6-phosphate phosphatase.

Thus, in an additional and/or alternative embodiment, the genetically engineered microbial cell contains a nucleic acid molecule comprising and expressing a nucleotide sequence encoding an N-acetylmannosamine-6-phosphate phosphatase.

In an additional and/or alternative embodiment, the genetically engineered microbial cell comprises sialic acid synthase activity. The sialic acid synthase catalyzes the condensation of ManNAc and phosphoenolpyruvate (PEP) to N-acetylneuraminic acid (NeuNAc).

In an additional and/or alternative embodiment, the genetically engineered microbial cell comprises a sialic acid synthase or a functional variant thereof, preferably a heterologous sialic acid synthase. Examples of sialic acid synthases are known from a variety of bacterial species such as *Campylobacter jejuni, Streptococcus agalactiae, Butyrivibrio proteoclasticus, Methanobrevibacter ruminantium, Acetobacterium woodii, Desulfobacula toluolica, Escherichia coli, Prevotella nigrescens, Halorhabdus tiamatea, Desulfotignum phosphitoxidans*, or Candidatus Scalindua sp., Idomarina loihiensis, *Fusobacterium nucleatum* or *Neisseria meningitidis*. Preferably, the sialic acid synthase is the N-acetylneuraminic acid synthase NeuB of *C. jejuni* (SEQ ID NO. 89) as encoded by the *C. jejuni* neuB gene (SEQ ID NO. 90).

Thus, in an additional and/or alternative embodiment, the genetically engineered microbial cell contains a nucleic acid molecule comprising and expressing a nucleotide sequence selected from the group consisting of
i) nucleotide sequences encoding a polypeptide as represented by SEQ ID NO. 89;
ii) a nucleotide sequences as represented by SEQ ID NO. 90;
iii) nucleotide sequences having at least 80%, 90%, 95%, 96%, 97%, 98%, 99% or more than 99% sequence identity to the nucleotide sequences encoding a polypeptide as represented by SEQ ID NO. 89;
iv) nucleotide sequences having at least 80%, 90%, 95%, 96%, 97%, 98%, 99% or more than 99% sequence identity to one of the nucleotide sequences as represented by SEQ ID NO. 90;
v) nucleotide sequences which are complementary to any one of the nucleotide sequences of i, ii, iii and iv; and
vi) fragments of any one of the nucleotide sequences of i, ii, iii, iv and v;
wherein said nucleotide sequence is operably linked to at least one nucleic acid expression control sequence effecting transcription and/or translation of said nucleotide sequence in the genetically engineered microbial cell to provide intracellular N-acetylneuraminic acid synthase activity.

The genetically engineered microbial cell possesses cytidine 5'-monophospho-(CMP)-N-acetylneuraminic acid synthetase activity for transferring cytidine 5'-monophosphate onto N-acetylneuraminic acid to generate a CMP-activated N-acetylneuraminic acid (CMP-NeuNAc). Several 5'-monophospho-(CMP)-sialic acid synthetases are known in the art and have been described, e.g. 5'-monophospho(CMP)-sialic acid synthetases from *E. coli, Neisseria meningitidis, Campylobacter jejuni, Streptococcus* sp., etc.

In an additional and/or alternative embodiment, the genetically engineered microbial cell contains a cytidine 5'-monophospho-(CMP)-N-acetylneuraminic acid synthetase, preferably a heterologous cytidine 5'-monophospho- (CMP)-N-acetylneuraminic acid synthetase, more preferably the N-acetylneuraminate cytidyltransferase NeuA from *E. coli. E. coli* NeuA (UnitProtKB—P13266; SEQ ID NO. 91) is encoded by the *E. coli* neuA gene (SEQ ID NO. 92).

Thus, in an additional and/or alternative embodiment, the genetically engineered microbial cell contains a nucleic acid molecule comprising and expressing a nucleotide sequence selected from the group consisting of
i) nucleotide sequences encoding a polypeptide as represented by SEQ ID NO. 91;
ii) a nucleotide sequences as represented by SEQ ID NO. 92;
iii) nucleotide sequences having at least 80%, 90%, 95%, 96%, 97%, 98%, 99% or more than 99% sequence identity to the nucleotide sequences encoding a polypeptide as represented by SEQ ID NO. 91;
iv) nucleotide sequences having at least 80%, 90%, 95%, 96%, 97%, 98%, 99% or more than 99% sequence identity to one of the nucleotide sequences as represented by SEQ ID NO. 92;
v) nucleotide sequences which are complementary to any one of the nucleotide sequences of i, ii, iii and iv; and
vi) fragments of any one of the nucleotide sequences of i, ii, iii, iv and v;
wherein said nucleotide sequence is operably linked to at least one nucleic acid expression control sequence effecting transcription and/or translation of said nucleotide sequence in the genetically engineered microbial cell to provide N-acetylneuraminate cytidyltransferase activity.

The genetically engineered microbial cell possesses sialyltransferase activity, preferably a heterologous sialyltransferase activity, and more preferably a sialyltransferase activity selected from the group consisting of $\alpha$-2,3-sialyltransferase activity, $\alpha$-2,6-sialyltransferase activity and/or $\alpha$-2,8-sialyltransferase activity. The sialyltransferase activity is capable of transferring the N-acetylneuraminic acid moiety from the CMP-NeuNAc to an acceptor molecule, wherein said acceptor molecule is a saccharide molecule, to provide a sialylated saccharide.

In an additional and/or alternative embodiment, the genetically engineered microbial cell contains at least one sialyltransferase, preferably at least one heterologous sialyltransferase, wherein said sialyltransferase is capable of possessing an $\alpha$-2,3-sialyltransferase activity and/or an $\alpha$-2,6-sialyltransferase activity and/or an $\alpha$-2,8-sialyltransferase activity for transferring the NeuNAc moiety from CMP-NeuNAc as donor substrate to the acceptor saccharide.

The term "sialyltransferase" as used herein refers to polypeptides being capable of possessing sialyltransferase activity. "Sialyltransferase activity" refers to the transfer of a sialic acid residue, preferably of an N-acetylneuraminic acid (Neu5Ac) residue, from a donor substrate to an acceptor molecule. The term "sialyltransferase" comprises functional fragments of the sialyltransferases described herein, functional variants of the sialyltransferases described herein, and functional fragments of the functional variants. "Functional" in this regard means that the fragments and/or variants are capable of possessing sialyltransferase activity. Functional fragments of a sialyltransferase encompass truncated versions of a sialyltransferase as encoded by it naturally occurring gene, which truncated version is capable of possessing sialyltransferase activity. Examples of truncated versions are sialyltransferases which do not comprise a so-called leader sequence which typically directs the polypeptide to a specific subcellular localization. Typically, such leader sequences are removed from the polypeptide during its subcellular transport, and are also absent in the naturally occurring mature sialyltransferase.

The heterologous sialyltransferase is capable of transferring a sialic acid residue from a donor substrate to an acceptor molecule. The term "capable of" with respect to the heterologous sialyltransferase refers to the sialyltransferase activity of the heterologous sialyltransferase and the provision that suitable reaction conditions are required for the heterologous sialyltransferase to possess its enzymatic activity. In the absence of suitable reaction conditions, the heterologous sialyltransferase does not possess its enzymatic activity, but retains its enzymatic activity and possesses its enzymatic activity when suitable reaction conditions are restored. Suitable reaction conditions include the presence of a suitable donor substrate, the presence of suitable acceptor molecules, the presence of essential cofactors such as—for example—monovalent or divalent ions, a pH value in an appropriate range, a suitable temperature and the like. It is not necessary that the optimum values for each and every factor effecting the enzymatic reaction of the heterologous sialyltransferase is met, but the reaction conditions have to be such that the heterologous sialyltransferase performs its enzymatic activity. Accordingly, the term "capable of" excludes any conditions upon which the enzymatic activity of the heterologous sialyltransferase has been irreversibly impaired and also excluded exposure of the heterologous sialyltransferase to any such condition. Instead, "capable of" means that the sialyltransferase is enzymatically active, i.e. possesses its sialyltransferase activity, if permissive reactions conditions (where all requirements being necessary for the sialyltransferase to perform its enzymatic activity) are provided to the sialyltransferase.

Sialyltransferases can be distinguished on the type of sugar linkage they form. As used herein, the terms "α-2,3-sialyltransferase" and "α-2,3-sialyltransferase activity" refer to polypeptides and their enzymatic activity which add a sialic acid residue with an α-2,3 linkage to galactose, N-acetylgalactosamine or a galactose or N-acetylgalactosamine residue of the acceptor molecule. Likewise, the terms "α-2,6-sialyltransferase" and "α-2,6-sialyltransferase activity" refer to polypeptides and their enzymatic activity which add a sialic acid residue with an α-2,6 linkage to galactose, N-acetylgalactosamine or a galactose or N-acetylgalactosamine residue of the acceptor molecule. Likewise, the terms "α-2,8-sialyltransferase" and "α-2,8-sialyltransferase activity" refer to polypeptides and their enzymatic activity which add a sialic acid residue with an α-2,8 linkage to galactose, N-acetylgalactosamine or a galactose or N-acetylgalactosamine residue of the acceptor molecule.

In an additional and/or alternative embodiment, the genetically engineered microbial cell contains a heterologous sialyltransferase that is preferably selected from the group consisting of I. polypeptides comprising or consisting of an amino acid sequence as represented by any one of SEQ ID NOs: 1 to 33;

II. polypeptides comprising or consisting of an amino acid sequence having a sequence identity of at least 80%, 90%, 95%, 96%, 97%, 98%, 99% or more than 99% to any one of the amino acid sequences as represented by any one of SEQ ID NOs: 1 to 33; and III. fragments of any one of the polypeptides of I. and II.

In an additional and/or alternative embodiment, the genetically engineered microbial cell has been transformed to contain a nucleic acid molecule which comprises and expresses a nucleotide sequence encoding the heterologous sialyltransferase. Preferably, a nucleotide sequence as can be inferred from Table 1. In an additional and/or alternative embodiment, the nucleotide sequence is selected from the group consisting of i. nucleotide sequences encoding a polypeptide as represented by any one of SEQ ID NOs: 1 to 33;

ii. nucleotide sequences as represented by any one of SEQ ID NOs: 34 to 66;

iii. nucleotide sequences having at least 80%, 90%, 95%, 96%, 97%, 98%, 99% or more than 99% sequence identity to one of the nucleotide sequences to one of the nucleotide sequences encoding a polypeptide as represented by any one of SEQ ID NOs: 1 to 33;

iv. nucleotide sequences having a sequence identity of at least 80%, 90%, 95%, 96%, 97%, 98%, 99% or more than 99% to any one of the nucleotide sequences represented by SEQ ID NOs: 34 to 66;

v. nucleotide sequences which are complementary to any one of the nucleotide sequences of i, ii, iii and iv; and vi. fragments of any one of the nucleotide sequences of i, ii, iii, iv and v;

wherein said nucleotide sequence is operably linked to at least one nucleic acid expression control sequence effecting transcription and/or translation of said nucleotide sequence in the genetically engineered microbial cell to provide sialyltransferase activity.

| Origin of the sialyltransferase gene | accession number of the sialyltransferase gene | Cloned as full length (FL) gene or without signal peptide (A) |
| --- | --- | --- |
| *Neisseria meningitidis* | U60660 | FL (SEQ ID NO: 5) |
| *Campylobacter jejuni* strain OH4384 | AF130466 | FL (SEQ ID NO: 10) |
| *Campylobacter jejuni* strain OH4384 | AX934425 | FL (SEQ ID NO: 12) |
| *Helicobacter acinonychis* | NC_008229 | FL (SEQ ID NO: 11) |
| *Helicobacter acinonychis* | NC_008229 | FL (SEQ ID NO: 33) |
| *Photobacterium* sp. JT-ISH-224 | BAF92026 | Δ17 (SEQ ID NO: 29) |
| *Pasteurella dagmatis* strain DSM 22969 | AFY98851 | FL (SEQ ID NO: 7) |
| *Photobacterium* sp. JT-ISH-224 | BAF92025 | Δ20 (SEQ ID NO: 3) |
| *Vibrio* sp. JT-FAJ-16 | BAF91160 | Δ22 (SEQ ID NO: 2) |
| *Pasteurella multocida* PM70 | AAK02272 | Δ25 (SEQ ID NO: 4) |
| *Photobacterium damselae* JT0160 | BAA25316 | FL (SEQ ID NO: 31) |
| *Streptococcus agalactiae* | AB050723 | FL (SEQ ID NO: 17) |
| *Haemophilus-somnus*-2336 | ACA31578 | FL (SEQ ID NO: 26) |
| *Haemophilus ducreyi* 35000HP | AF101047 | FL (SEQ ID NO: 14) |
| *Haemophilus ducreyi* 35000HP | AAP95068 | FL (SEQ ID NO: 27) |
| *Photobacterium phosphoreum* JT-ISH-467 | BAF63530 | Δ20 (SEQ ID NO: 8) |
| *Photobacterium leiognathi* JT-SHIZ-119 | AB500947 | Δ15 (SEQ ID NO: 28) |

-continued

| Origin of the sialyltransferase gene | accession number of the sialyltransferase gene | Cloned as full length (FL) gene or without signal peptide (A) |
|---|---|---|
| *Photobacterium leiognathi* JT-SHIZ-145 | BAF91416 | Δ15 (SEQ ID NO: 30) |
| *Campylobacter coli* | YP_008473374 | FL (SEQ ID NO: 1) |
| *Vibrio harveyi* | WP_017817635 | Δ24 (SEQ ID NO: 21) |
| *Streptococcus entericus* | WP_018369230 | FL (SEQ ID NO: 13) |
| *Avibacterium paragallinarum* | WP_021724759 | FL (SEQ ID NO: 9) |
| *Haemophilus parahaemolyticus* HK385 | EIJ71207 | FL (SEQ ID NO: 19) |
| *Alistipes* sp. CAG: 268 | CDC95697 | Δ17 (SEQ ID NO: 22) |
| *Alistipes* sp. AL-1 | WP_032134786 | FL (SEQ ID NO: 15) |
| *Pasteurella multocida* PM70 | NC_002663 | FL (SEQ ID NO: 6) |
| *Campylobacter jejuni* strain 81-176 | AAL09368 | FL (SEQ ID NO: 16) |
| *Alistipes shahii* WAL 8301 | YP_007816735 | Δ21 (SEQ ID NO: 23) |
| *Actinobacillus suis* ATCC 33415 | AIJ32009 | FL (SEQ ID NO: 24) |
| *Actinobacillus capsulatus* DSM 19761 | WP_018652686 | FL (SEQ ID NO: 25) |
| *Bibersteinia trehalosi* USDA-ARS-USMARC-189 | AHG84654 | FL (SEQ ID NO: 18) |
| *Photobacterium damselae* subsp. *damselae* CIP 102761 | EEZ40509 | FL (SEQ ID NO: 32) |
| *Haemophilus somnus* 2336 | ACA31170 | FL (SEQ ID NO: 20) |

Table 1: List of sialyltransferase-encoding nucleotide sequences. The sialyltransferase-encoding nucleotide sequences were either cloned as full length constructs (FL) or without a predicted signal peptide (4) as compared to their wild-type protein coding regions. The number behind the A indicates the N-terminally amino acids deleted from the corresponding sequence.

The expression "any one of SEQ ID NOs: 1 to 33" refers to any one of the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13. SEQ ID NO: 14. SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33. The same principle applies to the expression "any one of SEQ ID NOs: 34 to 66". Generally speaking, the expression "any one of SEQ ID NOs: X to Z", wherein "X" and "Z" represent a natural number, refers to all sequences (nucleotide sequences or amino acid sequences) represented by any one of the "SEQ ID NOs" comprising an identification number from X to Z.

In addition, the genetically engineered microbial cell has been genetically engineered to express the nucleotide sequence encoding the heterologous sialyltransferase. To this end, the nucleotide sequence encoding the heterologous sialyltransferase is operably linked to at least one expression control effecting transcription and/or translation of said nucleotide sequence encoding the heterologous sialyltransferase in the genetically engineered cell.

The term "operably linked" as used herein, refers to a functional linkage between the nucleotide sequence encoding the heterologous sialyltransferase and a second nucleotide sequence, the nucleic acid expression control sequence (such as promoter, operator, enhancer, regulator, array of transcription factor binding sites, transcriptional terminator, ribosome binding site), wherein the expression control sequence affects transcription and/or translation of the nucleic acid corresponding to the nucleotide sequence encoding the heterologous sialyltransferase. Accordingly, the term "promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

In an additional and/or alternative embodiment, the heterologous sialyltransferase being capable of possessing α-2, 3-sialyltransferase activity is selected from the group consisting of I polypeptides comprising or consisting of an amino acid sequence as represented by any one of SEQ ID NOs: 1 to 27;

II. polypeptides comprising or consisting of an amino acid sequence having an identity of at least 80%, 90%, 95%, 96%, 97%, 98%, 99% or more than 99% to any of the amino acid sequences as represented by any one of SEQ ID NOs: 1 to 27; and III. fragments of any one of the polypeptides of I. and II.

In an additional and/or alternative embodiment, the genetically engineered microbial cell contains a nucleic acid molecule which comprises at least one nucleotide sequence encoding said heterologous sialyltransferase being capable of possessing α-2,3-sialyltransferase activity, wherein said at least one nucleotide sequence is selected from the group consisting of i. nucleotide sequences encoding a polypeptide as represented by any one of SEQ ID NOs: 1 to 27;

ii. nucleotide sequences as represented by any one of SEQ ID NOs: 34 to 60;

iii. nucleotide sequences having at least 80%, 90%, 95%, 96%, 97%, 98%, 99% or more than 99% sequence identity to one of the nucleotide sequences encoding a polypeptide as represented by any one of SEQ ID NOs: 1 to 27;

iv. nucleotide sequences having a sequence identity of at least 80%, 90%, 95%, 96%, 97%, 98%, 99% or more than 99% to any one of the nucleotide sequences represented by SEQ ID NOs: 34 to 60;

v. nucleotide sequences which are complementary to any one of the nucleotide sequences of i, ii, iii and iv; and vi. fragments of any one of the nucleotide sequences of i, ii, iii, iv and v;

wherein said nucleotide sequence is operably linked to at least one nucleic acid expression control sequence effecting transcription and/or translation of said nucleotide sequence in the genetically engineered cell to provide α-2,3-sialyltransferase activity.

In an additional and/or alternative embodiment, the heterologous sialyltransferase being capable of possessing α-2, 3-sialyltransferase activity has a relative efficacy of at least 100-fold, at least 200-fold, at least 300-fold, at least 1000-fold, at least 10,000-fold, as compared to the relative efficacy of the sialyltransferase as represented by SEQ ID NO: 27 by means of quantitative analysis of LNT sialylation using LC-MS/MS.

In another embodiment, the heterologous sialyltransferase is capable of possessing α-2,6-sialyltransferase activity.

In an additional embodiment, the heterologous sialyltransferase being capable of possessing α-2,6-sialyltransferase activity is selected from the group consisting of I. polypeptides comprising or consisting of an amino acid sequence as represented by any one of SEQ ID NOs: 28 to 33;

II. polypeptides comprising or consisting of an amino acid sequence having an identity of at least 80%, 90%, 95%, 96%, 97%, 98%, 99% or more than 99% to any of the amino acid sequences as represented by any one of SEQ ID NOs: 28 to 33; and III. fragments of any one of the polypeptides of I. and II.

In an additional and/or alternative embodiment, the genetically engineered microbial cell contains a nucleic acid molecule which comprises at least one nucleotide sequence encoding said heterologous sialyltransferase being capable of possessing α-2,6-sialyltransferase activity, wherein said at least one nucleotide sequence is selected from the group consisting of i. nucleotide sequences encoding a polypeptide as represented by any one of SEQ ID NOs: 28 to 33;

ii. nucleotide sequences as represented by any one of SEQ ID NOs: 61 to 66;

iii. nucleotide sequences having at least 80%, 90%, 95%, 96%, 97%, 98%, 99% or more than 99% sequence identity to one of the nucleotide sequences encoding a polypeptide as represented by any one of SEQ ID NOs: 28 to 33;

iv. nucleotide sequences having a sequence identity of at least 80%, 90%, 95%, 96%, 97%, 98%, 99% or more than 99% to any one of the nucleotide sequences represented by SEQ ID NOs: 61 to 66;

v. nucleotide sequences which are complementary to any one of the nucleotide sequences of i, ii, iii and iv; and vi. fragments of any one of the nucleotide sequences of i, ii, iii, iv and v;

wherein said nucleotide sequence is operably linked to at least one nucleic acid expression control sequence effecting transcription and/or translation of said nucleotide sequence in the genetically engineered cell to provide α-2,6-sialyltransferase activity.

In an additional and/or alternative embodiment, the heterologous sialyltransferase being capable of possessing α-2, 6-sialyltransferase activity has a relative efficacy of at least 100-fold, more preferably of at least 200-fold, most preferably of at least 300-fold, as compared to the relative efficacy of the sialyltransferase as represented by SEQ ID NO: 33 by means of quantitative analysis of LNT sialylation.

In an additional and/or alternative embodiment, the heterologous sialyltransferase is capable of possessing α-2,8-sialyltransferase activity. An example of a heterologous sialyltransferase is capable of possessing α-2,8-sialyltransferase activity is the sialyltransferase CstII of *Campylobacter jejuni* OH4384.

The sialyltransferase is capable of transferring a sialic acid residue, e.g. a N-acetylneuraminic acid (Neu5Ac) residue, from a donor substrate, e.g. CMP-Neu5Ac, to an acceptor molecule. The acceptor molecule is a saccharide molecule, preferably a saccharide molecule set forth in Table 2.

| Name | Abbreviation | Structure |
|------|--------------|-----------|
| N-acetylglucosamine | GlcNAc | GlcNAc |
| Galactose | Gal | Gal |
| N-acetylgalactosamine | GalNAc | GalNAc |
| Lactose | Lac | Gal(β1,4)Glc |
| N-acetyllactosamine | LacNAc | Gal(β1,4)GlcNAc |
| Lacto-N-biose | LNB | Gal(β1,3)GlcNAc |
| Lactulose | LacU | Gal(β1,4)Frc |
| Melibiose | Mel | Gal(α1,6)Glc |
| Raffinose | Raf | Gal(α1,6)Glc(α1,2)Frc |
| 2'-Fucosyllactose | 2'-FL | Fuc(α1,2)Gal(β1,4)Glc |
| 3-Fucosyllactose | 3-FL | Gal(β1,4)[Fuc(α1,3)]Glc |
| 2',3-Difucosyllactose | DFL | Fuc(α1,2)Gal(β1,4)[Fuc(α1,3)]Glc |
| 6'-Galactosyllactose | 6'-GL | Gal(β1,6)Gal(β1,4)Glc |
| 3'-Galactosyllactose | 3'-GL | Gal(β1,3)Gal(β1,4)Glc |
| Lacto-N-triose II | LNT II | GlcNAc(β1,3)Gal(β1,4)Glc |
| Lacto-N-tetraose | LNT | Gal(β1,3)GlcNAc(β1,3)Gal(β1,4)Glc |
| Lacto-N-neotetraose | LNnT | Gal(β1,4)GlcNAc(β1,3)Gal(β1,4)Glc |
| Lacto-N-fucopentaose I | LNFP I | Fuc(α1,2)Gal(β1,3)GlcNAc(β1,3)Gal(β1,4)Glc |
| Lacto-N-neofucopentaose I | LNnFP I | Fuc(α1,2)Gal(β1,4)GlcNAc(β1,3)Gal(β1,4)Glc |
| Lacto-N-fucopentaose II | LNFP II | Gal(β1,3)[Fuc(α1,4)]GlcNAc(β1,3)Gal(β1,4)Glc |
| Lacto-N-fucopentaose III | LNFP III | Gal(β1,4)[Fuc(α1,3)]GlcNAc(β1,3)Gal(β1,4)Glc |
| Lacto-N-fucopentaose V | LNFP V | Gal(β1,3)GlcNAc(β1,3)Gal(β1,4)[Fuc(α1,3)]Glc |
| Lacto-N-neofucopentaose V | LNnFP V | Gal(β1,4)GlcNAc(β1,3)Gal(β1,4)[Fuc(α1,3)]Glc |
| Lacto-N-difucohexaose I | LNDH I | Fuc(α1,2)Gal(β1,3)[Fuc(α1,4)]GlcNAc(β1,3)Gal(β1,4)Glc |
| Lacto-N-difucohexaose II | LND | Gal(β1,3)[Fuc(α1,4)]GlcNAc(β1,3)Gal(β1,4)[Fuc(α1,3)]Glc |
| Lacto-N-neodifucohexaose I | LNnDFH I | Gal(β1,4)[Fuc(α1,3)]GlcNAc(β1,3)Gal(β1,4)[Fuc(α1,3)]Glc |
| Lacto-N-hexaose | LNH | Gal(β1,4)GlcNAc(β1,6)[Gal(β1,3)GlcNAc(β1,3)]Gal(β1,4)Glc |
| Lacto-N-neohexaose | LNnH | Gal(β1,4)GlcNAc(β1,6)[Gal(β1,4)GlcNAc(β1,3)]Gal(β1,4)Glc |

-continued

| Name | Abbreviation | Structure |
|---|---|---|
| para-Lacto-N-hexaose | paraLNT | Gal(β1,3)GlcNAc(β1,3)Gal(β1,4)GlcNAc(β1,3)Gal(β1,4)Glc |
| para-Lacto-N-neohexaose | paraLNnH | Gal(β1,4)GlcNAc(β1,3)Gal(β1,4)GlcNAc(β1,3)Gal(β1,4)Glc |
| 3'-Sialyllactose | 3'-SL | Neu5Ac(α2,3)Gal(β1,4)Glc |
| 6'-Sialyllactose | 6'-SL | Neu5Ac(α2,6)Gal(β1,4)Glc |
| Sialyllacto-N-tetraose a | LSTa | Neu5Ac(α2,3)Gal(β1,3)GlcNAc(β1,3)Gal(β1,4)Glc |
| Sialyllacto-N-tetraose b | LSTb | Gal(β1,3)[Neu5Ac(α2,6)]GlcNAc(β1,3)Gal(β1,4)Glc |
| Sialyllacto-N-tetraose c | LSTc | Neu5Ac(α2,6)Gal(β1,4)GlcNAc(β1,3)Gal(β1,4)Glc |
| Fucosyllacto-N-sialylpentaose a | F-LST-a | Neu5Ac(α2,3)Gal(β1,3)[Fuc(α1,4)]GlcNAc(β1,3)Gal(β1,4)Glc |
| Fucosyllacto-N-sialylpentaose b | F-LST-b | Fuc(α1,2)Gal(β1,3)[Neu5Ac(α2,6)]GlcNAc(β1,3)Gal(β1,4)Glc |
| Fucosyllacto-N-sialylpentaose c | F-LST-c | Neu5Ac(α2,3)Gal(β1,3)GlcNAc(β1,3)Gal(β1,4)[Fuc(α1,3)]Glc |
| Disialyllacto-N-tetraose | DS-LNT | Neu5Ac(α2,3)Gal(β1,3)[Neu5Ac(α2,6)]GlcNAc(β1,3)Gal(β1,4)Glc |
| 3-Fucosyl-3'-sialyllactose | 3F-3'-SL | Neu5Ac(α2,3)Gal(β1,4)[Fuc(α1,3)]Glc |
| 3-Fucosyl-6'-sialyllactose | 3F-6'-SL | Neu5Ac(α2,6)Gal(β1,4)[Fuc(α1,3)]Glc |
| 3'-sialyl-N-acetyllactosamine | 3'-SLN | Neu5Ac(α2,3)Gal(β1,4)GlcNAc |
| 6'-sialyl-N-acetyllactosamine | 6'-SLN | Neu5Ac(α2,6)Gal(β1,4)GlcNAc |

Table 2: List of saccharides that may be used as acceptor substrate for the production of a sialylated saccharide. The sialylated saccharide itself may also be used as acceptor substrate for the production of a further sialylated saccharide.

In an additional and/or alternative embodiment, the acceptor molecule is a monosaccharide, preferably a monosaccharide selected from the group consisting of N-acetylglucosamine, galactose and N-acetylgalactosamine.

In an additional and/or alternative embodiment, the acceptor molecule is a disaccharide, preferably a disaccharide selected from the group consisting lactose, lactulose, N-acetyllactosamine, lacto-N-biose, lactulose and melibiose.

In an additional and/or alternative embodiment, the acceptor molecule is a trisaccharide, preferably a trisaccharide selected from the group consisting of raffinose, lacto-N-triose II, 2'-fucosyllactose, 3-fucosyllactose, 3'-sialyllactose, 6'-sialyllactose, 3'-sialyl-N-acetyllactosamine, 6'-sialyl-N-acetyllactosamine, 3'-galactosyllactose and 6'-galactosyllactose.

In an additional and/or alternative embodiment, the acceptor molecule is a tetrasaccharide, preferably a tetrasaccharide selected from the group consisting of lacto-N-tetraose, lacto-N-neotetraose, 2'3-difucosyllactose, 3-fucosyl-3'-sialyllactose and 3-fucosyl-6'-sialyllactose.

In an additional and/or alternative embodiment, the acceptor molecule is a pentasaccharide, preferably a pentasaccharide selected from the group consisting of sialyllacto-N-tetraose a, sialyllacto-N-tetraose b, sialyllacto-N-tetraose c, lacto-N-fucopentaose I, lacto-N-fucopentaose II, lacto-N-fucopentaose III, lacto-N-fucopentaose V, lacto-N-neofucopentaose I and lacto-N-neofucopentaose V.

The term "functional variant" as used herein, with respect to an enzyme as mentioned herein, refers to polypeptide variants of the designated enzymes without loss of activity, and which share at least 70%, preferably at least 80%, at least 85%, at least 90%, at least 95%, at least 98% or least 99% identity with the amino acid sequence of the designated enzyme. This takes into account the possibility of some variability in the genomic sequence data from which these polypeptides are derived, and also the possibility that some of the amino acids present in these polypeptides can be substituted without significantly affecting the enzyme's catalytic activity.

The term "functional variant" also includes polypeptide variants of the designated enzymes which represent truncated variants of the enzyme without significant loss of the catalytic activity. Thus, the amino acid sequence of the truncated variants may differ from the amino acid sequences of the designated enzyme in that one, two or a stretch of more than two consecutive amino acids are absent. The truncation may be at the amino terminus (N-terminus), at the carboxyl terminus (C-terminus) and/or within the amino acid sequence of the designated enzyme.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

It is to be understood that a microbial cell already carrying one or more genes encoding said enzymes, and expressing said genes in a manner sufficient to produce NeuNAc, CMP-NeuNAc and/or the sialylated saccharide does not need to be genetically engineered to complete sialic acid biosynthesis and to transfer a sialic acid moiety to a saccharide acceptor, but may nevertheless be genetically engineered to alter the expression level of one or more of said genes to increase the intracellular level of said one or more gene products such as—for example the quantity of glutamine:fructose-6-phosphate aminotransferase, glucosamine-6-phosphate N-acetyltransferase, N-acetylglucosamine-6-phosphate phosphatase, N-acetylglucosamine 2-epimerase and/or N-acetylneuraminic acid synthase, thus increasing the rate of Neu5Ac biosynthesis and, as a consequence, of the sialylated saccharide, in the genetically engineered cell.

In an additional and/or alternative embodiment, the genetically engineered microbial cell synthesizes more PEP than the wildtype of the cell. In an additional and/or alternative embodiment, the genetically engineered microbial cell has been genetically engineered to possess an enhanced PEP biosynthesis pathway. Preferably, the genetically engineered microbial cell has been genetically engineered to possess an increased phosphoenolpyruvate synthase activity, for example in that the ppsA gene encoding phosphoenolpyruvate synthase gene is overexpressed and/or in that the non-naturally-occurring microorganisms contains at least one additional copy of a nucleotide sequence allowing the expression of a phosphoenolpyruvate synthase or a functional variant thereof. Overexpression of ppsA enhances intracellular PEP synthesis such that more PEP is available for the production of sialic acid. For example, a suitable phosphoenolpyruvate synthase is PpsA of E. coli.

In an additional and/or alternative embodiment, the genetically engineered microbial cell contains a nucleic acid molecule comprising a nucleotide sequence encoding E. coli PpsA or a functional variant thereof. Said nucleotide sequence encoding *E. coli* PpsA or a functional variant thereof has a sequence identity of at least 80%, at least 85%, at least 90%, at least 95%, at least 98% or at least 99% to the *E. coli* ppsA gene.

In an additional and/or alternative embodiment, the genetically engineered microbial cell additionally comprises one or more genes encoding for a polypeptide being capable of possessing an enzymatic activity selected from the group consisting of sucrose permease, sucrose hydrolase, fructoki-nase, L-glutamine: D-fructose-6-phosphate aminotransfer-ase, glucosamine-6-phosphate-N-acetyltransferase, N-acetylglucosamine-2-epimerase, sialic acid synthase, phosphoenolpyruvate synthase, wherein preferably at least one of these genes, preferably all, is/are overexpressed in the genetically engineered microbial cell as compared to the wild-type microbial cell.

In an additional and/or alternative embodiment, a sialic acid catabolic pathway that naturally occurs in the progeni-tor cell line of the genetically engineered microbial cell has been disabled in the genetically engineered microbial cell.

In an additional and/or alternative embodiment of the method and the genetically engineered microbial cell, the genetically engineered microbial cell lacks or possesses a decreased activity, as compared to the progenitor cell of the genetically engineered microbial cell, of one or more enzy-matic activities selected from the group consisting of α-N-acetylgalactosaminidase (e.g. NagA), N-acetylglu-cosaminekinase (e.g. NagK), N-acetylneuraminate lyase (=N-acetylneuraminic acid aldolase, e.g. NanA), β-galacto-sidase, a glucosamine-6-phosphate deaminase, a N-acetyl-glucosamine-6-phosphate deacetylase, a N-acetylman-nosamine kinase and/or a N-acetylmannosamine-6-phosphate epimerase.

In an additional and/or alternative embodiment of the method and the genetically engineered microbial cell, the genetically engineered microbial cell additionally comprises one or more genes encoding for a polypeptide being capable of possessing an enzymatic activity selected from the group consisting of N-acetylglucosamine-1-phosphate uridyltrans-ferase, glucosamine-1-phosphate acetyl transferase, phos-phoglucosamine mutase, UDP-N-acetylglucosamine-2-epi-merase, UDP-galactose-4-epimerase, galactose-1-phosphate uridylyltransferase, phosphoglucomutase, glu-cose-1-phos-phate uridylyltransferase, phosphomannomutase, mannose-1-phosphate glucanosyltransferase, GDP-mannose-4,6-de-hydratase, GDP-L-fucose synthase and fucosekinase/L-fucose-1-phosphate-guanyltransferase.

In an additional and/or alternative embodiment, the genetically engineered microbial cell comprises at least one selected from the group consisting of a functional lactose permease, a functional sialic acid transporter (exporter), wherein preferably comprises and expresses at least one nucleotide sequence encoding one selected from the group consisting of a functional lactose permease, a functional sucrose permease, a functional sialic acid transporter (ex-porter), wherein preferably at least one of these nucleotide sequences is overexpressed in the cell.

In an additional and/or alternative embodiment, the genetically engineered microbial cell is further modified to be capable to transfer said sole carbon source into the cell via a mechanism, that is not consuming PEP.

In an additional and/or alternative embodiment, the genetically engineered microbial cell possesses a functional sucrose utilization system. Said functional sucrose utiliza-tion system enables cellular import of exogenously supplied sucrose and its hydrolysis such that the resulting monosaccharides glucose and fructose can be metabolically utilized by the genetically engineered cell's metabolism and for the desired sialylated oligosaccharide production.

In an additional and/or alternative embodiment, the genetically engineered microbial cell has been genetically modified to possess a functional sucrose utilization system. In an additional and/or alternative embodiment the sucrose utilization system of the non-naturally-occurring microor-ganism comprises a sucrose proton symport transport sys-tem, a fructokinase, an invertase and a sucrose operon repressor.

A suitable a sucrose proton symport transport system is CscB, encoded by the cscB gene, for example CscB of *E. coli* (UniProtKB-P30000) as encoded by the cscB gene of *E. coli*.

A suitable fructokinase (EC 2.7.1.4) is CscK, encoded by the cscK gene, for example CscK of *E. coli* (UniProtKB-P40713) as encoded by the cscK gene of *E. coli*.

A suitable invertase (EC 3.2.1.26) which hydrolysis ter-minal nonreducing β-D-fructofuranoside residues in 3-D-fructofuranosides is CscA, for example CscA of *E. coli* (UniProtKB-086076) as encoded by the cscA gene of *E. coli*.

A suitable sucrose operon repressor is CscR as encoded by the cscR gene, for example the CscR of *E. coli* (UniPro-tKB-P62604) as encoded by the cscR gene of *E. coli*.

In an additional and/or alternative embodiment, the genetically engineered cell has been genetically engineered to possess a sucrose proton symport transport system, a fructokinase, an invertase and a sucrose operon repressor or functional variants of any one of these proteins.

In an additional and/or alternative embodiment, the genetically engineered cell has been genetically engineered to possess a nucleic acid molecule comprising nucleotide sequences encoding a sucrose proton symport transport system, a fructokinase, an invertase and a sucrose operon repressor for the expression of said sucrose proton symport transport system, fructokinase, invertase and sucrose operon repressor. In an additional and/or alternative embodiment, the genetically engineered cell has been genetically engi-neered to express the genes cscB, cscK, cscA, preferably the *E. coli* genes cscB, cscK, cscA and cscR.

In an additional and/or alternative embodiment, the nucleotide sequence encoding a functional variant of CscB, CscK, CscA or CscR has a sequence identity or at least 80%, at least 85%, at least 90%, at least 95%, at least 98% or at least 99% to *E. coli* cscB, cscK, cscA or cscR, respectively.

In an additional and/or alternative embodiment, the non-naturally-occurring microorganism expresses a β-galacto-side permease and a β-galactosidase.

In an additional and/or alternative embodiment, the non-naturally-occurring microorganism has been genetically engineered to express a β-galactoside permease, preferably the *E. coli* lactose permease LacY (SEQ ID NO: 93) or a functional variant thereof and a β-galactosidase, preferably *E. coli* LacZ (SEQ ID NO: 95) or a functional variant thereof. In an additional and/or alternative embodiment, the non-naturally-occurring microorganism has been genetically engineered to carry a nucleic acid molecule comprising a nucleotide sequence encoding a β-galactoside permease, preferably a nucleotide sequence encoding the *E. coli* LacY (SEQ ID NO: 94) or a functional variant thereof, and/or a nucleotide sequence encoding a β-galactosidase, preferably a nucleotide sequence encoding *E. coli* LacZ (SEQ ID NO: 96) or a functional variant thereof.

In an additional and/or alternative embodiment, the nucleotide sequence encoding *E. coli* LacY or a functional variant thereof has a sequence identity to *E. coli* lacY of at least 80%, at least 85%, at least 90%, at least 95%, at least 98% or at least 99%.

In an additional and/or alternative embodiment, the nucleotide sequence encoding *E. coli* LacZ or a functional variant thereof has a sequence identity to *E. coli* lacZ of at least 80%, at least 85%, at least 90%, at least 95%, at least 98% or at least 99%.

A non-naturally-occurring microorganism that can produce CMPNeu5Ac, and which expresses a functional β-galactoside permease and a functional β-galactosidase allows the cultivation of said non-naturally-occurring microorganism on lactose as a sole carbon source.

The genetically engineered microbial cell that can produce sialylated saccharides may—optionally—include additional features, and may be genetically engineered to possess these additional features. These additional features are considered to improve the productivity of the non-naturally-occurring microorganism leading to higher sialylated saccharide yields.

In an additional and/or alternative embodiment the genetically engineered microbial cell has been genetically engineered to abolish UDP-glucose:undecaprenylphosphate glucose-1-phosphate transferase activity, preferably by deleting the wcaJ gene or a functional variant thereof, by impairing expression of the wcaJ gene or a functional variant thereof, or by abolishing the activity of the WcaJ enzyme by introducing mutations into the protein-coding region of the such that the polypeptide encoded by the altered nucleotide sequence does not possess enzymatic activity of WcaJ. WcaJ encodes a UDP-glucose: undecaprenylphosphate glucose-1-phosphate transferase. Said UDP-glucose: undecaprenylphosphate glucose-1-phosphate transferase is the first enzyme in colanic acid biosynthesis.

In an additional and/or alternative embodiment, the genetically engineered microbial cell has been genetically engineered in that the β-galactosidase gene (lacZ) has been deleted, in that the expression of the β-galactosidase gene is impaired or in that the nucleotide sequence of the protein coding region of the β-galactosidase gene is amended such that the polypeptide being encoded by said altered nucleotide sequence(s) does not possess the enzymatic activity of the β-galactosidase.

In an additional and/or alternative embodiment, the genetically engineered microbial cell has been genetically engineered in that the gene encoding the galactose kinase (e.g. ga/K gene) has been deleted, in that the expression of the galk gene is impaired or in that the nucleotide sequence of the protein coding region of the galK gene is amended such that the polypeptide being encoded by said altered nucleotide sequence(s) does not possess the enzymatic activity of the galactose kinase. Deletion or inactivation of the ga/K gene/GalK is advantageous in that the genetically engineered microbial cell can utilize galactose as an acceptor substrate for sialylation reactions only.

In an additional and/or alternative embodiment, the genetically engineered microbial cell has been genetically engineered in that the gene encoding the N-acetylgalactosaminidase (nagA) has been deleted, that its expression has been impaired or in that the nucleotide sequence of the protein coding region is amended such that the polypeptide being encoded by said altered nucleotide sequence(s) does not possess the enzymatic activity of an N-acetylgalactosaminidase. Deletion or inactivation of nagA/NagA is advantageous in that the genetically engineered microbial cell can utilize GlcNAc or GlcNAc-6-phosphate as an acceptor for sialylation reactions only.

In an additional and/or alternative embodiment the genetically engineered microbial cell has been genetically engineered to abolish fucose isomerase activity, preferably by the deletion the fucI gene, by impairing expression of the fucI gene, or by modifying the protein-coding region of the fucI gene such that the polypeptide being encoded by said altered nucleotide sequence does not possess fucose isomerase activity. For example, the *E. coli* L-fucose isomerase FucI (UniProtKB-P69922) is encoded by the *E. coli* fucI gene.

Fuculokinase catalyzes the phosphorylation of fucose. Fuculokinase is the second enzyme in the subpathway that synthesizes L-lactaldehyde and glycerone phosphate from L-fucose. The *E. coli* fuculokinase fucK (UniProtKB-P11553) is encoded by the *E. coli* fucK gene. *E. coli* fuculokinase can also phosphorylate, with lower efficiency, D-ribulose, D-xylulose and D-fructose.

In an additional and/or alternative embodiment the genetically engineered cell has been genetically engineered to abolish fucose isomerase activity, preferably by the deletion of the fucK gene or, by impairing expression of the fucK gene, or by introducing mutations into the protein-coding region of the fucK gene such that the polypeptide being encoded by said altered nucleotide sequence does not possess fucose isomerase activity.

N-acetylgalactosamine-6-phosphate deacetylase catalyzes the following reaction: N-acetyl-D-galactosamine 6-phosphate+$H_2O$→D-galactosamine 6-phosphate+acetate. N-acetylgalactosamine-6-phosphate deacetylase is encoded by the agaA gene. In *E. coli* the N-acetylgalactosamine-6-phosphate deacetylase AgaA (UniProtKB-P42906) is encoded by the *E. coli* agaA gene.

In an additional and/or alternative embodiment the genetically engineered microbial cell has been genetically engineered to abolish N-acetylgalactosamine-6-phosphate deacetylase activity, preferably by deletion of the agaA gene, by impairing expression of the agaA gene, or by introducing mutations into the protein-coding region of the agaA gene such that the polypeptide being encoded by said altered nucleotide sequence does not possess N-acetylgalactosamine-6-phosphate deacetylase activity.

In an additional and/or alternative embodiment, the at least one genetically engineered microbial cell possesses an increased production of one or more nucleotide-activated sugars selected from the group consisting of UDP-N-acetylglucosamine, UDP-galactose and GDP-fucose. Preferably, the at least one genetically engineered microbial cell has been further genetically engineered to possess an increased production of one or more of said nucleotide-activated sugars. The production of the at least one of said nucleotide activated sugars is increased in the further genetically engineered cell as compared to the production of the same nucleotide-activated sugar(s) in the progenitor cell of the further genetically engineered microbial cell prior to being further genetically engineered to possess an increased production of at least one of said nucleotide-activated sugars.

In an additional and/or alternative embodiment, the at least one microbial cell has been further genetically engineered to overexpress one or more genes encoding for a polypeptide being capable of possessing an enzymatic activity selected from the group consisting of L-glutamine:D-fructose-6-phosphate aminotransferase, N-acetylglucosamine-1-phosphate uridyltransferase, glucosamine-1-phosphate acetyl transferase, phosphoglucosamine mutase, UDP-galactose-4-epimerase, galactose-1-phosphate uridylyltransferase, phosphoglucomutase, glucose-1-phosphate uridylyltransferase, phosphomannomutase, mannose-1- phosphate guanosyltransferase, GDP-mannose-4,6-dehydratase, GDP-L-fucose synthase and fucose kinase/L-fucose-1-phosphateguanyltransferase.

Presently, and as understood in the general field, and here with respect to every polynucleotide or nucleic acid discussed herein respectively, said overexpression of one or more genes or polypeptides is an overexpression as compared to the progenitor cell of the further genetically engineered microbial cell prior to being further genetically engineered to possess overexpression of said one or more genes or polypeptides.

Overexpression of one or more of said genes increases the amount of the corresponding polypeptides, i.e. enzyme(s), in the genetically engineered microbial cell, and hence increases the corresponding enzymatic activity in the cell to enhance intracellular production of sialylated saccharides.

In an additional and/or alternative embodiment, the at least one genetically engineered cell lacks or possesses a decreased activity of one or more enzymatic activities selected from the group consisting of β-galactosidase activity, glucosamine-6-phosphate deaminase, N-acetylglucosamine-6-phosphate deacetylase, N-acetylmannosamine kinase, N-acetylmannosamine-6-phosphate epimerase and N-acetylneuraminic acid aldolase as compared to the cell prior to be genetically engineered.

In an additional and/or alternative embodiment, one or more of the genes encoding a β-galactosidase, a glucosamine-6-phosphate deaminase, a N-acetylglucosamine-6-phosphate deacetylase, a N-acetylmannosamine kinase, a N-acetylmannosamine-6-phosphate epimerase and a N-acetylneuraminic acid aldolase has/have been deleted from the genome of the genetically engineered cell or the expression of one or more of the genes encoding a β-galactosidase, a glucosamine-6-phosphate deaminase, a N-acetylglucosamine-6-phosphate deacetylase, a N-acetyl mannosamine kinase, a N-acetylmannosamine-6-phosphate epimerase and a N-acetylneuraminic acid aldolase has/have been inactivated or at least decrease in the genetically engineered cell by further genetically engineering of cell. The expression of said genes is decreased in the further genetically engineered cell as compared to the progenitor cell of the further genetically engineered cell prior to being further genetically engineered to possess a decreased expression of said genes.

The genetically engineered microbial cell, preferably a prokaryotic cell. Appropriate microbial cells include yeast cells, bacterial cells, archaebacterial cells, algae cells, and fungal cells.

In an additional and/or alternative embodiment, the genetically engineered microbial cell is a bacterial cell, preferably a bacterial cell selected from the group consisting of *Bacillus, Lactobacillus, Lactococcus, Enterococcus, Bifidobacterium, Sporolactobacillus* spp., *Micromonospora* spp., *Micrococcus* spp., *Rhodococcus* spp., and *Pseudomonas*. Suitable bacterial species are *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus, Bacillus circulans, Bifidobacterium longum, Bifidobacterium infantis, Bifidobacterium bifidum, Citrobacter freundii, Clostridium cellulolyticum, Clostridium ljungdahlii, Clostridium* autoethanogenum, *Clostridium acetobutylicum, Corynebacterium glutamicum, Enterococcus faecium, Enterococcus* thermophiles, *Escherichia coli, Erwinia herbicola* (*Pantoea agglomerans*), *Lactobacillus acidophilus, Lactobacillus salivarius, Lactobacillus plantarum, Lactobacillus helveticus, Lactobacillus delbrueckii, Lactobacillus*

*rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Pantoea citrea, Pectobacterium carotovorum, Proprionibacterium freudenreichii, Pseudomonas fluorescens, Pseudomonas aeruginosa, Streptococcus* thermophiles and *Xanthomonas campestris.*

In an alternative embodiment, the genetically engineered cell is a yeast cell, preferably selected from the group consisting of *Saccharomyces* sp., in particular *Saccharomyces cerevisiae, Saccharomycopsis* sp., *Pichia* sp., in particular *Pichia pastoris, Hansenula* sp., *Kluyveromyces* sp., *Yarrowia* sp., *Rhodotorula* sp., and *Schizosaccharomyces* sp.

The genetically engineered cell has been genetically engineered to comprise a NeuNAc biosynthesis pathway, a cytidine 5'-monophospho-(CMP)-sialic acid synthetase activity, and a sialyltransferase activity.

The term "genetically engineered" as used herein refers to the modification of the microbial cell's genetic make-up using molecular biological methods. The modification of the microbial cell's genetic make-up may include the transfer of genes within and/or across species boundaries, inserting, deleting, replacing and/or modifying nucleotides, triplets, genes, open reading frames, promoters, enhancers, terminators and other nucleotide sequences mediating and/or controlling gene expression. The modification of the microbial cell's genetic make-up aims to generate a genetically modified organism possessing particular, desired properties. Genetically engineered microbial cells can contain one or more genes that are not present in the native (not genetically engineered) form of the cell. Techniques for introducing exogenous nucleic acid molecules and/or inserting exogenous nucleic acid molecules (recombinant, heterologous) into a cell's hereditary information for inserting, deleting or altering the nucleotide sequence of a cell's genetic information are known to the skilled artisan. Genetically engineered microbial cells can contain one or more genes that are present in the native form of the cell, wherein said genes are modified and re-introduced into the microbial cell by artificial means. The term "genetically engineered" also encompasses microbial cells that contain a nucleic acid molecule being endogenous to the cell, and that has been modified without removing the nucleic acid molecule from the cell. Such modifications include those obtained by gene replacement, site-specific mutations, and related techniques.

The term "heterologous" as used herein refers to a polypeptide, amino acid sequence, nucleic acid molecule or nucleotide sequence that is foreign to a cell or organism, i.e. to a polypeptide, amino acid sequence, nucleic acid molecule or nucleotide sequence that does not naturally occurs in said cell or organism. A "heterologous sequence" or a "heterologous nucleic acid" or "heterologous polypeptide", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microbial host cell, thus representing a genetically modified host cell. Techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989). Accordingly, a "heterologous polypeptide" is a polypeptide that does not naturally occur in the cell, and a "heterologous sialyltransferase" is a sialyltransferase that does not naturally occur in the microbial cell.

In an aspect, provided is a method by means of which a sialylated saccharide can be produced by fermentation, i.e. by means of whole cell biocatalysis, using a genetically engineered microbial cell as set forth herein before. The production of said sialylated saccharide does not require addition of N-acetylglucosamine, N-acetylmannosamine and/or N-acetylneuraminic acid to the fermentation broth and/or cultivating the genetically engineered microbial cell in the presence of N-acetylglucosamine, N-acetylmannosamine and/or N-acetylneuraminic acid for the intracellular biosynthesis of the sialylated saccharide.

In the method, the at least one genetically engineered microbial cell is cultivated in a fermentation broth and under conditions which are permissive for the production of the saccharide comprising at least one N-acetylneuraminic acid moiety.

In an additional and/or alternative embodiment, the fermentation broth contains at least one carbon source, the at least one carbon source is preferably selected from the group consisting of glucose, fructose, sucrose, glycerol and combinations thereof.

While the process and the genetically modified/engineered microbial cell employs a carbon source in the fermentation broth, it is not necessary to add glucosamine and/or N-acetylneuraminic acid and/or N-acetylglucosamine and/or N-acetylmannosamine to the fermentation broth, since the N-acetylneuraminic acid is produced intracellularly by the genetically engineered microbial cell. Thus, in an additional and or alternative embodiment, the at least one genetically engineered microbial cell is cultivated in the absence of and/or without addition of one or more selected from the group consisting of glucosamine, N-acetylglucosamine, N-acetylmannosamine and N-acetylneuraminic acid. The genetically engineered microbial cell may be cultivated in the absence and/or without addition of galactose, as far as galactose is not supplied as an acceptor substrate for the sialyltransferase reaction. In an additional and/or alternative embodiment, the at least one genetically engineered microbial cell is cultivated in the presence of one or more monosaccharides (e.g. galactose), disaccharides (e.g. lactose), trisaccharides (e.g. lacto-N-triose II), tetrasaccharides (e.g. lacto-N-tetraose) and/or pentasaccharides (e.g. sialyllacto-N-tetraose a).

According to an additional and/or alternative embodiment, the at least one genetically engineered microbial cell is cultivated in the presence of at least one acceptor substrate selected from the group consisting of galactose, N-acetylgalactosamine, N-acetylglucosamine, lactose, lactulose, N-acetyllactosamine, lacto-N-biose, lacto-N-triose, 2'-fucosyllactose, 3-fucosyllactose, 3'-sialyllactose, 6'-sialyllactose, 3'-sialyl-N-acetyllactosamine, 6'-sialyl-N-acetyllactosamine, 3'-galactosyllactose, 6'-galactosyllactose, lacto-N-triose II, lacto-N-tetraose, lacto-N-neotetraose, 2'3-difucosyllactose, 3-fucosyl-3'-sialyllactose and 3-fucosyl-6'-sialyllactose. These substrates are imported into the cell and used as acceptor molecules in the cell.

The genetically engineered cell requires a carbon source for growth, proliferation and production of sialylated oligosaccharides. In an additional and/or alternative embodiment, the genetically engineered cell may grow on an inexpensive sole carbon source, such as—for example—glycerol, glucose or sucrose. Said sole carbon source provides an educt for CMP-sialic acid biosynthesis in the genetically engineered cell. Hence, for the production of sialylated oligosaccharides, it is not necessary to cultivate the genetically engineered cell in the presence of Neu5Ac, ManNAc, GlcNAc or glucosamine (GlcN).

The method comprises the optional step of recovering the sialylated saccharide that has been produced by the at least one genetically engineered microbial cell during its cultivation in the fermentation broth. The sialylated saccharide can be recovered from the fermentation broth after the genetically engineered microbial cells have been removed, for example by centrifugation, and/or can be recovered from the cells, for example in that the cells are harvested from the fermentation broth by centrifugation and are subjected to a cell lysis step. Subsequently, the sialylated saccharides can be further purified from the fermentation broth and/or cell lysates by suitable techniques known to the skilled artisan. Suitable techniques include microfiltration, ultrafiltration, diafiltration, simulated moving bed type chromatography, electrodialysis, reverse osmosis, gel filtration, anion exchange chromatography, cation exchange chromatography, and the like.

The method and the genetically engineered microbial cell that is employed in the method are used for the production of a sialylated saccharide. The term "sialylated saccharide" refers to a saccharide molecule comprising at least one N-acetylneuraminic acid moiety.

In an additional and/or alternative embodiment, the sialylated saccharide is an oligosaccharide. The term "oligosaccharide" as used herein refers to polymers of monosaccharide residues, wherein said polymers comprise at least two monosaccharide residues, but no more than 10 monosaccharide residues, preferably no more than 7 monosaccharide residues. The oligosaccharides are either a linear chain of monosaccharides or are branched. In addition, the monosaccharide residues of the oligosaccharides may feature a number of chemical modifications. Accordingly, the oligosaccharides may comprise one or more non-saccharide moieties. The term "sialylated oligosaccharide" as used herein refers to oligosaccharides comprising one or more N-acetylneuraminic acid moieties.

According to additional and/or alternative embodiment, the sialylated oligosaccharide is selected from the group consisting of 3'-sialyllactose, 6'-sialyllactose, sialyllacto-N-tetraose a, sialyllacto-N-tetraose b, sialyllacto-N-tetraose c, fucosylsialyllacto-N-tetraose a, fucosyl-sialyllacto-N-tetraose b, fucosyl-sialyllacto-N-tetraose c, disialyllacto-N-tetraose, fucosyldisialyllacto-N-tetraose I, fucosyldisialyl-lacto-N-tetraose II, 3'-sialylgalactose, 6'-sialylgalactose, 3'-sialyl-N-acetyllactosamine and 6'-sialyl-N-acetyllactosamine.

In another aspect of the invention, the use of a genetically engineered microbial cell as described herein before for the production of a sialylated saccharide in a whole cell fermentation process is provided, i.e. the sialylated saccharide is synthesized by the genetically engineered microbial cell.

In another aspect of the invention, a sialylated saccharide is provided that has been produced by the method and/or by using the genetically engineered microbial cell as described herein before. In an additional and/or alternative embodiment, the sialylated saccharide is a sialylated oligosaccharide, preferably a sialylated oligosaccharide selected from the group consisting of 3'-sialyllactose, 6'-sialyllactose, sialyllacto-N-tetraose a, sialyllacto-N-tetraose b, sialyllacto-N-tetraose c, fucosyl-sialyllacto-N-tetraose a, fucosyl-sialyllacto-N-tetraose b, fucosyl-sialyllacto-N-tetraose c, disialyllacto-N-tetraose, fucosyldisialyllacto-N-tetraose I, fucosyldisialyllacto-N-tetraose II, 3'-sialylgalactose, 6'-sialylgalactose, 3'-sialyl-N-acetyllactosamine and 6'-sialyl-N-acetyllactosamine.

In another aspect of the invention, provided is the use of a sialylated saccharide that has been produced by a method as described herein before and/or by using the genetically engineered microbial cell as described herein before for the manufacture of a nutritional composition.

Thus, according to another aspect of the invention, provided is a nutritional composition containing at least one sialylated saccharide, preferably at least one sialylated oligosaccharide, which has been produced by the method and/or by the genetically engineered microbial cell as described herein before. In an additional and/or alternative embodiment, the sialylated oligosaccharide is selected from the group consisting of 3'-sialyllactose, 6'-sialyllactose, sialyllacto-N-tetraose a, sialyllacto-N-tetraose b, sialyllacto-N-tetraose c, fucosyl-sialyllacto-N-tetraose a, fucosyl-sialyllacto-N-tetraose b, fucosyl-sialyllacto-N-tetraose c, disialyllacto-N-tetraose, fucosyldisialyllacto-N-tetraose I, fucosyldisialyllacto-N-tetraose II.

In an additional and/or alternative embodiment, the nutritional composition further contains at least one neutral HMO, preferably 2'-FL.

In an additional and/or alternative embodiment, the nutritional composition contains 3-SL, 6-SL and 2'-FL.

In an additional embodiment, the nutritional composition is selected from the group consisting of medicinal, pharmaceutical, formulations, infant formula and dietary supplements.

The nutritional composition may be present in liquid form or in solid form including, but not limited to, powders, granules, flakes and pellets.

The present invention will be further described with respect to particular embodiments, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

EXAMPLES

Figure 1:
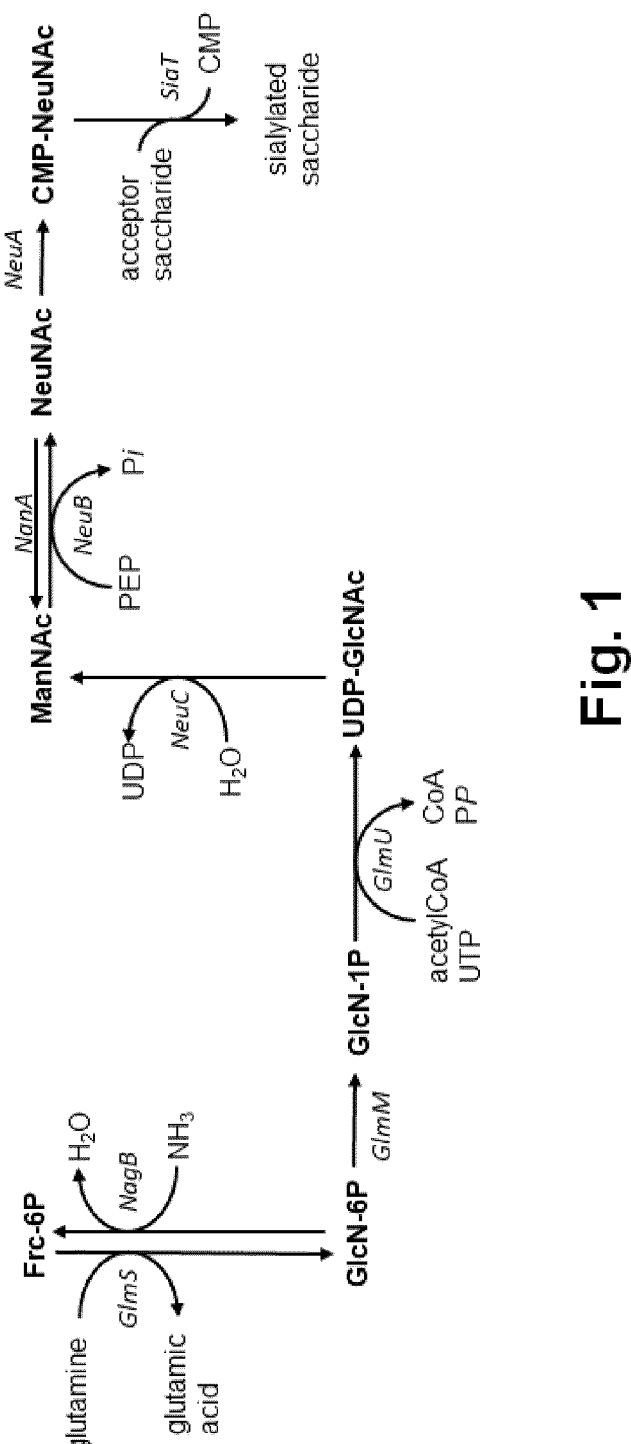
FIG. 1 is a schematic representation of a sialic acid biosynthesis pathway that may be employed by a genetically engineered microbial cell for the fermentative production of sialylated saccharides, wherein said sialic acid biosynthesis pathway utilizes UDP-GlcNAc.

FIGS. 1 to 3 show schemes displaying alternative pathways for intracellular biosynthesis of NeuNAc, CMP-NeuNAc and sialylated saccharides.

With cells genetically modified as described herein, the fermentative production of sialylated saccharides can be achieved. A provided sole carbon source (e.g. sucrose) gets imported into the microbial cell and is metabolized yielding fructose-6-phosphate (FIG. 1 to FIG. 3). Next, L-glutamine: D-fructose-6-phosphate aminotransferase (GlmS) effects conversion of fructose-6-phosphate to glucosamine-6-phosphate (FIG. 1 to FIG. 3), which in turn is metabolized by glucosamine-6-phosphate N-acetyltransferase (Gna1) to N-acetylglucosamine-6-phosphate (FIG. 2 and FIG. 3). N-acetylglucosamine-6-phosphate can be converted to i) N-acetylmannosamine-6-phosphate by an N-acetylglucosamine-6-phosphate epimerase (NanE) and further to N-acetylmannosamine by an N-acetylmannosamine-6-phosphate phosphatase (FIG. 3) or ii) to N-acetylglucosamine by an N-acetylglucosamine-6-phosphate phosphatase (YihX/YqaB) and further metabolized to N-acetylmannosamine by an N-acetylglucosamine 2-epimerase (Slr1975) (FIG. 2). Sialic acid synthase (NanA) converts N-acetylmannosamine into N-acetyl neuraminic acid, which gets converted into CMP-N-acetylneuraminic acid by CMP-sialic acid synthetase (FIG. 1 to FIG. 3). An acceptor substrate may be supplied to the culture broth and imported into the cell and modified or de novo synthesized by the recombinant host cell. The acceptor substrate is ligated with N-acetylneuraminic acid in a reaction catalyzed by a sialyltransferase (SiaT) yielding the sialylated saccharide, which may be exported into the culture broth.

Example 1: Production of Various Sialylated Oligosaccharides

Gene sequences of characterized or putative sialyltransferases were received from the literature and public databases. Since sialyltransferases are often described to exhibit higher activity when their signal peptide is deleted, we analyzed the corresponding protein sequences by the on-line prediction tool SignalP (Petersen et al., Nature Methods, 2011 Sep. 29; 8(10):785-6). Genes were synthetically synthesized by GenScript cooperation either, as annotated, in a full-length form or, when a signal peptide is predicted, as a truncated variant lacking the N-terminal signal peptide.

The sialyltransferases 1 to 26 were each subcloned as an operon with neuA into pDEST14 by SLIC using gene specific primers, yielding plasmids of the general kind: pDEST14-siaT-neuA. The remaining sialyltransferases 27 to 100 were directly subcloned by GenScript cooperation into plasmid pET11a using restriction sites NdeI and BamHI. Both expression systems allow the IPTG-inducible gene expression. For in vitro activity screenings, the plasmids were transformed to an E. coli BL21 (DE3) strain lacking LacZ activity.

The E. coli strains harboring the plasmids for siaT9 (α-2,3-sialyltransferase) and siaT18 (α-2,6-sialyltransferase) expression were grown at 30° C. in 100 ml shake flasks filled with 20 ml of 2YT medium supplemented with ampicillin 100 μg ml$^{-1}$. When the cultures reached an $OD_{600}$ of 0.1 to 0.3, gene expression was induced by addition of 0.3 mM IPTG and the incubation was continued for 12 to 16 hours. Cells were harvested by centrifugation and mechanically disrupted in a defined volume of 50 mM Tris-HCl pH7.5 using glass beads. The protein extract was kept on ice until the assay started. The in vitro assay was carried out in a total volume of 25 μl including 50 mM Tris-HCl PH7.5, 5 mM $MgCl_2$, 10 mM CMP-Neu5Ac and 5 to 20 mM of the appropriate acceptor substrates. The assay started with the addition of 3 μl protein extract and continued for 16 hours. Formation of sialylated oligosaccharides resulting from the activity of the sialyltransferases was determined by thin layer chromatography.

Therefore, samples were applied on Silica Gel 60 $F_{254}$ (Merck KGaA, Darmstadt, Germany)-plates. A mixture of butanol:acetone:acetic acid:$H_2O$ (35/35/7/23 (v/v/v/v)) was used as mobile phase. For detection of the separated substances, the TLC plate was soaked with thymol reagent (0.5 g thymol solved in 95 ml ethanol, 5 ml sulfuric acid added) and heated. Sialylated reaction products run slower than their acceptor substrates.

| Acceptor substrate | SiaT9 | SiaT18 |
|---|---|---|
| Galactose | + | + |
| Lactose | + | + |
| Lacto-N-tetraose | + | + |
| Sucrose | − | − |

Table 3: In vitro analyses determining sialyltransferase activities of two exemplary sialyltransferases depending on the supplied acceptor substrate. The formation of sialylated saccharides was determined by thin layer chromatography. (+) A sialylated reaction product was detectable. (−) A sialylated reaction product was not detectable.

Both sialyltransferases were capable to sialylate galactose or diverse oligosaccharides containing at least one galactose residue. No sialylated oligosaccharide was detectable when sucrose was applied to the reaction (Table 3).

Example 2: Metabolic Engineering of an E. coli BL21 (DE3) Strain for the Production of N-Acetylneuraminic Acid Metabolic engineering was achieved by the mutagenesis and deletions of specific endogenous genes and the genomic integration of heterologous genes. The genes lacZ and araA were inactivated by mutagenesis using mismatch-oligonucleotides as described by Ellis et al., (Proc. Natl. Acad. Sci. USA 98:6742-6746 (2001)).

Genomic deletions were generated according to the method of Datsenko and Wanner (Proc. Natl. Acad. Sci. USA 97:6640-6645 (2000)). To prevent the degradation of N-acetylglucosamine the following genes were deleted from the genome of E. coli strain BL21 (DE3): N-acetylglucosamine specific PTS enzyme II (nagE), N-acetylglucosamine-6-phosphate deacetylase (nagA), and glucosamine-6-phosphate deaminase (nagB). The whole N-acetylneuraminic acid catabolic gene cluster encoding N-acetylmannosamine kinase (nanK), N-acetylmannosamine-6-phosphate epimerase (nanE), N-acetylneuraminic acid aldolase (nanA) and the sialic acid permease (nanT) was also deleted. The genes manX, manY and manZ, encoding a phosphoenolpyruvate-dependent phosphotransferase system facilitating the import of glucosamine, were also deleted. The wzxC-wcaJ genes were also deleted. The wcaJ gene encodes an UDP-glucose:undecaprenyl phosphate glucose-1-phosphate transferase catalyzing the first step in colanic acid synthesis (Stevenson et al., J. Bacteriol. 1996, 178:4885-4893). In addition, the genes fucI and fucK and agaA were deleted, encoding L-fucose isomerase, L-fuculose kinase, and N-acetylgalactosamine-6-phosphate deacetylase, respectively.

The genomic integration of heterologous genes was achieved by transposition, using either the EZ-Tn5™ transposase (Epicentre, USA) or the hyperactive C9-mutant of the mariner transposase Himar1 (Proc. Natl. Acad. Sci. 1999, USA 96:11428-11433). To produce EZ-Tn5 transposomes the gene of interest together with a FRT-site flanked antibiotic resistance marker (alternatively the resistance marker gene was flanked by lox66-lox71 sites) was amplified. The resulting PCR-product carried at both termini the 19-bp Mosaic End recognition sites for the EZ-Tn5 transposase. For integration using Himar1 transposase expression constructs (operons) of interest were similarly cloned together with a FRT-site/lox66-lox71-site flanked by antibiotic resistance markers and transferred into the pEcomar vector, which encodes the hyperactive C9-mutant of the mariner transposase Himar1 under the control of the arabinose-inducible promoter ParaB. All genes were codon-optimized for expression in *E. coli* and prepared synthetically by GenScript Corp.

The expression fragment <Pter-lacY-FRT-aadA-FRT> was integrated by using the EZ-Tn5 transposase. After successful integration of the gene for the lactose importer LacY from *E. coli* K12 TG1 (GenBank: ABN72583) the resistance gene was eliminated from streptomycin resistant clones by the FLP recombinase encoded on plasmid pCP20 (Proc. Natl. Acad. Sci. 2000, USA 97:6640-6645). The csc-gene cluster from *E. coli* W (GenBank: CP002185.1), comprising the genes for sucrose permease, fructokinase, sucrose hydrolase, and a transcriptional repressor (genes cscB, cscK, cscA, and cscR, respectively), enabling the strain to grow on sucrose as a sole carbon source, was also inserted in the genome. This cluster was integrated into the genome of the *E. coli* BL21 (DE3) strain by transposition using plasmid pEcomar-cscABKR.

The resulting strain was further modified for the production of NeuNAc by the genomic integration of the following expression cassettes: <$P_{tet}$-Slr1975-gna1-lox66-aacC1-lox71> (SEQ ID NO. 97), <$P_{tet}$-neuB-lox66-kanR-lox71> (SEQ ID NO. 98), <$P_{tet}$-Slr1975-$P_{rs}$-neuB-FRT-dhfr-FRT> (SEQ ID NO. 99), <$P_{tet}$-glmS*-gna1-lox66-aacC1-lox71> (SEQ ID NO. 100) and <$P_{tet}$-ppsA-lox66-aacC1-lox71> (SEQ ID NO. 101). Except for the dhfr expression cassette, all resistance marker genes were removed in a stepwise manner from the genome (before the next round of gene integration) by introducing plasmid pKD-Cre (SEQ ID NO. 102) followed by selection on 2YT agar plates containing 100 μg·mL$^{-1}$ ampicillin and 100 mM L-arabinose at 30° C. Resistant clones were subsequently transferred to 2YT agar plates lacking ampicillin as well as the selective antibiotic used for genomic integration. The plates were incubated at 42° C. to cure the cells of the plasmid. Clones that were sensitive to ampicillin and the selective antibiotic were used for further experiments and modifications.

The gene sir1975 (GenBank: BAL35720) encodes *Synechocystis* sp. PCC6803 N-acetylglucosamine 2-epimerase. The gene gna1 (GenBank: NP_116637) encodes a glucosamine-6-phosphate acetyltransferase from *Saccharomyces cerevisiae*. The gene neuB (GenBank: AF305571) encodes a sialic acid synthase from *Campylobacter jejuni*. The gene glmS* is a mutated version of the *E. coli* L-glutamine: D-fructose-6-phosphate aminotransferase gene (Metab Eng. 2005 May; 7 (3): 201-14). The gene ppsA (GenBank: ACT43527) encodes the phosphoenolpyruvate synthase of *E. coli* BL21 (DE3).

For the generation of <$P_{tet}$-slr1975-gna1-lox66-aacC1-lox71>, the genes sir1975 and gna1 were subcloned as an operon behind the constitutive promotor Ptet and fused to the gentamycin resistance gene (flanked by lox66/lox71 sites) and inserted into the pEcomar vector by blunt-end ligation. The resulting expression cassette was integrated into the genome using vector pEcomar-slr195-gna1-aacC1 and the hyperactive C9-mutant of the mariner transposase Himar1 under the control of the arabinose-inducible promoter ParaB.

For the generation of <$P_{tet}$-neuB-lox66-kanR-lox71>, neuB was cloned behind the constitutive promotor Ptet and fused to the kanamycin resistance gene (flanked by lox66/lox71 sites). The resulting expression cassette was integrated into the genome using the EZ-Tn5 transposase. For the generation of <$P_{tet}$-Slr1975-$P_{rs}$-neuBFRT-dhfr-FRT>, the genes sir1975 and neuB were separately subcloned behind the constitutive promotors Ptet and Prs, respectively, and fused to the trimethoprim resistance gene (flanked by FRT sites). The resulting expression cassette was integrated into the genome by using the EZ-Tn5 transposase.

Expression cassette <$P_{tet}$-glmS*-gna1-lox66-aacC1-lox71> was generated by cloning glmS* and gna1 as an operon behind the constitutive promotor Ptet. This construct was further fused to the gentamycin resistance gene (flanked by lox66/lox71 sites). The resulting expression cassette was integrated into the genome by using the EZ-Tn5 transposase.

For the generation of <$P_{tet}$-ppsA-lox66-aacC1-lox71>, the ppsA gene was cloned behind the constitutive promoter Ptet and fused to the gentamycin resistance gene (flanked by lox66/lox71 sites). The resulting expression cassette was integrated into the genome by using the EZ-Tn5 transposase.

Altogether, the cumulative genome modifications gave rise to the Neu5Ac-producing strain *E. coli* #NANA1.

Example 3: Generation and Cultivation of a Microbial Cell Line for the Production of 3'-Sialyllactose Strain *E. coli* #NANA1 was further modified by the genomic integration of <$P_{tet}$-siaT9-Pts-neuA-lox66-aacC1-lox71> (SEQ ID NO: 103) by using the EZ-Tn5 transposase yielding a 3'-SL production strain. The gene siaT9 (GenBank: BAF91160), codon-optimized for expression in *E. coli* and prepared synthetically by GenScript, encodes an α-2,3-sialyltransferase from *Vibrio* sp. JT-FAJ-16. The gene neuA (GenBank: AF305571) encodes a CMP-sialic acid synthetase from *Campylobacter jejuni*.

Cultivation of the strain was conducted in 96-well plates. Therefore, single colonies of the strain were transferred from agar plates into microtiter plates containing 200 μL of the minimal medium containing 7 gl$^{-1}$ NH$_4$H$_2$PO$_4$, 7 gl$^{-1}$ K2HPO$_4$, 2 gl$^{-1}$ KOH, 0.3 gl$^{-1}$ citric acid, 5 gl$^{-1}$ NH$_4$Cl, 1 ml l$^{-1}$ antifoam, 0.1 mM CaCl$_2$, 8 mM MgSO$_4$, trace-elements and 2% sucrose as carbon source. Trace elements consisted of 0.101 g 1-1 nitrilotriacetic acid, pH 6.5, 0.056 gl$^{-1}$ ammonium ferric citrate, 0.01 gl$^{-1}$ MnCl$_2$×4 H$_2$O, 0.002 gl$^{-1}$ CoCl$_2$×6H$_2$O, 0.001 gl$^{-1}$ CuCl$_2$×2H$_2$O, 0.002 gl$^{-1}$ boric acid, 0.009 gl$^{-1}$ ZnSO$_4$×7H$_2$O, 0.001 gl$^{-1}$ Na$_2$MoO$_4$×2H$_2$O, 0.002 gl$^{-1}$ Na$_2$SeO$_3$, 0.002 gl$^{-1}$ NiSO$_4$×6 H$_2$O. Cultivation was conducted for approximately 20 hours at 30° C. under vigorous shaking. Subsequently, 50 μL of the culture broth was transferred to deepwell 96 well plates (2.0 mL) containing 400 μL of minimal medium per well.

After an incubation of another 48 hours, cultivation was stopped and the 3'-sialyllactose level in the supernatant was determined by mass spectrometry. Mass spectrometry analysis was performed by MRM (multiple reaction monitoring) using a LC Triple-Quadrupole MS detection system. Precursor ions are selected and analyzed in quadrupole 1, fragmentation takes place in the collision cell using argon as CID gas, selection of fragment ions is performed in quadrupole 3. Chromatographic separation of lactose, 3'-sialyllactose and 6'-sialyllactose after dilution of culture supernatant 1:100 with H$_2$O (LC/MS Grade), was performed on a XBridge Amide HPLC column (3.5 μm, 2.1 □ 50 mm (Waters, USA) with a XBridge Amide guard cartridge (3.5 μm, 2.1 □ 10 mm) (Waters, USA). Column oven temperature of the HPLC system was 50° C. The mobile phase was composed of acetonitrile:H$_2$O with 10 mM ammonium acetate. A 1 μl sample was injected into the instrument; the run was performed for 3.60 min with a flow rate of 400 μl/min. 3'-sialyllactose and 6'-sialyllactose were analyzed by MRM in ESI positive ionization mode. The mass spectrometer was operated at unit resolution. Sialyllactose forms an ion of m/z 656.2 [M+Na]. The precursor ion of sialyllactose was further fragmented in the collision cell into the fragment ions m/z 612.15, m/z 365.15 and m/z 314.15. Collision energy, Q1 and Q3 Pre Bias were optimized for each analyte individually. Quantification methods were established using commercially available standards (Carbosynth, Compton, UK). At the end of the cultivation a 3'-SL titer in the culture supernatant of approx. 0.6 g L$^{-1}$ was reached.

Example 4: Generation and Cultivation of a Microbial Cell Line for The Production of 6'-sialyllactose Strain *E. coli* #NANA1 was further modified by the genomic integration of <P$_{tet}$-SiaT18-P$_{t5}$-neuA-lox66-aacC1-lox71> (SEQ ID NO: 104) by using the EZ-Tn5 transposase yielding a 6'-SL production strain. The gene siaT18 (GenBank: AB500947), codon-optimized for expression in *E. coli* and prepared synthetically by GenScript, encodes an α-2,6-sialyltransferase from *Photobacterium leiognathi* JT-SHIZ-119. The gene neuA (GenBank: AF305571) encodes a CMP-sialic acid synthetase from *Campylobacter jejuni*.

As described in example 2, a cultivation in a 96-well plate was conducted using this 6'-SL production strain. At the end of the cultivation a 6'-SL titer in the culture supernatant of approx. 0.9 g L$^{-1}$ was reached.

Example 5: Composition of an Infant Formula Containing Sialyllactose

Infant Formula:
  Skimmed milk
  Vegetable oils (palm oil, rapeseed oil, sunflower oil)
  Human milk oligosaccharides
  L-Fucose
  6'-sialyllactose
  Skimmed milk powder
  Oil of *Mortierella* alpine
  Fish oil
  Calcium carbonate
  Potassium chloride
  Vitamin C
  Sodium chloride
  Vitamin E
  Iron acetate
  Zinc sulphate
  Niacin
  Calcium-D-panthothenate
  Copper sulphate
  Vitamin A
  Vitamin B1
  Vitamin B6
  Magnesium sulphate
  Potassium iodate
  Folic acid
  Vitamin K
  Sodium selenite
  Vitamin D

The invention claimed is:

1. A method for fermentative production of a saccharide comprising at least one N-acetylneuraminic acid moiety, the method comprising:
 a) providing at least one genetically engineered microbial cell which comprises:
  (i) a sialic acid biosynthesis pathway comprising a glucosamine-6-phosphate N-acetyltransferase, a N-acetylglucosamine-6-phosphate phosphatase and an N-acetylglucosamine 2-epimerase of SEQ ID NO: 84;
  (ii) a cytidine 5'-monophospho-(CMP)-N-acetyl-neuraminic acid synthetase;
  (iii) a heterologous sialyltransferase; and
  (iv) a glutamine:fructose-6-phosphate aminotransferase of SEQ ID NO: 70
 b) cultivating the at least one genetically-engineered microbial cell in a fermentation broth and under conditions permissive for production of said saccharide comprising at least one N-acetylneuraminic acid moiety; and, optionally
 c) recovering said saccharide comprising at least one N-acetylneuraminic acid moiety.

2. The method according to claim 1, wherein the at least one genetically engineered microbial cell comprises a nucleic acid molecule comprising and expressing a nucleotide sequence selected from the group consisting of:
 i) nucleotide sequences encoding a polypeptide as represented by SEQ ID NO: 91;
 ii) a nucleotide sequence as represented by SEQ ID NO: 92;
 iii) nucleotide sequences having at least 80% sequence similarity to the nucleotide sequences encoding a polypeptide as represented by SEQ ID NO: 91;
 iv) nucleotide sequences having at least 80% sequence similarity to the nucleotide sequences as represented by SEQ ID NO: 92;

v) nucleotide sequences which are complementary to any one of the nucleotide sequences of i, ii, iii and iv; and
 vi) fragments of any one of the nucleotide sequences of i, ii, iii, iv, and v.

3. The method according to claim 2, wherein the at least one genetically engineered microbial cell comprises a nucleic acid molecule comprising a nucleotide sequence with at least 90% sequence similarity to the nucleotide sequences encoding a polypeptide of SEQ ID NO: 91.

4. The method according to claim 2, wherein the at least one genetically engineered microbial cell comprises a nucleic acid molecule comprising a nucleotide sequence with at least 95%, 96%, 97%, 98%, or 99% sequence similarity to the nucleotide sequences encoding a polypeptide of SEQ ID NO: 91.

5. The method according to claim 2, wherein the at least one genetically engineered microbial cell comprises a nucleic acid molecule comprising a nucleotide sequence with greater than 99% sequence similarity to the nucleotide sequences encoding a polypeptide of SEQ ID NO: 91.

6. The method according to claim 2, wherein the at least one genetically engineered microbial cell comprises a nucleic acid molecule comprising a nucleotide sequence with at least 90% sequence similarity to SEQ ID NO: 92.

7. The method according to claim 2, wherein the at least one genetically engineered microbial cell comprises a nucleic acid molecule comprising a nucleotide sequence with at least 95%, 96%, 97%, 98%, or 99% sequence similarity to SEQ ID NO: 92.

8. The method according to claim 2, wherein the at least one genetically engineered microbial cell comprises a nucleic acid molecule comprising a nucleotide sequence with greater than 99% sequence similarity to SEQ ID NO: 92.

9. The method according to claim 1, wherein the at least one genetically engineered microbial cell comprises a heterologous sialyltransferase that is selected from the group consisting of:

I. polypeptides comprising an amino acid sequence encoded by a nucleotide sequence as represented by any one of SEQ ID NOs: 1 to 33;

II. polypeptides comprising an amino acid sequence having a sequence similarity of at least 80% to any one of the amino acid sequences encoded by a nucleotide sequence as represented by any one of SEQ ID NOs: 1 to 33; and III. fragments of any one of the polypeptides of I, and II.

10. The method according to claim 1, wherein the at least one genetically engineered microbial cell comprises a nucleic acid molecule which comprises and expresses a nucleotide sequence selected from the group consisting of:

i. nucleotide sequences as represented by any one of SEQ ID NOs: 1 to 33;

ii. nucleotide sequences encoding a polypeptide as represented by any one of SEQ ID NOs: 34 to 66;

iii. nucleotide sequences having at least 80% sequence similarity to one of the nucleotide sequences represented by any one of SEQ ID NOs: 1 to 33;

iv. nucleotide sequences encoding a polypeptide having a sequence similarity of at least 80% to any one of the amino acid sequences encoding a polypeptide represented by SEQ ID NOs: 34 to 66;

v. nucleotide sequences which are complementary to any one of the nucleotide sequences of i, ii, iii and iv; and vi. fragments of any one of the nucleotide sequences of i, ii, iii, iv and v.

11. The method according to claim 1, wherein an acceptor molecule is employed and is selected from the group consisting of N-acetylglucosamine, galactose, N-acetylgalactosamine, lactose, lactulose, N-acetyllactosamine, lacto-N-biose, melibiose, raffinose, lacto-N-triose II, 2'-fucosyllactose, 3-fucosyllactose, 3'-sialyllactose, 6'-sialyllactose, 3'-sialyl-N-acetyllactosamine, 6'-sialyl-N-acetyllactosamine, 3'-galactosyllactose, 6'-galactosyllactose, lacto-N-tetraose, lacto-N-neotetraose, 2'3-difucosyllactose, 3-fucosyl-3'-sialyllactose, 3-fucosyl-6'-sialyllactose, sialyllacto-N-tetraose a, sialyllacto-N-tetraose b, sialyllacto-N-tetraose c, lacto-N-fucopentaose I, lacto-N-fucopentaose II, lacto-N-fucopentaose III, lacto-N-fucopentaose V, lacto-N-neofucopentaose I and lacto-N-neofucopentaose V.

12. The method according to claim 1, wherein the fermentation broth comprises at least one carbon source, the at least one carbon source is optionally selected from the group consisting of glucose, fructose, sucrose, glycerol and combinations thereof.

13. The method according to claim 1, wherein the at least one genetically engineered microbial cell is cultivated in the absence of and/or without addition of one or more selected from the group consisting of glucosamine, N-acetylglucosamine, N-acetylmannosamine and N-acetylneuraminic acid.

14. The method according to claim 1, wherein the saccharide comprising at least one N-acetylneuraminic acid moiety is selected from the group consisting of 3'-sialylgalactose, 6'-sialylgalactose, 3'-sialyl-N-acetyllactosamine, 6'-sialyl-N-acetyllactosamine, 3'-sialyllactose, 6'-sialyllactose, sialyllacto-N-tetraose a, sialyllacto-N-tetraose b, sialyllacto-N-tetraose c, fucosylsialyllacto-N-tetraose a, fucosyl-sialyllacto-N-tetraose b, fucosyl-sialyllacto-N-tetraose c, disialyllacto-N-tetraose, fucosyldisialyllacto-N-tetraose I, and fucosyldisialyllacto-N-tetraose II.

15. The method according to claim 1, wherein the at least one genetically engineered microbial cell comprises a nucleotide sequence selected from the group consisting of:

i) nucleotide sequences encoding a polypeptide as represented by SEQ ID NO: 84:

ii) a nucleotide sequence as represented by SEQ ID NO: 86; and iii) nucleotide sequences which are complementary to any one of the nucleotide sequences of i) and ii).

16. The method of claim 1, wherein the at least one genetically engineered microbial cell comprises a gene encoding a phosphoenolpyruvate synthase and such gene has increased expression compared to expression by a wild type of the microbial cell.

17. A genetically-engineered microbial cell for fermentative production of a saccharide comprising at least one N-acetylneuraminic acid moiety, wherein the genetically-engineered microbial cell comprises:

(i) a synthetic sialic acid biosynthesis pathway comprising a glucosamine-6-phosphate N-acetyltransferase, a N-acetylglucosamine-6-phosphate phosphatase and an N-acetylglucosamine 2-epimerase of SEQ ID NO: 84;

(ii) a cytidine 5'-monophospho-(CMP)-N-acetyl-neuraminic acid synthetase;

(iii) a heterologous sialyltransferase; and (iv) a glutamine:fructose-6-phosphate aminotransferase of SEQ ID NO: 70.

\* \* \* \* \*

SEQUENCE LISTING

```
<160> NUMBER OF SEQ ID NOS: 104

<210> SEQ ID NO 1
<211> LENGTH: 1410
<212> TYPE: DNA
<213> ORGANISM: Campylobacter coli

<400> SEQUENCE: 1
atgcaaaacg tcattatcgc tggtaacggt ccgagcctgc aatcaatcaa ctatcaacgc      60
ctgccgaaag aatacgacat cttccgctgc aaccagttct acttcgaaga taaatactac     120
ctgggcaaaa acatcaaagc ggcctttttc aatccgtatc cgttcctgca gcaataccat     180
accgcgaaac agctggtgtt caacaacgaa tacaaaatcg aaaacatctt ttgtagcacg     240
ttcaatctgc cgttcatcga aaaagataac ttcatcaaca aattttacga tttctttccg     300
gacgctaaac tgggtcacaa aatcatcgaa aacctgaaag aattttacgc gtacatcaaa     360
tacaacgaaa tctacctgaa caaacgtatt accagcggca tctatatgtg cgcaattgct     420
atcgcgctgg gttataaaaa catttacctg tgtggcatcg atttctatga aggtgaaacg     480
atctacccgt tcaaagccat gtctaaaaac attaagaaaa tttttccgtg gatcaaagat     540
ttcaacccga gtaacttcca ttccaaagaa tacgacatcg aaatcctgaa actgctggaa     600
tcaatctaca aagttaacat ctacgcactg tgcgataact cggccctggc aaattacttc     660
ccgctgctgg tgaacaccga caattcattt gttctggaaa acaaatcgga tgactgtatc     720
aacgatatcc tgctgaccaa caatacgccg ggcattaact tctataaaag ccagatccaa     780
gtcaacaata ccgaaattct gctgctgaac tttcagaata tgatcagcgc caaagaaaac     840
gaaatttcta acctgaacaa aatcctgcaa gactcataca aaaccatcaa cacgaaagaa     900
```

-continued

```
aacgaaatta gtaatctgaa taaaatcctg caggattcct ataaaacgat taataccaaa      960
gaaaatgaaa tttcgaatct gaacaaaatc ctgcaggata aagacaaact gctgatcgtt     1020
aaagaaaacc tgctgaattt caaaagccgt catggtaaag ccaaatttcg cattcagaac     1080
caactgtctt ataaactggg ccaggcaatg atggtcaata gcaaatctct gctgggttat     1140
atccgtatgc cgtttgtgct gagttacatc aaagacaaac acaaacagga acaaaaaatc     1200
tatcaggaaa aaattaagaa agatccgagc ctgaccctgc cgccgctgga agattatccg     1260
gactacaaag aagctctgaa agaaaaagaa tgcctgacct atcgcctggg ccagacgctg     1320
attaaagcgg atcaagaatg gtacaaaggt ggctatgtga aaatgtggtt cgaaatcaaa     1380
aaactgaaga aagaatacaa aaagaaataa                                       1410
```

```
<210> SEQ ID NO 2
<211> LENGTH: 1146
<212> TYPE: DNA
<213> ORGANISM: Vibrio sp.

<400> SEQUENCE: 2
atgaacaacg acaactccac gaccaccaac aataacgcta ttgaaatcta tgtggatcgt       60
gcgaccctgc cgacgatcca gcaaatgacc aaaattgtta gccagaaaac gtctaacaaa      120
aaactgatct catggtcgcg ctacccgatt accgataaaa gcctgctgaa gaaaattaac      180
gcggaatttt tcaaagaaca atttgaactg acggaaagcc tgaaaaacat catcctgtct      240
gaaaacatcg ataacctgat cattcatggc aataccctgt ggagtattga tgtggttgac      300
attatcaaag aagtcaacct gctgggcaaa aatattccga tcgaactgca cttttatgat      360
gacggttccg ccgaatacgt tcgtatctac gaatttagta aactgccgga atccgaacag      420
aaatacaaaa ccagcctgtc taaaaacaac atcaaattct caatcgatgg caccgactcg      480
ttcaaaaaca cgatcgaaaa catctacggt ttcagccaac tgtatccgac cacgtaccac      540
atgctgcgtg cagatatctt cgacaccacg ctgaaaatta acccgctgcg cgaactgctg      600
tcaaacaaca tcaaacagat gaaatgggat tacttcaaag acttcaacta caaacaaaaa      660
gatatctttt actcactgac caacttcaac ccgaaagaaa tccaggaaga cttcaacaaa      720
aactcgaaca aaaacttcat cttcatcggc agtaactccg cgaccgccac ggcagaagaa      780
caaatcaata ttatcagcga agcgaagaaa gaaaacagca gcattatcac caattcaatt      840
tcggattatg acctgttttt caaaggtcat ccgtctgcca cgtttaacga acagattatc      900
aatgcacacg atatgatcga aatcaacaac aaaatcccgt cgaagctct gatcatgacc      960 ggcattctgc cggatgccgt tggcggtatg ggtagttccg tcttttttcag tatcccgaaa     1020 gaagtcaaaa acaaattcgt gttctataaa agtggtacgg atatcgaaaa taactccctg     1080
attcaggtga tgctgaaact gaatctgatt aaccgcgata tattaaact gatctctgac     1140 atttaa                                                                1146
```

```
<210> SEQ ID NO 3
<211> LENGTH: 1173
<212> TYPE: DNA
<213> ORGANISM: Photobacterium sp.

<400> SEQUENCE: 3
atgggctgta atagcgactc caaccacaac aactccgacg gcaacatcac caaaaacaaa       60
acgatcgaag tttatgtcga tcgtgcaacc ctgccgacga ttcagcaaat gacccagatc      120
```

-continued atcaacgaaa atagcaacaa caaaaaactg atttcatggt cgcgctaccc gatcaatgat      180
gaagaactgc tggaatcaat taacggctcg tttttcaaaa acaactctga actgatcaaa      240
agtctggatt ccatgattct gaccaatgac attaagaaag tgatcatcaa cggtaacacg      300
ctgtgggcgg ccgatgtggt taacatcatc aaatcaatcg aagcgttcgg caagaaaacc      360
gaaatcgaac tgaactttta tgatgacggt tcggccgaat atgtgcgtct gtacgacttt      420
agcaaactgc cggaatctga acaggaatac aaaattagcc tgtctaaaga taacattctg      480
agcagcatca acggcaccca gccgttcgaa aacgtcgtgg aaaacatcta cggtttcagt      540
caactgtacc cgaccacgta ccacatgctg cgtgccgata tctttgaaac caatctgccg      600
ctgcgcagtc tgaaaggcgt tctgtccaac aacatcaaac agatgaaatg ggattacttc      660
aaaaccttca acagccagca aaaagacaaa ttctacaact tcacgggttt taacccggat      720
gaaattatgg aacaatacaa agcaagcccg aacaaaaatt ttatcttcgt cggcaccaat      780
tctggcaccg caacggctga acagcaaatt gatatcctga ccgaagctaa aaacccgaac      840
agcccgatta tcacgaaatc gatccagggc ttcgacctgt tttttcaaagg tcatccgtct      900 gcaacctaca acaaacaaat catcgatgct cacaacatga tcgaaatcta caacaaaatc      960
ccgttcgaag cgctgatcat gaccgatgcc ctgccggatg cggtgggcgg tatgggcagc     1020
agcgtgtttt tcagcctgcc gaataccgtg gaaaacaaat tcattttcta taaatccgat     1080
acggacattg aaaacaatgc cctgatccag gttatgattg aactgaatat cgtgaaccgt     1140
aatgatgtga aactgatctc ggacctgcaa taa                                 1173

<210> SEQ ID NO 4
<211> LENGTH: 1167
<212> TYPE: DNA
<213> ORGANISM: Pasteurella multocida

<400> SEQUENCE: 4
atgaaaacga ttaccctgta tctggacccg gcgtccctgc cggcactgaa ccaactgatg       60
gattttacgc agaacaatga agacaaaacc catccgcgta tctttggcct gtctcgcttc      120
aaaattccgg ataacattat cacccaatat cagaatatcc actttgttga actgaaagac      180
aatcgtccga cggaagccct gttcaccatt ctggatcagt acccgggtaa cattgaactg      240
gacatccatc tgaatattgc tcacagcgtc cagctgattc gtccgatcct ggcgtatcgc      300
tttaaacatc tggatcgtgt gtccatccag cgcctgaacc tgtatgatga cggctcaatg      360
gaatacgttg atctggaaaa agaagaaaac aaagacatct cggcagaaat taaacaagct      420
gaaaaacagc tgagccatta tctgctgacg ggtaaaatca aattcgataa cccgaccatt      480
gcgcgctacg tttggcagtc tgcctttccg gtcaaatatc acttcctgag tacggactac      540
tttgaaaaag cagaatttct gcaaccgctg aaagaatatc tggcggaaaa ttaccagaaa      600
atggattgga cggcctatca gcaactgacc ccggaacagc aagcatttta cctgaccctg      660
gttggcttca acgacgaagt caaacagagt ctggaagtgc agcaagcgaa atttattttc      720
acgggcacca cgacctggga aggtaatacc gatgttcgtg aatattacgc ccagcaacag      780
ctgaacctgc tgaatcattt tacccaggcg ggcggcgacc tgtttattgg tgaccattac      840
aaaatttact tcaaaggtca cccgcgcggc ggtgaaatca cgattacat cctgaacaac      900 gcaaaaaaca tcacgaatat cccggctaat atctctttcg aagtgctgat gatgaccggc      960
ctgctgccgg ataaagtcgg cggtgtggct agctctctgt acttcagtct gccgaaagaa     1020
aaaattagtc acatcatctt caccagcaac aaacaggtca atcaaaaga agatgccctg     1080

-continued

```
aacaatccgt acgtgaaagt tatgcgtcgc ctgggtatta tcgatgaatc gcaagtgatc    1140
ttttgggaca gcctgaaaca gctgtaa                                         1167

<210> SEQ ID NO 5
<211> LENGTH: 1116
<212> TYPE: DNA
<213> ORGANISM: Neisseria meningitidis

<400> SEQUENCE: 5
atgggcctga aaaagcctg cctgaccgtg ctgtgtctga tcgtgttttg cttcggcatc      60 tttttatacgt tcgatcgtgt gaaccagggt gaacgcaatg cagttagtct gctgaaagaa    120
aaactgttta cgaagaagg cgaaccggtg aatctgatct tctgttacac cattctgcaa      180
atgaaagttg ccgaacgtat tatggcacag catccgggtg aacgctttta tgtggttctg      240
atgagcgaaa accgtaacga aaatacgat tactacttca accagatcaa agataaagcg       300
gaacgcgcct atttctttca cctgccgtac ggcctgaaca aaagttttaa tttcattccg      360
acgatggcgg aactgaaagt gaaaagcatg ctgctgccga aagttaaacg tatctatctg      420
gcaagcctgg aaaaagtgtc tattgcggcc tttctgagca cctacccgga tgcggaaatc      480
aaaaccttcg atgatggcac gggtaatctg attcagagct ctagttatct gggcgatgaa      540
ttttctgtta acggtacgat caaacgtaat ttcgcccgca tgatgatcgg tgattggtct      600
attgcgaaaa cccgcaacgc cagtgatgaa cattacacga tcttcaaagg cctgaaaaac      660
atcatggatg atggtcgtcg caaaatgacc tacctgccgc tgttcgatgc gtctgaactg      720
aaaacgggcg atgaaaccgg cggtacggtg cgtattctgc tgggtagccc ggataaagaa      780
atgaaagaaa tctctgaaaa agcagcgaaa aacttcaaaa tccagtatgt tgccccgcac      840
ccgcgtcaga cctacggcct gagtggtgtg accacgctga acagcccgta tgttattgaa      900
gattacatcc tgcgtgaaat taagaaaaac ccgcataccc gctatgaaat ctacacgttt      960
ttcagcggcg ccgcactgac catgaaagat tttccgaacg tgcacgttta tgcactgaaa    1020
ccggcgtctc tgccggaaga ttattggctg aaaccggtgt acgcgctgtt tacccagagt    1080
ggtattccga tcctgacgtt cgatgataaa aattaa                             1116

<210> SEQ ID NO 6
<211> LENGTH: 852
<212> TYPE: DNA
<213> ORGANISM: Pasteurella multocida

<400> SEQUENCE: 6
atggataaat ttgcagaaca tgaaattccg aaagcagtga tcgttgctgg caacggtgaa      60
agtctgtccc agattgatta tcgtctgctg ccgaaaaact acgacgtctt ccgttgcaac      120
caattctact tcgaagaacg ctacttcctg ggcaataaaa tcaaagccgt tgtttttcacc     180 ccgggtgttt ttctggaaca gtattacacg ctgtatcatc tgaaacgcaa caatgaatac       240
tttgtcgata acgtgattct gagctctttc aatcacccga ccgtggacct ggaaaaatca       300
cagaaaatcc aagcactgtt catcgatgtt atcaacggct acgaaaaata cctgtcgaaa       360
ctgaccgctt cgatgtttta tctgcgttac aaagaactgt atgaaaatca gcgcattacg       420
agcggtgttt acatgtgcgc tgtcgcgatc gccatgggct ataccgatat ttacctgacg       480
ggtatcgact tttatcaagc gtctgaagaa aactacgcct cgataacaa aaaaccgaat        540 attatccgtc tgctgccgga ctttcgcaaa gaaaaaaccc tgttcagcta tcattctaaa      600
```

-continued

```
gatattgacc tggaagcgct gtcatttctg cagcaacatt accacgtgaa cttctactca      660
atctcgccga tgagtccgct gtccaaacat tttccgatcc cgacggttga agatgactgt      720
gaaaccacgt tcgtcgcccc gctgaaagaa aactatatta atgacatcct gctgccgccg      780
cactttgtct atgaaaaact gggcgtggat aaactggcgg ccgcactgga acatcaccat      840
caccatcact aa                                                          852
```

<210> SEQ ID NO 7
<211> LENGTH: 1158
<212> TYPE: DNA
<213> ORGANISM: Pasteurella dagmatis

<400> SEQUENCE: 7

```
atgaccattt acctggaccc ggcgtctctg ccgaccctga accaactgat gcattttacg       60
aaagaaagcg aagacaaaga aaccgcacgt atttttggct tctctcgctt taaactgccg      120
gaaaaaatca cggaacagta caacaacatc catttcgtgg aaatcaaaaa caatcgtccg      180
acggaagata ttttcaccat cctggaccag tacccggaaa aactggaact ggatctgcat      240
ctgaacattg cacacagcat ccagctgttt catccgattc tgcaatatcg tttcaaacac      300
ccggatcgca ttagtatcaa atccctgaac ctgtatgatg acggcaccat ggaatacgtt      360
gatctggaaa aagaagaaaa caaagacatc aaaagtgcga tcaaaaaagc cgaaaaacag      420
ctgtccgatt atctgctgac gggtaaaatt aactttgaca atccgaccct ggcacgctac      480
gtttggcagt cacaatatcc ggtcaaatac catttcctgt cgacggaata ttttgaaaaa      540
gctgaattcc tgcagccgct gaaaacctat ctggcgggca ataccaaaa atggattgg       600 tcagcctatg aaaaactgtc gccggaacag caaacgtttt acctgaaact ggtcggtttc      660
agtgatgaaa ccaaacagct gtttcacacg gaacaaacca atttattttt cacgggcacc      720
acgacctggg agggtaacac cgatatccgt gaatattacg cgaaacagca actgaatctg      780
ctgaaacatt ttacccacag cgaaggcgac ctgtttatcg gtgaccagta caaaatctac      840
ttcaaaggcc atccgcgcgg cggtgatatt aacgactata tcctgaaaca cgcaaaagat      900
attacgaaca tcccggctaa tattagcttc gaaatcctga tgatgaccgg tctgctgccg      960
gacaaagtcg gcggtgtggc gagctctctg tacttctctc tgccgaaaga aaaaatcagc     1020
cacattatct tcacctctaa caagaaaatt aaaaacaaag aagatgccct gaatgacccg     1080
tacgtgcgtg ttatgctgcg tctgggtatg attgacaaaa gccaaattat cttctgggat     1140
tctctgaaac aactgtaa                                                    1158
```

<210> SEQ ID NO 8
<211> LENGTH: 1173
<212> TYPE: DNA
<213> ORGANISM: Photobacterium phosphoreum

<400> SEQUENCE: 8

```
atgggctgta actccgatag caaacacaat aacagtgatg gcaatattac caaaaacaaa       60
acgatcgaag tctatgtgga ccgtgcgacc ctgccgacga ttcagcaaat gacccagatc      120
atcaacgaaa atagcaacaa caaaaaactg atttcatggt cgcgttaccc gatcaatgat      180
gaaacgctgc tggaatcaat taatggctcg ttttttcaaaa accgcccgga actgatcaaa      240
agtctggatt ccatgattct gaccaacgaa attaagaaag tgatcatcaa cggtaacacg      300
ctgtgggcag ttgacgtggt taatattatc aaaagcattg aagctctggg caagaaaacc      360
gaaatcgaac tgaacttcta tgatgacggt tctgcggaat atgtgcgtct gtacgatttt      420
```

-continued

```
agccgcctgc cggaatctga acaggaatac aaaattagcc tgtctaaaga taacattcag       480
agcagcatca acggcaccca accgttcgac aacagcatcg aaaacatcta cggtttctct       540
cagctgtatc cgaccacgta ccacatgctg cgtgccgata tctttgaaac caatctgccg       600
ctgacgagtc tgaaacgcgt tatctccaac aacatcaaac agatgaaatg ggattacttc       660
accacgttca attcccagca gaaaaacaaa ttttacaact tcaccggctt caacccggaa       720
aaaatcaaag aacaatacaa agcgagtccg cacgaaaatt ttattttcat tggcaccaac       780
tccggcaccg ccaccgcaga acagcaaatt gatatcctga ccgaagccaa aaaaccggac       840
tcaccgatta tcaccaacag cattcagggc ctggacctgt ttttcaaagg tcatccgtct       900
gcgacctata accagcaaat tatcgacgcc cacaacatga tcgaaatcta caacaaaatc       960
ccgttcgaag cactgatcat gaccgatgca ctgccggacg ctgttggcgg tatgggtagt      1020
tccgtctttt tctcactgcc gaataccgtc gaaaacaaat tcattttcta taaatcggat      1080
acggacattg aaaacaatgc tctgatccag gttatgatcg aactgaatat cgtgaaccgc      1140
aatgatgtga aactgattag tgacctgcaa taa                                   1173
```

```
<210> SEQ ID NO 9
<211> LENGTH: 1254
<212> TYPE: DNA
<213> ORGANISM: Avibacterium paragallinarum

<400> SEQUENCE: 9
```

```
atgcgtaaaa tcatcacctt cttcagcctg ttcttctcga tctcagcgtg gtgtcaaaaa        60
atggaaatct acctggacta tgcgtcgctg ccgagcctga acatgatcct gaacctggtt       120
gaaaacaaaa acaacgaaaa agtcgaacgt attatcggct cgaacgcctt tgatttcaac       180
aaagaaattc tgaatagctt ctctaaagaa cgtatcgaat ttagtaaagt ctccattctg       240
gatatcaaag aattttcaga caaactgtac ctgaacattg aaaatcgga tacgccggtg       300 gacctgatta tccataccaa tctggatcac tcagttcgtt cgctgctgag catctttaaa       360
accctgagtc cgctgttcca taaaatcaac atcgaaaaac tgtacctgta cgatgacggc       420
agcggtaact atgttgatct gtaccagcac cgccaagaaa tatttctgc gattctgatc       480 gaagcccaga aaaactgaa agacgcgctg gaaatcgtg aaacggatac cgacaaactg       540
catagcctga cgcgctatac ctggcacaaa atctttccga cggaatatat cctgctgcgt       600
ccggattacc tggatattga cgaaaaaatg caaccgctga acatttcct gagcgatacc       660 atcgtgtcta tggacctgtc tcgctttagt catttctcca aaaaccagaa agaactgttt       720
ctgaaaatca cgcacttcga tcaaaacatc ttcaacgaac tgaacatcgg caccaaaaac       780
aaagaataca aaacgttcat cttcaccggc accacgacct gggaaaaaga taagaaaaaa       840
cgtctgaaca cgcgaaact gcagacggaa attctggaat cttttatcaa accgaacggc       900
aaattctacc tgggtaacga tatcaaaatc tttttcaaag gccacccgaa aggtgatgac       960
attaacgact acattatccg caaaaccggc gcagaaaaaa ttccggctaa catcccgttt      1020
gaagttctga tgatgacgaa tagtctgccg gattatgtcg cggtattat gagtaccgtg      1080 tactttccc tgccgccgaa aaatattgat aaagtggttt tcctgggttc cgaaaaaatc      1140
aaaaacgaaa acgacgccaa atcacagacc ctgtcgaaac tgatgctgat gctgaacgtc      1200
atcacgccgg aacagatttt cttttgaagaa atgccgaacc cgattaactt ttaa           1254
```

```
<210> SEQ ID NO 10
```

-continued

```
<211> LENGTH: 1293
<212> TYPE: DNA
<213> ORGANISM: Campylobacter jejuni

<400> SEQUENCE: 10
atgacccgca cccgtatgga aaacgaactg attgtgagca aaaacatgca gaacattatt      60
atcgccggta acggtccgag cctgaaaaat attaactata aacgtctgcc gcgcgaatac     120
gatgtgttcc gttgcaacca gttctacttc gaagacaaat actacctggg caagaaaatt     180
aaagccgtgt ttttcaatcc gggcgtgttt ctgcaacaat atcataccgc aaaacagctg     240
attctgaaaa acgaatacga aatcaaaaac atcttttgta gcaccttcaa tctgccgttt     300
atcgaatcta cgatttcct gcaccaattt tataactttt tcccggacgc taaactgggc     360
tacgaagtca tcgaaaacct gaaagaattt acgcgtacca tcaaatacaa cgaaatctac     420
ttcaacaaac gcatcaccctc tggcgtgtat atgtgcgcga ttgccatcgc actgggttat     480
aaaacgattt acctgtgtgg catcgatttc tatgaaggtg acgttattta cccgtttgaa     540
gcaatgagta ccaacattaa aacgatcttc ccgggtatca agatttcaa accgagtaac     600 tgccattcca agaatatga catcgaagcg ctgaaactgc tgaaaagcat ctacaaagtt     660
aacatctacg ccctgtgtga tgacagtatt ctggcaaatc atttcccgct gtccattaac     720
atcaacaaca acttcacccct ggaaaacaaa cacaacaact caatcaacga tattctgctg     780
accgacaata cgccgggcgt ctcgtttat aaaaatcagc tgaaagccga taacaaaatc     840
atgctgaact ctacaacat cctgcatagc aaagataacc tgatcaaatt cctgaacaaa     900
gaaatcgctg ttctgaaaaa acagaccacg caacgtgcta aagcgcgcat tcagaaccac     960
ctgagctata aactgggcca agccctgatt atcaatagca aatctgtcct gggtttcctg    1020
tctctgccgt ttattatcct gtcaattgtg atctcgcaca aacaggaaca aaaagcgtat    1080
aaattcaaag tgaagaaaaa cccgaacctg gcactgccgc cgctggaaac ctatccggat    1140
tacaacgaag ccctgaaaga aaaagaatgc ttcacgtaca aactgggcga agaatttatc    1200
aaagcaggta aaaactggta tggcgaaggt tacatcaaat ttatcttcaa agatgttccg    1260
cgtctgaaac gtgaatttga aaaaggcgaa taa    1293
```

```
<210> SEQ ID NO 11
<211> LENGTH: 1188
<212> TYPE: DNA
<213> ORGANISM: Heliobacter acinonychis

<400> SEQUENCE: 11
atgaataaga aaccgctgat tattgctggc aacgggccaa gcatcaaaga cttagattat      60
gcgttgttcc cgaaagactt tgatgtattc cgatgtaatc aattctactt cgaggacaaa     120
tactatttag ggcgggaaat aaaaggggtg ttctttaacg cgcacgtctt cgatctccaa     180
atgaagatca ctaaagccat agtcaaaaac ggggaatatc acccggacca catatattgc     240
acacatgtcg aaccgtacgg ttacgttaac ggaaaccagc aactcatgca agagtacctg     300
gaaaaacatt ttgtgggagt ccgaagcacg tacgcatacc tgaaagatct agagccattc     360
tttattctgc acagtaagta tcgcaacttc tacgaccagc acttcacaac gggcatcatg     420
atgctactgg tggccatcca attgggatac aaagaaatat acctgtgcgg aatagacttc     480
tacgaaaacg gattcggaca tttctacgag aaccaagggg gattctttga agaggatagc     540
gatccgatgc acgataagaa catagacatc caagcactgg aactggcaaa gaaatacgcg     600
aaaatctacg cactggtacc gaacagcgcc ctagtgaaaa tgattccgtt gagcagccaa     660
```

-continued

```
aaaggagttc tggaaaaggt gaaggaccgg atcgggttgg gcgagtttaa gagagagaaa      720
ttcgggcaaa aagaattgga aagacagaag gaattagaac gacaaaaaga gctcgaacgc      780
caaaaggagc ttgaacgtca aaaggaactt gaacgacaaa aagagttgga gaggcagaaa      840
gaactcgaac gccaaaaaga attagagaga cagaaggaat tagagcgcca aaaggagctt      900
gagcgtcaaa aagaattaga gaggcagaag gagttagaaa ggcagaaaga actggagaga      960
cagaaagaac tcgaaaggca gaaggagttg gaacgccaaa aagaactaga attagaacga     1020
tccttaaaag cacgattgaa agcggtactc gcgagcaaag gcatccgcgg cgacaacctg     1080
ataatcgtaa gtttaaaaga cacctaccga ctgtttaaag ggggatttgc gttactcttg     1140
gacctgaagg cgctaaagtc aatcattaaa gcattcctga agagataa                  1188

<210> SEQ ID NO 12
<211> LENGTH: 783
<212> TYPE: DNA
<213> ORGANISM: Campylobacter jejuni

<400> SEQUENCE: 12
atgggcaaaa aagtgattat tgcgggcaac ggcccgagcc tgaaagaaat tgattatagc       60
cgtctgccga acgattttga tgtgtttcgc tgcaaccagt tttatttcga agataaatat      120
tacctgggca aaaatgcaa agcggtgttc tataatccga tcctgttctt cgaacagtat       180
tacaccctga aacatctgat tcagaaccag gaatatgaaa ccgaactgat catgtgcagc      240
aactataacc aggcgcatct ggaaaacgaa aactttgtga aaaccttcta cgattatttt      300
ccggatgcgc atctgggcta tgattttttc aaacagctga agatttcaa cgcgtacttc       360 aaattccacg aaatctattt caaccagcgt attaccagcg gcgtgtatat gtgcgcggtg      420
gcgattgcgc tgggctataa agaaatttat ctgagcggca tcgatttta tcagaacggc       480 agcagctatg cgtttgatac caaacagaaa aacctgctga aactggcccc gaactttaaa      540
aacgataaca gccactatat tggccatagc aaaaacaccg atatcaaagc gctggaattt      600
ctggaaaaaa cctataaaat caaactgtat tgcctgtgcc cgaacagcct gctggccaac      660
tttattgaac tggcaccgaa tctgaacagc aacttcatca tccaggaaaa aaacaactat      720
accaaagata ttctgattcc gagcagcgaa gcgtatggca aattcagcaa aaacatcaac      780
taa                                                                     783

<210> SEQ ID NO 13
<211> LENGTH: 897
<212> TYPE: DNA
<213> ORGANISM: Streptococcus entericus

<400> SEQUENCE: 13
atgaagaaag tctacttctg ccatacggtc taccatctgc tgattaccct gtgcaaaatt       60
agcgttgaag aacaagttga aattattgtg ttcgataccg ttagtaatca tgaactgatt      120
gtccagaaaa tccgcgacgt gtttgttaac accacggtgc tgttcgcaga acaaaatacc      180 gattttttcca ttctggaaat cgatcgcgct acggacattt atgtgttcaa cgactggacc      240
ccgatcggcg cgtatctgcg taaaaacaaa ctgtttttacc atctgatcga agatggttat      300
aactaccacg aatataacgt ttacgcgaat gccctgacca tgaaacgtcg cctgctgaac      360
ttcgtgctgc gtcgcgaaga accgtcaggc ttttcgcgtt atgttcgcag cattgaagtt      420
aaccgtgtca aatacctgcc gaatgattgc cgcaaaagca aatgggttga aaaaccgcgt      480
```

-continued

```
tctgccctgt tcgaaaatct ggtcccggaa cataaacaga aaatcatcac gatcttcggc      540
ctggaaaact atcaagatag cctgcgcggt gtcctggtgc tgacccagcc gctggtgcaa      600
gactactggg atcgcgacat taccacggaa gaagaacagc tggaatttta tcgtcaaatc      660
gtggaatctt acggcgaagg tgaacaggtg ttttttcaaaa ttcacccgcg tgataaagtt      720
gactatagct ctctgaccaa cgtcattttt ctgaagaaaa acgtcccgat ggaagtgtac      780
gaactgattg ccgattgtca ttttaccaaa ggtatcacgc acagttccac cgcactggac      840
ttcctgtcct gtgtggataa gaaaatcacc ctgaaacaaa tgaaagcaaa tagttaa        897

<210> SEQ ID NO 14
<211> LENGTH: 888
<212> TYPE: DNA
<213> ORGANISM: Haemophilus ducreyi

<400> SEQUENCE: 14
atgaaagaaa tcgccatcat ctccaaccaa cgcatgttct tcctgtactg tctgctgacc       60
aataaaaatg tcgaagacgt gttcttcatt tttgaaaaag gcgcgatgcc gaacaatctg      120
accagcattt ctcatttcat cgtgctggat cacagtaaat ccgaatgcta tgactttttc      180
tacttcaact tcatcagttg taaatatcgt ctgcgcggcc tggatgttta cggtgcagac      240
catatcaaag gcgctaaatt ttttcctggaa cgtcaccgct tttttcgtggt tgaagatggt      300 atgatgaact acagcaaaaa catgtacgca ttctctctgt tccgtacccg caatccggtg      360
attctgccgg gcggttttca tccgaacgtt aaaaccatct tcctgacgaa agataatccg      420
attccggacc agatcgctca caaacgtgaa atcatcaaca tcaaaaccct gtggcaagcg      480
aaaaccgcca cggaaaaaac gaaaattctg agcttttttcg aaatcgatat gcaggaaatt      540
tcagttatca aaaaccgctc gtttgtcctg tatacccaac cgctgtcaga agataaaactg      600 ctgacggaag cggaaaaaat tgacatctat cgtaccattc tgacgaaata caaccattcg      660
cagaccgtta tcaaaccgca cccgcgcgat aaaacggact ataaacaact gtttccggat      720
gcctatgtca tgaaaggcac ctacccgagt gaactgctga cgctgctggg tgtcaacttc      780
aacaaagtga tcaccctgtt ttccacggcg gtcttcgatt atccgaaaga aaaaatcgac      840
ttctacggca ccgcggtgca tccgaaactg ctggatttct ttgactaa             888

<210> SEQ ID NO 15
<211> LENGTH: 1467
<212> TYPE: DNA
<213> ORGANISM: Alistipes sp.

<400> SEQUENCE: 15
atggccctgc tgagcggtac cgccgcatgc tcagatgacg aagtctcgca gaacctgatc       60
gtgattaatg gcggtgaaca ttttctgagc ctggatggtc tggcccgtgc aggtaaaatt      120
agcgtgctgg caccggctcc gtggcgtgtt acgaaagcag ctggtgatac ctggtttcgc      180
ctgagcgcaa ccgaaggtcc ggctggttac agcgaagtgg aactgtctct ggatgaaaat      240
ccgggtgccg cacgtagcgc acagctggcg tttgcctgtg gtgatgcgat tgtgccgttc      300
cgcctgagtc aaggcgcact gtccgctggt tatgattcac cggactatta cttttacgtt      360
accttcggca cgatgccgac cctgtatgcc ggtatccatc tgctgagcca cgataaaccg      420
ggctatgtct tttactcacg ttcgaaaacg tttgacccgg ccgaattccc ggcacgtgct      480
gaagttacca ccgcagctga tcgtaccgcc gatgcaaccc aggccgaaat ggaagcaatg      540
gctcgcgaaa tgaaacgtcg catcctggaa attaactctg cggatccgac cgccgtgttt      600
```

```
ggcctgtatg ttgatgacct gcgttgccgc attggctacg attggttcgt ggcgcagggt    660
atcgacagtg cccgtgtcaa agtgagcatg ctgtctgatg gcaccggcac gtacaacaat    720 tttttataact acttcggtga cgcggccacg gcggaacaaa attgggaaag ttatgcgtcc    780
gaagttgaag ccctggattg gaatcacggc ggtcgttatc cggaaacccg ctcgctgccg    840
gaatttgaaa gctacacgtg gccgtattac ctgtctaccc gtccggatta tcgcctggtg    900
gttcaggacg gcagtctgct ggaaagctct tgtccgttta ttaccgaaaa actgggtgaa    960
atggaaatcg aatccattca accgtatgaa atgctgtcag ccctgccgga aagttcccgt    1020
aaacgctttt atgatatggc aggcttcgat tacgacaaat ttgcagctct gttcgatgcg    1080
tccccgaaga aaaacctgat tatcattggt acctctcatg cggatgatgc cagtgcacgt    1140
ctgcagcgtg attacgttgc acgcatcatg gaacagtatg cgctcaata cgatgtcttt    1200 ttcaaaccgc acccggcaga caccacgtca gctggttatg aaacggaatt tccgggcctg    1260
accctgctgc cgggtcaaat gccgtttgaa atcttcgttt ggtccctgat tgatcgtgtc    1320
gacatgatcg gcggttatcc gtcaacggtc tttctgaccg ttccggtcga taaagtgcgc    1380
tttatttttg ccgcggatgc agcttctctg gtgcgtccgc tgaatatcct gttccgcgat    1440
gcgaccgacg ttgaatggat gcagtaa                                         1467

<210> SEQ ID NO 16
<211> LENGTH: 876
<212> TYPE: DNA
<213> ORGANISM: Campylobacter jejuni

<400> SEQUENCE: 16
atgaagaaag tgattatcgc cggcaatggt ccgagcctga agaaattga ttattctcgt      60 ctgccgaatg atttcgacgt ctttcgctgc aaccagttct actttgaaga caaatattac    120
ctgggcaaaa aatgtaaagc cgtgttttat accccgaact ttttctttga acagtattac    180
acgctgaaac atctgattca gaaccaagaa tatgaaaccg aactgatcat gtgctcaaac    240
tacaatcaag cacatctgga aaacgaaaac ttcgtcaaaa cgttctacga ttacttcccg    300
gacgctcacc tgggttacga tttctttaaa cagctgaaag aattcaacgc gtacttcaaa    360
ttccacgaaa tctacttcaa ccaacgtatc acctcaggcg tgtatatgtg tgcggttgcc    420
attgcactgg gttataaaga aatttacctg tcgggcatcg atttttatca gaatggtagc    480
tcttacgcct tcgacacgaa acaagaaaat ctgctgaaac tggcaccgga ttttaaaaac    540
gaccgctcac attatattgg ccactcgaaa aacaccgata tcaaagctct ggaattcctg    600
gaaaaaacgt acaaaatcaa actgtactgc ctgtgtccga atagtctgct ggctaacttt    660
atcgaactgg cgccgaacct gaattccaac ttcatcatcc aggagaaaaa caactacacc    720
aaagatatcc tgatcccgag ttccgaagcg tacggcaaat ttagcaaaaa catcaacttc    780
aagaaaatta aaatcaaaga aaacgtgtat tacaaactga ttaaagatct gctgcgtctg    840
ccgtctgaca tcaaacatta ttttaaaggt aaataa                              876

<210> SEQ ID NO 17
<211> LENGTH: 939
<212> TYPE: DNA
<213> ORGANISM: Streptococcus agalactiae

<400> SEQUENCE: 17
atgacgaatc gcaaaatcta tgtctgccac accctgtacc atctgctgat ctgcctgtat     60
```

-continued

```
aaagaagaaa tctactcaaa tctggaaatt atcctgagca gcagcattcc ggatgtggac     120
aacctggaga aaaaactgaa aagcaaaacc atcaacatcc atattctgga agaatcctca     180
ggcgaatctg aagaactgct gagtgttctg aaagatgcag gtctgtctta cagtaaattc     240
gatagcaact gcttcatctt caacgacgct accccgattg gccgtacgct gatcaaacac     300
ggtatttatt acaatctgat cgaagatggc ctgaactgtt ttacctactc gattttcagc     360
cagaaactgt ggaaatacta cgtgaaaaaa tacatcctgc ataaaattca accgcacggc     420
ttttcccgct actgcctggg tatcgaagtg aacagtctgg ttaatctgcc gaaagatccg     480
cgttacaaaa aattcatcga agtcccgcgc aaagaactgt tcgacaatgt tacggaatac     540
cagaaagaaa tggcgatcaa cctgtttggc gccgtccgtg tgtctattaa atccccgtca     600
gttctggtcc tgacccagcc gctgtccatc gataaagaat ttatgtcata caacaacaaa     660
atcgaaacgt cggaagaaca attcaacttc tacaaaagca tcgtgaacga atacatcaac     720
aaaggttaca acgtctacct gaaagtgcat ccgcgtgatg tggttgacta ttctaaactg     780
ccggttgaac tgctgccgag taacgtcccg atggaaatta tcgaactgat gctgaccggc     840
cgctttgaat gcggtattac ccatagcagc accgccctgg atttcctgac ctgtgtggac     900
aagaaaatta cgctggttga tctgaaagac attaaataa                           939
```

```
<210> SEQ ID NO 18
<211> LENGTH: 1233
<212> TYPE: DNA
<213> ORGANISM: Bibersteinia trehalosi

<400> SEQUENCE: 18
```

```
atggaattct gcaaaatggc aacgacgcaa aaaatctgtg tctacctgga ctatgctacg      60
atcccgagcc tgaactacat cctgcacttt gcgcaacatt cgaagatca ggaaaccatt      120 cgtctgtttg cctgtcccg cttccacatt ccggaatcag tcatccagcg ctatccgaaa      180
ggtgtggttc aattttaccc gaaccaggaa aaagacttca gcgcgctgct gctggccctg      240
aaaaacatcc tgatcgaagt taaacagcaa cagcgtaaat gcgaaatcga actgcatctg      300
aacctgtttc actatcagct gctgctgctg ccgttcctga gtctgtatct ggatacccag      360
gactactgtc atctgacgct gaaattttac gatgacggct ctgaagcgat tagtgccctg      420
caggaactgg cactggctcc ggatctggcg gcccaaatcc agtttgaaaa acaacagttc      480
gacgaactgg tcgtgaaaaa atcgtttaaa ctgtcgctgc tgagccgcta ttttttggggt      540 aaactgttcg aaagcgaata catttggttc aatcaagcaa tcctgcagaa agctgaactg      600
caaattctga acaggaaat cagctctagt cgtcagatgg attttgcaat ttatcaacag      660
atgtccgacg aacaaaaaca gctggtgctg aaattctga acatcgatct gaataaagtt      720
gcttacctga acaactgat ggaaaaccag ccgtcttttc tgttcctggg caccacgctg      780
tttaatatta cccaggaaac caaaacgtgg ctgatgcaga tgcatgtgga tctgatccaa      840
cagtattgcc tgccgagcgg ccagttttc aacaataaag ccggctatct gtgttttttac      900 aaaggtcacc cgaacgaaaa agaaatgaac caaatgatcc tgtctcagtt caaaaacctg      960
atcgcgctgc cggatgacat tccgctggaa atcctgctgc tgctgggcgt tattccgagt     1020
aaagtcggcg gttttgcatc ctcagctctg tttaacttca ccccggcgca gatcgaaaat     1080
attatctttt tcacgccgcg ttatttcgaa aaagataatc gcctgcacgc cacgcaatac     1140
cgtctgatga gggcctgat tgaactgggt tatctggacg ctgaaaaatc tgtgacccac     1200
tttgaaatca tgcaactgct gacgaaagaa taa                                  1233
```

```
<210> SEQ ID NO 19
<211> LENGTH: 1221
<212> TYPE: DNA
<213> ORGANISM: Haemophilus parahaemolyticus

<400> SEQUENCE: 19
atgaccgaac agtacatcaa aaacgtggaa gtttacctgg attacgcgac catcccgacg      60
ctgaactact tctaccattt caccgaaaac aaagatgaca tcgccacgat tcgtctgttt     120
ggcctgggtc gcttcaacat cagtaaatcc atcatcgaaa gctacccgga aggcattatc     180
cgttactgcc cgattatctt tgaagatcaa accgcatttc agcaactgtt cattaccctg     240
ctgacggaag acagtttttg tcagtatcgc tttaacttcc atattaacct gtttcactcc     300
tggaaaatgc tgatcccgct gctgcatatt atctggcagt ttaaacacaa agtcctggat     360
attaaactga acttctatga tgacggcagt gaaggtctgg tgacgctgtc caaaatcgaa     420
cagaactaca gctctgaaat cctgcaaaaa atcatcgata tcgactcaca gtcgttttat     480
gcagataaac tgtctttcct ggatgaagac attgctcgtt acctgtggaa cagtctgttt     540
gaatcccatt attacctgct gaacgacttc ctgctgaaaa acgaaaaact gtcactgctg     600
aaaaactcga tcaaatactg ccacatcatg gatctggaac gctacctgca gtttacccaa     660
gaagaaaaag acttttttcaa cgaactgctg ggcatcaaca tccagagtct ggaagataaa     720
atcaaaatct tccagcagaa gaaaaccttt attttcacgg gtaccacgat cttcagcctg     780
ccgaaagaag aagaagaaac cctgtatcgt ctgcatctga acgcaatcct gaattatatt     840 caccccgaacg gcaaatactt tattggcgat ggtttcacgc tggttatcaa aggtcatccg     900
caccagaaag aaatgaacag ccgcctggaa aaatctttttg aaaaagctgt catgctgccg     960
gataatatcc cgttcgaaat tctgtatctg atcggctgca aaccggacaa aattggcggt    1020
tttgtgagca cctcttactt cagctgtgat aagaaaaaca ttgcggacct gctgtttatc    1080
tctgcccgtc aagaagaagt tcgcaaaaac gattacctgt ttaacatcca gtaccaactg    1140
cgtgacatga tgattaaaac cggtttttatc caggaagaaa aaacgcactt ctactcagat    1200
atcccgatct tcatctcgta a                                             1221

<210> SEQ ID NO 20
<211> LENGTH: 903
<212> TYPE: DNA
<213> ORGANISM: Haemophilus somnus

<400> SEQUENCE: 20
atgaaatata acatcaaaat taaagctatc gtcatcgtgt cgagcctgcg tatgctgctg      60
atcttcctga tgctgaataa ataccacctg gatgaagttc tgtttgtctt caacgaaggc     120
ttcgaactgc ataaaaaata caaaatcaaa cactatgtgg cgattaaaaa gaaaattacc     180
aaattctggc gtctgtacta caaactgtac ttctaccgtt tcaaaattga ccgcatcccg     240
gtttatggcg cagatcatct gggttggacc gactattttc tgaaatactt cgatttctac     300
ctgattgaag acggcatcgc taacttctcc ccgaaacgtt acgaaattaa cctgacgcgc     360
aatatcccgg tctttggttt ccataaaacc gtgaagaaaa tttacctgac gagtctggaa     420
aatgttccgt ccgatattcg tcataaagtc gaactgatca gcctggaaca cctgtggaaa     480
acccgcacgg cgcaggaaca acacaacatc ctggatttct ttgcctttaa tctggacagc     540
ctgatctctc tgaaaatgaa aaaatacatc ctgttcaccc agtgcctgtc agaagatcgc     600
```

-continued

```
gtcatttcgg aacaggaaaa aatcgcgatc taccaacata tcatcaaaaa ctacgatgaa        660
cgtctgctgg ttatcaaacc gcacccgcgc gaaaccacgg actatcagaa atactttgaa        720
aatgtcttcg tgtaccaaga tgtggttccg agcgaactgt ttgaactgct ggacgtgaac        780
ttcgaacgtg ttattaccct gttttctacg gccgtgttca aatatgatcg caatatcgtt        840
gacttctacg gtacgcgcat ccacgacaaa atctatcaat ggttcggcga catcaaattc        900
taa                                                                     903

<210> SEQ ID NO 21
<211> LENGTH: 1146
<212> TYPE: DNA
<213> ORGANISM: Vibrio harveyi

<400> SEQUENCE: 21
atggattctt cgccggaaaa caccagctct acgctggaaa tttacatcga ttcagcaacc         60
ctgccgtcgc tgcagcacat ggtgaaaatt atcgacgaac aaagtggcaa caaaaaactg        120
atcaactgga aacgttatcc gatcgatgac gaactgctgc tggataaaat caacgctctg        180
agcttttctg ataccacgga cctgacccgt tatatggaaa gtattctgct gatcggcgat        240
attaaacgcg tggttattaa cggtaatagt ctgtccaact acaatattgt cggcgtgatg        300
cgctccatca acgccctggg tctggatctg gacgttgaaa tcaattttta tgatgacggt        360
tcagcagaat atgtccgtct gtacaacttc tcgcagctgc cggaagctga cgcgaactg         420 ctggtgtcaa tgtcgaaaaa caatattctg gcggccgtta acggcatcgg ttcttatgat        480
agcggctctc cggaaaatat ttacggtttt gcgcagattt atccggccac ctaccacatg        540
ctgcgtgcgg acattttcga tacggacctg gaaatcggcc tgattcgcga tatcctgggt        600
gacaacgtca aacagatgaa atggggccaa tttctgggtt tcaacgaaga acagaaagaa        660
ctgttttatc aactgaccag cttcaacccg gataaaatcc aggcgcaata caaagaatct        720
ccgaacaaaa acttcgtttt cgtcggcacc aacagtcgtt ccgcaacggc tgaacagcaa        780
atcaacatca tcaaagaagc caaaaaactg gatagcgaaa ttatcccgaa cagcatcgat        840
ggctatgacc tgtttttcaa aggtcatccg agcgcgacct acaaccagca aattgttgat        900
gcccacgaca tgaccgaaat ctataatcgc acgccgtttg aagtcctggc aatgacgagt        960
tccctgccgg atgctgtggg cggtatgggc tcatcgctgt ttttctcact gccgaaaacc       1020
gtggaaacga aattcatttt ctataaaagt ggcaccgata ttgaatccaa tgcgctgatc       1080
caggttatgc tgaaactggg tatcattacg gacgaaaaag tgcgctttac gacggacatc       1140
aaataa                                                                 1146

<210> SEQ ID NO 22
<211> LENGTH: 1452
<212> TYPE: DNA
<213> ORGANISM: Alistipes sp.

<400> SEQUENCE: 22
atggccagct gttctgatga cgataaagaa cagacgggtt ttcaaatcga cgatggctct         60
ggtttcctga gtctggatgc agctgcgcgt agtggctcca ttgccatcac cgcaaacaat        120
tcatggtcgg tgacgcagga taaagacagc gaatggctga ccctgagcac cacgtctggt        180
gcagcaggtc gtaccgaaat tggtatcatg ctggaagcga acccgggcga agctcgtaat        240
gcgggtctga cctttaactc tggcggtcgc acgtatccgt tcgtgattac ccagagtgcc        300
catgttacgg cagattttga cgatgctgac cactgctttt atatcacctt tggtaccctg        360
```

-continued

```
ccgaccctgt atgcaggtct gcatgtgctg tcccacgata aaccgtcata tgtgtttttc          420
cagcgttccc aaacctttcg cccggaagaa ttcccggccc atgcagaagt tacgattgct          480
gcggatccgt cagctaatgc gaccgatgaa gacatggaac gtatgcgcac ggccatgaaa          540
cagcaaattc tgaaaatcaa cgttgaagat ccgaccgcag ttttttggcct gtatgtcgac         600 gatctgcgtt gtggcattgg ttacgattgg ttcgtcgccc agggtatcga cagtacccgc          660
gtgaaagtta gtatgctgtc cgatggcacc ggcacgtaca acaacttcta caactacttc          720
ggcgatccgg ccaccgcaga acaaaactgg gaaaattacg ccgcacaggt ggaagcgctg          780
gattggcaac acggcggtcg ttttccggaa acccgcatgc cggatggttt tgacttctat          840
gaatggccgt attacctggc aacgcgtccg aactaccgcc tggttctgca ggacgatgac          900
ctgctggaag cgacgtctcc gtttatgacc gaacgtctgc agcaaatgcg caccgaatcg          960
aaacagccgt atgaactgct ggccagcctg ccggctgaag cccgtcaacg cttttttccgt       1020 atggctggct ttgattacga cgcgtttgct gcgctgttcg atgccagccc gaagaaaaac        1080
ctggtcatta tcggcacgtc acatacctcg gaagaaagcg aagcacagca agccgcatat        1140
gtggaacgta ttatcggcga ttatggtacc gcctacgaca ttttctttaa accgcacccg        1200
gcagatagct ctagttccaa ctacgaagaa cgctttgaag gtctgaccct gctgccgggt        1260
cagatgccgt ttgaaatttt cgtctggtcg ctgctggata aagtggacct gatcggcggt        1320
tattcatcga cggtgtttct gaccgtcccg gtggaaaaaa ccggctttat tttcgctgcg        1380
aatgctgaaa gcctgccgcg cccgctgaac gttctgttcc gtaatgcgga acatgtccgc        1440
tggatccagt aa                                                              1452
```

```
<210> SEQ ID NO 23
<211> LENGTH: 1452
<212> TYPE: DNA
<213> ORGANISM: Alistipes shahii

<400> SEQUENCE: 23
```

```
atggacgatg gcaccccgag tgtcagcatc aacggcggca ccgacttcct gagcctggac           60
cacctggcac gcagcggcaa aatcacggtc aacgcaccgg ctccgtggtc tgtgaccctg          120
gccccggaaa attacggcca ggatgaaaaa ccggactggc tgaccctgag cgccgaagaa          180
ggcccggcag gttatagcga aatcgatgtt acctttgcgg aaaacccggg tccggccgt           240 tccgcatcac tgctgttcag ctgcgatggt aaaaccctgg cctttacggt ttcgcagagc          300
gcaggcggta cgggtttcga tgctccggac tattactttt atatttcggt cggcaccatg          360
ccgacgctgt actcgggtct gcatctgctg agccacgata aaccgtctta tgttagttac          420
gaacgtgcga gcacctttga tgcggccgaa ttcccggacc gcgcgtttgt ctatccggtg          480
gccgatccga ccggtcatgc aaccaacgaa gaactgcgtg cgatgagcga agccatgaaa          540
cgtcgcatcc tggaaattaa tgcagaagat ccgaccgctg ttttcggtct gtgggtcgat          600
gacctgcgtt gccgcctggg ctacgattgg tttgtggctc aaggtatcga ctctgcgcgc          660
gtgaaagtta cgatgctgag tgatggcacc gcgacgtata acaattttca taactacttc          720
ggtgacgcag ctaccgccga acagaactgg aatgattatg cggccgaagt tgaagcactg          780
gactggaatc atggcggtcg ttatccggaa acccgtgccc cggaagaatt cgcctcctac          840
acctggccgt attacctgtc aacgcgtccg gattatcgcc tgatgctgca aaacagctct          900
ctgatggaaa gttcctgtcc gtttatcgca gatcgcctgg cagctatgaa aatggaatcc          960
```

-continued

```
gtgcagccgt atgaactgct gacggcactg ccggaagctt caaaacagca attctatcgt      1020
atggccaaat ttgattacgc acgctttgct ggcctgttcg acctgtctcc gaagaaaaac      1080
ctgattatca ttggtacctc tcattcatcg gcggccagtg aacagcaaca ggcagcttac      1140
gtcgaacgta tcattcaaca gtatggcagt gattacgaca ttttctttaa accgcacccg      1200
gcagatagct ctagtgctgg ttatccggac cgctttgaag gtctgaccct gctgccgggt      1260
cagatgccgt ttgaaatctt cgtttgggcg ctgctggata aaatcgacat gattggcggt      1320
tatccgtcca ccacgtttat ttcagtgccg ctggataaag ttggctttct gttcgcggcc      1380
gatgccgacg gtctggtccg cccgctgaat atcctgttcc gtgacgctgc aaatgtcgaa      1440
tggattcaat aa                                                          1452
```

```
<210> SEQ ID NO 24
<211> LENGTH: 1206
<212> TYPE: DNA
<213> ORGANISM: Actinobacillus suis

<400> SEQUENCE: 24
atggaacgca cgccgcaact gcaagcggtg gacatttaca ttgacttcgc aacgatcccg        60
agcctgagct actttctgca ctttctgaaa cataaacacg atgatcagcg tctgcgtctg       120
ttcagcctgg cccgtttttga aatgccgcaa accctgattg aacagtatga aggcattatc      180
cagttctcgc gcaacgtgga acataatgtt gaaccgctgc tggaacagct gcaaacgatc       240
ctgtcacaag aaggtaaaca gtttgaactg catctgcacc tgaacctgtt tcattcgttc       300
gaaatgtttc tgaatctgag cccgacctac acgcagtaca aagaaaaaat ctctaaaatc       360
gttctgcacc tgtatgatga cggcagtgaa ggtgtcatga acagtacca actgcagaaa        420 agctctagtc tggtgcagga tctggcggcc accaaagcat ctctggttag cctgttcgaa       480
aacggcgaag ttcgtttag ccagattgat ctgatccgtt atgtctggaa tgctgtgctg        540
gaaacccatt attacctgct gtctgatcac tttctgctgg acgaaaaact gcagccgctg       600
aaagcagaac tgggccatta ccaactgctg aacctgagtg cttatcagta cctgtcctca       660
gaagatctgc tgtggctgaa acagattctg aaaatcgaca ccgaactgga aagcctgatg       720
caaaaactga cggcgcagcc ggtgtatttc tttagcggta ccacgttttt caacatcagt       780
ttcgaagata acaacgtct ggcgaatatc catgccattc tgatccgcga cacctggac        840 ccgaactccc agctgtttat tggcgaaccg tacctgtttg tcttcaaagg tcatccgaac       900
tcaccggaaa ttaatcaggc cctgcgtgaa tattacccga cgttatctt cctgccggaa        960 aatattccgt ttgaaatcct gaccctgctg ggcttctccc gcaaaaaat tggcggtttt       1020 gcgtcaacga tccacgttaa ttccgaacag tcaaaactgg ccaaactgtt tttcctgacc      1080
tcgacggatg aacaagaacg ccagctgagc gacggttata ttaaacaata cgcactggct      1140
caggctatgc tggaaatgca actggtctcg caagaacaag tctattactg ctcgctgtcg      1200
tcgtaa                                                                 1206
```

```
<210> SEQ ID NO 25
<211> LENGTH: 1206
<212> TYPE: DNA
<213> ORGANISM: Actinobacillus capsulatus

<400> SEQUENCE: 25
atggaacgca tcccgcaact gcaagctgtc gatatttaca ttgacttcgc cacgatcccg        60
agcctgtcct actttctgca ctttctgaaa cataaacacg atcatcagcg tctgcgcctg       120
```

-continued

```
ttcagcctgg cgcgttttga aatgccgcag accgtcattg aacaatatga aggcattatc        180
cagttctcac gcaacgtgga acacaatgtt gaacaactgc tggaacagct gcaaacgatc        240
ctgtcgcagg aaggtaaaca atttgaactg cacctgcatc tgaacctgtt tcacagtttc        300
gaaatgtttc tgaatctgtc cccgacctac acgaaataca agaaaaaat ctcaaaaatc         360 gttctgcatc tgtatgatga cggctcggaa ggtgtcatga acagtacca actgcagcaa         420 agtaactccc tggcacagga tctggctagc accaaagcgt cactggtttc gctgttcaaa        480
aacggcgaag gtgccttttc tcagattgat ctgatccgtt atgtctggaa tgcagtgctg        540
gaaacccact attacctgct gtcagaccac tttctggccc atgaaaaact gcagccgctg        600
aaaattgaac tgggccatta ccagctgctg aatctgtctg cctatcaata cctgagctct        660
gaagatctgc tgtggctgaa acaaattctg aaaatcgacg cagaactgga aagtctgatg        720
cataaactga ccacgcagcc ggtgtatttc tttagcggta ccacgttttt caacatttcg        780
ttcgaagata aacagcgtct ggccaatatc cacgcaattc tgatccgcga acatctggac        840
ccgaacagtc agctgtttat cggcgaaccg tacctgtttg ttttcaaagg tcacccgaac        900
tccccggaaa ttaatcaggc tctgcgcgaa tattacccga acgcgatctt cctgccggaa        960
aatattccgt ttgaaatcct gaccctgctg ggcttcagcc cgcagaaaat tggcggtttt       1020
gcttctacga tccatgtgaa cagcgaacaa tctaaactgg cgaaactgtt tttcctgacc       1080
agtacggatg aacaggaacg taatcgctcc gacggttata ttaaacagta cgcgctggcc       1140
caagcaatgc tggaaatgca actggtctcg caagaacaag tctactactg ctcgctgtcg       1200
tcgtaa                                                                  1206

<210> SEQ ID NO 26
<211> LENGTH: 936
<212> TYPE: DNA
<213> ORGANISM: Haemophilus somnus

<400> SEQUENCE: 26
atgttccgtg aagacaatat gaacctgatt atctgctgta cgccgctgca agtgattatc        60
gccgaaaaaa ttatcgaacg ctatccggaa cagaaatttt atggcgttat gctggaatca       120
ttctacaacg ataaattcga cttctacgaa aacaaactga acatctgtg ccacgaattt        180 ttctgtatca aaatcgcacg tttcaaactg gaacgctata aaaacctgct gtcactgctg        240
aaaatcaaaa acaaaacctt cgatcgtgtc ttcctggcta acatcgaaaa acgctacatc        300
catatcatcc tgtcgaacat tttctttaaa gaactgtaca ccttcgatga cggcacggcg        360
aacatcgccc cgaatagtca tctgtatcaa gaatacgatc actccctgaa aaaacgtatt        420
accgacatcc tgctgccgaa ccattacaac agcaacaaag tgaaaaacat cagcaaactg        480
cactactcta tctaccgctg caaaaacaac atcatcgata acatcgaata catgccgctg        540
tttaacctgg agaaaaaata cacggcacag gataaaagta tttccatcct gctgggtcaa        600
ccgattttct atgacgaaga gaaaaacatt cgtctgatca agaagtcat cgccaaattc        660 aaaatcgatt actacttccc gcacccgcgc gaagattact acatcgacaa cgtgtcttac        720
atcaaaaccc cgctgatctt tgaagaattt tacgcggaac gttcaatcga aaattcgatc        780
aaaatctata ccttttttcag ctctgccgtg ctgaacatcg ttacgaaaga aaatattgat        840
cgcatctacg cactgaaacc gaaactgacg gaaaaagcgt atctggattg ttacgacatc        900
ctgaaagatt tcggtatcaa agttatcgac atctaa                                  936
```

```
<210> SEQ ID NO 27
<211> LENGTH: 1200
<212> TYPE: DNA
<213> ORGANISM: Haemophilus ducreyi

<400> SEQUENCE: 27
atgctgattc aacagaacct ggaaatctac ctggactacg caaccatccc gagcctggcc        60
tgctttatgc acttcattca acacaaagat gacgtcgata gtattcgtct gtttggcctg       120
gcacgcttcg atatcccgca gtccattatc gaccgttacc cggctaacca cctgttttat       180
cacaacatcg ataatcgcga cctgaccgca gtgctgaacc agctggcgga tattctggcc       240
caggaaaata aacgttttca aatcaacctg catctgaacc tgtttcacag cattgacctg       300 ttttcgcta tttatccgat ctaccagcaa tatcagcata aaatttctac catccagctg       360
caactgtacg atgacggcag cgaaggtatt gttacgcagc attctctgtg caaaattgcg       420
gatctggaac agctgatcct gcaacacaaa aacgtgctgc tggaactgct gaccaaaggc       480
acggccaacg ttccgaatcc gaccctgctg cgttatctgt ggaacaatat tatcgattca       540
cagtttcatc tgatctcgga ccattttctg caacacccga aactgcaacc gctgaaacgt       600
ctgctgaaac gctacaccat tctggatttt acgtgttatc cgcgcttcaa tgccaacag       660 aaacaactgc tgaaagaaat tctgcatatc tcaaacgaac tggaaaatct gctgaaactg       720
ctgaaacagc acaacacctt tctgttcacg ggcaccacgg cgtttaatct ggatcaggaa       780
aaactggacc tgctgaccca actgcatatc ctgctgctga cgaacacca gaatccgcat        840 tcaacgcact acattggcaa caattatctg ctgctgatca aaggtcatgc aaactcgccg       900
gctctgaatc ataccctggc gctgcacttt ccggatgcga ttttcctgcc ggccaatatt       960
ccgtttgaaa tcttcgcgat gctgggcttt acgccgaaca aaatgggcgg tttcgccagc      1020
acctcttaca ttaattatcc gacggaaaac atcaatcacc tgtttttcct gaccagtgat      1080
cagccgtcca ttcgcacgaa atggctggac tacgaaaaac aatttggtct gatgtattcc      1140
ctgctggcaa tgcagaaaat caacgaagat caggcgttta tgtgcaccat tcacaattaa      1200

<210> SEQ ID NO 28
<211> LENGTH: 1494
<212> TYPE: DNA
<213> ORGANISM: Photobacterium leiognathi

<400> SEQUENCE: 28
atgtgtaacg ataatcaaaa tacggtcgat gttgttgtga gcaccgttaa cgataacgtc        60
atcgaaaaca acacgtacca agttaaaccg atcgataccc cgaccacgtt tgacagttac       120
tcctggattc agacgtgcgg caccccgatc ctgaaagatg acgaaaaata ttcactgtcg       180
tttgatttcg tcgccccgga actggatcag gacgaaaaat ctgtttcga atttaccggc       240 gatgttgacg gtaaacgtta tgtcacgcag accaacctga cggtggttgc accgaccctg       300
gaagtttacg tcgatcatgc tagtctgccg tccctgcagc aactgatgaa aatcatccag       360
cagaaaaacg aatactcaca gaatgaacgt ttcatttcgt ggggccgcat cggtctgacg       420
gaagataacg cggaaaaact gaatgcccat atttatccgc tggcaggcaa caatacctca       480
caggaactgg tggatgcagt gatcgattac gctgactcga aaaaccgtct gaatctggaa       540
ctgaacacga ataccgcgca cagctttccg aacctggccc cgattctgcg cattatcagc       600
tctaaaagca acatcctgat ctctaacatc aacctgtacg atgacggcag tgctgaatat       660
gtgaacctgt acaattggaa agataccgaa gacaaatccg tgaaactgag cgattctttc       720
```

-continued

```
ctggttctga aagactactt taacggtatt agttccgaaa aaccgagcgg catctatggt      780
cgctacaact ggcatcaact gtataatacg tcttattact tcctgcgtaa agattacctg      840
accgttgaac cgcagctgca cgacctgcgc gaatatctgg gcggtagtct gaaacaaatg      900
tcctgggatg gctttccaca gctgtcgaaa ggtgacaaag aactgttcct gaacattgtc      960
ggctttgatc aggaaaaact gcagcaagaa taccagcaat cagaactgcc gaatttcgtg     1020
tttacgggca ccacgacctg ggcaggcggt gaaaccaaag aatattacgc tcagcaacag     1080
gtgaacgtcg tgaacaatgc gattaatgaa accagcccgt attacctggg ccgtgaacat     1140
gacctgtttt tcaaaggtca cccgcgcggc ggtattatca atgatattat cctgggcagt     1200
ttcaacaata tgattgacat cccggccaaa gtgtcctttg aagttctgat gatgacgggt     1260
atgctgccgg ataccgtggg cggtattgcg tcatccgctgt attttagcat cccggccgaa     1320
aaagtctctt tcattgtgtt taccagctct gatacgatca ccgatcgtga agacgcgctg     1380
aaatctccgc tggtgcaggt tatgatgacc ctgggcattg ttaaagaaaa agatgtgctg     1440
ttctggtcgg atctgccgga ttgttcctcg ggtgtttgta ttgctcagta ttaa           1494
```

```
<210> SEQ ID NO 29
<211> LENGTH: 1497
<212> TYPE: DNA
<213> ORGANISM: Photobacterium sp.

<400> SEQUENCE: 29
```

```
atgagtgaag aaaacaccca gtccattatt aaaaacgaca tcaacaaaac catcatcgat       60
gaagaatacg ttaacctgga accgatcaac cagtctaaca tcagtttac caaacatagc       120 tgggtccaga cctgcggtac gcagcaactg ctgacggaac aaaacaaaga atcaatttcg      180
ctgagcgtgg ttgcgccgcg tctggatgac gatgaaaaat actgtttcga tttcaacggt      240
gttagtaata aaggcgaaaa atacatcacc aaagtcacgc tgaatgtcgt ggcaccgtct      300
ctggaagttt atgtggatca tgctagtctg ccgaccctgc aacaactgat ggatattatc      360
aaatcggaag aagaaacccc gaccgcacag cgttacattg cttggggccg catcgtgccg      420
acggacgaac agatgaaaga actgaatatt accagctttg cgctgatcaa caatcacacg      480
ccggccgatc tggttcagga aattgtcaaa caggcgcaaa ccaaacatcg tctgaacgtg      540
aaactgagca gcaatacggc ccactcgttt gacaatctgg ttccgattct gaaagaactg      600
aacagcttca caatgtgac cgttacgaat atcgatctgt atgacgatgg cagcgcggaa       660
tatgttaacc tgtacaattg gcgcgacacc ctgaacaaaa cggataatct gaaaattggc      720
aaagactatc tggaagatgt cattaacggt atcaatgaag ataccagcaa caccggcacg      780
agttccgtgt acaattggca gaaactgtat ccggctaact accattttct gcgtaaagat      840
tatctgaccc tggaaccgtc cctgcacgaa ctgcgcgact acattggtga ttcactgaaa      900
cagatgcaat gggacggctt caaaaaattc aactcgaaac agcaagaact gtttctgagc      960
atcgtgaatt cgataaaca gaaactgcaa aacgaataca attcatcgaa cctgccgaat      1020
tttgtgttca ccggtaccac ggtttgggca ggcaaccacg aacgcgaata ctacgctaaa     1080
cagcaaatca cgttatcaa caacgccatc aacgaaagct ctccgcatta tctgggtaat     1140
tcctacgacc tgtttttcaa aggccacccg ggcggtggca ttatcaacac cctgatcatg     1200
cagaattatc cgtcaatggt cgatattccg tccaaaatct catttgaagt gctgatgatg     1260
accgacatgc tgccggatgc cgtggcaggt attgcgagtt ccctgtactt cacgatcccg     1320
```

-continued

```
gccgaaaaaa tcaaattcat cgttttcacc tctacggaaa ccattacgga tcgtgaaacc   1380
gccctgcgta gtccgctggt ccaggtgatg attaaactgg gcatcgtgaa agaagaaaat   1440
gtgctgttct gggcggacct gccgaattgc gaaacgggtg tctgtattgc tgtctga      1497
```

```
<210> SEQ ID NO 30
<211> LENGTH: 1449
<212> TYPE: DNA
<213> ORGANISM: Photobacterium leiognathi

<400> SEQUENCE: 30
atgaacgata atcaaaatac ggtggacgtg gtggtctcaa ccgtcaacga taacgtgatc     60
gaaaacaaca cgtaccaagt caaaccgatc gataccccga ccacgttcga ctcatactcg    120
tggattcaga cgtgcggcac cccgatcctg aaagatgacg aaaaatatag cctgtctttt    180
gatttcgttg ccccggaact ggatcaagac gaaaaattct gtttcgaatt taccggcgat    240
gtggatggta acgttatgt gacgcagacc aacctgacgg tggttgcacc gaccctggaa     300
gtttacgtcg atcatgcttc actgccgtcg ctgcagcaac tgatgaaaat catccagcag    360
aaaaacgaat acagccagaa tgaacgcttt atttcttggg ccgtatccg cctgacggaa     420 gataacgcgg aaaaactgaa tgcccatatt tatccgctgg caggcaacaa taccagccag    480
gaactggtgg acgcagttat cgattacgct gactctaaaa accgtctgaa tctggaactg    540
aacacgaata ccgccacag tttccgtaac attgcgccga tcctgcgcgc caccagctct    600
aaaaacaaca tcctgatctc caacatcaac ctgtacgatg acggtagtgc tgaatatgtg    660
tccctgtaca actggaaaga taccgacaat aaatcacaga aactgagtga ttccttctg    720 gttctgaaag actacctgaa tggcatcagt tccgaaaaac cgaacggtat ttatagcatc    780
tacaattggc atcagctgta tcactcatcg tattacttcc tgcgtaaaga ttacctgacg    840
gtggaaacca aactgcacga cctgcgcgaa tatctgggcg gttcactgaa acaaatgtcg    900
tgggatacct ttagccagct gtctaaaggc gacaaagaac tgttcctgaa cattgttggt    960
tttgatcagg aaaaactgca gcaagaatac cagcaaagcg aactgccgaa tttcgtcttt   1020
acgggcacca cgacctgggc aggcggtgaa accaaagaat attacgctca gcaacaggtg   1080
aacgtcgtga acaatgcgat taatgaaacc tctccgtatt acctgggccg tgaacatgac   1140
ctgtttttca aaggtcaccc gcgcggcggt attatcaatg atattatcct gggctcattc   1200
aacaatatga ttgacatccc ggccaaagtt tcgtttgaag tcctgatgat gacgggtatg   1260
ctgccggata ccgttggcgg tattgcgagc agcctgtatt ttagtatccc ggccgaaaaa   1320
gtgtccttca ttgttttttac cagttccgat acgatcaccg atcgcgaaga cgcgctgaaa   1380
agtccgctgg tccaagtgat gatgaccctg ggcattgtga agaaaaaga gtgctgttc    1440 tggtgctaa                                                          1449
```

```
<210> SEQ ID NO 31
<211> LENGTH: 2028
<212> TYPE: DNA
<213> ORGANISM: Photobacterium damsela

<400> SEQUENCE: 31
atgaaaaaga tcctgaccgt cctgagcatc tttatcctga gcgcctgtaa tagcgacaac     60
acctctctga agaaaccgt ctccagcaac agcgcggatg tggttgaaac ggaaacctat    120
cagctgaccc cgattgacgc cccgagcagc tttctgagcc attcttggga acagacgtgc    180
ggcaccccga tcctgaatga aagtgataaa caagcgattt cctttgactt cgtggccccg    240
```

```
gaactgaaac aggatgaaaa atactgtttc acgttcaaag gcatcaccgg tgaccaccgc        300
tacattacga acaccaccct gaccgttgtg gcaccgacgc tggaagtgta tatcgatcat        360
gctagtctgc cgagcctgca acaactgatt cacattatcc aggcgaaaga tgaatacccg        420
tcaaaccaac gctttgtttc gtggaaacgt gttaccgtcg atgcggacaa cgccaataaa        480
ctgaatattc atacctatcc gctgaaaggc aacaatacgt caccggaaat ggttgcggcc        540
atcgatgaat atgcacaatc gaaaaaccgc ctgaatattg aattttacac gaataccgct        600
catgtcttca acaatctgcc gccgattatc cagccgctgt acaacaacga aaaagtcaaa        660
atttcacaca tctcgctgta cgatgacggt agttccgaat atgtgagtct gtaccagtgg        720 aaagatacc cgaacaaaat tgaaacgctg gaaggcgaag tgagcctgct ggcaaattat        780
ctggctggca ccagcccgga tgcaccgaaa ggcatgggta accgttataa ttggcataaa        840
ctgtacgata ccgactatta ctttctgcgc gaagattatc tggacgtgga agcgaacctg        900
cacgatctgc gtgactacct gggttcatcg gcaaaacaga tgccgtggga tgaatttgct        960
aaactgagtg actcccagca aaccctgttt ctggatatcg ttggcttcga caaagaacag       1020
ctgcaacaac agtattcaca atcgccgctg ccgaattta tttttaccgg caccaccacc        1080
tgggcgggcg gtgaaacgaa agaatattac gcccaacagc aagtgaacgt tattaacaat       1140
gccatcaatg aaaccagccc gtattacctg ggcaaagatt acgacctgtt tttcaaaggt       1200
catccggcag gcggtgtgat caacgatatt atcctgggca gttttccgga catgattaat       1260
atcccggcta aaatttcctt cgaagtgctg atgatgaccg atatgctgcc ggacacggtt       1320
gcaggtatcg ctagctctct gtattttacc attccggcgg ataaagtgaa ctttatcgtt       1380
ttcacgagtt ccgatacgat taccgaccgt gaagaagccc tgaaaagccc gctggtccag       1440
gtgatgctga ccctgggcat cgtcaaagaa aaagatgtgc tgttctgggc agaccacaaa       1500
gttaatagca tggaagtcgc gattgatgaa gcctgcaccc gcattatcgc aaaacgtcag       1560
ccgacggctt ctgatctgcg cctggtgatt gcgattatca aaacgatcac cgatctggaa       1620
cgtattggcg acgttgccga atctattgcg aaagtcgcgc tggaatcttt ttctaacaaa       1680
cagtacaatc tgctggttag cctggaatct ctgggtcaac ataccgtgcg catgctgcac       1740
gaagttctgg atgcattcgc tcgtatggac gtcaaagcag ctatcgaagt gtatcaggaa       1800
gatgaccgca tcgatcaaga atacgaaagt attgtccgtc agctgatggc ccacatgatg       1860
gaagatccgt catcgattcc gaacgttatg aaagtcatgt gggcggcccg ttccatcgaa       1920
cgcgttggtg atcgttgcca gaatatttgt gaatacatca tctacttcgt gaaaggcaaa       1980
gatgttcgcc acaccaaacc ggatgacttc ggtacgatgc tggactaa              2028
```

```
<210> SEQ ID NO 32
<211> LENGTH: 1533
<212> TYPE: DNA
<213> ORGANISM: Photobacterium damsela

<400> SEQUENCE: 32
atgaaaaaga tcctgaccgt cctgagcatc tttatcctga cgcctgtaa tagcgacaac         60 acctctctga aagaaaccgt ctccagcaac agcgcggatg tggttgaaac ggaaacctat        120
cagctgaccc cgattgacgc cccgagcagc tttctgagcc attcttggga acagacgtgc        180
ggcaccccga tcctgaatga aagtgataaa caagcgattt cctttgactt cgtggcccg        240 gaactgaaac aggatgaaaa atactgtttc acgttcaaag gcatcaccgg tgaccaccgc        300
```

-continued

```
tacattacga acaccaccct gaccgttgtg gcaccgacgc tggaagtgta tatcgatcat      360
gctagtctgc cgagcctgca acaactgatt cacattatcc aggcgaaaga tgaatacccg      420
tcaaaccaac gctttgtttc gtggaaacgt gttaccgtcg atgcggacaa cgccaataaa      480
ctgaatattc atacctatcc gctgaaaggc aacaatacgt caccggaaat ggttgcggcc      540
atcgatgaat atgcacaatc gaaaaaccgc ctgaatattg aattttacac gaataccgct      600
catgtcttca caatctgcc gccgattatc cagccgctgt acaacaacga aaaagtcaaa      660
atttcacaca tctcgctgta cgatgacggt agttccgaat atgtgagtct gtaccagtgg      720
aaagataccc cgaacaaaat tgaaacgctg gaaggcgaag tgagcctgct ggcaaattat      780
ctggctggca ccagcccgga tgcaccgaaa ggcatgggta accgttataa ttggcataaa      840
ctgtacgata ccgactatta ctttctgcgc gaagattatc tggacgtgga agcgaacctg      900
cacgatctgc gtgactacct gggttcatcg gcaaaacaga tgccgtggga tgaatttgct      960
aaactgagtg actcccagca aaccctgttt ctggatatcg ttggcttcga caaagaacag     1020
ctgcaacaac agtattcaca atcgccgctg ccgaatttta tttttaccgg caccaccacc     1080
tgggcgggcg gtgaaacgaa agaatattac gcccaacagc aagtgaacgt tattaacaat     1140
gccatcaatg aaaccagccc gtattacctg ggcaaagatt acgacctgtt tttcaaaggt     1200
catccggcag gcggtgtgat caacgatatt atcctgggca gtttttccgga catgattaat     1260 atcccggcta aaatttcctt cgaagtgctg atgatgaccg atatgctgcc ggacacggtt     1320
gcaggtatcg ctagctctct gtattttacc attccggcgg ataaagtgaa ctttatcgtt     1380
ttcacgagtt ccgatacgat taccgaccgt gaagaagccc tgaaaagccc gctggtccag     1440
gtgatgctga ccctgggcat cgtcaaagaa aaagatgtgc tgttctgggc agacctgccg     1500
gactgctcgt ctggtgtgtg tatcgacaaa taa                                  1533
```

```
<210> SEQ ID NO 33
<211> LENGTH: 1269
<212> TYPE: DNA
<213> ORGANISM: Heliobacter acinonychis

<400> SEQUENCE: 33
```

```
atggggacca ttaaaaagcc cttaatcata gcaggaaatg gtccatcaat taaggaccta       60
gactatgctt tatttccaaa agacttcgat gtctttcgct gcaaccagtt ttacttcgag      120
gataaatatt acctaggacg cgaaataaaa ggagtgttct ttaacccttg tgtattaagc      180
agtcaaatgc aaacagtgca ataccttatg gacaatggcg aatatagcat agaacgcttc      240 tttttgcagtg tttcaacaga tcgccacgat tttgatgggg attaccaaac gatttttaccg     300 gtagacggtt atttaaaagc acactatccg ttcgtctgcg atacattcag cttattcaaa      360
ggtcacgaag aaatcttaaa acacgtgaaa taccacctga aaacgtacag caaagaactt      420
agtgcgggtg tcttaatgtt attgagtgca gtggtattag atacaaaga aatatacctta      480 gtaggaatcg acttcggcgc ctcatcttgg gggcacttct atgacgaaag ccaatcccaa      540
cactttagca atcacatggc agattgtcac aatatctatt acgacatgct gactatttgt      600
ctctgtcaaa agtatgcaaa attgtacgca ttagcaccca attcaccatt atcacatttg      660
cttacactaa atccacaggc caaatacccca tttgaactat tagataaacc tatcgggtat      720
actagcgacc taattattag tagcccgttg gaagagaagt tgctcgaatt taagaatatc      780
gaagagaagt tgcttgagtt caaaaacata gaagagaaac tcttagagtt caagaatatt      840
gaagagaaac tattagaatt taaaaacatc gaggaaaaac ttttggagtt caaaaatata      900
```

-continued

```
gaagagaaac tcctagagtt caagaacatt gaggaaaagt tgcttgagtt caaaaatatt     960
gaggaaaagt tgctcgaatt taagaatatc gaggaaaaac ttttggaatt taagaacata    1020
gaagaaaagt tactcgaatt taaaaacatt gaagagaaac tattggaatt taaaaatata    1080
gaggaaaagt tacttgagtt caaaaacata gaggaaaagt tacttgaatt taagaacata    1140
gaagagaaac ttctcgcaag ccgactgaac aacattctac gtaaaatcaa gcggaaaata    1200
cttccattct tttggggcgg aggtgtaacc ccaacattaa aagttagttt ccgttgggga    1260
gctgcataa                                                            1269
```

```
<210> SEQ ID NO 34
<211> LENGTH: 469
<212> TYPE: PRT
<213> ORGANISM: Campylobacter coli

<400> SEQUENCE: 34

Met Gln Asn Val Ile Ile Ala Gly Asn Gly Pro Ser Leu Gln Ser Ile
1               5                   10                  15

Asn Tyr Gln Arg Leu Pro Lys Glu Tyr Asp Ile Phe Arg Cys Asn Gln
            20                  25                  30

Phe Tyr Phe Glu Asp Lys Tyr Tyr Leu Gly Lys Asn Ile Lys Ala Ala
        35                  40                  45

Phe Phe Asn Pro Tyr Pro Phe Leu Gln Gln Tyr His Thr Ala Lys Gln
    50                  55                  60

Leu Val Phe Asn Asn Glu Tyr Lys Ile Glu Asn Ile Phe Cys Ser Thr
65                  70                  75                  80

Phe Asn Leu Pro Phe Ile Glu Lys Asp Asn Phe Ile Asn Lys Phe Tyr
                85                  90                  95

Asp Phe Phe Pro Asp Ala Lys Leu Gly His Lys Ile Ile Glu Asn Leu
            100                 105                 110

Lys Glu Phe Tyr Ala Tyr Ile Lys Tyr Asn Glu Ile Tyr Leu Asn Lys
        115                 120                 125

Arg Ile Thr Ser Gly Ile Tyr Met Cys Ala Ile Ala Ile Ala Leu Gly
    130                 135                 140

Tyr Lys Asn Ile Tyr Leu Cys Gly Ile Asp Phe Tyr Glu Gly Glu Thr
145                 150                 155                 160

Ile Tyr Pro Phe Lys Ala Met Ser Lys Asn Ile Lys Lys Ile Phe Pro
                165                 170                 175

Trp Ile Lys Asp Phe Asn Pro Ser Asn Phe His Ser Lys Glu Tyr Asp
            180                 185                 190

Ile Glu Ile Leu Lys Leu Leu Glu Ser Ile Tyr Lys Val Asn Ile Tyr
        195                 200                 205

Ala Leu Cys Asp Asn Ser Ala Leu Ala Asn Tyr Phe Pro Leu Leu Val
    210                 215                 220

Asn Thr Asp Asn Ser Phe Val Leu Glu Asn Lys Ser Asp Asp Cys Ile
225                 230                 235                 240

Asn Asp Ile Leu Leu Thr Asn Asn Thr Pro Gly Ile Asn Phe Tyr Lys
                245                 250                 255

Ser Gln Ile Gln Val Asn Asn Thr Glu Ile Leu Leu Leu Asn Phe Gln
            260                 265                 270

Asn Met Ile Ser Ala Lys Glu Asn Glu Ile Ser Asn Leu Asn Lys Ile
        275                 280                 285

Leu Gln Asp Ser Tyr Lys Thr Ile Asn Thr Lys Glu Asn Glu Ile Ser
    290                 295                 300
```

```
Asn Leu Asn Lys Ile Leu Gln Asp Ser Tyr Lys Thr Ile Asn Thr Lys
305                 310                 315                 320

Glu Asn Glu Ile Ser Asn Leu Asn Lys Ile Leu Gln Asp Lys Asp Lys
                325                 330                 335

Leu Leu Ile Val Lys Glu Asn Leu Leu Asn Phe Lys Ser Arg His Gly
            340                 345                 350

Lys Ala Lys Phe Arg Ile Gln Asn Gln Leu Ser Tyr Lys Leu Gly Gln
        355                 360                 365

Ala Met Met Val Asn Ser Lys Ser Leu Leu Gly Tyr Ile Arg Met Pro
    370                 375                 380

Phe Val Leu Ser Tyr Ile Lys Asp Lys His Lys Gln Glu Gln Lys Ile
385                 390                 395                 400

Tyr Gln Glu Lys Ile Lys Lys Asp Pro Ser Leu Thr Leu Pro Pro Leu
                405                 410                 415

Glu Asp Tyr Pro Asp Tyr Lys Glu Ala Leu Lys Glu Lys Glu Cys Leu
            420                 425                 430

Thr Tyr Arg Leu Gly Gln Thr Leu Ile Lys Ala Asp Gln Glu Trp Tyr
        435                 440                 445

Lys Gly Gly Tyr Val Lys Met Trp Phe Glu Ile Lys Lys Leu Lys Lys
    450                 455                 460

Glu Tyr Lys Lys Lys
465

<210> SEQ ID NO 35
<211> LENGTH: 381
<212> TYPE: PRT
<213> ORGANISM: Vibrio sp.

<400> SEQUENCE: 35

Met Asn Asn Asp Asn Ser Thr Thr Thr Asn Asn Asn Ala Ile Glu Ile
1               5                   10                  15

Tyr Val Asp Arg Ala Thr Leu Pro Thr Ile Gln Gln Met Thr Lys Ile
            20                  25                  30

Val Ser Gln Lys Thr Ser Asn Lys Lys Leu Ile Ser Trp Ser Arg Tyr
        35                  40                  45

Pro Ile Thr Asp Lys Ser Leu Leu Lys Lys Ile Asn Ala Glu Phe Phe
    50                  55                  60

Lys Glu Gln Phe Glu Leu Thr Glu Ser Leu Lys Asn Ile Ile Leu Ser
65                  70                  75                  80

Glu Asn Ile Asp Asn Leu Ile Ile His Gly Asn Thr Leu Trp Ser Ile
                85                  90                  95

Asp Val Val Asp Ile Ile Lys Glu Val Asn Leu Leu Gly Lys Asn Ile
            100                 105                 110

Pro Ile Glu Leu His Phe Tyr Asp Asp Gly Ser Ala Glu Tyr Val Arg
        115                 120                 125

Ile Tyr Glu Phe Ser Lys Leu Pro Glu Ser Glu Gln Lys Tyr Lys Thr
    130                 135                 140

Ser Leu Ser Lys Asn Asn Ile Lys Phe Ser Ile Asp Gly Thr Asp Ser
145                 150                 155                 160

Phe Lys Asn Thr Ile Glu Asn Ile Tyr Gly Phe Ser Gln Leu Tyr Pro
                165                 170                 175

Thr Thr Tyr His Met Leu Arg Ala Asp Ile Phe Asp Thr Thr Leu Lys
            180                 185                 190

Ile Asn Pro Leu Arg Glu Leu Leu Ser Asn Asn Ile Lys Gln Met Lys
```

-continued

```
            195                 200                 205

Trp Asp Tyr Phe Lys Asp Phe Asn Tyr Lys Gln Lys Asp Ile Phe Tyr
    210                 215                 220

Ser Leu Thr Asn Phe Asn Pro Lys Glu Ile Gln Glu Asp Phe Asn Lys
225                 230                 235                 240

Asn Ser Asn Lys Asn Phe Ile Phe Ile Gly Ser Asn Ser Ala Thr Ala
                    245                 250                 255

Thr Ala Glu Glu Gln Ile Asn Ile Ile Ser Glu Ala Lys Lys Glu Asn
                260                 265                 270

Ser Ser Ile Ile Thr Asn Ser Ile Ser Asp Tyr Asp Leu Phe Phe Lys
            275                 280                 285

Gly His Pro Ser Ala Thr Phe Asn Glu Gln Ile Ile Asn Ala His Asp
        290                 295                 300

Met Ile Glu Ile Asn Asn Lys Ile Pro Phe Glu Ala Leu Ile Met Thr
305                 310                 315                 320

Gly Ile Leu Pro Asp Ala Val Gly Gly Met Gly Ser Ser Val Phe Phe
                325                 330                 335

Ser Ile Pro Lys Glu Val Lys Asn Lys Phe Val Phe Tyr Lys Ser Gly
            340                 345                 350

Thr Asp Ile Glu Asn Asn Ser Leu Ile Gln Val Met Leu Lys Leu Asn
            355                 360                 365

Leu Ile Asn Arg Asp Asn Ile Lys Leu Ile Ser Asp Ile
    370                 375                 380

<210> SEQ ID NO 36
<211> LENGTH: 390
<212> TYPE: PRT
<213> ORGANISM: Photobacterium sp.

<400> SEQUENCE: 36

Met Gly Cys Asn Ser Asp Ser Asn His Asn Asn Ser Asp Gly Asn Ile
1               5                   10                  15

Thr Lys Asn Lys Thr Ile Glu Val Tyr Val Asp Arg Ala Thr Leu Pro
                20                  25                  30

Thr Ile Gln Gln Met Thr Gln Ile Ile Asn Glu Asn Ser Asn Asn Lys
            35                  40                  45

Lys Leu Ile Ser Trp Ser Arg Tyr Pro Ile Asn Asp Glu Glu Leu Leu
    50                  55                  60

Glu Ser Ile Asn Gly Ser Phe Phe Lys Asn Asn Ser Glu Leu Ile Lys
65                  70                  75                  80

Ser Leu Asp Ser Met Ile Leu Thr Asn Asp Ile Lys Lys Val Ile Ile
                85                  90                  95

Asn Gly Asn Thr Leu Trp Ala Ala Asp Val Val Asn Ile Ile Lys Ser
                100                 105                 110

Ile Glu Ala Phe Gly Lys Lys Thr Glu Ile Glu Leu Asn Phe Tyr Asp
            115                 120                 125

Asp Gly Ser Ala Glu Tyr Val Arg Leu Tyr Asp Phe Ser Lys Leu Pro
        130                 135                 140

Glu Ser Glu Gln Glu Tyr Lys Ile Ser Leu Ser Lys Asp Asn Ile Leu
145                 150                 155                 160

Ser Ser Ile Asn Gly Thr Gln Pro Phe Glu Asn Val Val Glu Asn Ile
                165                 170                 175

Tyr Gly Phe Ser Gln Leu Tyr Pro Thr Thr Tyr His Met Leu Arg Ala
                180                 185                 190
```

-continued

```
Asp Ile Phe Glu Thr Asn Leu Pro Leu Arg Ser Leu Lys Gly Val Leu
        195                 200                 205

Ser Asn Asn Ile Lys Gln Met Lys Trp Asp Tyr Phe Lys Thr Phe Asn
    210                 215                 220

Ser Gln Gln Lys Asp Lys Phe Tyr Asn Phe Thr Gly Phe Asn Pro Asp
225                 230                 235                 240

Glu Ile Met Glu Gln Tyr Lys Ala Ser Pro Asn Lys Asn Phe Ile Phe
                245                 250                 255

Val Gly Thr Asn Ser Gly Thr Ala Thr Ala Glu Gln Gln Ile Asp Ile
                260                 265                 270

Leu Thr Glu Ala Lys Asn Pro Asn Ser Pro Ile Ile Thr Lys Ser Ile
        275                 280                 285

Gln Gly Phe Asp Leu Phe Phe Lys Gly His Pro Ser Ala Thr Tyr Asn
        290                 295                 300

Lys Gln Ile Ile Asp Ala His Asn Met Ile Glu Ile Tyr Asn Lys Ile
305                 310                 315                 320

Pro Phe Glu Ala Leu Ile Met Thr Asp Ala Leu Pro Asp Ala Val Gly
                325                 330                 335

Gly Met Gly Ser Ser Val Phe Phe Ser Leu Pro Asn Thr Val Glu Asn
                340                 345                 350

Lys Phe Ile Phe Tyr Lys Ser Asp Thr Asp Ile Glu Asn Asn Ala Leu
        355                 360                 365

Ile Gln Val Met Ile Glu Leu Asn Ile Val Asn Arg Asn Asp Val Lys
        370                 375                 380

Leu Ile Ser Asp Leu Gln
385                 390
```

```
<210> SEQ ID NO 37
<211> LENGTH: 388
<212> TYPE: PRT
<213> ORGANISM: Pasteurella multocida

<400> SEQUENCE: 37

Met Lys Thr Ile Thr Leu Tyr Leu Asp Pro Ala Ser Leu Pro Ala Leu
1                   5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asp Ile His Leu Asn Ile Ala His Ser Val Gln Leu Ile Arg Pro Ile
                85                  90                  95

Leu Ala Tyr Arg Phe Lys His Leu Asp Arg Val Ser Ile Gln Arg Leu
            100                 105                 110

Asn Leu Tyr Asp Asp Gly Ser Met Glu Tyr Val Asp Leu Glu Lys Glu
            115                 120                 125

Glu Asn Lys Asp Ile Ser Ala Glu Ile Lys Gln Ala Glu Lys Gln Leu
        130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175
```

```
Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
            195                 200                 205

Leu Thr Pro Glu Gln Gln Ala Phe Tyr Leu Thr Leu Val Gly Phe Asn
    210                 215                 220

Asp Glu Val Lys Gln Ser Leu Glu Val Gln Gln Ala Lys Phe Ile Phe
225                 230                 235                 240

Thr Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Gly Gly
            260                 265                 270

Asp Leu Phe Ile Gly Asp His Tyr Lys Ile Tyr Phe Lys Gly His Pro
            275                 280                 285

Arg Gly Gly Glu Ile Asn Asp Tyr Ile Leu Asn Asn Ala Lys Asn Ile
            290                 295                 300

Thr Asn Ile Pro Ala Asn Ile Ser Phe Glu Val Leu Met Met Thr Gly
305                 310                 315                 320

Leu Leu Pro Asp Lys Val Gly Gly Val Ala Ser Ser Leu Tyr Phe Ser
                325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
            355                 360                 365

Arg Arg Leu Gly Ile Ile Asp Glu Ser Gln Val Ile Phe Trp Asp Ser
    370                 375                 380

Leu Lys Gln Leu
385
```

```
<210> SEQ ID NO 38
<211> LENGTH: 371
<212> TYPE: PRT
<213> ORGANISM: Neisseria meningitidis

<400> SEQUENCE: 38
```

```
Met Gly Leu Lys Lys Ala Cys Leu Thr Val Leu Cys Leu Ile Val Phe
1               5                   10                  15

Cys Phe Gly Ile Phe Tyr Thr Phe Asp Arg Val Asn Gln Gly Glu Arg
            20                  25                  30

Asn Ala Val Ser Leu Leu Lys Glu Lys Leu Phe Asn Glu Glu Gly Glu
            35                  40                  45

Pro Val Asn Leu Ile Phe Cys Tyr Thr Ile Leu Gln Met Lys Val Ala
    50                  55                  60

Glu Arg Ile Met Ala Gln His Pro Gly Glu Arg Phe Tyr Val Val Leu
65                  70                  75                  80

Met Ser Glu Asn Arg Asn Glu Lys Tyr Asp Tyr Tyr Phe Asn Gln Ile
                85                  90                  95

Lys Asp Lys Ala Glu Arg Ala Tyr Phe Phe His Leu Pro Tyr Gly Leu
            100                 105                 110

Asn Lys Ser Phe Asn Phe Ile Pro Thr Met Ala Glu Leu Lys Val Lys
            115                 120                 125

Ser Met Leu Leu Pro Lys Val Lys Arg Ile Tyr Leu Ala Ser Leu Glu
            130                 135                 140

Lys Val Ser Ile Ala Ala Phe Leu Ser Thr Tyr Pro Asp Ala Glu Ile
```

-continued

```
145                150                155                160

Lys Thr Phe Asp Asp Gly Thr Gly Asn Leu Ile Gln Ser Ser Ser Tyr
               165                170                175

Leu Gly Asp Glu Phe Ser Val Asn Gly Thr Ile Lys Arg Asn Phe Ala
               180                185                190

Arg Met Met Ile Gly Asp Trp Ser Ile Ala Lys Thr Arg Asn Ala Ser
               195                200                205

Asp Glu His Tyr Thr Ile Phe Lys Gly Leu Lys Asn Ile Met Asp Asp
           210                215                220

Gly Arg Arg Lys Met Thr Tyr Leu Pro Leu Phe Asp Ala Ser Glu Leu
225                230                235                240

Lys Thr Gly Asp Glu Thr Gly Gly Thr Val Arg Ile Leu Leu Gly Ser
               245                250                255

Pro Asp Lys Glu Met Lys Glu Ile Ser Glu Lys Ala Ala Lys Asn Phe
               260                265                270

Lys Ile Gln Tyr Val Ala Pro His Pro Arg Gln Thr Tyr Gly Leu Ser
               275                280                285

Gly Val Thr Thr Leu Asn Ser Pro Tyr Val Ile Glu Asp Tyr Ile Leu
           290                295                300

Arg Glu Ile Lys Lys Asn Pro His Thr Arg Tyr Glu Ile Tyr Thr Phe
305                310                315                320

Phe Ser Gly Ala Ala Leu Thr Met Lys Asp Phe Pro Asn Val His Val
               325                330                335

Tyr Ala Leu Lys Pro Ala Ser Leu Pro Glu Asp Tyr Trp Leu Lys Pro
               340                345                350

Val Tyr Ala Leu Phe Thr Gln Ser Gly Ile Pro Ile Leu Thr Phe Asp
               355                360                365

Asp Lys Asn
           370

<210> SEQ ID NO 39
<211> LENGTH: 283
<212> TYPE: PRT
<213> ORGANISM: Pasteurella multocida

<400> SEQUENCE: 39

Met Asp Lys Phe Ala Glu His Glu Ile Pro Lys Ala Val Ile Val Ala
1               5                  10                 15

Gly Asn Gly Glu Ser Leu Ser Gln Ile Asp Tyr Arg Leu Leu Pro Lys
               20                 25                 30

Asn Tyr Asp Val Phe Arg Cys Asn Gln Phe Tyr Phe Glu Glu Arg Tyr
           35                 40                 45

Phe Leu Gly Asn Lys Ile Lys Ala Val Phe Phe Thr Pro Gly Val Phe
       50                 55                 60

Leu Glu Gln Tyr Tyr Thr Leu Tyr His Leu Lys Arg Asn Asn Glu Tyr
65                 70                 75                 80

Phe Val Asp Asn Val Ile Leu Ser Ser Phe Asn His Pro Thr Val Asp
               85                 90                 95

Leu Glu Lys Ser Gln Lys Ile Gln Ala Leu Phe Ile Asp Val Ile Asn
               100                105                110

Gly Tyr Glu Lys Tyr Leu Ser Lys Leu Thr Ala Phe Asp Val Tyr Leu
           115                120                125

Arg Tyr Lys Glu Leu Tyr Glu Asn Gln Arg Ile Thr Ser Gly Val Tyr
       130                135                140
```

```
Met Cys Ala Val Ala Ile Ala Met Gly Tyr Thr Asp Ile Tyr Leu Thr
145                 150                 155                 160

Gly Ile Asp Phe Tyr Gln Ala Ser Glu Glu Asn Tyr Ala Phe Asp Asn
                165                 170                 175

Lys Lys Pro Asn Ile Ile Arg Leu Leu Pro Asp Phe Arg Lys Glu Lys
            180                 185                 190

Thr Leu Phe Ser Tyr His Ser Lys Asp Ile Asp Leu Glu Ala Leu Ser
        195                 200                 205

Phe Leu Gln Gln His Tyr His Val Asn Phe Tyr Ser Ile Ser Pro Met
    210                 215                 220

Ser Pro Leu Ser Lys His Phe Pro Ile Pro Thr Val Glu Asp Asp Cys
225                 230                 235                 240

Glu Thr Thr Phe Val Ala Pro Leu Lys Glu Asn Tyr Ile Asn Asp Ile
                245                 250                 255

Leu Leu Pro Pro His Phe Val Tyr Glu Lys Leu Gly Val Asp Lys Leu
                260                 265                 270

Ala Ala Ala Leu Glu His His His His His His
            275                 280

<210> SEQ ID NO 40
<211> LENGTH: 385
<212> TYPE: PRT
<213> ORGANISM: Pasteurella dagmatis

<400> SEQUENCE: 40

Met Thr Ile Tyr Leu Asp Pro Ala Ser Leu Pro Thr Leu Asn Gln Leu
1               5                   10                  15

Met His Phe Thr Lys Glu Ser Glu Asp Lys Glu Thr Ala Arg Ile Phe
                20                  25                  30

Gly Phe Ser Arg Phe Lys Leu Pro Glu Lys Ile Thr Glu Gln Tyr Asn
            35                  40                  45

Asn Ile His Phe Val Glu Ile Lys Asn Asn Arg Pro Thr Glu Asp Ile
        50                  55                  60

Phe Thr Ile Leu Asp Gln Tyr Pro Glu Lys Leu Glu Leu Asp Leu His
65                  70                  75                  80

Leu Asn Ile Ala His Ser Ile Gln Leu Phe His Pro Ile Leu Gln Tyr
                85                  90                  95

Arg Phe Lys His Pro Asp Arg Ile Ser Ile Lys Ser Leu Asn Leu Tyr
            100                 105                 110

Asp Asp Gly Thr Met Glu Tyr Val Asp Leu Glu Lys Glu Glu Asn Lys
        115                 120                 125

Asp Ile Lys Ser Ala Ile Lys Lys Ala Glu Lys Gln Leu Ser Asp Tyr
    130                 135                 140

Leu Leu Thr Gly Lys Ile Asn Phe Asp Asn Pro Thr Leu Ala Arg Tyr
145                 150                 155                 160

Val Trp Gln Ser Gln Tyr Pro Val Lys Tyr His Phe Leu Ser Thr Glu
                165                 170                 175

Tyr Phe Glu Lys Ala Glu Phe Leu Gln Pro Leu Lys Thr Tyr Leu Ala
            180                 185                 190

Gly Lys Tyr Gln Lys Met Asp Trp Ser Ala Tyr Glu Lys Leu Ser Pro
        195                 200                 205

Glu Gln Gln Thr Phe Tyr Leu Lys Leu Val Gly Phe Ser Asp Glu Thr
    210                 215                 220

Lys Gln Leu Phe His Thr Glu Gln Thr Lys Phe Ile Phe Thr Gly Thr
225                 230                 235                 240
```

-continued

```
Thr Thr Trp Glu Gly Asn Thr Asp Ile Arg Glu Tyr Tyr Ala Lys Gln
            245                 250                 255

Gln Leu Asn Leu Leu Lys His Phe Thr His Ser Glu Gly Asp Leu Phe
            260                 265                 270

Ile Gly Asp Gln Tyr Lys Ile Tyr Phe Lys Gly His Pro Arg Gly Gly
            275                 280                 285

Asp Ile Asn Asp Tyr Ile Leu Lys His Ala Lys Asp Ile Thr Asn Ile
    290                 295                 300

Pro Ala Asn Ile Ser Phe Glu Ile Leu Met Met Thr Gly Leu Leu Pro
305                 310                 315                 320

Asp Lys Val Gly Gly Val Ala Ser Ser Leu Tyr Phe Ser Leu Pro Lys
                325                 330                 335

Glu Lys Ile Ser His Ile Ile Phe Thr Ser Asn Lys Lys Ile Lys Asn
            340                 345                 350

Lys Glu Asp Ala Leu Asn Asp Pro Tyr Val Arg Val Met Leu Arg Leu
            355                 360                 365

Gly Met Ile Asp Lys Ser Gln Ile Ile Phe Trp Asp Ser Leu Lys Gln
    370                 375                 380

Leu
385

<210> SEQ ID NO 41
<211> LENGTH: 390
<212> TYPE: PRT
<213> ORGANISM: Photobacterium phosphoreum

<400> SEQUENCE: 41

Met Gly Cys Asn Ser Asp Ser Lys His Asn Asn Ser Asp Gly Asn Ile
1               5                   10                  15

Thr Lys Asn Lys Thr Ile Glu Val Tyr Val Asp Arg Ala Thr Leu Pro
            20                  25                  30

Thr Ile Gln Gln Met Thr Gln Ile Ile Asn Glu Asn Ser Asn Asn Lys
        35                  40                  45

Lys Leu Ile Ser Trp Ser Arg Tyr Pro Ile Asn Asp Glu Thr Leu Leu
    50                  55                  60

Glu Ser Ile Asn Gly Ser Phe Phe Lys Asn Arg Pro Glu Leu Ile Lys
65                  70                  75                  80

Ser Leu Asp Ser Met Ile Leu Thr Asn Glu Ile Lys Lys Val Ile Ile
                85                  90                  95

Asn Gly Asn Thr Leu Trp Ala Val Asp Val Val Asn Ile Ile Lys Ser
            100                 105                 110

Ile Glu Ala Leu Gly Lys Lys Thr Glu Ile Glu Leu Asn Phe Tyr Asp
            115                 120                 125

Asp Gly Ser Ala Glu Tyr Val Arg Leu Tyr Asp Phe Ser Arg Leu Pro
    130                 135                 140

Glu Ser Glu Gln Glu Tyr Lys Ile Ser Leu Ser Lys Asp Asn Ile Gln
145                 150                 155                 160

Ser Ser Ile Asn Gly Thr Gln Pro Phe Asp Asn Ser Ile Glu Asn Ile
                165                 170                 175

Tyr Gly Phe Ser Gln Leu Tyr Pro Thr Thr Tyr His Met Leu Arg Ala
            180                 185                 190

Asp Ile Phe Glu Thr Asn Leu Pro Leu Thr Ser Leu Lys Arg Val Ile
            195                 200                 205

Ser Asn Asn Ile Lys Gln Met Lys Trp Asp Tyr Phe Thr Thr Phe Asn
```

-continued

```
            210             215             220

Ser Gln Gln Lys Asn Lys Phe Tyr Asn Phe Thr Gly Phe Asn Pro Glu
225                 230                 235                 240

Lys Ile Lys Glu Gln Tyr Lys Ala Ser Pro His Glu Asn Phe Ile Phe
                245                 250                 255

Ile Gly Thr Asn Ser Gly Thr Ala Thr Ala Glu Gln Gln Ile Asp Ile
                260                 265                 270

Leu Thr Glu Ala Lys Lys Pro Asp Ser Pro Ile Ile Thr Asn Ser Ile
            275                 280                 285

Gln Gly Leu Asp Leu Phe Phe Lys Gly His Pro Ser Ala Thr Tyr Asn
        290                 295                 300

Gln Gln Ile Ile Asp Ala His Asn Met Ile Glu Ile Tyr Asn Lys Ile
305                 310                 315                 320

Pro Phe Glu Ala Leu Ile Met Thr Asp Ala Leu Pro Asp Ala Val Gly
                325                 330                 335

Gly Met Gly Ser Ser Val Phe Phe Ser Leu Pro Asn Thr Val Glu Asn
                340                 345                 350

Lys Phe Ile Phe Tyr Lys Ser Asp Thr Asp Ile Glu Asn Asn Ala Leu
            355                 360                 365

Ile Gln Val Met Ile Glu Leu Asn Ile Val Asn Arg Asn Asp Val Lys
        370                 375                 380

Leu Ile Ser Asp Leu Gln
385                 390

<210> SEQ ID NO 42
<211> LENGTH: 417
<212> TYPE: PRT
<213> ORGANISM: Avibacterium paragallinarum

<400> SEQUENCE: 42

Met Arg Lys Ile Ile Thr Phe Phe Ser Leu Phe Phe Ser Ile Ser Ala
1               5                   10                  15

Trp Cys Gln Lys Met Glu Ile Tyr Leu Asp Tyr Ala Ser Leu Pro Ser
                20                  25                  30

Leu Asn Met Ile Leu Asn Leu Val Glu Asn Lys Asn Asn Glu Lys Val
            35                  40                  45

Glu Arg Ile Ile Gly Phe Glu Arg Phe Asp Phe Asn Lys Glu Ile Leu
        50                  55                  60

Asn Ser Phe Ser Lys Glu Arg Ile Glu Phe Ser Lys Val Ser Ile Leu
65                  70                  75                  80

Asp Ile Lys Glu Phe Ser Asp Lys Leu Tyr Leu Asn Ile Glu Lys Ser
                85                  90                  95

Asp Thr Pro Val Asp Leu Ile Ile His Thr Asn Leu Asp His Ser Val
                100                 105                 110

Arg Ser Leu Leu Ser Ile Phe Lys Thr Leu Ser Pro Leu Phe His Lys
            115                 120                 125

Ile Asn Ile Glu Lys Leu Tyr Leu Tyr Asp Asp Gly Ser Gly Asn Tyr
        130                 135                 140

Val Asp Leu Tyr Gln His Arg Gln Glu Asn Ile Ser Ala Ile Leu Ile
145                 150                 155                 160

Glu Ala Gln Lys Lys Leu Lys Asp Ala Leu Glu Asn Arg Glu Thr Asp
                165                 170                 175

Thr Asp Lys Leu His Ser Leu Thr Arg Tyr Thr Trp His Lys Ile Phe
                180                 185                 190
```

-continued

```
Pro Thr Glu Tyr Ile Leu Leu Arg Pro Asp Tyr Leu Asp Ile Asp Glu
            195                 200             205

Lys Met Gln Pro Leu Lys His Phe Leu Ser Asp Thr Ile Val Ser Met
    210             215                 220

Asp Leu Ser Arg Phe Ser His Phe Ser Lys Asn Gln Lys Glu Leu Phe
225                 230             235                 240

Leu Lys Ile Thr His Phe Asp Gln Asn Ile Phe Asn Glu Leu Asn Ile
                245                 250                 255

Gly Thr Lys Asn Lys Glu Tyr Lys Thr Phe Ile Phe Thr Gly Thr Thr
            260                 265             270

Thr Trp Glu Lys Asp Lys Lys Lys Arg Leu Asn Asn Ala Lys Leu Gln
            275                 280             285

Thr Glu Ile Leu Glu Ser Phe Ile Lys Pro Asn Gly Lys Phe Tyr Leu
    290             295             300

Gly Asn Asp Ile Lys Ile Phe Phe Lys Gly His Pro Lys Gly Asp Asp
305             310             315                 320

Ile Asn Asp Tyr Ile Ile Arg Lys Thr Gly Ala Glu Lys Ile Pro Ala
                325             330                 335

Asn Ile Pro Phe Glu Val Leu Met Met Thr Asn Ser Leu Pro Asp Tyr
            340             345             350

Val Gly Gly Ile Met Ser Thr Val Tyr Phe Ser Leu Pro Pro Lys Asn
            355             360             365

Ile Asp Lys Val Val Phe Leu Gly Ser Glu Lys Ile Lys Asn Glu Asn
    370             375             380

Asp Ala Lys Ser Gln Thr Leu Ser Lys Leu Met Leu Met Leu Asn Val
385             390             395                 400

Ile Thr Pro Glu Gln Ile Phe Phe Glu Glu Met Pro Asn Pro Ile Asn
            405             410             415

Phe
```

```
<210> SEQ ID NO 43
<211> LENGTH: 430
<212> TYPE: PRT
<213> ORGANISM: Campylobacter jejuni

<400> SEQUENCE: 43
```

```
Met Thr Arg Thr Arg Met Glu Asn Glu Leu Ile Val Ser Lys Asn Met
1               5                   10                  15

Gln Asn Ile Ile Ile Ala Gly Asn Gly Pro Ser Leu Lys Asn Ile Asn
            20                  25                  30

Tyr Lys Arg Leu Pro Arg Glu Tyr Asp Val Phe Arg Cys Asn Gln Phe
            35                  40                  45

Tyr Phe Glu Asp Lys Tyr Tyr Leu Gly Lys Lys Ile Lys Ala Val Phe
    50                  55                  60

Phe Asn Pro Gly Val Phe Leu Gln Gln Tyr His Thr Ala Lys Gln Leu
65                  70                  75                  80

Ile Leu Lys Asn Glu Tyr Glu Ile Lys Asn Ile Phe Cys Ser Thr Phe
                85                  90                  95

Asn Leu Pro Phe Ile Glu Ser Asn Asp Phe Leu His Gln Phe Tyr Asn
            100                 105                 110

Phe Phe Pro Asp Ala Lys Leu Gly Tyr Glu Val Ile Glu Asn Leu Lys
            115                 120                 125

Glu Phe Tyr Ala Tyr Ile Lys Tyr Asn Glu Ile Tyr Phe Asn Lys Arg
    130                 135                 140
```

-continued

```
Ile Thr Ser Gly Val Tyr Met Cys Ala Ile Ala Ile Ala Leu Gly Tyr
145                 150                 155                 160

Lys Thr Ile Tyr Leu Cys Gly Ile Asp Phe Tyr Glu Gly Asp Val Ile
                165                 170                 175

Tyr Pro Phe Glu Ala Met Ser Thr Asn Ile Lys Thr Ile Phe Pro Gly
            180                 185                 190

Ile Lys Asp Phe Lys Pro Ser Asn Cys His Ser Lys Glu Tyr Asp Ile
        195                 200                 205

Glu Ala Leu Lys Leu Leu Lys Ser Ile Tyr Lys Val Asn Ile Tyr Ala
    210                 215                 220

Leu Cys Asp Asp Ser Ile Leu Ala Asn His Phe Pro Leu Ser Ile Asn
225                 230                 235                 240

Ile Asn Asn Asn Phe Thr Leu Glu Asn Lys His Asn Asn Ser Ile Asn
                245                 250                 255

Asp Ile Leu Leu Thr Asp Asn Thr Pro Gly Val Ser Phe Tyr Lys Asn
                260                 265                 270

Gln Leu Lys Ala Asp Asn Lys Ile Met Leu Asn Phe Tyr Asn Ile Leu
        275                 280                 285

His Ser Lys Asp Asn Leu Ile Lys Phe Leu Asn Lys Glu Ile Ala Val
    290                 295                 300

Leu Lys Lys Gln Thr Thr Gln Arg Ala Lys Ala Arg Ile Gln Asn His
305                 310                 315                 320

Leu Ser Tyr Lys Leu Gly Gln Ala Leu Ile Ile Asn Ser Lys Ser Val
                325                 330                 335

Leu Gly Phe Leu Ser Leu Pro Phe Ile Ile Leu Ser Ile Val Ile Ser
                340                 345                 350

His Lys Gln Glu Gln Lys Ala Tyr Lys Phe Lys Val Lys Lys Asn Pro
            355                 360                 365

Asn Leu Ala Leu Pro Pro Leu Glu Thr Tyr Pro Asp Tyr Asn Glu Ala
    370                 375                 380

Leu Lys Glu Lys Glu Cys Phe Thr Tyr Lys Leu Gly Glu Glu Phe Ile
385                 390                 395                 400

Lys Ala Gly Lys Asn Trp Tyr Gly Glu Gly Tyr Ile Lys Phe Ile Phe
                405                 410                 415

Lys Asp Val Pro Arg Leu Lys Arg Glu Phe Glu Lys Gly Glu
                420                 425                 430
```

```
<210> SEQ ID NO 44
<211> LENGTH: 395
<212> TYPE: PRT
<213> ORGANISM: Heliobacter acinonychis

<400> SEQUENCE: 44
```

```
Met Asn Lys Lys Pro Leu Ile Ile Ala Gly Asn Gly Pro Ser Ile Lys
1               5                   10                  15

Asp Leu Asp Tyr Ala Leu Phe Pro Lys Asp Phe Asp Val Phe Arg Cys
                20                  25                  30

Asn Gln Phe Tyr Phe Glu Asp Lys Tyr Tyr Leu Gly Arg Glu Ile Lys
            35                  40                  45

Gly Val Phe Phe Asn Ala His Val Phe Asp Leu Gln Met Lys Ile Thr
        50                  55                  60

Lys Ala Ile Val Lys Asn Gly Glu Tyr His Pro Asp His Ile Tyr Cys
65                  70                  75                  80

Thr His Val Glu Pro Tyr Gly Tyr Val Asn Gly Asn Gln Gln Leu Met
                85                  90                  95
```

-continued

```
Gln Glu Tyr Leu Glu Lys His Phe Val Gly Val Arg Ser Thr Tyr Ala
            100                 105                 110

Tyr Leu Lys Asp Leu Glu Pro Phe Phe Ile Leu His Ser Lys Tyr Arg
            115                 120                 125

Asn Phe Tyr Asp Gln His Phe Thr Thr Gly Ile Met Met Leu Leu Val
            130                 135                 140

Ala Ile Gln Leu Gly Tyr Lys Glu Ile Tyr Leu Cys Gly Ile Asp Phe
145                 150                 155                 160

Tyr Glu Asn Gly Phe Gly His Phe Tyr Glu Asn Gln Gly Gly Phe Phe
                165                 170                 175

Glu Glu Asp Ser Asp Pro Met His Asp Lys Asn Ile Asp Ile Gln Ala
                180                 185                 190

Leu Glu Leu Ala Lys Lys Tyr Ala Lys Ile Tyr Ala Leu Val Pro Asn
                195                 200                 205

Ser Ala Leu Val Lys Met Ile Pro Leu Ser Ser Gln Lys Gly Val Leu
            210                 215                 220

Glu Lys Val Lys Asp Arg Ile Gly Leu Gly Glu Phe Lys Arg Glu Lys
225                 230                 235                 240

Phe Gly Gln Lys Glu Leu Glu Arg Gln Lys Glu Leu Glu Arg Gln Lys
                245                 250                 255

Glu Leu Glu Arg Gln Lys Glu Leu Glu Arg Gln Lys Glu Leu Glu Arg
                260                 265                 270

Gln Lys Glu Leu Glu Arg Gln Lys Glu Leu Glu Arg Gln Lys Glu Leu
            275                 280                 285

Glu Arg Gln Lys Glu Leu Glu Arg Gln Lys Glu Leu Glu Arg Gln Lys
            290                 295                 300

Glu Leu Glu Arg Gln Lys Glu Leu Glu Arg Gln Lys Glu Leu Glu Arg
305                 310                 315                 320

Gln Lys Glu Leu Glu Arg Gln Lys Glu Leu Glu Arg Gln Lys Glu Leu
                325                 330                 335

Glu Leu Glu Arg Ser Leu Lys Ala Arg Leu Lys Ala Val Leu Ala Ser
            340                 345                 350

Lys Gly Ile Arg Gly Asp Asn Leu Ile Ile Val Ser Leu Lys Asp Thr
            355                 360                 365

Tyr Arg Leu Phe Lys Gly Gly Phe Ala Leu Leu Leu Asp Leu Lys Ala
            370                 375                 380

Leu Lys Ser Ile Ile Lys Ala Phe Leu Lys Arg
385                 390                 395

<210> SEQ ID NO 45
<211> LENGTH: 260
<212> TYPE: PRT
<213> ORGANISM: Campylobacter jejuni

<400> SEQUENCE: 45

Met Gly Lys Lys Val Ile Ile Ala Gly Asn Gly Pro Ser Leu Lys Glu
1               5                   10                  15

Ile Asp Tyr Ser Arg Leu Pro Asn Asp Phe Asp Val Phe Arg Cys Asn
                20                  25                  30

Gln Phe Tyr Phe Glu Asp Lys Tyr Tyr Leu Gly Lys Lys Cys Lys Ala
            35                  40                  45

Val Phe Tyr Asn Pro Ile Leu Phe Phe Glu Gln Tyr Tyr Thr Leu Lys
            50                  55                  60

His Leu Ile Gln Asn Gln Glu Tyr Glu Thr Glu Leu Ile Met Cys Ser
```

-continued

```
        65                    70                    75                    80
Asn Tyr Asn Gln Ala His Leu Glu Asn Glu Asn Phe Val Lys Thr Phe
                85                    90                    95
Tyr Asp Tyr Phe Pro Asp Ala His Leu Gly Tyr Asp Phe Phe Lys Gln
                100                   105                   110
Leu Lys Asp Phe Asn Ala Tyr Phe Lys Phe His Glu Ile Tyr Phe Asn
                115                   120                   125
Gln Arg Ile Thr Ser Gly Val Tyr Met Cys Ala Val Ala Ile Ala Leu
                130                   135                   140
Gly Tyr Lys Glu Ile Tyr Leu Ser Gly Ile Asp Phe Tyr Gln Asn Gly
145                   150                   155                   160
Ser Ser Tyr Ala Phe Asp Thr Lys Gln Lys Asn Leu Leu Lys Leu Ala
                165                   170                   175
Pro Asn Phe Lys Asn Asp Asn Ser His Tyr Ile Gly His Ser Lys Asn
                180                   185                   190
Thr Asp Ile Lys Ala Leu Glu Phe Leu Glu Lys Thr Tyr Lys Ile Lys
                195                   200                   205
Leu Tyr Cys Leu Cys Pro Asn Ser Leu Leu Ala Asn Phe Ile Glu Leu
                210                   215                   220
Ala Pro Asn Leu Asn Ser Asn Phe Ile Ile Gln Glu Lys Asn Asn Tyr
225                   230                   235                   240
Thr Lys Asp Ile Leu Ile Pro Ser Ser Glu Ala Tyr Gly Lys Phe Ser
                245                   250                   255
Lys Asn Ile Asn
                260

<210> SEQ ID NO 46
<211> LENGTH: 298
<212> TYPE: PRT
<213> ORGANISM: Streptococcus entericus

<400> SEQUENCE: 46

Met Lys Lys Val Tyr Phe Cys His Thr Val Tyr His Leu Leu Ile Thr
1               5                     10                    15
Leu Cys Lys Ile Ser Val Glu Glu Gln Val Glu Ile Ile Val Phe Asp
                20                    25                    30
Thr Val Ser Asn His Glu Leu Ile Val Gln Lys Ile Arg Asp Val Phe
                35                    40                    45
Val Asn Thr Thr Val Leu Phe Ala Glu Gln Asn Thr Asp Phe Ser Ile
        50                    55                    60
Leu Glu Ile Asp Arg Ala Thr Asp Ile Tyr Val Phe Asn Asp Trp Thr
65                    70                    75                    80
Pro Ile Gly Ala Tyr Leu Arg Lys Asn Lys Leu Phe Tyr His Leu Ile
                85                    90                    95
Glu Asp Gly Tyr Asn Tyr His Glu Tyr Asn Val Tyr Ala Asn Ala Leu
                100                   105                   110
Thr Met Lys Arg Arg Leu Leu Asn Phe Val Leu Arg Arg Glu Glu Pro
                115                   120                   125
Ser Gly Phe Ser Arg Tyr Val Arg Ser Ile Glu Val Asn Arg Val Lys
                130                   135                   140
Tyr Leu Pro Asn Asp Cys Arg Lys Ser Lys Trp Val Glu Lys Pro Arg
145                   150                   155                   160
Ser Ala Leu Phe Glu Asn Leu Val Pro Glu His Lys Gln Lys Ile Ile
                165                   170                   175
```

-continued

```
Thr Ile Phe Gly Leu Glu Asn Tyr Gln Asp Ser Leu Arg Gly Val Leu
            180                 185                 190

Val Leu Thr Gln Pro Leu Val Gln Asp Tyr Trp Asp Arg Asp Ile Thr
            195                 200                 205

Thr Glu Glu Glu Gln Leu Glu Phe Tyr Arg Gln Ile Val Glu Ser Tyr
        210                 215                 220

Gly Glu Gly Glu Gln Val Phe Phe Lys Ile His Pro Arg Asp Lys Val
225                 230                 235                 240

Asp Tyr Ser Ser Leu Thr Asn Val Ile Phe Leu Lys Lys Asn Val Pro
                245                 250                 255

Met Glu Val Tyr Glu Leu Ile Ala Asp Cys His Phe Thr Lys Gly Ile
            260                 265                 270

Thr His Ser Ser Thr Ala Leu Asp Phe Leu Ser Cys Val Asp Lys Lys
            275                 280                 285

Ile Thr Leu Lys Gln Met Lys Ala Asn Ser
    290                 295
```

```
<210> SEQ ID NO 47
<211> LENGTH: 295
<212> TYPE: PRT
<213> ORGANISM: Haemophilus ducreyi

<400> SEQUENCE: 47
```

```
Met Lys Glu Ile Ala Ile Ile Ser Asn Gln Arg Met Phe Phe Leu Tyr
1               5                   10                  15

Cys Leu Leu Thr Asn Lys Asn Val Glu Asp Val Phe Phe Ile Phe Glu
            20                  25                  30

Lys Gly Ala Met Pro Asn Asn Leu Thr Ser Ile Ser His Phe Ile Val
            35                  40                  45

Leu Asp His Ser Lys Ser Glu Cys Tyr Asp Phe Phe Tyr Phe Asn Phe
    50                  55                  60

Ile Ser Cys Lys Tyr Arg Leu Arg Gly Leu Asp Val Tyr Gly Ala Asp
65                  70                  75                  80

His Ile Lys Gly Ala Lys Phe Phe Leu Glu Arg His Arg Phe Phe Val
                85                  90                  95

Val Glu Asp Gly Met Met Asn Tyr Ser Lys Asn Met Tyr Ala Phe Ser
            100                 105                 110

Leu Phe Arg Thr Arg Asn Pro Val Ile Leu Pro Gly Gly Phe His Pro
            115                 120                 125

Asn Val Lys Thr Ile Phe Leu Thr Lys Asp Asn Pro Ile Pro Asp Gln
    130                 135                 140

Ile Ala His Lys Arg Glu Ile Ile Asn Ile Lys Thr Leu Trp Gln Ala
145                 150                 155                 160

Lys Thr Ala Thr Glu Lys Thr Lys Ile Leu Ser Phe Phe Glu Ile Asp
                165                 170                 175

Met Gln Glu Ile Ser Val Ile Lys Asn Arg Ser Phe Val Leu Tyr Thr
            180                 185                 190

Gln Pro Leu Ser Glu Asp Lys Leu Leu Thr Glu Ala Glu Lys Ile Asp
            195                 200                 205

Ile Tyr Arg Thr Ile Leu Thr Lys Tyr Asn His Ser Gln Thr Val Ile
        210                 215                 220

Lys Pro His Pro Arg Asp Lys Thr Asp Tyr Lys Gln Leu Phe Pro Asp
225                 230                 235                 240

Ala Tyr Val Met Lys Gly Thr Tyr Pro Ser Glu Leu Leu Thr Leu Leu
                245                 250                 255
```

-continued

```
Gly Val Asn Phe Asn Lys Val Ile Thr Leu Phe Ser Thr Ala Val Phe
            260                 265             270

Asp Tyr Pro Lys Glu Lys Ile Asp Phe Tyr Gly Thr Ala Val His Pro
            275                 280             285

Lys Leu Leu Asp Phe Phe Asp
            290             295

<210> SEQ ID NO 48
<211> LENGTH: 488
<212> TYPE: PRT
<213> ORGANISM: Alistipes sp.

<400> SEQUENCE: 48

Met Ala Leu Leu Ser Gly Thr Ala Ala Cys Ser Asp Asp Glu Val Ser
1               5                   10                  15

Gln Asn Leu Ile Val Ile Asn Gly Gly Glu His Phe Leu Ser Leu Asp
            20                  25                  30

Gly Leu Ala Arg Ala Gly Lys Ile Ser Val Leu Ala Pro Ala Pro Trp
            35                  40                  45

Arg Val Thr Lys Ala Ala Gly Asp Thr Trp Phe Arg Leu Ser Ala Thr
            50                  55                  60

Glu Gly Pro Ala Gly Tyr Ser Glu Val Glu Leu Ser Leu Asp Glu Asn
65                  70                  75                  80

Pro Gly Ala Ala Arg Ser Ala Gln Leu Ala Phe Ala Cys Gly Asp Ala
            85                  90                  95

Ile Val Pro Phe Arg Leu Ser Gln Gly Ala Leu Ser Ala Gly Tyr Asp
            100                 105                 110

Ser Pro Asp Tyr Tyr Phe Tyr Val Thr Phe Gly Thr Met Pro Thr Leu
            115                 120                 125

Tyr Ala Gly Ile His Leu Leu Ser His Asp Lys Pro Gly Tyr Val Phe
            130                 135                 140

Tyr Ser Arg Ser Lys Thr Phe Asp Pro Ala Glu Phe Pro Ala Arg Ala
145                 150                 155                 160

Glu Val Thr Thr Ala Ala Asp Arg Thr Ala Asp Ala Thr Gln Ala Glu
            165                 170                 175

Met Glu Ala Met Ala Arg Glu Met Lys Arg Arg Ile Leu Glu Ile Asn
            180                 185                 190

Ser Ala Asp Pro Thr Ala Val Phe Gly Leu Tyr Val Asp Asp Leu Arg
            195                 200                 205

Cys Arg Ile Gly Tyr Asp Trp Phe Val Ala Gln Gly Ile Asp Ser Ala
            210                 215                 220

Arg Val Lys Val Ser Met Leu Ser Asp Gly Thr Gly Thr Tyr Asn Asn
225                 230                 235                 240

Phe Tyr Asn Tyr Phe Gly Asp Ala Ala Thr Ala Glu Gln Asn Trp Glu
            245                 250                 255

Ser Tyr Ala Ser Glu Val Glu Ala Leu Asp Trp Asn His Gly Gly Arg
            260                 265                 270

Tyr Pro Glu Thr Arg Ser Leu Pro Glu Phe Glu Ser Tyr Thr Trp Pro
            275                 280                 285

Tyr Tyr Leu Ser Thr Arg Pro Asp Tyr Arg Leu Val Val Gln Asp Gly
            290                 295                 300

Ser Leu Leu Glu Ser Ser Cys Pro Phe Ile Thr Glu Lys Leu Gly Glu
305                 310                 315                 320

Met Glu Ile Glu Ser Ile Gln Pro Tyr Glu Met Leu Ser Ala Leu Pro
```

-continued

```
                325               330               335

Glu Ser Ser Arg Lys Arg Phe Tyr Asp Met Ala Gly Phe Asp Tyr Asp
            340               345               350

Lys Phe Ala Ala Leu Phe Asp Ala Ser Pro Lys Lys Asn Leu Ile Ile
            355               360               365

Ile Gly Thr Ser His Ala Asp Asp Ala Ser Ala Arg Leu Gln Arg Asp
            370               375               380

Tyr Val Ala Arg Ile Met Glu Gln Tyr Gly Ala Gln Tyr Asp Val Phe
385               390               395               400

Phe Lys Pro His Pro Ala Asp Thr Thr Ser Ala Gly Tyr Glu Thr Glu
            405               410               415

Phe Pro Gly Leu Thr Leu Leu Pro Gly Gln Met Pro Phe Glu Ile Phe
            420               425               430

Val Trp Ser Leu Ile Asp Arg Val Asp Met Ile Gly Gly Tyr Pro Ser
            435               440               445

Thr Val Phe Leu Thr Val Pro Val Asp Lys Val Arg Phe Ile Phe Ala
            450               455               460

Ala Asp Ala Ala Ser Leu Val Arg Pro Leu Asn Ile Leu Phe Arg Asp
465               470               475               480

Ala Thr Asp Val Glu Trp Met Gln
                485

<210> SEQ ID NO 49
<211> LENGTH: 291
<212> TYPE: PRT
<213> ORGANISM: Campylobacter jejuni

<400> SEQUENCE: 49

Met Lys Lys Val Ile Ile Ala Gly Asn Gly Pro Ser Leu Lys Glu Ile
1               5               10               15

Asp Tyr Ser Arg Leu Pro Asn Asp Phe Asp Val Phe Arg Cys Asn Gln
            20               25               30

Phe Tyr Phe Glu Asp Lys Tyr Tyr Leu Gly Lys Lys Cys Lys Ala Val
            35               40               45

Phe Tyr Thr Pro Asn Phe Phe Phe Glu Gln Tyr Tyr Thr Leu Lys His
            50               55               60

Leu Ile Gln Asn Gln Glu Tyr Glu Thr Glu Leu Ile Met Cys Ser Asn
65               70               75               80

Tyr Asn Gln Ala His Leu Glu Asn Glu Asn Phe Val Lys Thr Phe Tyr
            85               90               95

Asp Tyr Phe Pro Asp Ala His Leu Gly Tyr Asp Phe Phe Lys Gln Leu
            100               105               110

Lys Glu Phe Asn Ala Tyr Phe Lys Phe His Glu Ile Tyr Phe Asn Gln
            115               120               125

Arg Ile Thr Ser Gly Val Tyr Met Cys Ala Val Ala Ile Ala Leu Gly
            130               135               140

Tyr Lys Glu Ile Tyr Leu Ser Gly Ile Asp Phe Tyr Gln Asn Gly Ser
145               150               155               160

Ser Tyr Ala Phe Asp Thr Lys Gln Glu Asn Leu Leu Lys Leu Ala Pro
            165               170               175

Asp Phe Lys Asn Asp Arg Ser His Tyr Ile Gly His Ser Lys Asn Thr
            180               185               190

Asp Ile Lys Ala Leu Glu Phe Leu Glu Lys Thr Tyr Lys Ile Lys Leu
            195               200               205
```

-continued

```
Tyr Cys Leu Cys Pro Asn Ser Leu Leu Ala Asn Phe Ile Glu Leu Ala
    210                 215                 220
```

```
Pro Asn Leu Asn Ser Asn Phe Ile Ile Gln Glu Lys Asn Asn Tyr Thr
225                 230                 235                 240
```

```
Lys Asp Ile Leu Ile Pro Ser Ser Glu Ala Tyr Gly Lys Phe Ser Lys
                245                 250                 255
```

```
Asn Ile Asn Phe Lys Lys Ile Lys Ile Lys Glu Asn Val Tyr Tyr Lys
                260                 265                 270
```

```
Leu Ile Lys Asp Leu Leu Arg Leu Pro Ser Asp Ile Lys His Tyr Phe
                275                 280                 285
```

```
Lys Gly Lys
    290
```

```
<210> SEQ ID NO 50
<211> LENGTH: 312
<212> TYPE: PRT
<213> ORGANISM: Streptococcus agalactiae
```

```
<400> SEQUENCE: 50
```

```
Met Thr Asn Arg Lys Ile Tyr Val Cys His Thr Leu Tyr His Leu Leu
1               5                   10                  15
```

```
Ile Cys Leu Tyr Lys Glu Glu Ile Tyr Ser Asn Leu Glu Ile Ile Leu
                20                  25                  30
```

```
Ser Ser Ser Ile Pro Asp Val Asp Asn Leu Glu Lys Lys Leu Lys Ser
        35                  40                  45
```

```
Lys Thr Ile Asn Ile His Ile Leu Glu Glu Ser Ser Gly Glu Ser Glu
    50                  55                  60
```

```
Glu Leu Leu Ser Val Leu Lys Asp Ala Gly Leu Ser Tyr Ser Lys Phe
65                  70                  75                  80
```

```
Asp Ser Asn Cys Phe Ile Phe Asn Asp Ala Thr Pro Ile Gly Arg Thr
                85                  90                  95
```

```
Leu Ile Lys His Gly Ile Tyr Tyr Asn Leu Ile Glu Asp Gly Leu Asn
                100                 105                 110
```

```
Cys Phe Thr Tyr Ser Ile Phe Ser Gln Lys Leu Trp Lys Tyr Tyr Val
            115                 120                 125
```

```
Lys Lys Tyr Ile Leu His Lys Ile Gln Pro His Gly Phe Ser Arg Tyr
    130                 135                 140
```

```
Cys Leu Gly Ile Glu Val Asn Ser Leu Val Asn Leu Pro Lys Asp Pro
145                 150                 155                 160
```

```
Arg Tyr Lys Lys Phe Ile Glu Val Pro Arg Lys Glu Leu Phe Asp Asn
                165                 170                 175
```

```
Val Thr Glu Tyr Gln Lys Glu Met Ala Ile Asn Leu Phe Gly Ala Val
                180                 185                 190
```

```
Arg Val Ser Ile Lys Ser Pro Ser Val Leu Val Leu Thr Gln Pro Leu
            195                 200                 205
```

```
Ser Ile Asp Lys Glu Phe Met Ser Tyr Asn Asn Lys Ile Glu Thr Ser
    210                 215                 220
```

```
Glu Glu Gln Phe Asn Phe Tyr Lys Ser Ile Val Asn Glu Tyr Ile Asn
225                 230                 235                 240
```

```
Lys Gly Tyr Asn Val Tyr Leu Lys Val His Pro Arg Asp Val Val Asp
                245                 250                 255
```

```
Tyr Ser Lys Leu Pro Val Glu Leu Leu Pro Ser Asn Val Pro Met Glu
                260                 265                 270
```

```
Ile Ile Glu Leu Met Leu Thr Gly Arg Phe Glu Cys Gly Ile Thr His
                275                 280                 285
```

Ser Ser Thr Ala Leu Asp Phe Leu Thr Cys Val Asp Lys Lys Ile Thr
    290                 295                 300

Leu Val Asp Leu Lys Asp Ile Lys
305                 310

<210> SEQ ID NO 51
<211> LENGTH: 410
<212> TYPE: PRT
<213> ORGANISM: Bibersteinia trehalosi

<400> SEQUENCE: 51

Met Glu Phe Cys Lys Met Ala Thr Thr Gln Lys Ile Cys Val Tyr Leu
1               5                   10                  15

Asp Tyr Ala Thr Ile Pro Ser Leu Asn Tyr Ile Leu His Phe Ala Gln
            20                  25                  30

His Phe Glu Asp Gln Glu Thr Ile Arg Leu Phe Gly Leu Ser Arg Phe
        35                  40                  45

His Ile Pro Glu Ser Val Ile Gln Arg Tyr Pro Lys Gly Val Val Gln
    50                  55                  60

Phe Tyr Pro Asn Gln Glu Lys Asp Phe Ser Ala Leu Leu Leu Ala Leu
65                  70                  75                  80

Lys Asn Ile Leu Ile Glu Val Lys Gln Gln Gln Arg Lys Cys Glu Ile
                85                  90                  95

Glu Leu His Leu Asn Leu Phe His Tyr Gln Leu Leu Leu Pro Phe
            100                 105                 110

Leu Ser Leu Tyr Leu Asp Thr Gln Asp Tyr Cys His Leu Thr Leu Lys
        115                 120                 125

Phe Tyr Asp Asp Gly Ser Glu Ala Ile Ser Ala Leu Gln Glu Leu Ala
    130                 135                 140

Leu Ala Pro Asp Leu Ala Ala Gln Ile Gln Phe Glu Lys Gln Gln Phe
145                 150                 155                 160

Asp Glu Leu Val Val Lys Lys Ser Phe Lys Leu Ser Leu Leu Ser Arg
                165                 170                 175

Tyr Phe Trp Gly Lys Leu Phe Glu Ser Glu Tyr Ile Trp Phe Asn Gln
            180                 185                 190

Ala Ile Leu Gln Lys Ala Glu Leu Gln Ile Leu Lys Gln Glu Ile Ser
        195                 200                 205

Ser Ser Arg Gln Met Asp Phe Ala Ile Tyr Gln Gln Met Ser Asp Glu
    210                 215                 220

Gln Lys Gln Leu Val Leu Glu Ile Leu Asn Ile Asp Leu Asn Lys Val
225                 230                 235                 240

Ala Tyr Leu Lys Gln Leu Met Glu Asn Gln Pro Ser Phe Leu Phe Leu
                245                 250                 255

Gly Thr Thr Leu Phe Asn Ile Thr Gln Glu Thr Lys Thr Trp Leu Met
            260                 265                 270

Gln Met His Val Asp Leu Ile Gln Gln Tyr Cys Leu Pro Ser Gly Gln
        275                 280                 285

Phe Phe Asn Asn Lys Ala Gly Tyr Leu Cys Phe Tyr Lys Gly His Pro
    290                 295                 300

Asn Glu Lys Glu Met Asn Gln Met Ile Leu Ser Gln Phe Lys Asn Leu
305                 310                 315                 320

Ile Ala Leu Pro Asp Asp Ile Pro Leu Glu Ile Leu Leu Leu Leu Gly
                325                 330                 335

Val Ile Pro Ser Lys Val Gly Gly Phe Ala Ser Ser Ala Leu Phe Asn

-continued

```
              340                 345                 350

Phe Thr Pro Ala Gln Ile Glu Asn Ile Ile Phe Phe Thr Pro Arg Tyr
        355                 360                 365

Phe Glu Lys Asp Asn Arg Leu His Ala Thr Gln Tyr Arg Leu Met Gln
        370                 375                 380

Gly Leu Ile Glu Leu Gly Tyr Leu Asp Ala Glu Lys Ser Val Thr His
385                 390                 395                 400

Phe Glu Ile Met Gln Leu Leu Thr Lys Glu
                405                 410

<210> SEQ ID NO 52
<211> LENGTH: 406
<212> TYPE: PRT
<213> ORGANISM: Haemophilus parahaemolyticus

<400> SEQUENCE: 52

Met Thr Glu Gln Tyr Ile Lys Asn Val Glu Val Tyr Leu Asp Tyr Ala
1                   5                  10                  15

Thr Ile Pro Thr Leu Asn Tyr Phe Tyr His Phe Thr Glu Asn Lys Asp
                20                  25                  30

Asp Ile Ala Thr Ile Arg Leu Phe Gly Leu Gly Arg Phe Asn Ile Ser
        35                  40                  45

Lys Ser Ile Ile Glu Ser Tyr Pro Glu Gly Ile Ile Arg Tyr Cys Pro
    50                  55                  60

Ile Ile Phe Glu Asp Gln Thr Ala Phe Gln Gln Leu Phe Ile Thr Leu
65                  70                  75                  80

Leu Thr Glu Asp Ser Phe Cys Gln Tyr Arg Phe Asn Phe His Ile Asn
                85                  90                  95

Leu Phe His Ser Trp Lys Met Leu Ile Pro Leu Leu His Ile Ile Trp
                100                 105                 110

Gln Phe Lys His Lys Val Leu Asp Ile Lys Leu Asn Phe Tyr Asp Asp
            115                 120                 125

Gly Ser Glu Gly Leu Val Thr Leu Ser Lys Ile Glu Gln Asn Tyr Ser
            130                 135                 140

Ser Glu Ile Leu Gln Lys Ile Ile Asp Ile Asp Ser Gln Ser Phe Tyr
145                 150                 155                 160

Ala Asp Lys Leu Ser Phe Leu Asp Glu Asp Ile Ala Arg Tyr Leu Trp
                165                 170                 175

Asn Ser Leu Phe Glu Ser His Tyr Tyr Leu Leu Asn Asp Phe Leu Leu
                180                 185                 190

Lys Asn Glu Lys Leu Ser Leu Leu Lys Asn Ser Ile Lys Tyr Cys His
            195                 200                 205

Ile Met Asp Leu Glu Arg Tyr Leu Gln Phe Thr Gln Glu Glu Lys Asp
        210                 215                 220

Phe Phe Asn Glu Leu Leu Gly Ile Asn Ile Gln Ser Leu Glu Asp Lys
225                 230                 235                 240

Ile Lys Ile Phe Gln Gln Lys Lys Thr Phe Ile Phe Thr Gly Thr Thr
                245                 250                 255

Ile Phe Ser Leu Pro Lys Glu Glu Glu Glu Thr Leu Tyr Arg Leu His
                260                 265                 270

Leu Asn Ala Ile Leu Asn Tyr Ile His Pro Asn Gly Lys Tyr Phe Ile
        275                 280                 285

Gly Asp Gly Phe Thr Leu Val Ile Lys Gly His Pro His Gln Lys Glu
    290                 295                 300
```

-continued

```
Met Asn Ser Arg Leu Glu Lys Ser Phe Glu Lys Ala Val Met Leu Pro
305                 310                 315                 320

Asp Asn Ile Pro Phe Glu Ile Leu Tyr Leu Ile Gly Cys Lys Pro Asp
                325                 330                 335

Lys Ile Gly Gly Phe Val Ser Thr Ser Tyr Phe Ser Cys Asp Lys Lys
            340                 345                 350

Asn Ile Ala Asp Leu Leu Phe Ile Ser Ala Arg Gln Glu Glu Val Arg
        355                 360                 365

Lys Asn Asp Tyr Leu Phe Asn Ile Gln Tyr Gln Leu Arg Asp Met Met
    370                 375                 380

Ile Lys Thr Gly Phe Ile Gln Glu Glu Lys Thr His Phe Tyr Ser Asp
385                 390                 395                 400

Ile Pro Ile Phe Ile Ser
            405
```

```
<210> SEQ ID NO 53
<211> LENGTH: 300
<212> TYPE: PRT
<213> ORGANISM: Haemophilus somnus

<400> SEQUENCE: 53

Met Lys Tyr Asn Ile Lys Ile Lys Ala Ile Val Ile Val Ser Ser Leu
1               5                   10                  15

Arg Met Leu Leu Ile Phe Leu Met Leu Asn Lys Tyr His Leu Asp Glu
            20                  25                  30

Val Leu Phe Val Phe Asn Glu Gly Phe Glu Leu His Lys Lys Tyr Lys
        35                  40                  45

Ile Lys His Tyr Val Ala Ile Lys Lys Lys Ile Thr Lys Phe Trp Arg
    50                  55                  60

Leu Tyr Tyr Lys Leu Tyr Phe Tyr Arg Phe Lys Ile Asp Arg Ile Pro
65                  70                  75                  80

Val Tyr Gly Ala Asp His Leu Gly Trp Thr Asp Tyr Phe Leu Lys Tyr
            85                  90                  95

Phe Asp Phe Tyr Leu Ile Glu Asp Gly Ile Ala Asn Phe Ser Pro Lys
            100                 105                 110

Arg Tyr Glu Ile Asn Leu Thr Arg Asn Ile Pro Val Phe Gly Phe His
        115                 120                 125

Lys Thr Val Lys Lys Ile Tyr Leu Thr Ser Leu Glu Asn Val Pro Ser
    130                 135                 140

Asp Ile Arg His Lys Val Glu Leu Ile Ser Leu Glu His Leu Trp Lys
145                 150                 155                 160

Thr Arg Thr Ala Gln Glu Gln His Asn Ile Leu Asp Phe Phe Ala Phe
            165                 170                 175

Asn Leu Asp Ser Leu Ile Ser Leu Lys Met Lys Lys Tyr Ile Leu Phe
            180                 185                 190

Thr Gln Cys Leu Ser Glu Asp Arg Val Ile Ser Glu Gln Glu Lys Ile
        195                 200                 205

Ala Ile Tyr Gln His Ile Ile Lys Asn Tyr Asp Glu Arg Leu Leu Val
    210                 215                 220

Ile Lys Pro His Pro Arg Glu Thr Thr Asp Tyr Gln Lys Tyr Phe Glu
225                 230                 235                 240

Asn Val Phe Val Tyr Gln Asp Val Val Pro Ser Glu Leu Phe Glu Leu
            245                 250                 255

Leu Asp Val Asn Phe Glu Arg Val Ile Thr Leu Phe Ser Thr Ala Val
            260                 265                 270
```

```
Phe Lys Tyr Asp Arg Asn Ile Val Asp Phe Tyr Gly Thr Arg Ile His
        275                 280                 285

Asp Lys Ile Tyr Gln Trp Phe Gly Asp Ile Lys Phe
        290                 295                 300

<210> SEQ ID NO 54
<211> LENGTH: 381
<212> TYPE: PRT
<213> ORGANISM: Vibrio harveyi

<400> SEQUENCE: 54

Met Asp Ser Ser Pro Glu Asn Thr Ser Ser Thr Leu Glu Ile Tyr Ile
1               5                   10                  15

Asp Ser Ala Thr Leu Pro Ser Leu Gln His Met Val Lys Ile Ile Asp
            20                  25                  30

Glu Gln Ser Gly Asn Lys Lys Leu Ile Asn Trp Lys Arg Tyr Pro Ile
        35                  40                  45

Asp Asp Glu Leu Leu Leu Asp Lys Ile Asn Ala Leu Ser Phe Ser Asp
    50                  55                  60

Thr Thr Asp Leu Thr Arg Tyr Met Glu Ser Ile Leu Leu Ile Gly Asp
65              70                  75                  80

Ile Lys Arg Val Val Ile Asn Gly Asn Ser Leu Ser Asn Tyr Asn Ile
            85                  90                  95

Val Gly Val Met Arg Ser Ile Asn Ala Leu Gly Leu Asp Leu Asp Val
            100                 105                 110

Glu Ile Asn Phe Tyr Asp Asp Gly Ser Ala Glu Tyr Val Arg Leu Tyr
        115                 120                 125

Asn Phe Ser Gln Leu Pro Glu Ala Glu Arg Glu Leu Leu Val Ser Met
    130                 135                 140

Ser Lys Asn Asn Ile Leu Ala Ala Val Asn Gly Ile Gly Ser Tyr Asp
145                 150                 155                 160

Ser Gly Ser Pro Glu Asn Ile Tyr Gly Phe Ala Gln Ile Tyr Pro Ala
            165                 170                 175

Thr Tyr His Met Leu Arg Ala Asp Ile Phe Asp Thr Asp Leu Glu Ile
            180                 185                 190

Gly Leu Ile Arg Asp Ile Leu Gly Asp Asn Val Lys Gln Met Lys Trp
        195                 200                 205

Gly Gln Phe Leu Gly Phe Asn Glu Glu Gln Lys Glu Leu Phe Tyr Gln
    210                 215                 220

Leu Thr Ser Phe Asn Pro Asp Lys Ile Gln Ala Gln Tyr Lys Glu Ser
225                 230                 235                 240

Pro Asn Lys Asn Phe Val Phe Val Gly Thr Asn Ser Arg Ser Ala Thr
            245                 250                 255

Ala Glu Gln Gln Ile Asn Ile Ile Lys Glu Ala Lys Lys Leu Asp Ser
            260                 265                 270

Glu Ile Ile Pro Asn Ser Ile Asp Gly Tyr Asp Leu Phe Phe Lys Gly
        275                 280                 285

His Pro Ser Ala Thr Tyr Asn Gln Gln Ile Val Asp Ala His Asp Met
    290                 295                 300

Thr Glu Ile Tyr Asn Arg Thr Pro Phe Glu Val Leu Ala Met Thr Ser
305                 310                 315                 320

Ser Leu Pro Asp Ala Val Gly Gly Met Gly Ser Ser Leu Phe Phe Ser
            325                 330                 335

Leu Pro Lys Thr Val Glu Thr Lys Phe Ile Phe Tyr Lys Ser Gly Thr
```

-continued

```
                 340              345              350

Asp Ile Glu Ser Asn Ala Leu Ile Gln Val Met Leu Lys Leu Gly Ile
         355              360              365

Ile Thr Asp Glu Lys Val Arg Phe Thr Thr Asp Ile Lys
    370              375              380

<210> SEQ ID NO 55
<211> LENGTH: 483
<212> TYPE: PRT
<213> ORGANISM: Alistipes sp.

<400> SEQUENCE: 55

Met Ala Ser Cys Ser Asp Asp Asp Lys Glu Gln Thr Gly Phe Gln Ile
1               5               10              15

Asp Asp Gly Ser Gly Phe Leu Ser Leu Asp Ala Ala Ala Arg Ser Gly
            20              25              30

Ser Ile Ala Ile Thr Ala Asn Asn Ser Trp Ser Val Thr Gln Asp Lys
        35              40              45

Asp Ser Glu Trp Leu Thr Leu Ser Thr Thr Ser Gly Ala Ala Gly Arg
    50              55              60

Thr Glu Ile Gly Ile Met Leu Glu Ala Asn Pro Gly Glu Ala Arg Asn
65              70              75              80

Ala Gly Leu Thr Phe Asn Ser Gly Gly Arg Thr Tyr Pro Phe Val Ile
            85              90              95

Thr Gln Ser Ala His Val Thr Ala Asp Phe Asp Asp Ala Asp His Cys
        100             105             110

Phe Tyr Ile Thr Phe Gly Thr Leu Pro Thr Leu Tyr Ala Gly Leu His
    115             120             125

Val Leu Ser His Asp Lys Pro Ser Tyr Val Phe Phe Gln Arg Ser Gln
    130             135             140

Thr Phe Arg Pro Glu Glu Phe Pro Ala His Ala Glu Val Thr Ile Ala
145             150             155             160

Ala Asp Pro Ser Ala Asn Ala Thr Asp Glu Asp Met Glu Arg Met Arg
            165             170             175

Thr Ala Met Lys Gln Gln Ile Leu Lys Ile Asn Val Glu Asp Pro Thr
            180             185             190

Ala Val Phe Gly Leu Tyr Val Asp Asp Leu Arg Cys Gly Ile Gly Tyr
            195             200             205

Asp Trp Phe Val Ala Gln Gly Ile Asp Ser Thr Arg Val Lys Val Ser
    210             215             220

Met Leu Ser Asp Gly Thr Gly Thr Tyr Asn Asn Phe Tyr Asn Tyr Phe
225             230             235             240

Gly Asp Pro Ala Thr Ala Glu Gln Asn Trp Glu Asn Tyr Ala Ala Gln
            245             250             255

Val Glu Ala Leu Asp Trp Gln His Gly Gly Arg Phe Pro Glu Thr Arg
            260             265             270

Met Pro Asp Gly Phe Asp Phe Tyr Glu Trp Pro Tyr Tyr Leu Ala Thr
            275             280             285

Arg Pro Asn Tyr Arg Leu Val Leu Gln Asp Asp Asp Leu Leu Glu Ala
    290             295             300

Thr Ser Pro Phe Met Thr Glu Arg Leu Gln Gln Met Arg Thr Glu Ser
305             310             315             320

Lys Gln Pro Tyr Glu Leu Leu Ala Ser Leu Pro Ala Glu Ala Arg Gln
            325             330             335
```

-continued

Arg Phe Phe Arg Met Ala Gly Phe Asp Tyr Asp Ala Phe Ala Ala Leu
            340                 345                 350

Phe Asp Ala Ser Pro Lys Lys Asn Leu Val Ile Ile Gly Thr Ser His
        355                 360                 365

Thr Ser Glu Glu Ser Glu Ala Gln Gln Ala Ala Tyr Val Glu Arg Ile
    370                 375                 380

Ile Gly Asp Tyr Gly Thr Ala Tyr Asp Ile Phe Phe Lys Pro His Pro
385                 390                 395                 400

Ala Asp Ser Ser Ser Ser Asn Tyr Glu Glu Arg Phe Glu Gly Leu Thr
                405                 410                 415

Leu Leu Pro Gly Gln Met Pro Phe Glu Ile Phe Val Trp Ser Leu Leu
            420                 425                 430

Asp Lys Val Asp Leu Ile Gly Gly Tyr Ser Ser Thr Val Phe Leu Thr
        435                 440                 445

Val Pro Val Glu Lys Thr Gly Phe Ile Phe Ala Ala Asn Ala Glu Ser
    450                 455                 460

Leu Pro Arg Pro Leu Asn Val Leu Phe Arg Asn Ala Glu His Val Arg
465                 470                 475                 480

Trp Ile Gln

<210> SEQ ID NO 56
<211> LENGTH: 483
<212> TYPE: PRT
<213> ORGANISM: Alistipes shahii

<400> SEQUENCE: 56

Met Asp Asp Gly Thr Pro Ser Val Ser Ile Asn Gly Gly Thr Asp Phe
1               5                   10                  15

Leu Ser Leu Asp His Leu Ala Arg Ser Gly Lys Ile Thr Val Asn Ala
            20                  25                  30

Pro Ala Pro Trp Ser Val Thr Leu Ala Pro Glu Asn Tyr Gly Gln Asp
        35                  40                  45

Glu Lys Pro Asp Trp Leu Thr Leu Ser Ala Glu Glu Gly Pro Ala Gly
    50                  55                  60

Tyr Ser Glu Ile Asp Val Thr Phe Ala Glu Asn Pro Gly Pro Ala Arg
65                  70                  75                  80

Ser Ala Ser Leu Leu Phe Ser Cys Asp Gly Lys Thr Leu Ala Phe Thr
                85                  90                  95

Val Ser Gln Ser Ala Gly Gly Thr Gly Phe Asp Ala Pro Asp Tyr Tyr
            100                 105                 110

Phe Tyr Ile Ser Val Gly Thr Met Pro Thr Leu Tyr Ser Gly Leu His
        115                 120                 125

Leu Leu Ser His Asp Lys Pro Ser Tyr Val Ser Tyr Glu Arg Ala Ser
    130                 135                 140

Thr Phe Asp Ala Ala Glu Phe Pro Asp Arg Ala Phe Val Tyr Pro Val
145                 150                 155                 160

Ala Asp Pro Thr Gly His Ala Thr Asn Glu Glu Leu Arg Ala Met Ser
                165                 170                 175

Glu Ala Met Lys Arg Arg Ile Leu Glu Ile Asn Ala Glu Asp Pro Thr
            180                 185                 190

Ala Val Phe Gly Leu Trp Val Asp Asp Leu Arg Cys Arg Leu Gly Tyr
        195                 200                 205

Asp Trp Phe Val Ala Gln Gly Ile Asp Ser Ala Arg Val Lys Val Thr
    210                 215                 220

-continued

```
Met Leu Ser Asp Gly Thr Ala Thr Tyr Asn Asn Phe His Asn Tyr Phe
225                 230                 235                 240

Gly Asp Ala Ala Thr Ala Glu Gln Asn Trp Asn Asp Tyr Ala Ala Glu
                245                 250                 255

Val Glu Ala Leu Asp Trp Asn His Gly Gly Arg Tyr Pro Glu Thr Arg
                260                 265                 270

Ala Pro Glu Glu Phe Ala Ser Tyr Thr Trp Pro Tyr Tyr Leu Ser Thr
                275                 280                 285

Arg Pro Asp Tyr Arg Leu Met Leu Gln Asn Ser Ser Leu Met Glu Ser
                290                 295                 300

Ser Cys Pro Phe Ile Ala Asp Arg Leu Ala Ala Met Lys Met Glu Ser
305                 310                 315                 320

Val Gln Pro Tyr Glu Leu Leu Thr Ala Leu Pro Glu Ala Ser Lys Gln
                325                 330                 335

Gln Phe Tyr Arg Met Ala Lys Phe Asp Tyr Ala Arg Phe Ala Gly Leu
                340                 345                 350

Phe Asp Leu Ser Pro Lys Lys Asn Leu Ile Ile Ile Gly Thr Ser His
                355                 360                 365

Ser Ser Ala Ala Ser Glu Gln Gln Gln Ala Ala Tyr Val Glu Arg Ile
                370                 375                 380

Ile Gln Gln Tyr Gly Ser Asp Tyr Asp Ile Phe Phe Lys Pro His Pro
385                 390                 395                 400

Ala Asp Ser Ser Ser Ala Gly Tyr Pro Asp Arg Phe Glu Gly Leu Thr
                405                 410                 415

Leu Leu Pro Gly Gln Met Pro Phe Glu Ile Phe Val Trp Ala Leu Leu
                420                 425                 430

Asp Lys Ile Asp Met Ile Gly Gly Tyr Pro Ser Thr Thr Phe Ile Ser
                435                 440                 445

Val Pro Leu Asp Lys Val Gly Phe Leu Phe Ala Ala Asp Ala Asp Gly
                450                 455                 460

Leu Val Arg Pro Leu Asn Ile Leu Phe Arg Asp Ala Ala Asn Val Glu
465                 470                 475                 480

Trp Ile Gln
```

```
<210> SEQ ID NO 57
<211> LENGTH: 401
<212> TYPE: PRT
<213> ORGANISM: Actinobacillus suis

<400> SEQUENCE: 57
```

```
Met Glu Arg Thr Pro Gln Leu Gln Ala Val Asp Ile Tyr Ile Asp Phe
1               5                   10                  15

Ala Thr Ile Pro Ser Leu Ser Tyr Phe Leu His Phe Leu Lys His Lys
                20                  25                  30

His Asp Asp Gln Arg Leu Arg Leu Phe Ser Leu Ala Arg Phe Glu Met
                35                  40                  45

Pro Gln Thr Leu Ile Glu Gln Tyr Glu Gly Ile Ile Gln Phe Ser Arg
                50                  55                  60

Asn Val Glu His Asn Val Glu Pro Leu Leu Glu Gln Leu Gln Thr Ile
65                  70                  75                  80

Leu Ser Gln Glu Gly Lys Gln Phe Glu Leu His Leu His Leu Asn Leu
                85                  90                  95

Phe His Ser Phe Glu Met Phe Leu Asn Leu Ser Pro Thr Tyr Thr Gln
                100                 105                 110
```

-continued

```
Tyr Lys Glu Lys Ile Ser Lys Ile Val Leu His Leu Tyr Asp Asp Gly
        115                 120                 125

Ser Glu Gly Val Met Lys Gln Tyr Gln Leu Gln Lys Ser Ser Ser Leu
        130                 135                 140

Val Gln Asp Leu Ala Ala Thr Lys Ala Ser Leu Val Ser Leu Phe Glu
145                 150                 155                 160

Asn Gly Glu Gly Ser Phe Ser Gln Ile Asp Leu Ile Arg Tyr Val Trp
                165                 170                 175

Asn Ala Val Leu Glu Thr His Tyr Tyr Leu Leu Ser Asp His Phe Leu
                180                 185                 190

Leu Asp Glu Lys Leu Gln Pro Leu Lys Ala Glu Leu Gly His Tyr Gln
                195                 200                 205

Leu Leu Asn Leu Ser Ala Tyr Gln Tyr Leu Ser Ser Glu Asp Leu Leu
        210                 215                 220

Trp Leu Lys Gln Ile Leu Lys Ile Asp Thr Glu Leu Glu Ser Leu Met
225                 230                 235                 240

Gln Lys Leu Thr Ala Gln Pro Val Tyr Phe Phe Ser Gly Thr Thr Phe
                245                 250                 255

Phe Asn Ile Ser Phe Glu Asp Lys Gln Arg Leu Ala Asn Ile His Ala
                260                 265                 270

Ile Leu Ile Arg Glu His Leu Asp Pro Asn Ser Gln Leu Phe Ile Gly
        275                 280                 285

Glu Pro Tyr Leu Phe Val Phe Lys Gly His Pro Asn Ser Pro Glu Ile
        290                 295                 300

Asn Gln Ala Leu Arg Glu Tyr Tyr Pro Asn Val Ile Phe Leu Pro Glu
305                 310                 315                 320

Asn Ile Pro Phe Glu Ile Leu Thr Leu Leu Gly Phe Ser Pro Gln Lys
                325                 330                 335

Ile Gly Gly Phe Ala Ser Thr Ile His Val Asn Ser Glu Gln Ser Lys
                340                 345                 350

Leu Ala Lys Leu Phe Phe Leu Thr Ser Thr Asp Glu Gln Glu Arg Gln
        355                 360                 365

Leu Ser Asp Gly Tyr Ile Lys Gln Tyr Ala Leu Ala Gln Ala Met Leu
        370                 375                 380

Glu Met Gln Leu Val Ser Gln Glu Gln Val Tyr Tyr Cys Ser Leu Ser
385                 390                 395                 400

Ser
```

```
<210> SEQ ID NO 58
<211> LENGTH: 401
<212> TYPE: PRT
<213> ORGANISM: Actinobacillus capsulatus

<400> SEQUENCE: 58

Met Glu Arg Ile Pro Gln Leu Gln Ala Val Asp Ile Tyr Ile Asp Phe
1               5                   10                  15

Ala Thr Ile Pro Ser Leu Ser Tyr Phe Leu His Phe Leu Lys His Lys
                20                  25                  30

His Asp His Gln Arg Leu Arg Leu Phe Ser Leu Ala Arg Phe Glu Met
        35                  40                  45

Pro Gln Thr Val Ile Glu Gln Tyr Glu Gly Ile Ile Gln Phe Ser Arg
        50                  55                  60

Asn Val Glu His Asn Val Glu Gln Leu Leu Glu Gln Leu Gln Thr Ile
65                  70                  75                  80
```

-continued

```
Leu Ser Gln Glu Gly Lys Gln Phe Glu Leu His Leu His Leu Asn Leu
              85              90              95

Phe His Ser Phe Glu Met Phe Leu Asn Leu Ser Pro Thr Tyr Thr Lys
              100             105             110

Tyr Lys Glu Lys Ile Ser Lys Ile Val Leu His Leu Tyr Asp Asp Gly
              115             120             125

Ser Glu Gly Val Met Lys Gln Tyr Gln Leu Gln Gln Ser Asn Ser Leu
    130             135             140

Ala Gln Asp Leu Ala Ser Thr Lys Ala Ser Leu Val Ser Leu Phe Lys
145             150             155             160

Asn Gly Glu Gly Ala Phe Ser Gln Ile Asp Leu Ile Arg Tyr Val Trp
              165             170             175

Asn Ala Val Leu Glu Thr His Tyr Tyr Leu Leu Ser Asp His Phe Leu
              180             185             190

Ala His Glu Lys Leu Gln Pro Leu Lys Ile Glu Leu Gly His Tyr Gln
              195             200             205

Leu Leu Asn Leu Ser Ala Tyr Gln Tyr Leu Ser Ser Glu Asp Leu Leu
    210             215             220

Trp Leu Lys Gln Ile Leu Lys Ile Asp Ala Glu Leu Glu Ser Leu Met
225             230             235             240

His Lys Leu Thr Thr Gln Pro Val Tyr Phe Phe Ser Gly Thr Thr Phe
              245             250             255

Phe Asn Ile Ser Phe Glu Asp Lys Gln Arg Leu Ala Asn Ile His Ala
              260             265             270

Ile Leu Ile Arg Glu His Leu Asp Pro Asn Ser Gln Leu Phe Ile Gly
              275             280             285

Glu Pro Tyr Leu Phe Val Phe Lys Gly His Pro Asn Ser Pro Glu Ile
    290             295             300

Asn Gln Ala Leu Arg Glu Tyr Tyr Pro Asn Ala Ile Phe Leu Pro Glu
305             310             315             320

Asn Ile Pro Phe Glu Ile Leu Thr Leu Leu Gly Phe Ser Pro Gln Lys
              325             330             335

Ile Gly Gly Phe Ala Ser Thr Ile His Val Asn Ser Glu Gln Ser Lys
              340             345             350

Leu Ala Lys Leu Phe Phe Leu Thr Ser Thr Asp Glu Gln Glu Arg Asn
              355             360             365

Arg Ser Asp Gly Tyr Ile Lys Gln Tyr Ala Leu Ala Gln Ala Met Leu
    370             375             380

Glu Met Gln Leu Val Ser Gln Glu Gln Val Tyr Tyr Cys Ser Leu Ser
385             390             395             400

Ser
```

<210> SEQ ID NO 59
<211> LENGTH: 311
<212> TYPE: PRT
<213> ORGANISM: Haemophilus somnus

<400> SEQUENCE: 59

```
Met Phe Arg Glu Asp Asn Met Asn Leu Ile Ile Cys Cys Thr Pro Leu
1               5               10              15

Gln Val Ile Ile Ala Glu Lys Ile Ile Glu Arg Tyr Pro Glu Gln Lys
              20              25              30

Phe Tyr Gly Val Met Leu Glu Ser Phe Tyr Asn Asp Lys Phe Asp Phe
              35              40              45
```

-continued

```
Tyr Glu Asn Lys Leu Lys His Leu Cys His Glu Phe Phe Cys Ile Lys
    50                  55                  60

Ile Ala Arg Phe Lys Leu Glu Arg Tyr Lys Asn Leu Leu Ser Leu Leu
65                  70                  75                  80

Lys Ile Lys Asn Lys Thr Phe Asp Arg Val Phe Leu Ala Asn Ile Glu
                85                  90                  95

Lys Arg Tyr Ile His Ile Ile Leu Ser Asn Ile Phe Phe Lys Glu Leu
                100                 105                 110

Tyr Thr Phe Asp Asp Gly Thr Ala Asn Ile Ala Pro Asn Ser His Leu
                115                 120                 125

Tyr Gln Glu Tyr Asp His Ser Leu Lys Lys Arg Ile Thr Asp Ile Leu
    130                 135                 140

Leu Pro Asn His Tyr Asn Ser Asn Lys Val Lys Asn Ile Ser Lys Leu
145                 150                 155                 160

His Tyr Ser Ile Tyr Arg Cys Lys Asn Asn Ile Ile Asp Asn Ile Glu
                165                 170                 175

Tyr Met Pro Leu Phe Asn Leu Glu Lys Lys Tyr Thr Ala Gln Asp Lys
                180                 185                 190

Ser Ile Ser Ile Leu Leu Gly Gln Pro Ile Phe Tyr Asp Glu Glu Lys
                195                 200                 205

Asn Ile Arg Leu Ile Lys Glu Val Ile Ala Lys Phe Lys Ile Asp Tyr
    210                 215                 220

Tyr Phe Pro His Pro Arg Glu Asp Tyr Tyr Ile Asp Asn Val Ser Tyr
225                 230                 235                 240

Ile Lys Thr Pro Leu Ile Phe Glu Glu Phe Tyr Ala Glu Arg Ser Ile
                245                 250                 255

Glu Asn Ser Ile Lys Ile Tyr Thr Phe Phe Ser Ser Ala Val Leu Asn
                260                 265                 270

Ile Val Thr Lys Glu Asn Ile Asp Arg Ile Tyr Ala Leu Lys Pro Lys
                275                 280                 285

Leu Thr Glu Lys Ala Tyr Leu Asp Cys Tyr Asp Ile Leu Lys Asp Phe
    290                 295                 300

Gly Ile Lys Val Ile Asp Ile
305                 310
```

<210> SEQ ID NO 60
<211> LENGTH: 399
<212> TYPE: PRT
<213> ORGANISM: Haemophilus ducreyi

<400> SEQUENCE: 60

```
Met Leu Ile Gln Gln Asn Leu Glu Ile Tyr Leu Asp Tyr Ala Thr Ile
1               5                   10                  15

Pro Ser Leu Ala Cys Phe Met His Phe Ile Gln His Lys Asp Asp Val
                20                  25                  30

Asp Ser Ile Arg Leu Phe Gly Leu Ala Arg Phe Asp Ile Pro Gln Ser
            35                  40                  45

Ile Ile Asp Arg Tyr Pro Ala Asn His Leu Phe Tyr His Asn Ile Asp
    50                  55                  60

Asn Arg Asp Leu Thr Ala Val Leu Asn Gln Leu Ala Asp Ile Leu Ala
65                  70                  75                  80

Gln Glu Asn Lys Arg Phe Gln Ile Asn Leu His Leu Asn Leu Phe His
                85                  90                  95

Ser Ile Asp Leu Phe Phe Ala Ile Tyr Pro Ile Tyr Gln Gln Tyr Gln
                100                 105                 110
```

-continued

```
His Lys Ile Ser Thr Ile Gln Leu Gln Leu Tyr Asp Asp Gly Ser Glu
        115                 120                 125

Gly Ile Val Thr Gln His Ser Leu Cys Lys Ile Ala Asp Leu Glu Gln
        130                 135                 140

Leu Ile Leu Gln His Lys Asn Val Leu Leu Glu Leu Leu Thr Lys Gly
145                 150                 155                 160

Thr Ala Asn Val Pro Asn Pro Thr Leu Leu Arg Tyr Leu Trp Asn Asn
                165                 170                 175

Ile Ile Asp Ser Gln Phe His Leu Ile Ser Asp His Phe Leu Gln His
                180                 185                 190

Pro Lys Leu Gln Pro Leu Lys Arg Leu Leu Lys Arg Tyr Thr Ile Leu
                195                 200                 205

Asp Phe Thr Cys Tyr Pro Arg Phe Asn Ala Glu Gln Lys Gln Leu Leu
        210                 215                 220

Lys Glu Ile Leu His Ile Ser Asn Glu Leu Glu Asn Leu Leu Lys Leu
225                 230                 235                 240

Leu Lys Gln His Asn Thr Phe Leu Phe Thr Gly Thr Thr Ala Phe Asn
                245                 250                 255

Leu Asp Gln Glu Lys Leu Asp Leu Leu Thr Gln Leu His Ile Leu Leu
                260                 265                 270

Leu Asn Glu His Gln Asn Pro His Ser Thr His Tyr Ile Gly Asn Asn
                275                 280                 285

Tyr Leu Leu Leu Ile Lys Gly His Ala Asn Ser Pro Ala Leu Asn His
        290                 295                 300

Thr Leu Ala Leu His Phe Pro Asp Ala Ile Phe Leu Pro Ala Asn Ile
305                 310                 315                 320

Pro Phe Glu Ile Phe Ala Met Leu Gly Phe Thr Pro Asn Lys Met Gly
                325                 330                 335

Gly Phe Ala Ser Thr Ser Tyr Ile Asn Tyr Pro Thr Glu Asn Ile Asn
                340                 345                 350

His Leu Phe Phe Leu Thr Ser Asp Gln Pro Ser Ile Arg Thr Lys Trp
                355                 360                 365

Leu Asp Tyr Glu Lys Gln Phe Gly Leu Met Tyr Ser Leu Leu Ala Met
        370                 375                 380

Gln Lys Ile Asn Glu Asp Gln Ala Phe Met Cys Thr Ile His Asn
385                 390                 395

<210> SEQ ID NO 61
<211> LENGTH: 497
<212> TYPE: PRT
<213> ORGANISM: Photobacterium leiognathi

<400> SEQUENCE: 61

Met Cys Asn Asp Asn Gln Asn Thr Val Asp Val Val Val Ser Thr Val
1               5                   10                  15

Asn Asp Asn Val Ile Glu Asn Asn Thr Tyr Gln Val Lys Pro Ile Asp
                20                  25                  30

Thr Pro Thr Thr Phe Asp Ser Tyr Ser Trp Ile Gln Thr Cys Gly Thr
        35                  40                  45

Pro Ile Leu Lys Asp Asp Glu Lys Tyr Ser Leu Ser Phe Asp Phe Val
        50                  55                  60

Ala Pro Glu Leu Asp Gln Asp Glu Lys Phe Cys Phe Glu Phe Thr Gly
65                  70                  75                  80

Asp Val Asp Gly Lys Arg Tyr Val Thr Gln Thr Asn Leu Thr Val Val
```

-continued

```
                    85                  90                  95
Ala Pro Thr Leu Glu Val Tyr Val Asp His Ala Ser Leu Pro Ser Leu
            100                 105                 110

Gln Gln Leu Met Lys Ile Ile Gln Gln Lys Asn Glu Tyr Ser Gln Asn
            115                 120                 125

Glu Arg Phe Ile Ser Trp Gly Arg Ile Gly Leu Thr Glu Asp Asn Ala
            130                 135                 140

Glu Lys Leu Asn Ala His Ile Tyr Pro Leu Ala Gly Asn Asn Thr Ser
145                 150                 155                 160

Gln Glu Leu Val Asp Ala Val Ile Asp Tyr Ala Asp Ser Lys Asn Arg
                    165                 170                 175

Leu Asn Leu Glu Leu Asn Thr Asn Thr Ala His Ser Phe Pro Asn Leu
                    180                 185                 190

Ala Pro Ile Leu Arg Ile Ile Ser Ser Lys Ser Asn Ile Leu Ile Ser
                    195                 200                 205

Asn Ile Asn Leu Tyr Asp Asp Gly Ser Ala Glu Tyr Val Asn Leu Tyr
            210                 215                 220

Asn Trp Lys Asp Thr Glu Asp Lys Ser Val Lys Leu Ser Asp Ser Phe
225                 230                 235                 240

Leu Val Leu Lys Asp Tyr Phe Asn Gly Ile Ser Ser Glu Lys Pro Ser
                    245                 250                 255

Gly Ile Tyr Gly Arg Tyr Asn Trp His Gln Leu Tyr Asn Thr Ser Tyr
                    260                 265                 270

Tyr Phe Leu Arg Lys Asp Tyr Leu Thr Val Glu Pro Gln Leu His Asp
                    275                 280                 285

Leu Arg Glu Tyr Leu Gly Gly Ser Leu Lys Gln Met Ser Trp Asp Gly
            290                 295                 300

Phe Ser Gln Leu Ser Lys Gly Asp Lys Glu Leu Phe Leu Asn Ile Val
305                 310                 315                 320

Gly Phe Asp Gln Glu Lys Leu Gln Gln Glu Tyr Gln Gln Ser Glu Leu
                    325                 330                 335

Pro Asn Phe Val Phe Thr Gly Thr Thr Thr Trp Ala Gly Gly Glu Thr
            340                 345                 350

Lys Glu Tyr Tyr Ala Gln Gln Gln Val Asn Val Val Asn Asn Ala Ile
            355                 360                 365

Asn Glu Thr Ser Pro Tyr Tyr Leu Gly Arg Glu His Asp Leu Phe Phe
            370                 375                 380

Lys Gly His Pro Arg Gly Gly Ile Ile Asn Asp Ile Ile Leu Gly Ser
385                 390                 395                 400

Phe Asn Asn Met Ile Asp Ile Pro Ala Lys Val Ser Phe Glu Val Leu
                    405                 410                 415

Met Met Thr Gly Met Leu Pro Asp Thr Val Gly Gly Ile Ala Ser Ser
            420                 425                 430

Leu Tyr Phe Ser Ile Pro Ala Glu Lys Val Ser Phe Ile Val Phe Thr
            435                 440                 445

Ser Ser Asp Thr Ile Thr Asp Arg Glu Asp Ala Leu Lys Ser Pro Leu
            450                 455                 460

Val Gln Val Met Met Thr Leu Gly Ile Val Lys Glu Lys Asp Val Leu
465                 470                 475                 480

Phe Trp Ser Asp Leu Pro Asp Cys Ser Ser Gly Val Cys Ile Ala Gln
                    485                 490                 495

Tyr
```

```
<210> SEQ ID NO 62
<211> LENGTH: 498
<212> TYPE: PRT
<213> ORGANISM: Photobacterium sp.

<400> SEQUENCE: 62

Met Ser Glu Glu Asn Thr Gln Ser Ile Ile Lys Asn Asp Ile Asn Lys
1               5                   10                  15

Thr Ile Ile Asp Glu Glu Tyr Val Asn Leu Glu Pro Ile Asn Gln Ser
            20                  25                  30

Asn Ile Ser Phe Thr Lys His Ser Trp Val Gln Thr Cys Gly Thr Gln
        35                  40                  45

Gln Leu Leu Thr Glu Gln Asn Lys Glu Ser Ile Ser Leu Ser Val Val
    50                  55                  60

Ala Pro Arg Leu Asp Asp Asp Glu Lys Tyr Cys Phe Asp Phe Asn Gly
65                  70                  75                  80

Val Ser Asn Lys Gly Glu Lys Tyr Ile Thr Lys Val Thr Leu Asn Val
                85                  90                  95

Val Ala Pro Ser Leu Glu Val Tyr Val Asp His Ala Ser Leu Pro Thr
            100                 105                 110

Leu Gln Gln Leu Met Asp Ile Ile Lys Ser Glu Glu Glu Asn Pro Thr
        115                 120                 125

Ala Gln Arg Tyr Ile Ala Trp Gly Arg Ile Val Pro Thr Asp Glu Gln
    130                 135                 140

Met Lys Glu Leu Asn Ile Thr Ser Phe Ala Leu Ile Asn Asn His Thr
145                 150                 155                 160

Pro Ala Asp Leu Val Gln Glu Ile Val Lys Gln Ala Gln Thr Lys His
            165                 170                 175

Arg Leu Asn Val Lys Leu Ser Ser Asn Thr Ala His Ser Phe Asp Asn
            180                 185                 190

Leu Val Pro Ile Leu Lys Glu Leu Asn Ser Phe Asn Asn Val Thr Val
            195                 200                 205

Thr Asn Ile Asp Leu Tyr Asp Asp Gly Ser Ala Glu Tyr Val Asn Leu
    210                 215                 220

Tyr Asn Trp Arg Asp Thr Leu Asn Lys Thr Asp Asn Leu Lys Ile Gly
225                 230                 235                 240

Lys Asp Tyr Leu Glu Asp Val Ile Asn Gly Ile Asn Glu Asp Thr Ser
            245                 250                 255

Asn Thr Gly Thr Ser Ser Val Tyr Asn Trp Gln Lys Leu Tyr Pro Ala
            260                 265                 270

Asn Tyr His Phe Leu Arg Lys Asp Tyr Leu Thr Leu Glu Pro Ser Leu
        275                 280                 285

His Glu Leu Arg Asp Tyr Ile Gly Asp Ser Leu Lys Gln Met Gln Trp
    290                 295                 300

Asp Gly Phe Lys Lys Phe Asn Ser Lys Gln Gln Glu Leu Phe Leu Ser
305                 310                 315                 320

Ile Val Asn Phe Asp Lys Gln Lys Leu Gln Asn Glu Tyr Asn Ser Ser
            325                 330                 335

Asn Leu Pro Asn Phe Val Phe Thr Gly Thr Thr Val Trp Ala Gly Asn
            340                 345                 350

His Glu Arg Glu Tyr Tyr Ala Lys Gln Gln Ile Asn Val Ile Asn Asn
        355                 360                 365

Ala Ile Asn Glu Ser Ser Pro His Tyr Leu Gly Asn Ser Tyr Asp Leu
    370                 375                 380
```

-continued

```
Phe Phe Lys Gly His Pro Gly Gly Gly Ile Ile Asn Thr Leu Ile Met
385             390             395             400

Gln Asn Tyr Pro Ser Met Val Asp Ile Pro Ser Lys Ile Ser Phe Glu
                405             410             415

Val Leu Met Met Thr Asp Met Leu Pro Asp Ala Val Ala Gly Ile Ala
            420             425             430

Ser Ser Leu Tyr Phe Thr Ile Pro Ala Glu Lys Ile Lys Phe Ile Val
        435             440             445

Phe Thr Ser Thr Glu Thr Ile Thr Asp Arg Glu Thr Ala Leu Arg Ser
    450             455             460

Pro Leu Val Gln Val Met Ile Lys Leu Gly Ile Val Lys Glu Glu Asn
465             470             475             480

Val Leu Phe Trp Ala Asp Leu Pro Asn Cys Glu Thr Gly Val Cys Ile
            485             490             495

Ala Val
```

```
<210> SEQ ID NO 63
<211> LENGTH: 482
<212> TYPE: PRT
<213> ORGANISM: Photobacterium leiognathi

<400> SEQUENCE: 63
```

```
Met Asn Asp Asn Gln Asn Thr Val Asp Val Val Val Ser Thr Val Asn
1               5               10              15

Asp Asn Val Ile Glu Asn Asn Thr Tyr Gln Val Lys Pro Ile Asp Thr
            20              25              30

Pro Thr Thr Phe Asp Ser Tyr Ser Trp Ile Gln Thr Cys Gly Thr Pro
        35              40              45

Ile Leu Lys Asp Asp Glu Lys Tyr Ser Leu Ser Phe Asp Phe Val Ala
    50              55              60

Pro Glu Leu Asp Gln Asp Glu Lys Phe Cys Phe Glu Phe Thr Gly Asp
65              70              75              80

Val Asp Gly Lys Arg Tyr Val Thr Gln Thr Asn Leu Thr Val Val Ala
            85              90              95

Pro Thr Leu Glu Val Tyr Val Asp His Ala Ser Leu Pro Ser Leu Gln
            100             105             110

Gln Leu Met Lys Ile Ile Gln Gln Lys Asn Glu Tyr Ser Gln Asn Glu
        115             120             125

Arg Phe Ile Ser Trp Gly Arg Ile Arg Leu Thr Glu Asp Asn Ala Glu
    130             135             140

Lys Leu Asn Ala His Ile Tyr Pro Leu Ala Gly Asn Asn Thr Ser Gln
145             150             155             160

Glu Leu Val Asp Ala Val Ile Asp Tyr Ala Asp Ser Lys Asn Arg Leu
            165             170             175

Asn Leu Glu Leu Asn Thr Asn Thr Gly His Ser Phe Arg Asn Ile Ala
            180             185             190

Pro Ile Leu Arg Ala Thr Ser Ser Lys Asn Asn Ile Leu Ile Ser Asn
        195             200             205

Ile Asn Leu Tyr Asp Asp Gly Ser Ala Glu Tyr Val Ser Leu Tyr Asn
    210             215             220

Trp Lys Asp Thr Asp Asn Lys Ser Gln Lys Leu Ser Asp Ser Phe Leu
225             230             235             240

Val Leu Lys Asp Tyr Leu Asn Gly Ile Ser Ser Glu Lys Pro Asn Gly
            245             250             255
```

```
Ile Tyr Ser Ile Tyr Asn Trp His Gln Leu Tyr His Ser Ser Tyr Tyr
            260                 265                 270

Phe Leu Arg Lys Asp Tyr Leu Thr Val Glu Thr Lys Leu His Asp Leu
            275                 280                 285

Arg Glu Tyr Leu Gly Gly Ser Leu Lys Gln Met Ser Trp Asp Thr Phe
        290                 295                 300

Ser Gln Leu Ser Lys Gly Asp Lys Glu Leu Phe Leu Asn Ile Val Gly
    305                 310                 315                 320

Phe Asp Gln Glu Lys Leu Gln Gln Gly Tyr Gln Gln Ser Glu Leu Pro
                325                 330                 335

Asn Phe Val Phe Thr Gly Thr Thr Thr Trp Ala Gly Gly Glu Thr Lys
                340                 345                 350

Glu Tyr Tyr Ala Gln Gln Gln Val Asn Val Val Asn Asn Ala Ile Asn
            355                 360                 365

Glu Thr Ser Pro Tyr Tyr Leu Gly Arg Glu His Asp Leu Phe Phe Lys
        370                 375                 380

Gly His Pro Arg Gly Gly Ile Ile Asn Asp Ile Ile Leu Gly Ser Phe
    385                 390                 395                 400

Asn Asn Met Ile Asp Ile Pro Ala Lys Val Ser Phe Glu Val Leu Met
                405                 410                 415

Met Thr Gly Met Leu Pro Asp Thr Val Gly Gly Ile Ala Ser Ser Leu
                420                 425                 430

Tyr Phe Ser Ile Pro Ala Glu Lys Val Ser Phe Ile Val Phe Thr Ser
            435                 440                 445

Ser Asp Thr Ile Thr Asp Arg Glu Asp Ala Leu Lys Ser Pro Leu Val
        450                 455                 460

Gln Val Met Met Thr Leu Gly Ile Val Lys Glu Lys Asp Val Leu Phe
    465                 470                 475                 480

Trp Cys

<210> SEQ ID NO 64
<211> LENGTH: 675
<212> TYPE: PRT
<213> ORGANISM: Photobacterium damsela

<400> SEQUENCE: 64

Met Lys Lys Ile Leu Thr Val Leu Ser Ile Phe Ile Leu Ser Ala Cys
1               5                   10                  15

Asn Ser Asp Asn Thr Ser Leu Lys Glu Thr Val Ser Ser Asn Ser Ala
            20                  25                  30

Asp Val Val Glu Thr Glu Thr Tyr Gln Leu Thr Pro Ile Asp Ala Pro
        35                  40                  45

Ser Ser Phe Leu Ser His Ser Trp Glu Gln Thr Cys Gly Thr Pro Ile
    50                  55                  60

Leu Asn Glu Ser Asp Lys Gln Ala Ile Ser Phe Asp Phe Val Ala Pro
65                  70                  75                  80

Glu Leu Lys Gln Asp Glu Lys Tyr Cys Phe Thr Phe Lys Gly Ile Thr
                85                  90                  95

Gly Asp His Arg Tyr Ile Thr Asn Thr Thr Leu Thr Val Val Ala Pro
            100                 105                 110

Thr Leu Glu Val Tyr Ile Asp His Ala Ser Leu Pro Ser Leu Gln Gln
        115                 120                 125

Leu Ile His Ile Ile Gln Ala Lys Asp Glu Tyr Pro Ser Asn Gln Arg
    130                 135                 140
```

```
Phe Val Ser Trp Lys Arg Val Thr Val Asp Ala Asp Asn Ala Asn Lys
145                 150                 155                 160

Leu Asn Ile His Thr Tyr Pro Leu Lys Gly Asn Asn Thr Ser Pro Glu
                165                 170                 175

Met Val Ala Ala Ile Asp Glu Tyr Ala Gln Ser Lys Asn Arg Leu Asn
            180                 185                 190

Ile Glu Phe Tyr Thr Asn Thr Ala His Val Phe Asn Asn Leu Pro Pro
            195                 200                 205

Ile Ile Gln Pro Leu Tyr Asn Asn Glu Lys Val Lys Ile Ser His Ile
    210                 215                 220

Ser Leu Tyr Asp Asp Gly Ser Ser Glu Tyr Val Ser Leu Tyr Gln Trp
225                 230                 235                 240

Lys Asp Thr Pro Asn Lys Ile Glu Thr Leu Glu Gly Glu Val Ser Leu
                245                 250                 255

Leu Ala Asn Tyr Leu Ala Gly Thr Ser Pro Asp Ala Pro Lys Gly Met
            260                 265                 270

Gly Asn Arg Tyr Asn Trp His Lys Leu Tyr Asp Thr Asp Tyr Tyr Phe
            275                 280                 285

Leu Arg Glu Asp Tyr Leu Asp Val Glu Ala Asn Leu His Asp Leu Arg
    290                 295                 300

Asp Tyr Leu Gly Ser Ser Ala Lys Gln Met Pro Trp Asp Glu Phe Ala
305                 310                 315                 320

Lys Leu Ser Asp Ser Gln Gln Thr Leu Phe Leu Asp Ile Val Gly Phe
                325                 330                 335

Asp Lys Glu Gln Leu Gln Gln Gln Tyr Ser Gln Ser Pro Leu Pro Asn
            340                 345                 350

Phe Ile Phe Thr Gly Thr Thr Thr Trp Ala Gly Gly Glu Thr Lys Glu
            355                 360                 365

Tyr Tyr Ala Gln Gln Gln Val Asn Val Ile Asn Asn Ala Ile Asn Glu
    370                 375                 380

Thr Ser Pro Tyr Tyr Leu Gly Lys Asp Tyr Asp Leu Phe Phe Lys Gly
385                 390                 395                 400

His Pro Ala Gly Gly Val Ile Asn Asp Ile Ile Leu Gly Ser Phe Pro
                405                 410                 415

Asp Met Ile Asn Ile Pro Ala Lys Ile Ser Phe Glu Val Leu Met Met
            420                 425                 430

Thr Asp Met Leu Pro Asp Thr Val Ala Gly Ile Ala Ser Ser Leu Tyr
            435                 440                 445

Phe Thr Ile Pro Ala Asp Lys Val Asn Phe Ile Val Phe Thr Ser Ser
    450                 455                 460

Asp Thr Ile Thr Asp Arg Glu Glu Ala Leu Lys Ser Pro Leu Val Gln
465                 470                 475                 480

Val Met Leu Thr Leu Gly Ile Val Lys Glu Lys Asp Val Leu Phe Trp
                485                 490                 495

Ala Asp His Lys Val Asn Ser Met Glu Val Ala Ile Asp Glu Ala Cys
            500                 505                 510

Thr Arg Ile Ile Ala Lys Arg Gln Pro Thr Ala Ser Asp Leu Arg Leu
            515                 520                 525

Val Ile Ala Ile Ile Lys Thr Ile Thr Asp Leu Glu Arg Ile Gly Asp
    530                 535                 540

Val Ala Glu Ser Ile Ala Lys Val Ala Leu Glu Ser Phe Ser Asn Lys
545                 550                 555                 560
```

-continued

```
Gln Tyr Asn Leu Leu Val Ser Leu Glu Ser Leu Gly Gln His Thr Val
            565                 570                 575

Arg Met Leu His Glu Val Leu Asp Ala Phe Ala Arg Met Asp Val Lys
            580                 585                 590

Ala Ala Ile Glu Val Tyr Gln Glu Asp Asp Arg Ile Asp Gln Glu Tyr
            595                 600                 605

Glu Ser Ile Val Arg Gln Leu Met Ala His Met Met Glu Asp Pro Ser
        610                 615                 620

Ser Ile Pro Asn Val Met Lys Val Met Trp Ala Ala Arg Ser Ile Glu
625                 630                 635                 640

Arg Val Gly Asp Arg Cys Gln Asn Ile Cys Glu Tyr Ile Ile Tyr Phe
                645                 650                 655

Val Lys Gly Lys Asp Val Arg His Thr Lys Pro Asp Asp Phe Gly Thr
            660                 665                 670

Met Leu Asp
        675

<210> SEQ ID NO 65
<211> LENGTH: 510
<212> TYPE: PRT
<213> ORGANISM: Photobacterium damsela

<400> SEQUENCE: 65

Met Lys Lys Ile Leu Thr Val Leu Ser Ile Phe Ile Leu Ser Ala Cys
1               5                   10                  15

Asn Ser Asp Asn Thr Ser Leu Lys Glu Thr Val Ser Ser Asn Ser Ala
            20                  25                  30

Asp Val Val Glu Thr Glu Thr Tyr Gln Leu Thr Pro Ile Asp Ala Pro
            35                  40                  45

Ser Ser Phe Leu Ser His Ser Trp Glu Gln Thr Cys Gly Thr Pro Ile
        50                  55                  60

Leu Asn Glu Ser Asp Lys Gln Ala Ile Ser Phe Asp Phe Val Ala Pro
65                  70                  75                  80

Glu Leu Lys Gln Asp Glu Lys Tyr Cys Phe Thr Phe Lys Gly Ile Thr
                85                  90                  95

Gly Asp His Arg Tyr Ile Thr Asn Thr Thr Leu Thr Val Val Ala Pro
            100                 105                 110

Thr Leu Glu Val Tyr Ile Asp His Ala Ser Leu Pro Ser Leu Gln Gln
        115                 120                 125

Leu Ile His Ile Ile Gln Ala Lys Asp Glu Tyr Pro Ser Asn Gln Arg
        130                 135                 140

Phe Val Ser Trp Lys Arg Val Thr Val Asp Ala Asp Asn Ala Asn Lys
145                 150                 155                 160

Leu Asn Ile His Thr Tyr Pro Leu Lys Gly Asn Asn Thr Ser Pro Glu
                165                 170                 175

Met Val Ala Ala Ile Asp Glu Tyr Ala Gln Ser Lys Asn Arg Leu Asn
            180                 185                 190

Ile Glu Phe Tyr Thr Asn Thr Ala His Val Phe Asn Asn Leu Pro Pro
        195                 200                 205

Ile Ile Gln Pro Leu Tyr Asn Asn Glu Lys Val Lys Ile Ser His Ile
        210                 215                 220

Ser Leu Tyr Asp Asp Gly Ser Ser Glu Tyr Val Ser Leu Tyr Gln Trp
225                 230                 235                 240

Lys Asp Thr Pro Asn Lys Ile Glu Thr Leu Glu Gly Glu Val Ser Leu
                245                 250                 255
```

-continued

```
Leu Ala Asn Tyr Leu Ala Gly Thr Ser Pro Asp Ala Pro Lys Gly Met
            260                 265                 270

Gly Asn Arg Tyr Asn Trp His Lys Leu Tyr Asp Thr Asp Tyr Tyr Phe
            275                 280                 285

Leu Arg Glu Asp Tyr Leu Asp Val Glu Ala Asn Leu His Asp Leu Arg
        290                 295                 300

Asp Tyr Leu Gly Ser Ser Ala Lys Gln Met Pro Trp Asp Glu Phe Ala
305                 310                 315                 320

Lys Leu Ser Asp Ser Gln Gln Thr Leu Phe Leu Asp Ile Val Gly Phe
                325                 330                 335

Asp Lys Glu Gln Leu Gln Gln Gln Tyr Ser Gln Ser Pro Leu Pro Asn
            340                 345                 350

Phe Ile Phe Thr Gly Thr Thr Thr Trp Ala Gly Gly Glu Thr Lys Glu
            355                 360                 365

Tyr Tyr Ala Gln Gln Gln Val Asn Val Ile Asn Asn Ala Ile Asn Glu
        370                 375                 380

Thr Ser Pro Tyr Tyr Leu Gly Lys Asp Tyr Asp Leu Phe Phe Lys Gly
385                 390                 395                 400

His Pro Ala Gly Gly Val Ile Asn Asp Ile Ile Leu Gly Ser Phe Pro
                405                 410                 415

Asp Met Ile Asn Ile Pro Ala Lys Ile Ser Phe Glu Val Leu Met Met
            420                 425                 430

Thr Asp Met Leu Pro Asp Thr Val Ala Gly Ile Ala Ser Ser Leu Tyr
            435                 440                 445

Phe Thr Ile Pro Ala Asp Lys Val Asn Phe Ile Val Phe Thr Ser Ser
        450                 455                 460

Asp Thr Ile Thr Asp Arg Glu Glu Ala Leu Lys Ser Pro Leu Val Gln
465                 470                 475                 480

Val Met Leu Thr Leu Gly Ile Val Lys Glu Lys Asp Val Leu Phe Trp
                485                 490                 495

Ala Asp Leu Pro Asp Cys Ser Ser Gly Val Cys Ile Asp Lys
                500                 505                 510

<210> SEQ ID NO 66
<211> LENGTH: 422
<212> TYPE: PRT
<213> ORGANISM: Heliobacter acinonychis

<400> SEQUENCE: 66

Met Gly Thr Ile Lys Lys Pro Leu Ile Ile Ala Gly Asn Gly Pro Ser
1               5                   10                  15

Ile Lys Asp Leu Asp Tyr Ala Leu Phe Pro Lys Asp Phe Asp Val Phe
            20                  25                  30

Arg Cys Asn Gln Phe Tyr Phe Glu Asp Lys Tyr Tyr Leu Gly Arg Glu
            35                  40                  45

Ile Lys Gly Val Phe Phe Asn Pro Cys Val Leu Ser Ser Gln Met Gln
        50                  55                  60

Thr Val Gln Tyr Leu Met Asp Asn Gly Glu Tyr Ser Ile Glu Arg Phe
65                  70                  75                  80

Phe Cys Ser Val Ser Thr Asp Arg His Asp Phe Asp Gly Asp Tyr Gln
                85                  90                  95

Thr Ile Leu Pro Val Asp Gly Tyr Leu Lys Ala His Tyr Pro Phe Val
            100                 105                 110

Cys Asp Thr Phe Ser Leu Phe Lys Gly His Glu Glu Ile Leu Lys His
```

-continued

```
            115                 120                 125

Val Lys Tyr His Leu Lys Thr Tyr Ser Lys Glu Leu Ser Ala Gly Val
    130                 135                 140

Leu Met Leu Leu Ser Ala Val Val Leu Gly Tyr Lys Glu Ile Tyr Leu
145                 150                 155                 160

Val Gly Ile Asp Phe Gly Ala Ser Ser Trp Gly His Phe Tyr Asp Glu
                165                 170                 175

Ser Gln Ser Gln His Phe Ser Asn His Met Ala Asp Cys His Asn Ile
                180                 185                 190

Tyr Tyr Asp Met Leu Thr Ile Cys Leu Cys Gln Lys Tyr Ala Lys Leu
                195                 200                 205

Tyr Ala Leu Ala Pro Asn Ser Pro Leu Ser His Leu Leu Thr Leu Asn
    210                 215                 220

Pro Gln Ala Lys Tyr Pro Phe Glu Leu Leu Asp Lys Pro Ile Gly Tyr
225                 230                 235                 240

Thr Ser Asp Leu Ile Ile Ser Ser Pro Leu Glu Glu Lys Leu Leu Glu
                245                 250                 255

Phe Lys Asn Ile Glu Glu Lys Leu Leu Glu Phe Lys Asn Ile Glu Glu
                260                 265                 270

Lys Leu Leu Glu Phe Lys Asn Ile Glu Glu Lys Leu Leu Glu Phe Lys
    275                 280                 285

Asn Ile Glu Glu Lys Leu Leu Glu Phe Lys Asn Ile Glu Glu Lys Leu
    290                 295                 300

Leu Glu Phe Lys Asn Ile Glu Glu Lys Leu Leu Glu Phe Lys Asn Ile
305                 310                 315                 320

Glu Glu Lys Leu Leu Glu Phe Lys Asn Ile Glu Glu Lys Leu Leu Glu
                325                 330                 335

Phe Lys Asn Ile Glu Glu Lys Leu Leu Glu Phe Lys Asn Ile Glu Glu
                340                 345                 350

Lys Leu Leu Glu Phe Lys Asn Ile Glu Glu Lys Leu Leu Glu Phe Lys
    355                 360                 365

Asn Ile Glu Glu Lys Leu Leu Glu Phe Lys Asn Ile Glu Glu Lys Leu
    370                 375                 380

Leu Ala Ser Arg Leu Asn Asn Ile Leu Arg Lys Ile Lys Arg Lys Ile
385                 390                 395                 400

Leu Pro Phe Phe Trp Gly Gly Gly Val Thr Pro Thr Leu Lys Val Ser
                405                 410                 415

Phe Arg Trp Gly Ala Ala
                420

<210> SEQ ID NO 67
<211> LENGTH: 609
<212> TYPE: PRT
<213> ORGANISM: Escherichia coli

<400> SEQUENCE: 67

Met Cys Gly Ile Val Gly Ala Ile Ala Gln Arg Asp Val Ala Glu Ile
1                 5                  10                  15

Leu Leu Glu Gly Leu Arg Arg Leu Glu Tyr Arg Gly Tyr Asp Ser Ala
                20                  25                  30

Gly Leu Ala Val Val Asp Ala Glu Gly His Met Thr Arg Leu Arg Arg
            35                  40                  45

Leu Gly Lys Val Gln Met Leu Ala Gln Ala Ala Glu Glu His Pro Leu
    50                  55                  60
```

-continued

```
His Gly Gly Thr Gly Ile Ala His Thr Arg Trp Ala Thr His Gly Glu
65              70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
        130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
                180                 185                 190

Asp Gln Leu Ala Leu Leu Pro Val Thr Arg Arg Phe Ile Phe Leu Glu
            195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
            325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
    370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
        450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
```

-continued

```
                    485                 490                 495
Ala Tyr Ala Ala Gly Glu Leu Lys His Gly Pro Leu Ala Leu Ile Asp
            500                 505                 510

Ala Asp Met Pro Val Ile Val Val Ala Pro Asn Asn Glu Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Glu Val Ile Ala Pro Ile Phe
            565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
            595                 600                 605

Glu
```

```
<210> SEQ ID NO 68
<211> LENGTH: 1830
<212> TYPE: DNA
<213> ORGANISM: Escherichia coli

<400> SEQUENCE: 68
atgtgtggaa ttgttggcgc gatcgcgcaa cgtgatgtag cagaaatcct tcttgaaggt       60
ttacgtcgtc tggaataccg cggatatgac tctgccggtc tggccgttgt tgatgcagaa      120
ggtcatatga cccgcctgcg tcgcctcggt aaagtccaga tgctggcaca ggcagcggaa      180
gaacatcctc tgcatggcgg cactggtatt gctcacactc gctgggcgac ccacggtgaa      240
ccttcagaag tgaatgcgca tccgcatgtt tctgaacaca ttgtggtggt gcataacggc      300
atcatcgaaa accatgaacc gctgcgtgaa gagctaaaag cgcgtggcta taccttcgtt      360
tctgaaaccg acaccgaagt gattgcccat ctggtgaact gggagctgaa acaaggcggg      420
actctgcgtg aggccgttct gcgtgctatc ccgcagctgc gtggtgcgta cggtacagtg      480
atcatggact cccgtcaccc ggataccctg ctggcggcac gttctggtag tccgctggtg      540
attggcctgg ggatgggcga aaactttatc gcttctgacc agctggcgct gttgccggtg      600
acccgtcgct ttatcttcct tgaagagggc gatattgcgg aaatcactcg ccgttcggta      660
aacatcttcg ataaaactgg cgcggaagta aaacgtcagg atatcgaatc caatctgcaa      720
tatgacgcgg cgataaagg catttaccgt cactacatgc agaaagagat ctacgaacag      780
ccgaacgcga tcaaaaacac ccttaccgga cgcatcagcc acggtcaggt tgatttaagc      840
gagctgggac cgaacgccga cgaactgctg tcgaaggttg agcatattca gatcctcgcc      900
tgtggtactt cttataactc cggtatggtt tcccgctact ggtttgaatc gctagcaggt      960
attccgtgcg acgtcgaaat cgcctctgaa ttccgctatc gcaaatctgc cgtgcgtcgt     1020
aacagcctga tgatcacctt gtcacagtct ggcgaaaccg cggatacccct ggctggcctg     1080 cgtctgtcga aagagctggg ttaccttggt tcactggcaa tctgtaacgt tccgggttct     1140
tctctggtgc gcgaatccga tctggcgcta atgaccaacg cgggtacaga aatcggcgtg     1200
gcatccacta aagcattcac cactcagtta actgtgctgt tgatgctggt ggcgaagctg     1260
tctcgcctga aaggtctgga tgcctccatt gaacatgaca tcgtgcatgg tctgcaggcg     1320
ctgccgagcc gtattgagca gatgctgtct caggacaaac gcattgaagc gctggcagaa     1380
```

-continued

```
gatttctctg acaaacatca cgcgctgttc ctgggccgtg gcgatcagta cccaatcgcg      1440
ctggaaggcg cattgaagtt gaaagagatc tcttacattc acgctgaagc ctacgctgct      1500
ggcgaactga aacacggtcc gctggcgcta attgatgccg atatgccggt tattgttgtt      1560
gcaccgaaca acgaattgct ggaaaaactg aaatccaaca ttgaagaagt tcgcgcgcgt      1620
ggcggtcagt tgtatgtctt cgccgatcag gatgcgggtt ttgtaagtag cgataacatg      1680
cacatcatcg agatgccgca gtgtggaagag gtgattgcac cgatcttcta caccgttccg      1740
ctgcagctgc tggcttacca tgtcgcgctg atcaaaggca ccgacgttga ccagccgcgt      1800
aacctggcaa aatcggttac ggttgagtaa                                        1830
```

```
<210> SEQ ID NO 69
<211> LENGTH: 609
<212> TYPE: PRT
<213> ORGANISM: Escherichia coli

<400> SEQUENCE: 69

Met Cys Gly Ile Val Gly Ala Ile Ala Gln Arg Asp Val Ala Lys Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
            115                 120                 125

Ala His Leu Val Asn Trp Glu Leu Lys Gln Gly Gly Thr Leu Arg Glu
        130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
            195                 200                 205

Glu Gly Asp Ile Ala Glu Ile Thr Arg Arg Ser Val Asn Ile Phe Asp
        210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
```

-continued

```
              290                 295                 300
Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
                340                 345                 350

Thr Ala Asp Thr Leu Ala Gly Leu Arg Leu Ser Lys Glu Leu Gly Tyr
                355                 360                 365

Leu Gly Ser Leu Ala Ile Cys Asn Val Pro Gly Ser Ser Leu Val Arg
                370                 375                 380

Glu Ser Val Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
                420                 425                 430

Asp Ile Val His Gly Leu Gln Ala Leu Pro Ser Arg Ile Glu Gln Met
                435                 440                 445

Leu Pro Gln Asp Lys Arg Ile Glu Ala Leu Ala Glu Asp Phe Ser Asp
        450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
                500                 505                 510

Ala Asp Met Pro Val Ile Val Ala Pro Asn Asn Gly Leu Leu Glu
                515                 520                 525

Lys Leu Lys Ser Asn Ile Glu Glu Val Arg Ala Arg Gly Gly Gln Leu
        530                 535                 540

Tyr Val Phe Ala Asp Gln Asp Ala Gly Phe Val Ser Ser Asp Asn Met
545                 550                 555                 560

His Ile Ile Glu Met Pro His Val Glu Glu Val Ile Ala Pro Ile Phe
                565                 570                 575

Tyr Thr Val Pro Leu Gln Leu Leu Ala Tyr His Val Ala Leu Ile Lys
        580                 585                 590

Gly Thr Asp Val Asp Gln Pro Arg Asn Leu Ala Lys Ser Val Thr Val
        595                 600                 605

Glu
```

<210> SEQ ID NO 70
<211> LENGTH: 1830
<212> TYPE: DNA
<213> ORGANISM: Escherichia coli

<400> SEQUENCE: 70

```
atgtgcggta tcgttggtgc tatcgcacag cgtgatgtag cgaaaatcct cctggaaggt      60
ctgcgtcgtc tcgaataccg tggttacgac tctgccggtc tggcagtagt ggatgcagaa     120
ggtcacatga ctcgtctgcg tcgtctgggt aaagtgcaga tgctcgcgca ggcggcggaa     180
gaacacccac tccacggtgg tacgggtatc gcacacactc gttgggcaac ccacggtgaa     240
ccgtctgagg tcaacgcaca cccgcatgtt agcgagcaca tcgtagtcgt tcacaacggt     300
```

-continued

```
atcatcgaga accacgaacc actccgtgag gaactcaaag cccgtggtta caccttcgta      360
agcgaaaccg acacggaagt tatcgcccac ctcgttaact gggaactcaa acagggtggt      420
actctgcgtg aagcagttct gcgtgccatt ccacagctgc gtggtgcata cggtaccgtg      480
atcatggact ctcgtcatcc ggataccctg ctcgccgcac gttctggttc tccactcgtt      540
atcggtctgg gtatgggtga gaacttcatc gcctctgatc agctggccct gctcccagtt      600
acccgtcgct tcatcttcct ggaagagggt gacatcgccg aaatcacccg tcgttccgtt      660
aacatcttcg acaaaacggg tgcggaagtt aaacgtcagg acatcgagtc taacctgcag      720
tatgacgctg gtgacaaagg catctaccgt cactacatgc agaaagagat ctacgaacag      780
ccgaacgcga tcaaaaacac cctgaccggt cgtatctctc acggtcaggt tgacctgtct      840
gagctgggtc aaacgcggga cgaactcctg tccaaagtcg agcacatcca gatcctggct      900
tgtggtacct cttacaactc cggtatggtt tctcgttact ggttcgaatc tctggcaggt      960
atcccatgcg acgttgaaat cgcctccgaa ttccgttatc gtaaatctgc ggtacgtcgt     1020
aactccctca tgatcaccct gtctcagtct ggtgaaaccg ctgatactct ggcaggtctg     1080
cgtctcagca aagaactggg ttacctgggt tctctggcca tctgcaacgt tccgggttct     1140
agcctggttc gtgagtctgt gctggctctg atgaccaacg cgggtacgga gatcggtgtt     1200
gcctctacca aagcgttcac tacccagctc actgtcctgc tgatgctggt tgccaaactg     1260
tctcgtctca aaggcctcga cgctagcatc gaacacgaca tcgtacacgg tctgcaggcc     1320
ctcccatctc gtatcgagca gatgctgccg caggacaaac gtatcgaagc actggcagaa     1380
gacttcagcg acaaacacca cgcgctgttt ctgggtcgtg gtgaccagta cccaattgcg     1440
ctggaaggtg ccctgaaact gaaagagatc agctacatcc atgcagaggc atacgcagcg     1500
ggtgagctga acatggtcc actggccctg atcgacgcag atatgccggt tattgtggtt     1560
gctccgaaca acggcctgct ggagaaactg aaatccaaca tcgaggaagt acgtgcgcgt     1620
ggtggtcagc tgtacgtgtt tgctgaccag gacgcgggtt tcgtttccag cgacaacatg     1680
cacatcatcg aaatgccgca tgttgaagag gtaatcgcgc caatcttcta caccgtaccg     1740
ctgcagctgc tggcgtacca tgtagccctg atcaaaggta cggacgttga ccagccgcgt     1800
aacctggcga aatccgtgac cgtggaataa                                     1830
```

```
<210> SEQ ID NO 71
<211> LENGTH: 445
<212> TYPE: PRT
<213> ORGANISM: Escherichia coli

<400> SEQUENCE: 71

Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
            20                  25                  30

Ala Gly Lys Val Leu Ala Arg His Gly Ser Arg Lys Ile Ile Ile Gly
        35                  40                  45

Lys Asp Thr Arg Ile Ser Gly Tyr Met Leu Glu Ser Ala Leu Glu Ala
    50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95

Ile Val Ile Ser Ala Ser His Asn Pro Phe Tyr Asp Asn Gly Ile Lys
```

```
                 100                 105                 110
Phe Phe Ser Ile Asp Gly Thr Lys Leu Pro Asp Ala Val Glu Glu Ala
        115                 120                 125

Ile Glu Ala Glu Met Glu Lys Glu Ile Ser Cys Val Asp Ser Ala Glu
    130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
                165                 170                 175

Ile Val Val Asp Cys Ala Asn Gly Ala Thr Tyr His Ile Ala Pro Asn
                180                 185                 190

Val Leu Arg Glu Leu Gly Ala Asn Val Ile Ala Ile Gly Cys Glu Pro
            195                 200                 205

Asn Gly Val Asn Ile Asn Ala Glu Val Gly Ala Thr Asp Val Arg Ala
        210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
                245                 250                 255

Val Asp Gly Asp Gln Ile Met Tyr Ile Ile Ala Arg Glu Gly Leu Arg
                260                 265                 270

Gln Gly Gln Leu Arg Gly Gly Ala Val Gly Thr Leu Met Ser Asn Met
            275                 280                 285

Gly Leu Glu Leu Ala Leu Lys Gln Leu Gly Ile Pro Phe Ala Arg Ala
        290                 295                 300

Lys Val Gly Asp Arg Tyr Val Leu Glu Lys Met Gln Glu Lys Gly Trp
305                 310                 315                 320

Arg Ile Gly Ala Glu Asn Ser Gly His Val Ile Leu Leu Asp Lys Thr
                325                 330                 335

Thr Thr Gly Asp Gly Ile Val Ala Gly Leu Gln Val Leu Ala Ala Met
            340                 345                 350

Ala Arg Asn His Met Ser Leu His Asp Leu Cys Ser Gly Met Lys Met
        355                 360                 365

Phe Pro Gln Ile Leu Val Asn Val Arg Tyr Thr Ala Gly Ser Gly Asp
    370                 375                 380

Pro Leu Glu His Glu Ser Val Lys Ala Val Thr Ala Glu Val Glu Ala
385                 390                 395                 400

Ala Leu Gly Asn Arg Gly Arg Val Leu Leu Arg Lys Ser Gly Thr Glu
                405                 410                 415

Pro Leu Ile Arg Val Met Val Glu Gly Glu Asp Glu Ala Gln Val Thr
                420                 425                 430

Glu Phe Ala His Arg Ile Ala Asp Ala Val Lys Ala Val
            435                 440                 445
```

<210> SEQ ID NO 72
<211> LENGTH: 1338
<212> TYPE: DNA
<213> ORGANISM: Escherichia coli

<400> SEQUENCE: 72

```
atgagtaatc gtaaatattt cggtaccgat gggattcgtg tcgtgtagg ggatgcgccg        60 atcacacctg attttgtgct taagctgggt tgggccgcgg gtaaagtgct ggcgcgccac       120
ggctcccgta agattattat tggtaaagac acgcgtattt ctggctatat gctggagtca       180
```

-continued

```
gcactggaag cgggtctggc ggcagcgggc ctttccgcac tcttcactgg cccgatgcca          240
acaccggccg tggcttatct gacgcgtacc ttccgcgcag aggccggaat tgtgatatct          300
gcatcgcata acccgttcta cgataatggc attaaattct tctctatcga cggcaccaaa          360
ctgccggatg cggtagaaga ggccatcgaa gcggaaatgg aaaaggagat cagctgcgtt          420
gattcggcag aactgggtaa agccagccgt atcgttgatg ccgcgggtcg ctatatcgag          480
ttttgcaaag ccacgttccc gaacgaactt agcctcagtg aactgaagat tgtggtggat          540
tgtgcaaacg gtgcgactta tcacatcgcg ccgaacgtgc tgcgcgaact ggggggcgaac          600 gttatcgcta tcggttgtga gccaaacggt gtaaacatca atgccgaagt gggggctacc          660
gacgttcgcg cgctccaggc tcgtgtgctg gctgaaaaag cggatctcgg tattgccttc          720
gacggcgatg cgatcgcgt gattatggtt gaccatgaag gcaataaagt cgatggcgat          780
cagatcatgt atatcatcgc gcgtgaaggt cttcgtcagg gccagctgcg tggtggcgct          840
gtgggtacat tgatgagcaa catggggctt gaactggcgc tgaaacagtt aggaattcca          900
tttgcgcgcg cgaaagtggg tgaccgctac gtactggaaa aaatgcagga gaaaggctgg          960
cgtatcggtg cagagaattc cggtcatgtg atcctgctgg ataaaactac taccggtgac          1020
ggcatcgttg ctggcttgca ggtgctggcg gcgatggcac gtaaccatat gagcctgcac          1080
gacctttgca gcggcatgaa aatgttcccg cagattctgg ttaacgtacg ttacaccgca          1140
ggtagcggca tccacttga gcatgagtca gttaaagccg tgaccgcaga ggttgaagct          1200
gcgctgggca accgtggacg cgtgttgctg cgtaaatccg gcaccgaacc gttaattcgc          1260
gtgatggtgg aaggcgaaga cgaagcgcag gtgactgaat ttgcacaccg catcgccgat          1320
gcagtaaaag ccgtttaa                                                        1338
```

<210> SEQ ID NO 73
<211> LENGTH: 456
<212> TYPE: PRT
<213> ORGANISM: Escherichia coli

<400> SEQUENCE: 73

```
Met Leu Asn Asn Ala Met Ser Val Val Ile Leu Ala Ala Gly Lys Gly
1               5                   10                  15

Thr Arg Met Tyr Ser Asp Leu Pro Lys Val Leu His Thr Leu Ala Gly
            20                  25                  30

Lys Ala Met Val Gln His Val Ile Asp Ala Ala Asn Glu Leu Gly Ala
        35                  40                  45

Ala His Val His Leu Val Tyr Gly His Gly Gly Asp Leu Leu Lys Gln
    50                  55                  60

Ala Leu Lys Asp Asp Asn Leu Asn Trp Val Leu Gln Ala Glu Gln Leu
65                  70                  75                  80

Gly Thr Gly His Ala Met Gln Gln Ala Ala Pro Phe Phe Ala Asp Asp
                85                  90                  95

Glu Asp Ile Leu Met Leu Tyr Gly Asp Val Pro Leu Ile Ser Val Glu
            100                 105                 110

Thr Leu Gln Arg Leu Arg Asp Ala Lys Pro Gln Gly Gly Ile Gly Leu
        115                 120                 125

Leu Thr Val Lys Leu Asp Asp Pro Thr Gly Tyr Gly Arg Ile Thr Arg
    130                 135                 140

Glu Asn Gly Lys Val Thr Gly Ile Val Glu His Lys Asp Ala Thr Asp
145                 150                 155                 160

Glu Gln Arg Gln Ile Gln Glu Ile Asn Thr Gly Ile Leu Ile Ala Asn
```

```
              165               170               175
Gly Ala Asp Met Lys Arg Trp Leu Ala Lys Leu Thr Asn Asn Asn Ala
            180               185               190

Gln Gly Glu Tyr Tyr Ile Thr Asp Ile Ile Ala Leu Ala Tyr Gln Glu
        195               200               205

Gly Arg Glu Ile Val Ala Val His Pro Gln Arg Leu Ser Glu Val Glu
    210               215               220

Gly Val Asn Asn Arg Leu Gln Leu Ser Arg Leu Glu Arg Val Tyr Gln
225               230               235               240

Ser Glu Gln Ala Glu Lys Leu Leu Leu Ala Gly Val Met Leu Arg Asp
            245               250               255

Pro Ala Arg Phe Asp Leu Arg Gly Thr Leu Thr His Gly Arg Asp Val
            260               265               270

Glu Ile Asp Thr Asn Val Ile Ile Glu Gly Asn Val Thr Leu Gly His
            275               280               285

Arg Val Lys Ile Gly Thr Gly Cys Val Ile Lys Asn Ser Val Ile Gly
        290               295               300

Asp Asp Cys Glu Ile Ser Pro Tyr Thr Val Val Glu Asp Ala Asn Leu
305               310               315               320

Ala Ala Ala Cys Thr Ile Gly Pro Phe Ala Arg Leu Arg Pro Gly Ala
            325               330               335

Glu Leu Leu Glu Gly Ala His Val Gly Asn Phe Val Glu Met Lys Lys
            340               345               350

Ala Arg Leu Gly Lys Gly Ser Lys Ala Gly His Leu Thr Tyr Leu Gly
            355               360               365

Asp Ala Glu Ile Gly Asp Asn Val Asn Ile Gly Ala Gly Thr Ile Thr
    370               375               380

Cys Asn Tyr Asp Gly Ala Asn Lys Phe Lys Thr Ile Ile Gly Asp Asp
385               390               395               400

Val Phe Val Gly Ser Asp Thr Gln Leu Val Ala Pro Val Thr Val Gly
            405               410               415

Lys Gly Ala Thr Ile Ala Ala Gly Thr Thr Val Thr Arg Asn Val Gly
            420               425               430

Glu Asn Ala Leu Ala Ile Ser Arg Val Pro Gln Thr Gln Lys Glu Gly
        435               440               445

Trp Arg Arg Pro Val Lys Lys Lys
    450               455
```

```
<210> SEQ ID NO 74
<211> LENGTH: 1371
<212> TYPE: DNA
<213> ORGANISM: Escherichia coli

<400> SEQUENCE: 74
atgttgaata atgctatgag cgtagtgatc cttgccgcag gcaaaggcac gcgcatgtat      60
tccgatcttc cgaaagtgct gcataccctt gccgggaaag cgatggttca gcatgtcatt     120
gatgctgcga atgaattagg cgcagcgcac gttcacctgg tgtacggtca cggcggcgat     180
ctgctaaaac aggcgctgaa agacgacaac cttaactggg tgcttcaggc agagcagctg     240
ggtacgggtc atgcaatgca gcaggccgca ccttttctttg ccgatgatga agacatttta     300
atgctctacg cgacgtgcc gctgatctct gtcgaaacac tccagcgtct gcgtgatgct     360
aaaccgcagg gtggcattgg tctgctgacg gtgaaactgg atgatccgac cggttatgga     420 cgtatcacccc gtgaaaacgg caaagttacc ggcattgttg agcacaaaga tgccaccgac     480
```

-continued

```
gagcagcgtc agattcagga gatcaacacc ggcattctga ttgccaacgg cgcagatatg      540
aaacgctggc tggcgaagct gaccaacaat aatgctcagg gcgaatacta catcaccgac      600
attattgcgc tggcgtatca ggaagggcgt gaaatcgtcg ccgttcatcc gcaacgttta      660
agcgaagtag aaggcgtgaa taaccgcctg caactctccc gtctggagcg tgtttatcag      720
tccgaacagg ctgaaaaact gctgttagca ggcgttatgc tgcgcgatcc agcgcgtttt      780
gatctgcgtg gtacgctaac tcacgggcgc gatgttgaaa ttgatactaa cgttatcatc      840
gagggcaacg tgactctcgg tcatcgcgtg aaaattggca ccggttgcgt gattaaaaac      900
agcgtgattg cgatgattg cgaaatcagt ccgtataccg ttgtggaaga tgcgaatctg        960
gcagcggcct gtaccattgg cccgtttgcc cgtttgcgtc ctggtgctga gttgctggaa     1020
ggtgctcacg tcggtaactt cgttgagatg aaaaaagcgc gtctgggtaa aggctcgaaa     1080
gctggtcatc tgacttacct gggcgatgcg gaaattggcg ataacgttaa catcggcgcg     1140
ggaaccatta cctgcaacta cgatggtgcg aataaattta agaccattat cggcgacgat     1200
gtgtttgttg gttccgacac tcagctggtg gccccggtaa cagtaggcaa aggcgcgacc     1260
attgctgcgg gtacaactgt gacgcgtaat gtcggcgaaa atgcattagc tatcagccgt     1320
gtgccgcaga ctcagaaaga aggctggcgt cgtccggtaa agaaaaagtg a              1371
```

```
<210> SEQ ID NO 75
<211> LENGTH: 391
<212> TYPE: PRT
<213> ORGANISM: Escherichia coli

<400> SEQUENCE: 75

Met Lys Lys Ile Leu Tyr Val Thr Gly Ser Arg Ala Glu Tyr Gly Ile
1               5                   10                  15

Val Arg Arg Leu Leu Thr Met Leu Arg Glu Thr Pro Glu Ile Gln Leu
            20                  25                  30

Asp Leu Ala Val Thr Gly Met His Cys Asp Asn Ala Tyr Gly Asn Thr
        35                  40                  45

Ile His Ile Ile Glu Gln Asp Asn Phe Asn Ile Ile Lys Val Val Asp
    50                  55                  60

Ile Asn Ile Asn Thr Thr Ser His Thr His Ile Leu His Ser Met Ser
65                  70                  75                  80

Val Cys Leu Asn Ser Phe Gly Asp Phe Phe Ser Asn Asn Thr Tyr Asp
                85                  90                  95

Ala Val Met Val Leu Gly Asp Arg Tyr Glu Ile Phe Ser Val Ala Ile
            100                 105                 110

Ala Ala Ser Met His Asn Ile Pro Leu Ile His Ile His Gly Gly Glu
        115                 120                 125

Lys Thr Leu Ala Asn Tyr Asp Glu Phe Ile Arg His Ser Ile Thr Lys
    130                 135                 140

Met Ser Lys Leu His Leu Thr Ser Thr Glu Glu Tyr Lys Lys Arg Val
145                 150                 155                 160

Ile Gln Leu Gly Glu Lys Pro Gly Ser Val Phe Asn Ile Gly Ser Leu
                165                 170                 175

Gly Ala Glu Asn Ala Leu Ser Leu His Leu Pro Asn Lys Gln Glu Leu
            180                 185                 190

Glu Leu Lys Tyr Gly Ser Leu Leu Lys Arg Tyr Phe Val Val Val Phe
        195                 200                 205

His Pro Glu Thr Leu Ser Thr Gln Ser Val Asn Asp Gln Ile Asp Glu
```

-continued

```
        210             215             220

Leu Leu Ser Ala Ile Ser Phe Phe Lys Asn Thr His Asp Phe Ile Phe
225             230             235             240

Ile Gly Ser Asn Ala Asp Thr Gly Ser Asp Ile Ile Gln Arg Lys Val
            245             250             255

Lys Tyr Phe Cys Lys Glu Tyr Lys Phe Arg Tyr Leu Ile Ser Ile Arg
            260             265             270

Ser Glu Asp Tyr Leu Ala Met Ile Lys Tyr Ser Cys Gly Leu Ile Gly
        275             280             285

Asn Ser Ser Ser Gly Leu Ile Glu Val Pro Ser Leu Lys Val Ala Thr
    290             295             300

Ile Asn Ile Gly Asp Arg Gln Lys Gly Arg Val Arg Gly Ala Ser Val
305             310             315             320

Ile Asp Val Pro Val Glu Lys Asn Ala Ile Val Arg Gly Ile Asn Ile
            325             330             335

Ser Gln Asp Glu Lys Phe Ile Ser Val Val Gln Ser Ser Ser Asn Pro
            340             345             350

Tyr Phe Lys Glu Asn Ala Leu Ile Asn Ala Val Arg Ile Ile Lys Asp
            355             360             365

Phe Ile Lys Ser Lys Asn Lys Asp Tyr Lys Asp Phe Tyr Asp Ile Pro
    370             375             380

Glu Cys Thr Thr Ser Tyr Asp
385             390
```

```
<210> SEQ ID NO 76
<211> LENGTH: 1176
<212> TYPE: DNA
<213> ORGANISM: Escherichia coli

<400> SEQUENCE: 76
atgaaaaaaa tattatacgt aactggatct agagctgaat atggaatagt tcggagactt      60
ttgacaatgc taagagaaac tccagaaata cagcttgatt tggcagttac aggaatgcat     120
tgtgataatg cgtatggaaa tacaatacat attatagaac aagataattt taatattatc     180
aaggttgtgg atataaatat caatacaact tcacatactc acattctcca ttcaatgagt     240
gtttgcctca attcgtttgg tgattttttt tcaaataaca catatgatgc ggttatggtt     300
ttaggcgata gatatgaaat attttcagtc gctatcgcag catcaatgca taatattcca     360
ttaattcata ttcatggtgg tgaaaagaca ttagctaatt atgatgagtt tattaggcat     420
tcaattacta aaatgagtaa actccatctt acttctacag aagagtataa aaaacgagta     480
attcaactag gtgaaaagcc tggtagtgtg tttaatattg gttctcttgg tgcagaaaat     540
gctctttcat tgcatttacc aaataagcag gagttggaac taaatatgg ttcactgtta     600 aaacggtact ttgttgtagt attccatcct gaaacacttt ccacgcagtc ggttaatgat     660
caaatagatg agttattgtc agcgatttct ttttttaaaa atactcacga ctttatttt     720 attggcagta acgctgacac tggttctgat ataattcaga gaaaagtaaa atattttgc      780 aaagagtata agttcagata tttgatttct attcgttcag aagattattt ggcaatgatt     840
aaatactctt gtgggctaat tgggaactcc tcctctggtt taattgaggt tccatcttta     900
aaagttgcaa caattaacat tggtgatagg cagaaaggcc gtgttcgtgg agccagtgta     960
atagatgtac ccgttgaaaa aaatgcaatc gtcagaggga taaatatatc tcaagatgaa    1020
aaatttatta gtgttgtaca gtcatctagt aatccttatt ttaaagaaaa tgctttaatt    1080
```

-continued

```
aatgctgtta gaattattaa ggattttatt aaatcaaaaa ataaagatta caaagatttt    1140
tatgacatcc cggaatgtac caccagttat gactag                             1176
```

<210> SEQ ID NO 77
<211> LENGTH: 159
<212> TYPE: PRT
<213> ORGANISM: Saccharomyces cerevisiae

<400> SEQUENCE: 77

```
Met Ser Leu Pro Asp Gly Phe Tyr Ile Arg Arg Met Glu Glu Gly Asp
1               5                   10                  15

Leu Glu Gln Val Thr Glu Thr Leu Lys Val Leu Thr Thr Val Gly Thr
                20                  25                  30

Ile Thr Pro Glu Ser Phe Ser Lys Leu Ile Lys Tyr Trp Asn Glu Ala
        35                  40                  45

Thr Val Trp Asn Asp Asn Glu Asp Lys Lys Ile Met Gln Tyr Asn Pro
    50                  55                  60

Met Val Ile Val Asp Lys Arg Thr Glu Thr Val Ala Ala Thr Gly Asn
65                  70                  75                  80

Ile Ile Ile Glu Arg Lys Ile Ile His Glu Leu Gly Leu Cys Gly His
                85                  90                  95

Ile Glu Asp Ile Ala Val Asn Ser Lys Tyr Gln Gly Gln Gly Leu Gly
            100                 105                 110

Lys Leu Leu Ile Asp Gln Leu Val Thr Ile Gly Phe Asp Tyr Gly Cys
        115                 120                 125

Tyr Lys Ile Ile Leu Asp Cys Asp Glu Lys Asn Val Lys Phe Tyr Glu
    130                 135                 140

Lys Cys Gly Phe Ser Asn Ala Gly Val Glu Met Gln Ile Arg Lys
145                 150                 155
```

<210> SEQ ID NO 78
<211> LENGTH: 480
<212> TYPE: DNA
<213> ORGANISM: Saccharomyces cerevisiae

<400> SEQUENCE: 78

```
atgagcttac ccgatggatt ttatataagg cgaatggaag agggggattt ggaacaggtc     60
actgagacgc taaaggtttt gaccaccgtg ggcactatta cccccgaatc cttcagcaaa    120
ctcataaaat actggaatga agccacagta tggaatgata acgaagataa aaaaataatg    180
caatataacc ccatggtgat tgtggacaag cgcaccgaga cggttgccgc tacggggaat    240
atcatcatcg aaagaaagat cattcatgaa ctggggctat gtggccacat cgaggacatt    300
gcagtaaact ccaagtatca gggccaaggt ttgggcaagc tcttgattga tcaattggta    360
actatcggct ttgactacgg ttgttataag attattttag attgcgatga gaaaaatgtc    420
aaattctatg aaaaatgtgg gtttagcaac gcaggcgtgg aaatgcaaat tagaaaatag    480
```

<210> SEQ ID NO 79
<211> LENGTH: 188
<212> TYPE: PRT
<213> ORGANISM: Escherichia coli

<400> SEQUENCE: 79

```
Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
                20                  25                  30
```

```
His Tyr Gly Leu Gln Tyr Asp Ile Gln Ala Met Ile Ala Leu Asn Gly
        35              40              45

Ser Pro Thr Trp Arg Ile Ala Gln Ala Ile Ile Glu Leu Asn Gln Ala
    50              55              60

Asp Leu Asp Pro His Ala Leu Ala Arg Glu Lys Thr Glu Ala Val Arg
65              70              75              80

Ser Met Leu Leu Asp Ser Val Glu Pro Leu Pro Leu Val Asp Val Val
            85              90              95

Lys Ser Trp His Gly Arg Arg Pro Met Ala Val Gly Thr Gly Ser Glu
            100             105             110

Ser Ala Ile Ala Glu Ala Leu Leu Ala His Leu Gly Leu Arg His Tyr
            115             120             125

Phe Asp Ala Val Val Ala Ala Asp His Val Lys His His Lys Pro Ala
    130             135             140

Pro Asp Thr Phe Leu Leu Cys Ala Gln Arg Met Gly Val Gln Pro Thr
145             150             155             160

Gln Cys Val Val Phe Glu Asp Ala Asp Phe Gly Ile Gln Ala Ala Arg
            165             170             175

Ala Ala Gly Met Asp Ala Val Asp Val Arg Leu Leu
            180             185
```

```
<210> SEQ ID NO 80
<211> LENGTH: 199
<212> TYPE: PRT
<213> ORGANISM: Escherichia coli

<400> SEQUENCE: 80
```

```
Met Leu Tyr Ile Phe Asp Leu Gly Asn Val Ile Val Asp Ile Asp Phe
1               5               10              15

Asn Arg Val Leu Gly Ala Trp Ser Asp Leu Thr Arg Ile Pro Leu Ala
            20              25              30

Ser Leu Lys Lys Ser Phe His Met Gly Glu Ala Phe His Gln His Glu
            35              40              45

Arg Gly Glu Ile Ser Asp Glu Ala Phe Ala Glu Ala Leu Cys His Glu
    50              55              60

Met Ala Leu Pro Leu Ser Tyr Glu Gln Phe Ser His Gly Trp Gln Ala
65              70              75              80

Val Phe Val Ala Leu Arg Pro Glu Val Ile Ala Ile Met His Lys Leu
            85              90              95

Arg Glu Gln Gly His Arg Val Val Leu Ser Asn Thr Asn Arg Leu
            100             105             110

His Thr Thr Phe Trp Pro Glu Glu Tyr Pro Glu Ile Arg Asp Ala Ala
            115             120             125

Asp His Ile Tyr Leu Ser Gln Asp Leu Gly Met Arg Lys Pro Glu Ala
    130             135             140

Arg Ile Tyr Gln His Val Leu Gln Ala Glu Gly Phe Ser Pro Ser Asp
145             150             155             160

Thr Val Phe Phe Asp Asp Asn Ala Asp Asn Ile Glu Gly Ala Asn Gln
            165             170             175

Leu Gly Ile Thr Ser Ile Leu Val Lys Asp Lys Thr Thr Ile Pro Asp
            180             185             190

Tyr Phe Ala Lys Val Leu Cys
        195
```

<210> SEQ ID NO 81
<211> LENGTH: 567
<212> TYPE: DNA
<213> ORGANISM: Escherichia coli

<400> SEQUENCE: 81

```
atgtacgagc gttatgcagg tttaattttt gatatggatg cacaatcct ggatacggag        60 cctacgcacc gtaaagcgtg gcgcgaagta ttagggcact acggtcttca gtacgatatt       120
caggcgatga ttgcgcttaa tggatcgccc acctggcgta ttgctcaggc aattattgag       180
ctgaatcagg ccgatctcga cccgcatgcg ttagcgcgtg aaaaaacaga agcagtaaga       240
agtatgctgc tggatagcgt cgaaccgctt cctcttgttg atgtggtgaa aagttggcat       300
ggtcgtcgcc caatggctgt aggaacgggg agtgaaagcg ccatcgctga ggcattgctg       360
gcgcacctgg gattacgcca ttattttgac gccgtcgtcg ctgccgatca cgtcaaacac       420
cataaacccg cgccagacac attttttgttg tgcgcgcagc gtatgggcgt gcaaccgacg       480
cagtgtgtgg tctttgaaga tgccgatttc ggtattcagg cggcccgtgc agcaggcatg       540
gacgccgtgg atgttcgctt gctgtga                                          567
```

<210> SEQ ID NO 82
<211> LENGTH: 600
<212> TYPE: DNA
<213> ORGANISM: Escherichia coli

<400> SEQUENCE: 82

```
atgctctata tctttgattt aggtaatgtg attgtcgata tcgactttaa ccgtgtgctg        60
ggagcctgga gcgatttaac gcgtattccg ctggcatcgc ttaagaagag tttttcatatg      120 ggggaggcgt ttcatcagca tgagcgtggg gaaattagcg acgaagcgtt cgcagaggcg       180
ctgtgtcatg agatggctct accgctaagc tacgagcagt tctctcacgg ctggcaggcg       240
gtgtttgttg cgctgcgccc ggaagtgatc gccatcatgc ataaactgcg tgagcagggg       300
catcgcgtgg tggtgctttc caataccaac cgcctgcata ccaccttctg gccggaagaa       360
tacccggaaa ttcgtgatgc tgctgaccat atctatctgt cgcaagatct ggggatgcgc       420
aaacctgaag cacgaattta ccagcatgtt ttgcaggcgg aaggttttttc acccagcgat       480 acggtctttt tcgacgataa cgccgataat atagaaggag ccaatcagct gggcattacc       540
agtattctgg tgaaagataa aaccaccatc ccggactatt cgcgaaggt gttatgctaa       600
```

<210> SEQ ID NO 83
<211> LENGTH: 421
<212> TYPE: PRT
<213> ORGANISM: Bacteroides ovatus

<400> SEQUENCE: 83

```
Met Asp Ser Lys Asn Asn Ile Gly His Ser Ala Asp Ile Ser Leu Thr
1               5                   10                  15

Ala Glu Leu Pro Ile Pro Ile Tyr Asn Gly Asn Thr Ile Met Asp Phe
            20                  25                  30

Lys Lys Leu Ala Ser Leu Tyr Lys Asp Glu Leu Leu Asp Asn Val Leu
        35                  40                  45

Pro Phe Trp Leu Glu His Ser Gln Asp His Glu Tyr Gly Gly Tyr Phe
    50                  55                  60

Thr Cys Leu Asp Arg Glu Gly Lys Val Phe Asp Thr Asp Lys Phe Ile
65                  70                  75                  80

Trp Leu Gln Ser Arg Glu Val Trp Met Phe Ser Met Leu Tyr Asn Lys
```

-continued

```
                85              90              95
Val Glu Lys Arg Gln Glu Trp Leu Asp Cys Ala Ile Gln Gly Gly Glu
            100             105             110

Phe Leu Lys Lys Tyr Gly His Asp Gly Asn Tyr Asn Trp Tyr Phe Ser
            115             120             125

Leu Asp Arg Ser Gly Arg Pro Leu Val Glu Pro Tyr Asn Ile Phe Ser
            130             135             140

Tyr Thr Phe Ala Thr Met Ala Phe Gly Gln Leu Ser Leu Thr Thr Gly
145             150             155             160

Asn Gln Glu Tyr Ala Asp Ile Ala Lys Lys Thr Phe Asp Ile Ile Leu
                165             170             175

Ser Lys Val Asp Asn Pro Lys Gly Arg Trp Asn Lys Leu His Pro Gly
            180             185             190

Thr Arg Asn Leu Lys Asn Phe Ala Leu Pro Met Ile Leu Cys Asn Leu
            195             200             205

Ala Leu Glu Ile Glu His Leu Leu Asp Glu Thr Tyr Leu Arg Glu Thr
            210             215             220

Met Asp Thr Cys Ile His Glu Val Met Glu Val Phe Tyr Arg Pro Glu
225             230             235             240

Leu Gly Gly Ile Ile Val Glu Asn Val Asp Ile Asp Gly Asn Leu Val
                245             250             255

Asp Cys Phe Glu Gly Arg Gln Val Thr Pro Gly His Ala Ile Glu Ala
            260             265             270

Met Trp Phe Ile Met Asp Leu Gly Lys Arg Leu Asn Arg Pro Glu Leu
            275             280             285

Ile Glu Lys Ala Lys Glu Thr Thr Leu Thr Met Leu Asn Tyr Gly Trp
            290             295             300

Asp Lys Gln Tyr Gly Gly Ile Tyr Tyr Phe Met Asp Arg Asn Gly Cys
305             310             315             320

Pro Pro Gln Gln Leu Glu Trp Asp Gln Lys Leu Trp Trp Val His Ile
                325             330             335

Glu Thr Leu Ile Ser Leu Leu Lys Gly Tyr Gln Leu Thr Gly Asp Lys
                340             345             350

Lys Cys Leu Glu Trp Phe Glu Lys Val His Asp Tyr Thr Trp Glu His
            355             360             365

Phe Lys Asp Lys Glu Tyr Pro Glu Trp Tyr Gly Tyr Leu Asn Arg Arg
            370             375             380

Gly Glu Val Leu Leu Pro Leu Lys Gly Gly Lys Trp Lys Gly Cys Phe
385             390             395             400

His Val Pro Arg Gly Leu Tyr Gln Cys Trp Lys Thr Leu Glu Glu Ile
                405             410             415

Lys Asn Ile Val Ser
            420
```

```
<210> SEQ ID NO 84
<211> LENGTH: 391
<212> TYPE: PRT
<213> ORGANISM: Synechocystis sp.

<400> SEQUENCE: 84

Met Ile Ala His Arg Arg Gln Glu Leu Ala Gln Gln Tyr Tyr Gln Ala
1               5               10              15

Leu His Gln Asp Val Leu Pro Phe Trp Glu Lys Tyr Ser Leu Asp Arg
            20              25              30
```

-continued

```
Gln Gly Gly Gly Tyr Phe Thr Cys Leu Asp Arg Lys Gly Gln Val Phe
        35                  40                  45

Asp Thr Asp Lys Phe Ile Trp Leu Gln Asn Arg Gln Val Trp Gln Phe
    50                  55                  60

Ala Val Phe Tyr Asn Arg Leu Glu Pro Lys Pro Gln Trp Leu Glu Ile
65                  70                  75                  80

Ala Arg His Gly Ala Asp Phe Leu Ala Arg His Gly Arg Asp Gln Asp
                85                  90                  95

Gly Asn Trp Tyr Phe Ala Leu Asp Gln Glu Gly Lys Pro Leu Arg Gln
            100                 105                 110

Pro Tyr Asn Val Phe Ser Asp Cys Phe Ala Ala Met Ala Phe Ser Gln
            115                 120                 125

Tyr Ala Leu Ala Ser Gly Ala Gln Glu Ala Lys Ala Ile Ala Leu Gln
    130                 135                 140

Ala Tyr Asn Asn Val Leu Arg Arg Gln His Asn Pro Lys Gly Gln Tyr
145                 150                 155                 160

Glu Lys Ser Tyr Pro Gly Thr Arg Pro Leu Lys Ser Leu Ala Val Pro
                165                 170                 175

Met Ile Leu Ala Asn Leu Thr Leu Glu Met Glu Trp Leu Leu Pro Pro
            180                 185                 190

Thr Thr Val Glu Glu Val Leu Ala Gln Thr Val Arg Glu Val Met Thr
            195                 200                 205

Asp Phe Leu Asp Pro Glu Ile Gly Leu Met Arg Glu Ala Val Thr Pro
    210                 215                 220

Thr Gly Glu Phe Val Asp Ser Phe Glu Gly Arg Leu Leu Asn Pro Gly
225                 230                 235                 240

His Gly Ile Glu Ala Met Trp Phe Met Met Asp Ile Ala Gln Arg Ser
                245                 250                 255

Gly Asp Arg Gln Leu Gln Glu Gln Ala Ile Ala Val Val Leu Asn Thr
            260                 265                 270

Leu Glu Tyr Ala Trp Asp Glu Glu Phe Gly Gly Ile Phe Tyr Phe Leu
            275                 280                 285

Asp Arg Gln Gly His Pro Pro Gln Gln Leu Glu Trp Asp Gln Lys Leu
    290                 295                 300

Trp Trp Val His Leu Glu Thr Leu Val Ala Leu Ala Lys Gly His Gln
305                 310                 315                 320

Ala Thr Gly Gln Glu Lys Cys Trp Gln Trp Phe Glu Arg Val His Asp
                325                 330                 335

Tyr Ala Trp Ser His Phe Ala Asp Pro Glu Tyr Gly Glu Trp Phe Gly
            340                 345                 350

Tyr Leu Asn Arg Arg Gly Glu Val Leu Leu Asn Leu Lys Gly Gly Lys
            355                 360                 365

Trp Lys Gly Cys Phe His Val Pro Arg Ala Leu Trp Leu Cys Ala Glu
    370                 375                 380

Thr Leu Gln Leu Pro Val Ser
385                 390
```

<210> SEQ ID NO 85
<211> LENGTH: 1266
<212> TYPE: DNA
<213> ORGANISM: Bacteroides ovatus

<400> SEQUENCE: 85
atggatagta agaataacat tggtcattca gcagacatct ctttaactgc tgaattaccc        60

```
ataccaatct ataatggaaa tacgattatg gatttcaaaa aactggcaag tctgtacaag         120
gatgagctcc tggacaacgt ccttcctttc tggcttgaac attcacaaga ccatgagtat         180
ggtggttact tcacctgtct ggaccgtgaa ggaaaagtat tcgatacgga taagtttatt         240
tggctgcaaa gtcgtgaggt atggatgttc tccatgcttt acaacaaagt ggagaaacgt         300
caggaatggc tagactgtgc cattcagggt ggcgaatttc taaaaaaata tggacatgac         360
ggcaattata actggtattt ttccctcgac cgttcgggta gaccattggt agaaccgtac         420
aatatattct cgtatacatt cgctaccatg gctttcggac agttgagcct tacaaccggt         480
aatcaggaat atgcggacat tgccaagaaa actttcgata taatcctttc caaagtggat         540
aatccgaaag ggagatggaa taagcttcat ccgggtaccc gtaatctgaa gaactttgcc         600
ttgccaatga tcctctgtaa cttggcactg gagatagagc atttattgga tgaaacgtat         660
ctgcgggaaa caatggatac ttgtatccat gaagtgatgg aagttttcta tcgtcctgaa         720
ctcggaggta tcattgttga aaacgtggac atagacggta atttggtcga ttgtttttgaa        780 ggccgtcagg tgaccccggg acatgccatt gaagcgatgt ggtttatcat ggatctaggc        840
aagcgtctga atcgtccgga attgatagag aaagccaaag agactactct cacgatgctt        900
aattatggct gggacaagca atatggaggt atctactatt ttatggatcg taacggttgt        960
cctccccaac aattggagtg ggaccagaaa ctctggtggg tccatatcga aacgcttatt       1020
tccctgctga aaggctatca attgacggga gacaaaaaat gcttggaatg gtttgaaaag       1080
gtacatgact acacttggga gcatttcaag gataaagaat atcctgaatg gtatggctac       1140
ttgaaccgaa gaggcgaagt attgctacca ctcaaaggag gaaaatggaa aggatgcttc       1200
catgtgccaa gaggactgta tcagtgctgg aaaacattag aagaaataaa aaatatagta       1260
tcctaa                                                                   1266
```

<210> SEQ ID NO 86
<211> LENGTH: 1176
<212> TYPE: DNA
<213> ORGANISM: Synechocystis sp.

<400> SEQUENCE: 86

```
atgattgccc atcgccgtca ggagttagcc cagcaatatt accaggcttt acaccaggac          60
gtattgccct tttgggaaaa atattccctc gatcgccagg ggggcggtta ctttacctgc         120
ttagaccgta aaggccaggt ttttgacaca gataaattca tttggttaca aaaccgtcag         180
gtatggcagt ttgccgtttt ctacaaccgt ttggaaccaa aaccccaatg gttagaaatt         240
gcccgccatg gtgctgattt tttagctcgc cacggccgag atcaagacgg taattggtat         300
tttgctttgg atcaggaagg caaacccctg cgtcaaccct ataacgtttt ttccgattgc         360
ttcgccgcca tggcctttag tcaatatgcc ttagccagtg gggcgcagga agctaaagcc         420
attgccctgc aggcctacaa taacgtccta cgccgtcagc acaatcccaa aggtcaatac         480
gagaagtcct atccaggtac tagaccccctc aaatccctgg cggtgccgat gatttttagcc       540 aacctcaccc tggagatgga atggttatta ccgcctacta ccgtggaaga ggtgttggcc         600
caaaccgtca gagaagtgat gacggatttc ctcgacccag aaataggatt aatgcgggaa         660
gcggtgaccc ccacaggaga atttgttgat agttttgaag gcggttgct caacccagga         720 cacggcattg aagccatgtg gttcatgatg gacattgccc aacgctccgg cgatcgccag         780
ttacaggagc aagccattgc agtggtgttg aacaccctgg aatatgcctg ggatgaagaa         840
tttggtggca tattttattt ccttgatcgc cagggccacc ctccccaaca actggaatgg         900
```

```
gaccaaaagc tctggtgggt acatttggaa accctggttg ccctagccaa gggccaccaa      960
gccactggcc aagaaaaatg ttggcaatgg tttgagcggg tccatgatta cgcctggagt     1020
catttcgccg atcctgagta tggggaatgg tttggctacc tgaatcgccg gggagaggtg     1080
ttactcaacc taaaaggggg gaaatggaaa gggtgcttcc acgtgcccg agctctgtgg       1140 ctctgtgcgg aaactctcca acttccggtt agttaa                               1176
```

<210> SEQ ID NO 87
<211> LENGTH: 229
<212> TYPE: PRT
<213> ORGANISM: Escherichia coli

<400> SEQUENCE: 87

```
Met Ser Leu Leu Ala Gln Leu Asp Gln Lys Ile Ala Ala Asn Gly Gly
1               5                   10                  15

Leu Ile Val Ser Cys Gln Pro Val Pro Asp Ser Pro Leu Asp Lys Pro
            20                  25                  30

Glu Ile Val Ala Ala Met Ala Leu Ala Ala Glu Gln Ala Gly Ala Val
        35                  40                  45

Ala Ile Arg Ile Glu Gly Val Ala Asn Leu Gln Ala Thr Arg Ala Val
    50                  55                  60

Val Ser Val Pro Ile Ile Gly Ile Val Lys Arg Asp Leu Glu Asp Ser
65                  70                  75                  80

Pro Val Arg Ile Thr Ala Tyr Ile Glu Asp Val Asp Ala Leu Ala Gln
                85                  90                  95

Ala Gly Ala Asp Ile Ile Ala Ile Asp Gly Thr Asp Arg Pro Arg Pro
            100                 105                 110

Val Pro Val Glu Thr Leu Leu Ala Arg Ile His His His Gly Leu Leu
        115                 120                 125

Ala Met Thr Asp Cys Ser Thr Pro Glu Asp Gly Leu Ala Cys Gln Lys
    130                 135                 140

Leu Gly Ala Glu Ile Ile Gly Thr Thr Leu Ser Gly Tyr Thr Thr Pro
145                 150                 155                 160

Glu Thr Pro Glu Glu Pro Asp Leu Ala Leu Val Lys Thr Leu Ser Asp
                165                 170                 175

Ala Gly Cys Arg Val Ile Ala Glu Gly Arg Tyr Asn Thr Pro Ala Gln
            180                 185                 190

Ala Ala Asp Ala Met Arg His Gly Ala Trp Ala Val Thr Val Gly Ser
            195                 200                 205

Ala Ile Thr Arg Leu Glu His Ile Cys Gln Trp Tyr Asn Thr Ala Met
    210                 215                 220

Lys Lys Ala Val Leu
225
```

<210> SEQ ID NO 88
<211> LENGTH: 690
<212> TYPE: DNA
<213> ORGANISM: Escherichia coli

<400> SEQUENCE: 88

```
atgtcgttac ttgcacaact ggatcaaaaa atcgctgcta acggtggcct gattgtctcc      60
tgccagccgg ttccggacag cccgctcgat aaacccgaaa tcgtcgccgc catggcatta     120
gcggcagaac aggcgggcgc ggttgccatt cgcattgaag tgtgtggcaaa tctgcaagcc    180 acgcgtgcgg tggtgagcgt gccgattatt ggaattgtga aacgcgatct ggaggattct    240
```

-continued

```
ccggtacgca tcacggccta tattgaagat gttgatgcgc tggcgcaggc gggcgcggac      300
attatcgcca ttgacggcac cgaccgcccg cgtccggtgc ctgttgaaac gctgctggca      360
cgtattcacc atcacggttt actggcgatg accgactgct caacgccgga agacggcctg      420
gcatgccaaa agctgggagc cgaaattatt ggcactacgc tttctggcta taccacgcct      480
gaaacgccag aagagccgga tctggcgctg gtgaaaacgt tgagcgacgc cggatgtcgg      540
gtgattgccg aagggcgtta caacacgcct gctcaggcgg cggatgcgat cgccacggc      600 gcgtgggcgg tgacggtcgg ttctgcaatc acgcgtcttg agcacatttg tcagtggtac      660
aacacagcga tgaaaaaggc ggtgctatga                                       690
```

```
<210> SEQ ID NO 89
<211> LENGTH: 346
<212> TYPE: PRT
<213> ORGANISM: Campylobacter jejuni

<400> SEQUENCE: 89

Met Lys Glu Ile Lys Ile Gln Asn Ile Ile Ile Ser Glu Glu Lys Ala
1               5                   10                  15

Pro Leu Val Val Pro Glu Ile Gly Ile Asn His Asn Gly Ser Leu Glu
            20                  25                  30

Leu Ala Lys Ile Met Val Asp Ala Ala Phe Ser Ala Gly Ala Lys Ile
        35                  40                  45

Ile Lys His Gln Thr His Ile Val Glu Asp Glu Met Ser Lys Ala Ala
    50                  55                  60

Lys Lys Val Ile Pro Gly Asn Ala Lys Ile Ser Ile Tyr Glu Ile Met
65                  70                  75                  80

Gln Lys Cys Ala Leu Asp Tyr Lys Asp Glu Leu Ala Leu Lys Glu Tyr
                85                  90                  95

Thr Glu Lys Leu Gly Leu Val Tyr Leu Ser Thr Pro Phe Ser Arg Ala
            100                 105                 110

Gly Ala Asn Arg Leu Glu Asp Met Gly Val Ser Ala Phe Lys Ile Gly
            115                 120                 125

Ser Gly Glu Cys Asn Asn Tyr Pro Leu Ile Lys His Ile Ala Ala Phe
        130                 135                 140

Lys Lys Pro Met Ile Val Ser Thr Gly Met Asn Ser Ile Glu Ser Ile
145                 150                 155                 160

Lys Pro Thr Val Lys Ile Leu Leu Asp Asn Glu Ile Pro Phe Val Leu
                165                 170                 175

Met His Thr Thr Asn Leu Tyr Pro Thr Pro His Asn Leu Val Arg Leu
            180                 185                 190

Asn Ala Met Leu Glu Leu Lys Lys Glu Phe Ser Cys Met Val Gly Leu
            195                 200                 205

Ser Asp His Thr Thr Asp Asn Leu Ala Cys Leu Gly Ala Val Val Leu
        210                 215                 220

Gly Ala Cys Val Leu Glu Arg His Phe Thr Asp Ser Met His Arg Ser
225                 230                 235                 240

Gly Pro Asp Ile Val Cys Ser Met Asp Thr Lys Ala Leu Lys Glu Leu
                245                 250                 255

Ile Ile Gln Ser Glu Gln Met Ala Ile Ile Arg Gly Asn Asn Glu Ser
            260                 265                 270

Lys Lys Ala Ala Lys Gln Glu Gln Val Thr Ile Asp Phe Ala Phe Ala
        275                 280                 285
```

-continued

```
Ser Val Val Ser Ile Lys Asp Ile Lys Lys Gly Glu Val Leu Ser Met
    290             295             300

Asp Asn Ile Trp Val Lys Arg Pro Gly Leu Gly Gly Ile Ser Ala Ala
305             310             315             320

Glu Phe Glu Asn Ile Leu Gly Lys Lys Ala Leu Arg Asp Ile Glu Asn
                325             330             335

Asp Ala Gln Leu Ser Tyr Glu Asp Phe Ala
            340             345
```

<210> SEQ ID NO 90
<211> LENGTH: 1041
<212> TYPE: DNA
<213> ORGANISM: Campylobacter jejuni

<400> SEQUENCE: 90

```
atgaaagaaa taaaaataca aaatataatc ataagtgaag aaaaagcacc cttagtcgtg      60
cctgaaatag gcattaatca taatggcagt ttagaactag ctaaaattat ggtagatgca     120
gcctttagcg caggtgctaa gattataaag catcaaaccc acatcgttga agatgagatg     180
agtaaggccg ctaaaaaagt aattcctggt aatgcaaaaa taagcattta tgagattatg     240
caaaaatgtg ctttagatta taaagatgag ctagcactta agaatacac agaaaaatta     300 ggtcttgttt atcttagcac accttttct cgtgcaggtg caaaccgctt agaagatatg     360
ggagttagtc tttttaagat tggttcaggt gagtgtaata attatccgct tattaaacac     420
atagcagcct ttaaaaagcc tatgatagtt agcacaggaa tgaatagtat tgaaagtata     480
aaaccaactg taaaaatctt attagacaat gaaattccct ttgtttttaat gcactcgacc     540 aatctttacc caaccccgca taatcttgta agattaaacg ctatgcttga attaaaaaaa     600 gaatttttctt gcatggtagg cttaagcgac cacacaacag ataatcttgc gtgtttaggt     660
gcggttgcac ttggtgcttg tgtgcttgaa agacatttta ctgatagtat gcatagaagt     720
ggccctgata tagtttgttc tatggataca aaggctttaa aagagctaat tatccaaagt     780
gagcaaatgg ctataatgaa aggaaataat gaaagcaaaa aagcagctaa gcaagaacaa     840
gttacaattg atttttgcctt tgcaagcgta gttagcatta agatattaa aaaaggcgaa     900 gttttatcta tggacaatat ctgggttaaa agacctggac ttggtggaat tagtgcggct     960
gaatttgaaa atattttagg caaaaaaagca ttaagagata tagaaaatga tactcagtta    1020
agctatgagg atttttgcgtg a                                             1041
```

<210> SEQ ID NO 91
<211> LENGTH: 221
<212> TYPE: PRT
<213> ORGANISM: Escherichia coli

<400> SEQUENCE: 91

```
Met Ser Leu Ala Ile Ile Pro Ala Arg Gly Gly Ser Lys Gly Ile Lys
1               5               10              15

Asn Lys Asn Leu Val Leu Leu Asn Asn Lys Pro Leu Ile Tyr Tyr Thr
                20              25              30

Ile Lys Ala Ala Leu Asn Ala Lys Ser Ile Ser Lys Val Val Val Ser
        35              40              45

Ser Asp Ser Asp Glu Ile Leu Asn Tyr Ala Lys Ser Gln Asn Val Asp
    50              55              60

Ile Leu Lys Arg Pro Ile Ser Leu Ala Gln Asp Asp Thr Thr Ser Asp
65              70              75              80
```

-continued

```
Lys Val Leu Leu His Ala Leu Lys Phe Tyr Lys Asp Tyr Glu Asp Val
                85                  90                  95

Val Phe Leu Gln Pro Thr Ser Pro Leu Arg Thr Asn Ile His Ile Asn
               100                 105                 110

Glu Ala Phe Asn Leu Tyr Lys Asn Ser Asn Ala Asn Ala Leu Ile Ser
           115                 120                 125

Val Ser Glu Cys Asp Asn Lys Ile Leu Lys Ala Phe Val Cys Asn Asp
       130                 135                 140

Cys Gly Asp Leu Ala Gly Ile Cys Asn Asp Glu Tyr Pro Phe Met Pro
145                 150                 155                 160

Arg Gln Lys Leu Pro Lys Thr Tyr Met Ser Asn Gly Ala Ile Tyr Ile
               165                 170                 175

Leu Lys Ile Lys Glu Phe Leu Asn Asn Pro Ser Phe Leu Gln Ser Lys
           180                 185                 190

Thr Lys His Phe Leu Met Asp Glu Ser Ser Ser Leu Asp Ile Asp Cys
           195                 200                 205

Leu Glu Asp Leu Lys Lys Val Glu Gln Ile Trp Lys Lys
       210                 215                 220
```

<210> SEQ ID NO 92
<211> LENGTH: 666
<212> TYPE: DNA
<213> ORGANISM: Escherichia coli

<400> SEQUENCE: 92

```
atgagcctgg ccattatccc ggcacgtggc ggttctaaag gcatcaaaaa caaaaacctg      60
gttctgctga acaataaacc gctgatttat tacaccatca aagcggccct gaacgccaaa     120
agtattagca aagtggttgt gagctctgat tctgatgaaa tcctgaacta cgcaaaaagt     180
cagaacgttg atatcctgaa acgtccgatc agtctggcac aggatgatac cacgagcgat     240
aaagtgctgc tgcatgcgct gaaattctac aaagattacg aagatgttgt gttcctgcag     300
ccgaccagcc cgctgcgtac gaatattcac atcaacgaag cgttcaacct gtacaaaaac     360
agcaacgcaa acgcgctgat ttctgttagt gaatgcgata acaaaatcct gaaagcgttt     420
gtgtgcaatg attgtggcga tctggccggt atttgtaacg atgaataccc gttcatgccg     480
cgccagaaac tgccgaaaac ctatatgagc aatggtgcca tctacatcct gaaaatcaaa     540
gaattcctga caacccgag cttcctgcag tctaaaacga acatttcct gatggatgaa     600 agtagctctc tggatattga ttgcctggaa gatctgaaaa aagtggaaca gatctggaaa     660
aaataa                                                               666
```

<210> SEQ ID NO 93
<211> LENGTH: 417
<212> TYPE: PRT
<213> ORGANISM: Escherichia coli

<400> SEQUENCE: 93

```
Met Tyr Tyr Leu Lys Asn Thr Asn Phe Trp Met Phe Gly Leu Phe Phe
1               5                  10                  15

Phe Phe Tyr Phe Phe Ile Met Gly Ala Tyr Phe Pro Phe Phe Pro Ile
               20                  25                  30

Trp Leu His Asp Ile Asn His Ile Ser Lys Ser Asp Thr Gly Ile Ile
           35                  40                  45

Phe Ala Ala Ile Ser Leu Phe Ser Leu Leu Phe Gln Pro Leu Phe Gly
       50                  55                  60
```

-continued

```
Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
                85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
            115                 120                 125

Ile Glu Lys Val Ser Arg Arg Ser Asn Phe Glu Phe Gly Arg Ala Arg
        130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Ala Leu Ile Leu Ala Val Leu Leu Phe Phe Ala Lys Thr Asp Ala Pro
                180                 185                 190

Ser Ser Ala Thr Val Ala Asn Ala Val Gly Ala Asn His Ser Ala Phe
            195                 200                 205

Ser Leu Lys Leu Ala Leu Glu Leu Phe Arg Gln Pro Lys Leu Trp Phe
        210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
                245                 250                 255

Gly Thr Arg Val Phe Gly Tyr Val Thr Thr Met Gly Glu Leu Leu Asn
                260                 265                 270

Ala Ser Ile Met Phe Phe Ala Pro Leu Ile Ile Asn Arg Ile Gly Gly
            275                 280                 285

Lys Asn Ala Leu Leu Leu Ala Gly Thr Ile Met Ser Val Arg Ile Ile
        290                 295                 300

Gly Ser Ser Phe Ala Thr Ser Ala Leu Glu Val Val Ile Leu Lys Thr
305                 310                 315                 320

Leu His Met Phe Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
            340                 345                 350

Cys Phe Cys Phe Phe Lys Gln Leu Ala Met Ile Phe Met Ser Val Leu
            355                 360                 365

Ala Gly Asn Met Tyr Glu Ser Ile Gly Phe Gln Gly Ala Tyr Leu Val
        370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415

Ala
```

<210> SEQ ID NO 94
<211> LENGTH: 1254
<212> TYPE: DNA
<213> ORGANISM: Escherichia coli

<400> SEQUENCE: 94
atgtactatt taaaaaacac aaacttttgg atgttcggtt tattcttttt cttttacttt      60
tttatcatgg gagcctactt cccgttttc ccgatttggc tacatgacat caaccatatc     120

-continued

```
agcaaaagtg atacgggtat tattttttgcc gctatttctc tgttctcgct attattccaa      180
ccgctgtttg gtctgctttc tgacaaactc gggctgcgca aatacctgct gtggattatt      240
accggcatgt tagtgatgtt tgcgccgttc tttattttta tcttcgggcc actgttacaa      300
tacaacattt tagtaggatc gattgttggt ggtatttatc taggcttttg ttttaacgcc      360
ggtgcgccag cagtagaggc atttattgag aaagtcagcc gtcgcagtaa tttcgaattt      420
ggtcgcgcgc ggatgtttgg ctgtgttggc tgggcgctgt gtgcctcgat tgtcggcatc      480
atgttcacca tcaataatca gtttgttttc tggctgggct ctggctgtgc actcatcctc      540
gccgttttac tctttttcgc caaaacggat gcgccctctt ctgccacggt tgccaatgcg      600
gtaggtgcca accattcggc atttagcctt aagctggcac tggaactgtt cagacagcca      660
aaactgtggt ttttgtcact gtatgttatt ggcgtttcct gcacctacga tgtttttgac      720
caacagtttg ctaatttctt tacttcgttc tttgctaccg gtgaacaggg tacgcgggta      780
tttggctacg taacgacaat gggcgaatta cttaacgcct cgattatgtt ctttgcgcca      840
ctgatcatta atcgcatcgg tgggaaaaac gccctgctgc tggctggcac tattatgtct      900
gtacgtatta ttggctcatc gttcgccacc tcagcgctgg aagtggttat tctgaaaacg      960
ctgcatatgt ttgaagtacc gttcctgctg gtgggctgct ttaaatatat taccagccag     1020
tttgaagtgc gtttttcagc gacgatttat ctggtctgtt tctgcttctt taagcaactg     1080
gcgatgattt ttatgtctgt actggcgggc aatatgtatg aaagcatcgg tttccagggc     1140
gcttatctgg tgctgggtct ggtggcgctg ggcttcacct taatttccgt gttcacgctt     1200
agcggccccg gtccgctttc tctactgcgt cgtcaggtga atgaagtcgc ttaa           1254
```

<210> SEQ ID NO 95
<211> LENGTH: 1024
<212> TYPE: PRT
<213> ORGANISM: Escherichia coli

<400> SEQUENCE: 95

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175
```

-continued

```
Phe Leu Arg Ala Gly Glu Asn Arg Leu Ala Val Met Val Leu Arg Trp
        180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
        210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
                260                 265                 270

Ala Pro Phe Gly Gly Glu Ile Ile Asp Glu Arg Gly Gly Tyr Ala Asp
            275                 280                 285

Arg Val Thr Leu Arg Leu Asn Val Glu Asn Pro Lys Leu Trp Ser Ala
        290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
        370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
        435                 440                 445

Arg Asn His Pro Ser Val Ile Ile Trp Ser Leu Gly Asn Glu Ser Gly
        450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
        515                 520                 525

Gly Glu Thr Arg Pro Leu Ile Leu Cys Glu Tyr Ala His Ala Met Gly
        530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
            565                 570                 575

Ile Lys Tyr Asp Glu Asn Gly Asn Pro Trp Ser Ala Tyr Gly Gly Asp
            580                 585                 590
```

-continued

```
Phe Gly Asp Thr Pro Asn Asp Arg Gln Phe Cys Met Asn Gly Leu Val
        595             600             605

Phe Ala Asp Arg Thr Pro His Pro Ala Leu Thr Glu Ala Lys His Gln
        610             615             620

Gln Gln Phe Phe Gln Phe Arg Leu Ser Gly Gln Thr Ile Glu Val Thr
625             630             635             640

Ser Glu Tyr Leu Phe Arg His Ser Asp Asn Glu Leu Leu His Trp Met
            645             650             655

Val Ala Leu Asp Gly Lys Pro Leu Ala Ser Gly Glu Val Pro Leu Asp
            660             665             670

Val Ala Pro Gln Gly Lys Gln Leu Ile Glu Leu Pro Glu Leu Pro Gln
            675             680             685

Pro Glu Ser Ala Gly Gln Leu Trp Leu Thr Val Arg Val Val Gln Pro
        690             695             700

Asn Ala Thr Ala Trp Ser Glu Ala Gly His Ile Ser Ala Trp Gln Gln
705             710             715             720

Trp Arg Leu Ala Glu Asn Leu Ser Val Thr Leu Pro Ala Ala Ser His
            725             730             735

Ala Ile Pro His Leu Thr Thr Ser Glu Met Asp Phe Cys Ile Glu Leu
            740             745             750

Gly Asn Lys Arg Trp Gln Phe Asn Arg Gln Ser Gly Phe Leu Ser Gln
            755             760             765

Met Trp Ile Gly Asp Lys Lys Gln Leu Leu Thr Pro Leu Arg Asp Gln
    770             775             780

Phe Thr Arg Ala Pro Leu Asp Asn Asp Ile Gly Val Ser Glu Ala Thr
785             790             795             800

Arg Ile Asp Pro Asn Ala Trp Val Glu Arg Trp Lys Ala Ala Gly His
            805             810             815

Tyr Gln Ala Glu Ala Ala Leu Leu Gln Cys Thr Ala Asp Thr Leu Ala
            820             825             830

Asp Ala Val Leu Ile Thr Thr Ala His Ala Trp Gln His Gln Gly Lys
            835             840             845

Thr Leu Phe Ile Ser Arg Lys Thr Tyr Arg Ile Asp Gly Ser Gly Gln
    850             855             860

Met Ala Ile Thr Val Asp Val Glu Val Ala Ser Asp Thr Pro His Pro
865             870             875             880

Ala Arg Ile Gly Leu Asn Cys Gln Leu Ala Gln Val Ala Glu Arg Val
            885             890             895

Asn Trp Leu Gly Leu Gly Pro Gln Glu Asn Tyr Pro Asp Arg Leu Thr
            900             905             910

Ala Ala Cys Phe Asp Arg Trp Asp Leu Pro Leu Ser Asp Met Tyr Thr
            915             920             925

Pro Tyr Val Phe Pro Ser Glu Asn Gly Leu Arg Cys Gly Thr Arg Glu
    930             935             940

Leu Asn Tyr Gly Pro His Gln Trp Arg Gly Asp Phe Gln Phe Asn Ile
945             950             955             960

Ser Arg Tyr Ser Gln Gln Gln Leu Met Glu Thr Ser His Arg His Leu
            965             970             975

Leu His Ala Glu Glu Gly Thr Trp Leu Asn Ile Asp Gly Phe His Met
            980             985             990

Gly Ile Gly Gly Asp Asp Ser Trp  Ser Pro Ser Val Ser  Ala Glu Phe
        995             1000            1005

Gln Leu  Ser Ala Gly Arg Tyr  His Tyr Gln Leu Val  Trp Cys Gln
```

1010 1015 1020

Lys

<210> SEQ ID NO 96
<211> LENGTH: 3075
<212> TYPE: DNA
<213> ORGANISM: Escherichia coli

<400> SEQUENCE: 96
atgaccatga ttacggattc actggccgtc gttttacaac gtcgtgactg ggaaaaccct 60
ggcgttaccc aacttaatcg ccttgcagca catccccctt tcgccagctg gcgtaatagc 120
gaagaggccc gcaccgatcg cccttcccaa cagttgcgca gcctgaatgg cgaatggcgc 180
tttgcctggt ttccggcacc agaagcggtg ccggaaagct ggctggagtg cgatcttcct 240
gaggccgata ctgtcgtcgt cccctcaaac tggcagatgc acggttacga tgcgcccatc 300
tacaccaacg tgacctatcc cattacggtc aatccgccgt ttgttcccac ggagaatccg 360
acgggttgtt actcgctcac atttaatgtt gatgaaagct ggctacagga aggccagacg 420
cgaattattt ttgatggcgt taactcggcg tttcatctgt ggtgcaacgg gcgctgggtc 480
ggttacggcc aggacagtcg tttgccgtct gaatttgacc tgagcgcatt tttacgcgcc 540
ggagaaaacc gcctcgcggt gatggtgctg cgctggagtg acggcagtta tctggaagat 600
caggatatgt ggcggatgag cggcattttc cgtgacgtct cgttgctgca taaaccgact 660
acacaaatca gcgatttcca tgttgccact cgctttaatg atgatttcag ccgcgctgta 720
ctggaggctg aagttcagat gtgcggcgag ttgcgtgact acctacgggt aacagtttct 780
ttatggcagg gtgaaacgca ggtcgccagc ggcaccgcgc ctttcggcgg tgaaattatc 840
gatgagcgtg gtggttatgc cgatcgcgtc acactacgtc tgaacgtcga aaacccgaaa 900
ctgtggagcg ccgaaatccc gaatctctat cgtgcggtgg ttgaactgca caccgccgac 960
ggcacgctga ttgaagcaga agcctgcgat gtcggtttcc gcgaggtgcg gattgaaaat 1020
ggtctgctgc tgctgaacgg caagccgttg ctgattcgag gcgttaaccg tcacgagcat 1080
catcctctgc atggtcaggt catggatgag cagacgatgg tgcaggatat cctgctgatg 1140
aagcagaaca actttaacgc cgtgcgctgt tcgcattatc cgaaccatcc gctgtggtac 1200
acgctgtgcg accgctacgg cctgtatgtg gtggatgaag ccaatattga aacccacggc 1260
atggtgccaa tgaatcgtct gaccgatgat ccgcgctggc taccggcgat gagcgaacgc 1320
gtaacgcgaa tggtgcagcg cgatcgtaat cacccgagtg tgatcatctg gtcgctgggg 1380
aatgaatcag gccacggcgc taatcacgac gcgctgtatc gctggatcaa atctgtcgat 1440
ccttcccgcc cggtgcagta tgaaggcggc ggagccgaca ccacggccac cgatattatt 1500
tgcccgatgt acgcgcgcgt ggatgaagac cagcccttcc cggctgtgcc gaaatggtcc 1560
atcaaaaaat ggctttcgct acctggagag acgcgcccgc tgatcctttg cgaatacgcc 1620
cacgcgatgg gtaacagtct tggcggtttc gctaaatact ggcaggcgtt tcgtcagtat 1680
ccccgtttac agggcggctt cgtctgggac tgggtggatc agtcgctgat taaatatgat 1740
gaaaacggca acccgtggtc ggcttacggc ggtgattttg gcgatacgcc gaacgatcgc 1800
cagttctgta tgaacggtct ggtctttgcc gaccgcacgc cgcatccagc gctgacggaa 1860
gcaaaacacc agcagcagtt tttccagttc cgtttatccg ggcaaaccat cgaagtgacc 1920
agcgaatacc tgttccgtca tagcgataac gagctcctgc actggatggt ggcgctggat 1980
ggtaagccgc tggcaagcgg tgaagtgcct ctggatgtcg ctccacaagg taaacagttg 2040

-continued

```
attgaactgc ctgaactacc gcagccggag agcgccgggc aactctggct cacagtacgc      2100
gtagtgcaac cgaacgcgac cgcatggtca gaagccggac acatcagcgc ctggcagcag      2160
tggcgtctgg ctgaaaacct cagcgtgaca ctccccgccg cgtcccacgc catcccgcat      2220
ctgaccacca gcgaaatgga ttttgcatc gagctgggta ataagcgttg gcaatttaac      2280
cgccagtcag gctttctttc acagatgtgg attggcgata aaaaacaact gctgacgccg      2340
ctgcgcgatc agttcacccg tgcaccgctg gataacgaca ttggcgtaag tgaagcgacc      2400
cgcattgacc ctaacgcctg ggtcgaacgc tggaaggcgg cgggccatta ccaggccgaa      2460
gcagcgttgt tgcagtgcac ggcagataca cttgctgatg cggtgctgat tacgaccgct      2520
cacgcgtggc agcatcaggg gaaaaccta tttatcagcc ggaaaaccta ccggattgat      2580
ggtagtggtc aaatggcgat taccgttgat gttgaagtgg cgagcgatac accgcatccg      2640
gcgcggattg gcctgaactg ccagctggcg caggtagcag agcgggtaaa ctggctcgga      2700
ttagggccgc aagaaaacta tcccgaccgc cttactgccg cctgtttga ccgctgggat      2760 ctgccattgt cagacatgta tacccgtac gtcttcccga gcgaaaacgg tctgcgctgc      2820
gggacgcgcg aattgaatta tggcccacac cagtggcgcg cgacttcca gttcaacatc      2880 agccgctaca gtcaacagca actgatggaa accagccatc gccatctgct gcacgcggaa      2940
gaaggcacat ggctgaatat cgacggtttc catatgggga ttggtggcga cgactcctgg      3000
agcccgtcag tatcggcgga attccagctg agcgccggtc gctaccatta ccagttggtc      3060
tggtgtcaaa aataa                                                        3075
```

<210> SEQ ID NO 97
<211> LENGTH: 3123
<212> TYPE: DNA
<213> ORGANISM: Artificial Sequence
<220> FEATURE:
<223> OTHER INFORMATION: Expression cassette

<400> SEQUENCE: 97

```
ctgtctctta tacacatctc cggccagatg attaattcct aattttttgtt gacactctat       60 cattgataga gttattttac cactccctat cagtgataga gaaaagtgaa atgaatagtt      120
cgacaaaaat ctagaaataa ttttgtttaa ctttaagaag gagatataca aatgatcgct      180
caccgtcgtc aggaactggc tcaacagtat tatcaggctc tgcaccaaga tgtgctgccg      240
ttctgggaaa agtattcgct ggatcgtcaa ggcggtggct attttacctg cctggaccgc      300
aagggtcagt tttttgatac ggacaagttc atttggctgc aaaaccgtca agtgtggcaa      360
tttgcggttt tctacaatcg cctggaaccg aaaccgcagt ggctggaaat cgctcgtcat      420
ggtgcggatt ttctggcacg tcacggtcgt gatcaggacg gtaactggta tttcgccctg      480
gatcaggaag gcaaaccgct gcgccaaccg tacaatgtgt tttccgactg tttcgcggcg      540
atggcgttta gccagtatgc actggcttct ggtgctcaag aagcgaaggc cattgcactg      600
caagcgtata acaatgttct gcgtcgccag cataacccga aaggtcaata tgaaaagagt      660 taccccgggta cccgtccgct gaaatccctg gcagtgccga tgatcctggc taatctgacg      720
ctggaaatgg aatggctgct gccgccgacc acggtcgaag aagtgctggc ccagaccgtt      780
cgtgaagtca tgacggattt tctggacccg gaaattggcc tgatgcgcga agcagttacc      840
ccgacgggtg aatttgtcga ttcattcgaa ggccgcctgc tgaacccggg tcatggcatt      900
gaagcgatgt ggtttatgat ggatattgcc cagcgttcgg gtgaccgcca gctgcaagaa      960
```

```
caggctattg cggtggttct gaatacccctg gaatatgcat gggatgaaga atttggtggc      1020
atcttttact tcctggaccg tcaaggtcac ccgccgcagc aactggaatg ggatcagaaa      1080
ctgtggtggg tccatctgga aaccctggtg gccctggcaa aaggtcacca ggcgacgggc      1140
caagaaaagt gctggcagtg gtttgaacgc gtgcatgatt atgcatggag ccactttgct      1200
gacccggaat atggtgaatg gttcggctac ctgaaccgtc gcggtgaagt gctgctgaat      1260
ctgaaaggtg gcaaatggaa gggctgcttc cacgttccgc gtgcgctgtg gctgtgtgcc      1320
gaaaccctgc aactgccggt ctcttaataa tcgaaggaga tacaacatga gcttacccga      1380
tggattttat ataaggcgaa tggaagaggg ggatttggaa caggtcactg agacgctaaa      1440
ggttttgacc accgtgggca ctattacccc cgaatccttc agcaaactca taaaatactg      1500
gaatgaagcc acagtatgga atgataacga agataaaaaa ataatgcaat ataaccccat      1560
ggtgattgtg gacaagcgca ccgagacggt tgccgctacg gggaatatca tcatcgaaag      1620
aaagatcatt catgaactgg ggctatgtgg ccacatcgag gacattgcag taaactccaa      1680
gtatcagggc caaggtttgg gcaagctctt gattgatcaa ttggtaacta tcggctttga      1740
ctacggttgt tataagatta tttttagattg cgatgagaaa aatgtcaaat tctatgaaaa      1800
atgtgggttt agcaacgcag gcgtggaaat gcaaattaga aaatagaata actagcataa      1860
acccccttgg ggcctctaaa cgggtcttga ggggttttttt gctgaaacca atttgcctgg      1920
cggcagtagc gcggtggtcc cacctgaccc catgccgaac tcagaagtga aacgccgtag      1980
cgccgatggt agtgtgggggt ctccccatgc gagagtaggg aactgccagg catcaaataa      2040
aacgaaaggc tcagtcgaaa gactgggcct ttcgggatcc aggccggcct gttaagacgg      2100
ccagtgaatt cgagctcggt acctaccgtt cgtataatgt atgctatacg aagttatcga      2160
gctctagaga atgatcccct cattaggcca cacgttcaag tgcagcgcac accgtggaaa      2220
cggatgaagg cacgaaccca gttgacataa gcctgttcgg ttcgtaaact gtaatgcaag      2280
tagcgtatgc gctcacgcaa ctggtccaga accttgaccg aacgcagcgg tggtaacggc      2340
gcagtggcgg ttttcatggc ttgttatgac tgttttttttg tacagtctat gcctcgggca      2400
tccaagcagc aagcgcgtta cgccgtgggt cgatgtttga tgttatggag cagcaacgat      2460
gttacgcagc agcaacgatg ttacgcagca gggcagtcgc cctaaaacaa agttaggtgg      2520
ctcaagtatg ggcatcattc gcacatgtag gctcggccct gaccaagtca aatccatgcg      2580
ggctgctctt gatcttttttcg gtcgtgagtt cggagacgta gccacctact cccaacatca      2640
gccggactcc gattacctcg ggaacttgct ccgtagtaag acattcatcg cgcttgctgc      2700
cttcgaccaa gaagcggttg ttggcgctct cgcggcttac gttctgccca ggtttgagca      2760
gccgcgtagt gagatctata tctatgatct cgcagtctcc ggcgagcacc ggaggcaggg      2820
cattgccacc gcgctcatca atctcctcaa gcatgaggcc aacgcgcttg gtgcttatgt      2880
gatctacgtg caagcagatt acggtgacga tcccgcagtg gctctctata caaagttggg      2940
catacgggaa gaagtgatgc actttgatat cgacccaagt accgccacct aacaattcgt      3000
tcaagccgag atcgtagaat ttcgacgacc tgcagccaag cataacttcg tataatgtat      3060
gctatacgaa cggtaggatc ctctagagtc gacctgcagg catgagatgt gtataagaga      3120
cag                                                                   3123
```

<210> SEQ ID NO 98
<211> LENGTH: 2965
<212> TYPE: DNA
<213> ORGANISM: Artificial Sequence
<220> FEATURE:
<223> OTHER INFORMATION: Expression cassette

<400> SEQUENCE: 98

```
ctgtctctta tacacatctc cggccagatg attaattcct aattttttgtt gacactctat      60 cattgataga gttattttac cactccctat cagtgataga gaaaagtgaa atgaatagtt     120
cgacaaaaat ctagaaataa ttttgtttaa ctttaagaag gagatataca aatgaaagaa     180
atcaaaatcc agaacatcat catcagcgaa gaaaaagcgc cgctggttgt gccggaaatc     240
ggcattaacc ataatggtag tctggaactg gcaaaaatca tggtggatgc ggcctttagc     300
gccggtgcaa aaatcattaa acatcagacc cacattgtgg aagatgaaat gtctaaagca     360
gcgaaaaaag ttatcccggg caacgcgaaa atcagtatct acgaaatcat gcagaaatgc     420
gcgctggatt acaaagatga actggccctg aaagaatata ccgaaaaact gggtctggtg     480
tacctgtcta ccccgtttag tcgtgcgggt gcaaaccgtc tggaagatat gggtgttagt     540
gcgttcaaaa tcggcagcgg tgaatgtaac aattatccgc tgatcaaaca tattgccgca     600
tttaaaaaac cgatgattgt tagcaccggc atgaatagca tcgaatctat taaaccgacg     660
gtgaaaatcc tgctggataa cgaaattccg tttgttctga tgcataccac gaatctgtac     720 ccgacccccgc acaacctggt gcgtctgaat gccatgctgg aactgaaaaa agaattctct     780
tgcatggttg gtctgagtga tcacaccacg gataatctgg catgcctggg tgcagtggtt     840
ctgggtgcgt gtgtgctgga acgtcatttc accgatagca tgcaccgctc tggtccggat     900
attgtttgta gtatggatac gaaagcactg aaagaactga tcattcagag cgaacagatg     960
gcgatcattc gcggcaacaa tgaatctaaa aaagcggcca acaggaaca ggtgaccatc    1020 gattttgcat cgcgagtgt ggttagcatc aaagatatca aaaaaggcga agtgctgagc    1080
atggataata tttgggttaa acgtccgggt ctgggcggta tctctgcagc ggaatttgaa    1140
aacattctgg gcaaaaaagc actgcgcgat attgaaaatg atgcgcagct gtcttatgaa    1200
gatttcgcct aataaatcga tactagcata accccttggg gcctctaaac gcgtcgacac    1260
gcaaaaaggc catccgtcag gatggccttc tgcttaattt gatgcctggc agtttatggc    1320
gggcgtcctg cccgccaccc tccgggccgt tgcttcgcaa cgttcaaatc cgctcccggc    1380
ggatttgtcc tactcaggag agcgttcacc gacaaacaac agataaaacg aaaggcccag    1440
tctttcgact gagcctttcg ttttatttga tgcctggcag ttccctactc tcgcatgggg    1500 agacccccaca ctaccatccg gtatcgataa gcttgatggc gaagggggga tgtgctgcaa    1560
ggcgattaag ttgggtaacg ccagggtttt cccagtcacg acgttgtaaa acgacggcca    1620
gtgaattcga gctcggtacc taccgttcgt ataatgtatg ctatacgaag ttatcgagct    1680
ctagagaatg atccctccc tcacgctgcc gcaagcactc agggcgcaag gctgctaaa    1740 ggaagcggaa cacgtagaaa gccagtccgc agaaacggtg ctgaccccgg atgaatgtca    1800
gctactgggc tatctggaca agggaaaacg caagcgcaaa gagaaagcag gtagcttgca    1860
gtgggcttac atggcgatag ctagactggg cggttttatg gacagcaagc gaaccggaat    1920
tgccagctgg ggcgccctct ggtaaggttg ggaagccctg caaagtaaac tggatggctt    1980
tcttgccgcc aaggatctga tggcgcaggg gatcaagatc tgatcaagag acaggatgag    2040
gatcgtttcg catgattgaa caagatggat tgcacgcagg ttctccggcc gcttgggtgg    2100
agaggctatt cggctatgac tgggcacaac agacaatcgg ctgctctgat gccgccgtgt    2160
tccggctgtc agcgcagggg cgcccggttc tttttgtcaa gaccgacctg tccggtgccc    2220
```

```
tgaatgaact gcaggacgag gcagcgcggc tatcgtggct ggccacgacg ggcgttcctt      2280
gcgcagctgt gctcgacgtt gtcactgaag cgggaaggga ctggctgcta ttgggcgaag      2340
tgccggggca ggatctcctg tcatctcacc ttgctcctgc cgagaaagta tccatcatgg      2400
ctgatgcaat gcggcggctg catacgcttg atccggctac ctgcccattc gaccaccaag      2460
cgaaacatcg catcgagcga gcacgtactc ggatggaagc cggtcttgtc gatcaggatg      2520
atctggacga agagcatcag gggctcgcgc cagccgaact gttcgccagg ctcaaggcgc      2580
gcatgcccga cggcgaggat ctcgtcgtga cccatggcga tgcctgcttg ccgaatatca      2640
tggtggaaaa tggccgcttt tctggattca tcgactgtgg ccggctgggt gtggcggacc      2700
gctatcagga catagcgttg gctacccgtg atattgctga gagcttggc ggcgaatggg      2760 ctgaccgctt cctcgtgctt tacggtatcg ccgctcccga ttcgcagcgc atcgccttct      2820
atcgccttct tgacgagttc ttctgagcgg gactctggga atttcgacga cctgcagcca      2880
agcataactt cgtataatgt atgctatacg aacggtagga tcctctagag tcgacctgca      2940
ggcatgagat gtgtataaga gacag                                            2965
```

```
<210> SEQ ID NO 99
<211> LENGTH: 3904
<212> TYPE: DNA
<213> ORGANISM: Artificial Sequence
<220> FEATURE:
<223> OTHER INFORMATION: Expression cassette

<400> SEQUENCE: 99
ctgtctctta tacacatctc cggccagatg attaattcct aattttttgtt gacactctat      60 cattgataga gttattttac cactccctat cagtgataga gaaaagtgaa atgaatagtt      120
cgacaaaaat ctagaaataa tttttgtttaa ctttaagaag gagatataca aatgatcgct      180
caccgtcgtc aggaactggc tcaacagtat tatcaggctc tgcaccaaga tgtgctgccg      240
ttctgggaaa agtattcgct ggatcgtcaa ggcggtggc attttacctg cctgaccgc      300 aagggtcagg tttttgatac ggacaagttc atttggctgc aaaaccgtca agtgtggcaa      360
tttgcggttt tctacaatcg cctggaaccg aaaccgcagt ggctggaaat cgctcgtcat      420
ggtgcggatt ttctggcacg tcacggtcgt gatcaggacg gtaactggta tttcgccctg      480
gatcaggaag gcaaaccgct cgcgccaaccg tacaatgtgt tttccgactg tttcgcggcg      540 atggcgtta gccagtatgc actggcttct ggtgctcaag aagcgaaggc cattgcactg      600
caagcgtata acaatgttct gcgtcgccag cataacccga aaggtcaata tgaaaagagt      660 taccgggta cccgtccgct gaaatccctg gcagtgccga tgatcctggc taatctgacg      720
ctggaaatgg aatggctgct gccgccgacc acgtcgaag aagtgctggc ccagaccgtt      780
cgtgaagtca tgacggattt tctggacccg gaaattggcc tgatgcgcga agcagttacc      840
ccgacgggtg aatttgtcga ttcattcgaa ggccgcctgc tgaacccggg tcatggcatt      900
gaagcgatgt ggtttatgat ggatattgcc cagcgttcgg gtgaccgcca gctgcaagaa      960
caggctattg cggtggttct gaatacccctg gaatatgcat gggatgaaga atttggtggc      1020
atcttttact tcctggaccg tcaaggtcac ccgccgcagc aactggaatg ggatcagaaa      1080
ctgtggtggg tccatctgga aaccctggtg gccctggcaa aaggtcacca ggcgacgggc      1140
caagaaaagt gctggcagtg gtttgaacgc gtgcatgatt atgcatggag ccactttgct      1200
gacccggaat atggtgaatg gttcggctac ctgaaccgtc gcggtgaagt gctgctgaat      1260
ctgaaaggtg gcaaatggaa gggctgcttc cacgttccgc gtgcgctgtg gctgtgtgcc      1320
```

-continued

```
gaaaccctgc aactgccggt ctcttaattt cgtcgacaca caggaaacat attaaaaatt    1380
aaaacctgca ggagtttaaa cgcggccgcg atatcgttgt aaaacgacgg ccagtgcaag    1440
aatcataaaa aatttatttg ctttcaggaa aatttttctg tataatagat tcataaattt    1500
gagagaggag tttttgtgag cggataacaa ttccccatct tagtatatta gttaagtata    1560
aatacacaag gagatataca tatgaaagaa atcaaaatcc agaacatcat catcagcgaa    1620
gaaaaagcgc cgctggttgt gccggaaatc ggcattaacc ataatggtag tctggaactg    1680
gcaaaaatca tggtggatgc ggcctttagc gccggtgcaa aaatcattaa acatcagacc    1740
cacattgtgg aagatgaaat gtctaaagca gcgaaaaaag ttatcccggg caacgcgaaa    1800
atcagtatct acgaaatcat gcagaaatgc gcgctggatt acaaagatga actggccctg    1860
aaagaatata ccgaaaaact gggtctggtg tacctgtcta ccccgtttag tcgtgcgggt    1920 gcaaccgtc tggaagatat gggtgttagt gcgttcaaaa tcggcagcgg tgaatgtaac    1980
aattatccgc tgatcaaaca tattgccgca tttaaaaaac cgatgattgt tagcaccggc    2040
atgaatagca tcgaatctat taaaccgacg gtgaaaatcc tgctggataa cgaaattccg    2100
tttgttctga tgcataccac gaatctgtac ccgacccccgc acaacctggt gcgtctgaat    2160
gccatgctgg aactgaaaaa agaattctct tgcatggttg gtctgagtga tcacaccacg    2220
gataatctgg catgcctggg tgcagtggtt ctgggtgcgt gtgtgctgga acgtcatttc    2280
accgatagca tgcaccgctc tggtccggat attgtttgta gtatggatac gaaagcactg    2340
aaagaactga tcattcagag cgaacagatg gcgatcattc gcggcaacaa tgaatctaaa    2400
aaagcggcca acaggaaca ggtgaccatc gattttgcat cgcgagtgt ggttagcatc    2460 aaagatatca aaaaggcga agtgctgagc atggataata tttgggttaa acgtccgggt    2520
ctgggcggta tctctgcagc ggaatttgaa aacattctgg gcaaaaaagc actgcgcgat    2580
attgaaaatg atgcgcagct gtcttatgaa gatttcgcct aaaataacta gcataacccc    2640
ttggggcctc taaacgggtc ttgaggggtt ttttgctgaa accaatttgc ctggcggcag    2700
tagcgcggtg gtcccacctg accccatgcc gaactcagaa gtgaaacgcc gtagcgccga    2760
tggtagtgtg gggtctcccc atgcgagagt agggaactgc caggcatcaa ataaaacgaa    2820
aggctcagtc gaaagactgg gcctttcggg atccaggccg gcctgttaac gaattaatct    2880
tccgcggcgg tatcgataag cttgatatcg aattccgaag ttcctattct ctagaaagta    2940
taggaacttc aggtctgaag aggagtttac gtccagccaa gctagcttgg ctgcaggtcg    3000
tcgaaattct accgggtagg ggaggcgctt ttcccaaggc agtctggagc atgcgcttta    3060 gcagcccgc tgggcacttg gcgctacaca agtggcctct ggcctcgcac acattccaca    3120
tccaccggta ggcgccaacc ggctccgttc tttggtggcc ccttcgcgcc accttctact    3180
cctcccctag tcaggaagtt cccccccgcc ccgcagctcg cgtcgtgcag gacgtgacaa    3240
atggaagtag cacgtctcac tagtctcgtg cagatggaca gcaccgctga gcaatggaag    3300
cgggtaggcc tttgggggcag cggccaatag cagctttgct ccttcgcttt ctgggctcag    3360
gggcgggctc aggggggcggg gcgggcgccc gaaggtcctc cggaggcccg gcattctgca    3420
cgcttcaaaa gcgcacgtct gccgcgctgt tctcctcttc ctcatctccg ggcctttcga    3480
cctgcagcct gttgacaatt aatcatcggc atagtatatc ggcatagtat aatacgacaa    3540
ggtgaggaac taaaccatgg gtcaaagtag cgatgaagcc aacgctcccg ttgcagggca    3600
gtttgcgctt cccctgagtg ccacctttgg cttaggggat cgcgtacgca agaaatctgg    3660
```

-continued

```
tgccgcttgg cagggtcaag tcgtcggttg gtattgcaca aaactcactc ctgaaggcta    3720
tgcggtcgag tccgaatccc acccaggctc agtgcaaatt tatcctgtgg ctgcacttga    3780
acgtgtggcc taatgagggg atcaattctc tagagctcgc tgatcagaag ttcctattct    3840
ctagaaagta taggaacttc gatggcgcct catccctgaa gccaaagatg tgtataagag    3900
acag                                                                 3904

<210> SEQ ID NO 100
<211> LENGTH: 3793
<212> TYPE: DNA
<213> ORGANISM: Artificial Sequence
<220> FEATURE:
<223> OTHER INFORMATION: Expression cassette

<400> SEQUENCE: 100
ctgtctctta tacacatctc cggccagatg attaattcct aatttttgtt gacactctat      60
cattgataga gttattttac cactccctat cagtgataga gaaaagtgaa atgaatagtt     120
cgacaaaaat ctagaaataa ttttgtttgg cgtcgagaag gagatagaaa atgtgcggta     180
tcgttggtgc tatcgcacag cgtgatgtag cgaaaatcct cctggaaggt ctgcgtcgtc     240
tcgaataccg tggttacgac tctgccggtc tggcagtagt ggatgcagaa ggtcacatga     300
ctcgtctgcg tcgtctgggt aaagtgcaga tgctcgcgca ggcggcggaa gaacacccac     360
tccacggtgg tacgggtatc gcacacactc gttgggcaac ccacggtgaa ccgtctgagg     420
tcaacgcaca cccgcatgtt agcgagcaca tcgtagtcgt tcacaacggt atcatcgaga     480
accacgaacc actccgtgag gaactcaaag cccgtggtta caccttcgta agcgaaaccg     540
acacggaagt tatcgcccac ctcgttaact gggaactcaa acagggtggt actctgcgtg     600
aagcagttct gcgtgccatt ccacagctgc gtggtgcata cggtaccgtg atcatggact     660
ctcgtcatcc ggatacccctg ctcgccgcac gttctggttc tccactcgtt atcggtctgg     720
gtatgggtga gaacttcatc gcctctgatc agctggccct gctcccagtt acccgtcgct     780
tcatcttcct ggaagagggt gacatcgccg aaatcacccg tcgttccgtt aacatcttcg     840
acaaaacggg tgcggaagtt aaacgtcagg acatcgagtc taacctgcag tatgacgctg     900
gtgacaaagg catctaccgt cactacatgc agaaagagat ctacgaacag ccgaacgcga     960
tcaaaaacac cctgaccggt cgtatctctc acggtcaggt tgacctgtct gagctgggtc    1020
caaacgcgga cgaactcctg tccaaagtcg agcacatcca gatcctggct tgtggtacct    1080
cttacaactc cggtatggtt tctcgttact ggttcgaatc tctggcaggt atcccatgcg    1140
acgttgaaat cgcctccgaa ttccgttatc gtaaatctgc ggtacgtcgt aactccctca    1200 tgatcacccct gtctcagtct ggtgaaaccg ctgatactct ggcaggtctg cgtctcagca    1260
aagaactggg ttacctgggt tctctggcca tctgcaacgt tccgggttct agcctggttc    1320
gtgagtctgt gctggctctg atgaccaacg cgggtacgga gatcggtgtt gcctctacca    1380
aagcgttcac tacccagctc actgtcctgc tgatgctggt tgccaaactg tctcgtctca    1440
aaggcctcga cgctagcatc gaacacgaca tcgtacacgg tctgcaggcc ctcccatctc    1500
gtatcgagca gatgctgccg caggacaaac gtatcgaagc actggcagaa gacttcagcg    1560
acaaacacca cgcgctgttt ctgggtcgtg gtgaccagta cccaattgcg ctggaaggtg    1620
ccctgaaact gaaagagatc agctacatcc atgcagaggc atacgcagcg ggtgagctga    1680
aacatggtcc actggccctg atcgacgcag atatgccggt tattgtggtt gctccgaaca    1740
acggcctgct ggagaaactg aaatccaaca tcgaggaagt acgtgcgcgt ggtggtcagc    1800
```

```
tgtacgtgtt tgctgaccag gacgcgggtt tcgtttccag cgacaacatg cacatcatcg        1860
aaatgccgca tgttgaagag gtaatcgcgc caatcttcta caccgtaccg ctgcagctgc        1920
tggcgtacca tgtagccctg atcaaaggta cggacgttga ccagccgcgt aacctggcga        1980
aatccgtgac cgtggaataa cgaaggagat agaaccatga gcttacccga tggattttat        2040
ataaggcgaa tggaagaggg ggatttggaa caggtcactg agacgctaaa ggttttgacc        2100
accgtgggca ctattacccc cgaatccttc agcaaactca taaatactg gaatgaagcc         2160 acagtatgga atgataacga agataaaaaa ataatgcaat ataaccccat ggtgattgtg        2220
gacaagcgca ccgagacggt tgccgctacg gggaatatca tcatcgaaag aaagatcatt        2280
catgaactgg ggctatgtgg ccacatcgag gacattgcag taaactccaa gtatcagggc        2340
caaggtttgg gcaagctctt gattgatcaa ttggtaacta tcggctttga ctacggttgt        2400
tataagatta ttttagattg cgatgagaaa aatgtcaaat tctatgaaaa atgtgggttt        2460
agcaacgcag gcgtggaaat gcaaattaga aaatagcatc cgtatcggaa acactagcat        2520
aaccccttgg ggcctctaaa cgggtcttga ggggtttttt gctgaaacca atttgcctgg        2580
cggcagtagc gcggtggtcc cacctgaccc catgccgaac tcagaagtga aacgccgtag        2640
cgccgatggt agtgtggggt ctccccatgc gagagtaggg aactgccagg catcaaataa        2700
aacgaaaggc tcagtcgaaa gactgggcct ttcgcttcca caactttgta taataaagtt        2760
gtccccacgg ccagtgaatt cgagctcggt acctaccgtt cgtataatgt atgctatacg        2820
aagttatcga gctctagaga atgatcccct cattaggcca cacgttcaag tgcagcgcac        2880
accgtggaaa cggatgaagg cacgaaccca gttgacataa gcctgttcgg ttcgtaaact        2940
gtaatgcaag tagcgtatgc gctcacgcaa ctggtccaga accttgaccg aacgcagcgg        3000
tggtaacggc gcagtggcgg ttttcatggc ttgttatgac tgtttttttg tacagtctat        3060
gcctcgggca tccaagcagc aagcgcgtta cgccgtgggt cgatgtttga tgttatggag        3120
cagcaacgat gttacgcagc agcaacgatg ttacgcagca gggcagtcgc cctaaaacaa        3180
agttaggtgg ctcaagtatg gcatcattc gcacatgtag gctcggccct gaccaagtca         3240
aatccatgcg ggctgctctt gatcttttcg gtcgtgagtt cggagacgta gccacctact        3300
cccaacatca gccggactcc gattacctcg ggaacttgct ccgtagtaag acattcatcg        3360
cgcttgctgc cttcgaccaa gaagcggttg ttggcgctct cgcggcttac gttctgccca        3420
ggtttgagca gccgcgtagt gagatctata tctatgatct cgcagtctcc ggcgagcacc        3480
ggaggcaggg cattgccacc gcgctcatca atctcctcaa gcatgaggcc aacgcgcttg        3540
gtgcttatgt gatctacgtg caagcagatt acggtgacga tcccgcagtg gctctctata        3600
caaagttggg catacgggaa gaagtgatgc actttgatat cgacccaagt accgccacct        3660
aacaattcgt tcaagccgag atcgtagaat ttcgacgacc tgcagccaag cataacttcg        3720
tataatgtat gctatacgaa cggtaggatc ctctagagtc gacctgcagg catgagatgt        3780
gtataagaga cag                                                           3793
```

<210> SEQ ID NO 101
<211> LENGTH: 3847
<212> TYPE: DNA
<213> ORGANISM: Artificial Sequence
<220> FEATURE:
<223> OTHER INFORMATION: Expression cassette

<400> SEQUENCE: 101

-continued

```
ctgtctctta tacacatctc cggccagatg attaattcct aattttttgtt gacactctat       60 cattgataga gttattttac cactccctat cagtgataga gaaaagtgaa atgaatagtt      120
cgacaaaaat ctagaaataa ttttgtttgg cgtcgagaag gagatagaac catgtccaac      180
aatggctcgt caccgctggt gctttggtat aaccaactcg gcatgaatga tgtagacagg      240
gttgggggca aaaatgcctc cctgggtgaa atgattacta acctttccgg aatgggtgtt      300
tccgttccga atggtttcgc cacaaccgcc gacgcgttta accagtttct ggaccaaagc      360
ggcgtaaacc agcgcattta tgaactgctg gataaaacgg atattgacga tgttactcag      420
cttgcgaaag cgggcgcgca aatccgccag tggattatcg acactcccct ccagcctgag      480
ctggaaaacg ccatcagcga agcctatgca cagctttctg ccgatgacga aaacgcctct      540
tttgcggtgc gctcctccgc caccgcagaa gatatgccgg acgcttcttt tgccggtcag      600
caggaaacct tcctcaacgt tcagggtttt gacgccgttc tcgtggcagt gaaacatgta      660
tttgcttctc tgtttaacga tcgcgccatc tcttatcgtg tgcaccaggg ttacgatcac      720
cgtggtgtgg cgctctccgc cggtgttcaa cggatggtgc gctctgacct cgcatcatct      780
ggcgtgatgt tctccattga taccgaatcc ggctttgacc aggtggtgtt tatcacttcc      840
gcatggggcc ttggtgagat ggtcgtgcag ggtgcggtta acccggatga gttttacgtg      900
cataaaccga cactggcggc gaatcgcccg gctatcgtgc gccgcaccat ggggtcgaaa      960
aaaatccgca tggtttacgc gccgacccag gagcacggca gcaggttaa aatcgaagac     1020 gtaccgcagg aacagcgtga catcttctcg ctgaccaacg aagaagtgca ggaactggca     1080
aaacaggccg tacaaattga gaaacactac ggtcgcccga tggatattga gtgggcgaaa     1140
gatggccaca ccggtaaact gttcattgtg caggcgcgtc cggaaaccgt gcgctcacgc     1200
ggtcaggtca tggagcgtta tacgctgcat tcacagggta agattatcgc cgaaggccgt     1260
gctatcggtc atcgcatcgg tgcgggtccg gtgaaagtca tccatgatat cagcgaaatg     1320
aaccgcatcg aacctggtga cgtgctggtc actgacatga ccgacccgga ctgggaaccg     1380
atcatgaaga aagcatctgc catcgtcacc aaccgtggcg gtcgtacctg tcacgcggcg     1440
atcatcgctc gtgaactggg cattccggcg gtagtgggct gtggtgatgc aacagaacgg     1500
atgaaagacg gtgagaacgt cactgtttct tgtgccgaag gtgataccgg ttacgtctat     1560
gcggagttgc tggaatttag cgtgaaaagc tccagcgtag aaacgatgcc ggatctgccg     1620
ttgaaagtga tgatgaacgt cggtaacccg gaccgagctt tcgacttcgc ctgtctgccg     1680
aacgaaggcg tgggacttgc gcgtctggaa tttatcatca accgtatgat tggcgtccac     1740
ccacgcgcac tgcttgagtt tgacgatcag gaaccgcagt tgcaaaacga aatccgcgag     1800
atgatgaaag gttttgattc tccgcgtgaa ttttacgttg gtcgtctgac tgaagggatc     1860
gcgacgctgg gtgccgcgtt ttatccgaag cgcgtcattg tccgtctctc tgatttttaaa     1920 tcgaacgaat atgccaacct ggtcggtggt gagcgttacg agccagatga agagaacccg     1980
atgctcggct tccgtggcgc gggacgctat atttccgaca gcttccgcga ctgtttcgcg     2040
ctggagtgcg aagcagtgaa acgtgtgcgc aacgacatgg ggctgaccaa cgttgagatc     2100
atgatcccgt tcgtgcgaac cgtagatcag gcgaaagcgg tggttgagga actggcgcgt     2160 cagggctga aacgtggtga gaacgggctg aaaatcatca tgatgtgtga aatcccgtcc     2220
aacgccttgc tggccgagca gttcctcgaa tatttcgacg gcttctcaat ggctcaaac     2280 gacatgacgc agctggcgct cggtctggat cgtgactccg gcgtggtgtc tgaactgttc     2340
gatgagcgca acgatgcggt gaaagcactg ctgtcgatgg cgattcgtgc cgcgaagaaa     2400
```

-continued

```
caggycaaat atgtcgggat ttgcggtcag ggtccgtccg accacgaaga ctttgccgca    2460
tggttgatgg aagaggggat cgatagcctg tctctgaacc cggacaccgt ggtgcaaacc    2520
tggttaagcc tggctgaact gaagaaataa catccgtatc ggaaacacta gcataacccc    2580
ttggggcctc taaacgggtc ttgaggggtt ttttgctgaa accaatttgc ctggcggcag    2640
tagcgcggtg gtcccacctg accccatgcc gaactcagaa gtgaaacgcc gtagcgccga    2700
tggtagtgtg gggtctcccc atgcgagagt agggaactgc caggcatcaa ataaaacgaa    2760
aggctcagtc gaaagactgg gcctttcgct tccacaactt tgtataataa agttgtcccc    2820
acggccagtg aattcgagct cggtacctac cgttcgtata atgtatgcta tacgaagtta    2880
tcgagctcta gagaatgatc ccctcattag gccacacgtt caagtgcagc gcacaccgtg    2940
gaaacggatg aaggcacgaa cccagttgac ataagcctgt tcggttcgta aactgtaatg    3000
caagtagcgt atgcgctcac gcaactggtc cagaaccttg accgaacgca gcggtggtaa    3060
cggcgcagtg gcggtttttca tggcttgtta tgactgtttt tttgtacagt ctatgcctcg    3120
ggcatccaag cagcaagcgc gttacgccgt gggtcgatgt ttgatgttat ggagcagcaa    3180
cgatgttacg cagcagcaac gatgttacgc agcagggcag tcgccctaaa acaaagttag    3240
gtggctcaag tatgggcatc attcgcacat gtaggctcgg ccctgaccaa gtcaaatcca    3300
tgcgggctgc tcttgatctt ttcggtcgtg agttcggaga cgtagccacc tactcccaac    3360
atcagccgga ctccgattac ctcgggaact tgctccgtag taagacattc atcgcgcttg    3420
ctgccttcga ccaagaagcg gttgttggcg ctctcgcggc ttacgttctg cccaggtttg    3480
agcagccgcg tagtgagatc tatatctatg atctcgcagt ctccggcgag caccggaggc    3540
agggcattgc caccgcgctc atcaatctcc tcaagcatga ggccaacgcg cttggtgctt    3600
atgtgatcta cgtgcaagca gattacggtg acgatcccgc agtggctctc tatacaaagt    3660
tgggcatacg ggaagaagtg atgcactttg atatcgaccc aagtaccgcc acctaacaat    3720
tcgttcaagc cgagatcgta gaatttcgac gacctgcagc caagcataac ttcgtataat    3780
gtatgctata cgaacggtag gatcctctag agtcgacctg caggcatgag atgtgtataa    3840
gagacag                                                                3847
```

```
<210> SEQ ID NO 102
<211> LENGTH: 5554
<212> TYPE: DNA
<213> ORGANISM: Artificial Sequence
<220> FEATURE:
<223> OTHER INFORMATION: plasmid

<400> SEQUENCE: 102
catcgattta ttatgacaac ttgacggcta catcattcac ttttttcttca caaccggcac      60 ggaactcgct cgggctggcc ccggtgcatt ttttaaatac ccgcgagaaa tagagttgat     120
cgtcaaaacc aacattgcga ccgacggtgg cgataggcat ccgggtggtg ctcaaaagca     180
gcttcgcctg gctgatacgt tggtcctcgc gccagcttaa gacgctaatc cctaactgct     240
ggcggaaaag atgtgacaga cgcgacggcg acaagcaaac atgctgtgcg acgctggcga     300
tatcaaaatt gctgtctgcc aggtgatcgc tgatgtactg acaagcctcg cgtacccgat     360
tatccatcgg tggatggagc gactcgttaa tcgcttccat gcgccgcagt aacaattgct     420
caagcagatt tatcgccagc agctccgaat agcgcccttc cccttgcccg gcgttaatga     480
tttgcccaaa caggtcgctg aaatgcggct ggtgcgcttc atccgggcga agaaccccg      540
```

-continued

```
tattggcaaa tattgacggc cagttaagcc attcatgcca gtaggcgcgc ggacgaaagt    600
aaacccactg gtgataccat tcgcgagcct ccggatgacg accgtagtga tgaatctctc    660
ctggcgggaa cagcaaaata tcacccggtc ggcaaacaaa ttctcgtccc tgattttttca   720 ccacccctg accgcgaatg gtgagattga gaatataacc tttcattccc agcggtcggt     780
cgataaaaaa atcgagataa ccgttggcct caatcggcgt taaacccgcc accagatggg     840
cattaaacga gtatcccggc agcaggggat cattttgcgc ttcagccata cttttcatac     900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa aagtgtctat aatcacggca    1080
gaaaagtcca cattgattat ttgcacggcg tcacactttg ctatgccata gcatttttat    1140
ccataagatt agcggatcct acctgacgct ttttatcgca actctctact gtttctccat    1200
acccgttttt ttgggaattc gagctctaag gaggttataa aaaatgtcta atctgctgac    1260
ggtccaccaa aacctgccgg ctctgccggt cgatgctacc tctgatgaag ttcgcaaaaa    1320
cctgatggat atgtttcgtg atcgccaggc attcagcgaa catacctgga aaatgctgct    1380
gtccgtgtgc cgttcatggg cggcctggtg taaactgaac aatcgcaaat ggtttccggc    1440
ggaaccggaa gatgtccgtg actatctgct gtacctgcag gcccgcggtc tggcagttaa    1500
aacgatccag caacatctgg gccaactgaa tatgctgcac cgtcgctccg gtctgccgcg    1560
tccgagcgat tctaatgcgg tgtcactggt tatgcgtcgc attcgtaaag aaaacgtgga    1620
tgcaggcgaa cgcgctaaac aggcactggc ttttgaacgt accgatttcg accaagttcg    1680
ctcgctgatg gaaaacagcg atcgttgcca ggacatccgc aatctggcgt tcctgggtat    1740
tgcctataac accctgctgc gcattgcaga aatcgctcgt attcgcgtga aagatatcag    1800
ccgtacggac ggcggtcgca tgctgattca catcggccgt accaaaacgc tggtctctac    1860
cgcaggcgtg gaaaaagctc tgagtctggg tgtgacgaaa ctggttgaac gctggattag    1920
tgtctccggc gtggcggatg acccgaacaa ttacctgttt tgtcgtgttc gcaaaaatgg    1980
tgtcgcagct ccgtcagcca cctcgcagct gagcacgcgt gcactggaag gcatcttcga    2040
agctacccat cgcctgattt atggcgccaa agatgactcg ggtcaacgtt acctggcgtg    2100
gtctggtcac agtgcacgtg ttggtgccgc acgtgatatg gcccgtgccg gtgtttccat    2160
cccggaaatt atgcaggcag gcggttggac caacgttaat atcgtcatga actatattcg    2220
caatctggac tcggaaacgg gtgctatggt tcgcctgctg gaagacggtg actaatgagt    2280
gccggagttc atcgaaaaaa tggacgaggc actggctgaa attggttttg tatttgggga    2340
gcaatggcga tgacgcatcc tcacgataat atcgcgggtag gcgcaatcac tttcgtctac    2400
tccgttacaa agcgaggctg ggtatttccc ggcctttctg ttatccgaaa tccactgaaa    2460
gcacagcggc tggctgagga gataaataat aaacgagggg ctgtatgcac aaagcatctt    2520
ctgttgagtt aagaacgagt atcgagatgg cacatagcct tgctcaaatt ggaatcaggt    2580
ttgtgccaat accagtagaa acagacgaag aatccatggg tatggacagt tttcccttttg   2640 atatgtaacg gtgaacagtt gttctacttt tgtttgttag tcttgatgct tcactgatag    2700
atacaagagc cataagaacc tcagatcctt ccgtatttag ccagtatgtt ctctagtgtg    2760
gttcgttgtt tttgcgtgag ccatgagaac gaaccattga gatcatactt actttgcatg    2820
tcactcaaaa attttgcctc aaaactggtg agctgaattt ttgcagttaa agcatcgtgt    2880
agtgtttttc ttagtccgtt acgtaggtag gaatctgatg taatggttgt tggtattttg    2940
```

-continued

```
tcaccattca tttttatctg gttgttctca agttcggtta cgagatccat ttgtctatct   3000
agttcaactt ggaaaatcaa cgtatcagtc gggcggcctc gcttatcaac caccaatttc   3060
atattgctgt aagtgtttaa atctttactt attggtttca aaacccattg gttaagcctt   3120
ttaaactcat ggtagttatt ttcaagcatt aacatgaact taaattcatc aaggctaatc   3180
tctatatttg ccttgtgagt tttctttgt gttagttctt ttaataacca ctcataaatc    3240
ctcatagagt atttgtttc aaaagactta acatgttcca gattatattt tatgaatttt     3300
tttaactgga aaagataagg caatatctct tcactaaaaa ctaattctaa tttttcgctt   3360
gagaacttgg catagtttgt ccactggaaa atctcaaagc ctttaaccaa aggattcctg   3420
atttccacag ttctcgtcat cagctctctg gttgctttag ctaatacacc ataagcattt   3480
tccctactga tgttcatcat ctgagcgtat tggttataag tgaacgatac cgtccgttct   3540
ttccttgtag ggttttcaat cgtggggttg agtagtgcca cacagcataa aattagcttg   3600
gtttcatgct ccgttaagtc atagcgacta atcgctagtt catttgcttt gaaaacaact   3660
aattcagaca tacatctcaa ttggtctagg tgattttaat cactatacca attgagatgg   3720
gctagtcaat gataaattact agtccttttc ctttgagttg tgggtatctg taaattctgc   3780
tagacctttg ctggaaaact tgtaaattct gctagaccct ctgtaaattc cgctagacct   3840
ttgtgtgttt tttttgttta tattcaagtg gttataattt atagaataaa gaaagaataa   3900
aaaaagataa aaagaataga tcccagccct gtgtataact cactacttta gtcagttccg   3960
cagtattaca aaaggatgtc gcaaacgctg tttgctcctc tacaaaacag accttaaaac   4020
cctaaaggct taagtagcac cctcgcaagc tcggttgcgg ccgcaatcgg gcaaatcgct   4080
gaatattcct tttgtctccg accatcaggc acctgagtcg ctgtcttttt cgtgacattc   4140
agttcgctgc gctcacggct ctggcagtga atgggggtaa atggcactac aggcgccttt   4200
tatggattca tgcaaggaaa ctacccataa tacaagaaaa gcccgtcacg ggcttctcag   4260
ggcgttttat ggcgggtctg ctatgtggtg ctatctgact ttttgctgtt cagcagttcc   4320
tgccctctga ttttccagtc tgaccacttc ggattatccc gtgacaggtc attcagactg   4380
gctaatgcac ccagtaaggc agcggtatca tcaacggggt ctgacgctca gtggaacgaa   4440
aactcacgtt aagggatttt ggtcatgaga ttatcaaaaa ggatcttcac ctagatcctt   4500
ttaaattaaa aatgaagttt taaatcaatc taaagtatat atgagtaaac ttggtctgac   4560
agttaccaat gcttaatcag tgaggcacct atctcagcga tctgtctatt tcgttcatcc   4620
atagttgcct gactccccgt cgtgtagata actacgatac gggagggctt accatctggc   4680
cccagtgctg caatgatacc gcgagaccca cgctcaccgg ctccagattt atcagcaata   4740
aaccagccag ccggaagggc cgagcgcaga agtggtcctg caactttatc cgcctccatc   4800
cagtctatta attgttgccg ggaagctaga gtaagtagtt cgccagttaa tagtttgcgc   4860
aacgttgttg ccattgctac aggcatcgtg gtgtcacgct cgtcgtttgg tatggcttca   4920
ttcagctccg gttcccaacg atcaaggcga gttacatgat cccccatgtt gtgcaaaaaa   4980
gcggttagct ccttcggtcc tccgatcgtt gtcagaagta agttggccgc agtgttatca   5040
ctcatggtta tggcagcact gcataattct cttactgtca tgccatccgt aagatgcttt   5100
tctgtgactg gtgagtactc aaccaagtca ttctgagaat agtgtatgcg cgaccgagt    5160 tgctcttgcc cggcgtcaat acgggataat accgcgccac atagcagaac tttaaaagtg   5220
ctcatcattg gaaaacgttc ttcggggcga aaactctcaa ggatcttacc gctgttgaga   5280
```

-continued

```
tccagttcga tgtaacccac tcgtgcaccc aactgatctt cagcatcttt tacttcacc      5340 agcgtttctg ggtgagcaaa aacaggaagg caaaatgccg caaaaaaggg aataagggcg     5400
acacggaaat gttgaatact catactcttc cttttcaat attattgaag catttatcag      5460
ggttattgtc tcatgagcgg atacatattt gaatgtattt agaaaaataa acaaataggg     5520
gttccgcgca catttccccg aaaagtgcca cctg                                 5554
```

```
<210> SEQ ID NO 103
<211> LENGTH: 3415
<212> TYPE: DNA
<213> ORGANISM: Artificial Sequence
<220> FEATURE:
<223> OTHER INFORMATION: Expression cassette

<400> SEQUENCE: 103
ccggccagat gattaattcc taattttttgt tgacactcta tcattgatag agttatttta      60
ccactcccta tcagtgatag agaaaagtga aatgaatagt tcgacaaaaa tctagaaata     120
attttgttta actttaagaa ggagatatac aaatgaacaa cgacaactcc acgaccacca     180
acaataacgc tattgaaatc tatgtggatc gtgcgaccct gccgacgatc cagcaaatga     240
ccaaaattgt tagccagaaa acgtctaaca aaaaactgat ctcatggtcg cgctacccga     300
ttaccgataa aagcctgctg aagaaaatta acgcggaatt tttcaaagaa caatttgaac     360
tgacggaaag cctgaaaaac atcatcctgt ctgaaaacat cgataacctg atcattcatg     420
gcaataccct gtggagtatt gatgtggttg acattatcaa agaagtcaac ctgctgggca     480
aaaatattcc gatcgaactg cacttttatg atgacggttc cgccgaatac gttcgtatct     540
acgaatttag taaactgccg gaatccgaac agaaatacaa aaccagcctg tctaaaaaca     600
acatcaaatt ctcaatcgat ggcaccgact cgttcaaaaa cacgatcgaa aacatctacg     660
gtttcagcca actgtatccg accacgtacc acatgctgcg tgcagatatc ttcgacacca     720
cgctgaaaat taacccgctg cgcgaactgc tgtcaaacaa catcaaacag atgaaatggg     780
attacttcaa agacttcaac tacaaacaaa aagatatctt ttactcactg accaacttca     840
acccgaaaga aatccaggaa gacttcaaca aaaactcgaa caaaaacttc atcttcatcg     900
gcagtaactc cgcgaccgcc acggcagaag aacaaatcaa tattatcagc gaagcgaaga     960
aagaaaacag cagcattatc accaattcaa tttcggatta tgacctgtttt ttcaaaggtc    1020 atccgtctgc cacgtttaac gaacagatta tcaatgcaca cgatatgatc gaaatcaaca    1080
acaaaatccc gttcgaagct ctgatcatga ccggcattct gccggatgcc gttggcggta    1140
tgggtagttc cgtctttttc agtatcccga aagaagtcaa aaacaaattc gtgttctata    1200
aaagtggtac ggatatcgaa aataactccc tgattcaggt gatgctgaaa ctgaatctga    1260
ttaaccgcga taatattaaa ctgatctctg acatttaatt tcgtcgacac acaggaaaca    1320
tattaaaaat taaaacctgc aggagtttaa acgcggccgc gatatcgttg taaaacgacg    1380
gccagtgcaa gaatcataaa aaatttatttt gctttcagga aaattttttct gtataataga    1440 ttcataaatt tgagagagga gttttttgtga gcggataaca attccccatc ttagtatatt    1500
agttaagtat aaatacacaa ggagatatac atatgagcct ggccattatc ccggcacgtg    1560
gcggttctaa aggcatcaaa aacaaaaacc tggttctgct gaacaataaa ccgctgattt    1620
attacaccat caaagcggcc ctgaacgcca aaagtattag caaagtggtt gtgagctctg    1680
attctgatga aatcctgaac tacgcaaaaa gtcagaacgt tgatatcctg aaacgtccga    1740
tcagtctggc acaggatgat accacgagcg ataaagtgct gctgcatgcg ctgaaattct    1800
```

```
acaaagatta cgaagatgtt gtgttcctgc agccgaccag cccgctgcgt acgaatattc    1860
acatcaacga agcgttcaac ctgtacaaaa acagcaacgc aaacgcgctg atttctgtta    1920
gtgaatgcga taacaaaatc ctgaaagcgt ttgtgtgcaa tgattgtggc gatctggccg    1980
gtatttgtaa cgatgaatac ccgttcatgc cgcgccagaa actgccgaaa acctatatga    2040
gcaatggtgc catctacatc ctgaaaatca aagaattcct gaacaacccg agcttcctgc    2100
agtctaaaac gaaacatttc ctgatggatg aaagtagctc tctggatatt gattgcctgg    2160
aagatctgaa aaaagtggaa cagatctgga aaaataaaa tactgaaacc aatttgcctg     2220
gcggcagtag cgcggtggtc ccacctgacc ccatgccgaa ctcagaagtg aaacgccgta    2280
gcgccgatgg tagtgtgggg tctccccatg cgagagtagg gaactgccag gcatcaaata    2340
aaacgaaagg ctcagtcgaa agactgggcc tttcgcttcc acaactttgt ataataaagt    2400
tgtccccacg gccagtgaat tcgagctcgg tacctaccgt tcgtataatg tatgctatac    2460
gaagttatcg agctctagag aatgatcccc tcattaggcc acacgttcaa gtgcagcgca    2520
caccgtggaa acggatgaag gcacgaaccc agttgacata gcctgttcg gttcgtaaac     2580 tgtaatgcaa gtagcgtatg cgctcacgca actggtccag aaccttgacc gaacgcagcg    2640
gtggtaacgg cgcagtggcg gttttcatgg cttgttatga ctgttttttt gtacagtcta    2700
tgcctcgggc atccaagcag caagcgcgtt acgccgtggg tcgatgtttg atgttatgga    2760
gcagcaacga tgttacgcag cagcaacgat gttacgcagc agggcagtcg ccctaaaaca    2820
aagttaggtg gctcaagtat gggcatcatt cgcacatgta ggctcggccc tgaccaagtc    2880
aaatccatgc gggctgctct tgatcttttc ggtcgtgagt tcggagacgt agccacctac    2940
tcccaacatc agccggactc cgattacctc gggaacttgc tccgtagtaa gacattcatc    3000
gcgcttgctg ccttcgacca agaagcggtt gttggcgctc tcgcggctta cgttctgccc    3060
aggtttgagc agccgcgtag tgagatctat atctatgatc tcgcagtctc cggcgagcac    3120
cggaggcagg gcattgccac cgcgctcatc aatctcctca agcatgaggc caacgcgctt    3180
ggtgcttatg tgatctacgt gcaagcagat tacggtgacg atcccgcagt ggctctctat    3240
acaaagttgg gcatacggga agaagtgatg cactttgata tcgacccaag taccgccacc    3300
taacaattcg ttcaagccga gatcgtagaa tttcgacgac ctgcagccaa gcataacttc    3360
gtataatgta tgctatacga acggtaggat cctctagagt cgacctgcag gcatg         3415
```

<210> SEQ ID NO 104
<211> LENGTH: 3763
<212> TYPE: DNA
<213> ORGANISM: Artificial Sequence
<220> FEATURE:
<223> OTHER INFORMATION: Expression cassette

<400> SEQUENCE: 104

```
ccggccagat gattaattcc taattttttgt tgacactcta tcattgatag agttatttta    60
ccactcccta tcagtgatag agaaaagtga aatgaatagt tcgacaaaaa tctagaaata    120 attttgtttta actttaagaa ggagatatac aaatgtgtaa cgataatcaa aatacggtcg    180
atgttgttgt gagcaccgtt aacgataacg tcatcgaaaa caacacgtac caagttaaac    240
cgatcgatac cccgaccacg tttgacagtt actcctggat tcagacgtgc ggcaccccga    300
tcctgaaaga tgacgaaaaa tattcactgt cgtttgattt cgtcgccccg gaactggatc    360
aggacgaaaa attctgtttc gaatttaccg gcgatgttga cggtaaacgt tatgtcacgc    420
```

-continued

```
agaccaacct gacggtggtt gcaccgaccc tggaagttta cgtcgatcat gctagtctgc    480
cgtccctgca gcaactgatg aaaatcatcc agcagaaaaa cgaatactca cagaatgaac    540
gtttcatttc gtggggccgc atcggtctga cggaagataa cgcggaaaaa ctgaatgccc    600
atatttatcc gctggcaggc aacaatacct cacaggaact ggtggatgca gtgatcgatt    660
acgctgactc gaaaaaccgt ctgaatctgg aactgaacac gaataccgcg cacagctttc    720
cgaacctggc cccgattctg cgcattatca gctctaaaag caacatcctg atctctaaca    780
tcaacctgta cgatgacggc agtgctgaat atgtgaacct gtacaattgg aaagataccg    840
aagacaaatc cgtgaaactg agcgattctt cctggttct gaaagactac tttaacggta    900
ttagttccga aaaaccgagc ggcatctatg gtcgctacaa ctggcatcaa ctgtataata    960
cgtcttatta cttcctgcgt aaagattacc tgaccgttga accgcagctg cacgacctgc    1020
gcgaatatct gggcggtagt ctgaaacaaa tgtcctggga tggcttttca cagctgtcga    1080
aaggtgacaa agaactgttc ctgaacattg tcggctttga tcaggaaaaa ctgcagcaag    1140
aataccagca atcagaactg ccgaatttcg tgtttacggg caccacgacc tgggcaggcg    1200
gtgaaaccaa agaatattac gctcagcaac aggtgaacgt cgtgaacaat gcgattaatg    1260
aaaccagccc gtattacctg ggccgtgaac atgacctgtt tttcaaaggt cacccgcgcg    1320
gcggtattat caatgatatt atcctgggca gtttcaacaa tatgattgac atcccggcca    1380
aagtgtcctt tgaagttctg atgatgacgg gtatgctgcc ggataccgtg ggcggtattg    1440
cgtcatcgct gtattttagc atcccggccg aaaaagtctc tttcattgtg tttaccagct    1500
ctgatacgat caccgatcgt gaagacgcgc tgaaatctcc gctggtgcag gttatgatga    1560
ccctgggcat tgttaaagaa aaagatgtgc tgttctggtc ggatctgccg gattgttcct    1620
cgggtgtttg tattgctcag tattaatttc gtcgacacac aggaaacata ttaaaaatta    1680
aaacctgcag gagtttaaac gcggccgcga tatcgttgta aaacgacggc cagtgcaaga    1740
atcataaaaa atttatttgc tttcaggaaa attttctgt ataatagatt cataaatttg    1800
agagaggagt ttttgtgagc ggataacaat tccccatctt agtatattag ttaagtataa    1860
atacacaagg agatatacat atgagcctgg ccattatccc ggcacgtggc ggttctaaag    1920
gcatcaaaaa caaaaacctg gttctgctga acaataaacc gctgatttat tacaccatca    1980
aagcggccct gaacgccaaa agtattagca aagtggttgt gagctctgat tctgatgaaa    2040
tcctgaacta cgcaaaaagt cagaacgttg atatcctgaa acgtccgatc agtctggcac    2100
aggatgatac cacgagcgat aaagtgctgc tgcatgcgct gaaattctac aaagattacg    2160
aagatgttgt gttcctgcag ccgaccagcc cgctgcgtac gaatattcac atcaacgaag    2220
cgttcaacct gtacaaaaac agcaacgcaa acgcgctgat ttctgttagt gaatgcgata    2280
acaaaatcct gaaagcgttt gtgtgcaatg attgtggcga tctggccggt atttgtaacg    2340
atgaataccc gttcatgccg cgccagaaac tgccgaaaac ctatatgagc aatggtgcca    2400
tctacatcct gaaaatcaaa gaattcctga caacccgag cttcctgcag tctaaaacga    2460
aacatttcct gatggatgaa agtagctctc tggatattga ttgcctggaa gatctgaaaa    2520
aagtggaaca gatctggaaa aaataaaata ctgaaaccaa tttgcctggc ggcagtagcg    2580
cggtggtccc acctgacccc atgccgaact cagaagtgaa acgccgtagc gccgatggta    2640
gtgtggggtc tccccatgcg agagtaggga actgccaggc atcaaataaa acgaaaggct    2700
cagtcgaaag actgggcctt tcgcttccac aactttgtat aataaagttg tccccacggc    2760
cagtgaattc gagctcggta cctaccgttc gtataatgta tgctatacga agttatcgag    2820
```

-continued

```
ctctagagaa tgatccctc attaggccac acgttcaagt gcagcgcaca ccgtggaaac   2880
ggatgaaggc acgaacccag ttgacataag cctgttcggt tcgtaaactg taatgcaagt   2940
agcgtatgcg ctcacgcaac tggtccagaa ccttgaccga acgcagcggt ggtaacggcg   3000
cagtggcggt tttcatggct tgttatgact gtttttttgt acagtctatg cctcgggcat   3060
ccaagcagca agcgcgttac gccgtgggtc gatgtttgat gttatggagc agcaacgatg   3120
ttacgcagca gcaacgatgt tacgcagcag ggcagtcgcc ctaaaacaaa gttaggtggc   3180
tcaagtatgg gcatcattcg cacatgtagg ctcggccctg accaagtcaa atccatgcgg   3240
gctgctcttg atcttttcgg tcgtgagttc ggagacgtag ccacctactc ccaacatcag   3300
ccggactccg attacctcgg gaacttgctc cgtagtaaga cattcatcgc gcttgctgcc   3360
ttcgaccaag aagcggttgt tggcgctctc gcggcttacg ttctgcccag gtttgagcag   3420
ccgcgtagtg agatctatat ctatgatctc gcagtctccg gcgagcaccg gaggcagggc   3480
attgccaccg cgctcatcaa tctcctcaag catgaggcca acgcgcttgg tgcttatgtg   3540
atctacgtgc aagcagatta cggtgacgat cccgcagtgg ctctctatac aaagttgggc   3600
atacgggaag aagtgatgca ctttgatatc gacccaagta ccgccaccta acaattcgtt   3660
caagccgaga tcgtagaatt tcgacgacct gcagccaagc ataacttcgt ataatgtatg   3720
ctatacgaac ggtaggatcc tctagagtcg acctgcaggc atg                     3763
```